US009365863B2

(12) United States Patent
Burns et al.

(10) Patent No.: US 9,365,863 B2
(45) Date of Patent: *Jun. 14, 2016

(54) COMPOSITIONS AND METHODS FOR DEPLOYING A TRANSGENIC REFUGE SEED BLEND

(71) Applicant: Monsanto Technology LLC, St. Louis, MO (US)

(72) Inventors: Wen C. Burns, Chesterfield, MO (US); Catherine A. Chay, St. Louis, MO (US); Cheryl L. Cloninger, St. Louis, MO (US); Mingqi Deng, Chesterfield, MO (US); Stanislaw Flasinski, Chesterfield, MO (US); Kunsheng Wu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/262,233

(22) Filed: Apr. 25, 2014

(65) Prior Publication Data

US 2014/0338072 A1 Nov. 13, 2014

Related U.S. Application Data

(60) Provisional application No. 61/821,227, filed on May 8, 2013.

(51) Int. Cl.
*C12N 15/82* (2006.01)
*A01G 1/00* (2006.01)

(52) U.S. Cl.
CPC ............ *C12N 15/8286* (2013.01); *A01G 1/001* (2013.01); *C12N 15/8275* (2013.01)

(58) Field of Classification Search
CPC ................................................ C12N 15/8286
See application file for complete search history.

(56) References Cited

U.S. PATENT DOCUMENTS

| | | | |
|---|---|---|---|
| 4,766,203 A | 8/1988 | Kreig et al. | |
| 4,797,279 A | 1/1989 | Karamata et al. | |
| 4,910,016 A | 3/1990 | Gaertner et al. | |
| 5,378,625 A | 1/1995 | Donovan et al. | |
| 5,633,435 A | 5/1997 | Barry et al. | |
| 5,659,123 A | 8/1997 | Van Rie et al. | |
| 5,696,144 A | 12/1997 | Royalty et al. | |
| 5,753,507 A | 5/1998 | Ohta et al. | |
| 5,849,320 A | 12/1998 | Turnblad et al. | |
| 5,876,739 A | 3/1999 | Turnblad et al. | |
| 5,877,012 A | 3/1999 | Estruch | |
| 5,990,395 A | 11/1999 | Plaisted et al. | |
| 6,023,013 A | 2/2000 | English et al. | |
| 6,060,594 A | 5/2000 | English et al. | |
| 6,063,597 A | 5/2000 | English et al. | |
| 6,083,499 A | 7/2000 | Narva et al. | |
| 6,172,281 B1 | 1/2001 | Van Mellaert et al. | |
| 6,252,148 B1 | 6/2001 | Armstrong | |
| 6,551,962 B1 | 4/2003 | Pershing et al. | |
| 7,001,869 B2 | 2/2006 | Johnson | |
| 7,288,643 B2 | 10/2007 | Barbour et al. | |
| 7,323,556 B2 | 1/2008 | Bing et al. | |
| 7,361,813 B2 | 4/2008 | Steiner et al. | |
| 7,612,194 B2 | 11/2009 | Andersen et al. | |
| 7,943,819 B2 | 5/2011 | Baum et al. | |
| 8,062,840 B2 | 11/2011 | Anderson et al. | |
| 8,067,671 B2 | 11/2011 | Boukharov et al. | |
| 8,088,976 B2 | 1/2012 | Boukharov et al. | |
| 8,212,113 B2 | 7/2012 | Beazley et al. | |
| 8,232,456 B2 | 7/2012 | Long et al. | |
| 8,404,927 B2 | 3/2013 | Allen et al. | |
| 8,466,346 B2 | 6/2013 | DeFramond et al. | |
| 8,614,370 B2 | 12/2013 | Andersen et al. | |
| 8,618,358 B2 | 12/2013 | Feng et al. | |
| 8,686,230 B2 | 4/2014 | Beazley et al. | |
| 8,759,611 B2 | 6/2014 | Buam et al. | |
| 8,946,510 B2 | 2/2015 | Baum et al. | |
| 2003/0186813 A1 | 10/2003 | Pershing et al. | |
| 2004/0063582 A1 | 4/2004 | Johnson | |
| 2006/0112447 A1 | 5/2006 | Bogdanova et al. | |
| 2006/0127889 A1 | 6/2006 | Dotson et al. | |
| 2006/0272049 A1 | 11/2006 | Waterhouse et al. | |
| 2007/0124836 A1* | 5/2007 | Baum et al. | 800/279 |

(Continued)

FOREIGN PATENT DOCUMENTS

EP 2281447 A3 3/2011
WO WO 97/40162 10/1997

(Continued)

OTHER PUBLICATIONS

Nascimento. 2013. Brazil corn seed compaies offer almost 500 hybrids to growers. Agro News. http://news.agropages.com/News/NewsDetail---9371.htm.*
International Search Report and Written Opinion regarding International Application No. PCT/US14/35518, dated Sep. 25, 2014.
U.S. Appl. No. 10/780,151, filed Feb. 17, 2004, Pershing et al.
U.S. Appl. No. 11/686,725, filed Mar. 15, 2007, Head et al.
U.S. Appl. No. 14/304,715, filed Jun. 13, 2014, Carroll et al.
Agi et al., "Arthropod management: efficacy of seed mixes of transgenic Bt and nontransgenic cotton against bollworm *Helicoverpa zea* boddie," *J. Cotton Sci.* 5:74-80, 2001.
Amendment and Response to Office Action in U.S. Appl. No. 11/686,725, dated Jun. 26, 2012.
Amendment and Response to Office Action in U.S. Appl. No. 12/651,174, dated Jun. 6, 2012.
Amendment and Response to Office Action regarding U.S. Appl. No. 10/780,151, dated Apr. 19, 2010.
Amendment and Response to Office Action regarding U.S. Appl. No. 11/686,725, dated Mar. 18, 2011.
Armstrong et al., "Field evaluation of European corn borer in progeny of 173 transgenic corn event expressing an insecticidal protein from *Bacillus thuringiensis*," *Crop Sci.* 35(2):550-557, 1995.

(Continued)

*Primary Examiner* — Anne Kubelik
*Assistant Examiner* — Karen Redden
(74) *Attorney, Agent, or Firm* — Dentons US LLP; T. K. Ball, Esq.; Carine M. Doyle, Esq.

(57) ABSTRACT

Methods and compositions for deploying refuge seeds with transgenic crop seeds comprising event MON 87411 are provided. The refuge seeds can be non-transgenic seeds of a similar variety to that of the transgenic crop seeds, or the refuge seeds can be a transgenic variety, but lack event MON 87411 found in the transgenic crop seeds and serve as a refuge thereto.

22 Claims, 4 Drawing Sheets

(56) References Cited

U.S. PATENT DOCUMENTS

| | | | |
|---|---|---|---|
| 2007/0259785 | A1 | 11/2007 | Heck et al. |
| 2008/0028482 | A1 | 1/2008 | Beazley et al. |
| 2008/0226753 | A1 | 9/2008 | Cosgrove |
| 2009/0041869 | A1 | 2/2009 | Cosgrove |
| 2009/0068159 | A1 | 3/2009 | Baum et al. |
| 2010/0022390 | A1 | 1/2010 | Cosgrove |
| 2010/0029725 | A1 | 2/2010 | Cosgrove et al. |
| 2010/0179196 | A1* | 7/2010 | Pershing et al. .............. 514/341 |
| 2010/0192265 | A1 | 7/2010 | Andersen et al. |
| 2010/0210460 | A1 | 8/2010 | Coaldrake et al. |
| 2011/0004955 | A1 | 1/2011 | Abad et al. |
| 2011/0277180 | A1 | 11/2011 | Romano |
| 2011/0321185 | A1 | 12/2011 | Anderson et al. |
| 2012/0137387 | A1 | 5/2012 | Baum et al. |
| 2012/0164205 | A1 | 6/2012 | Baum et al. |
| 2012/0192317 | A1 | 7/2012 | Heck et al. |
| 2013/0232646 | A1 | 9/2013 | Baum et al. |
| 2013/0340111 | A1 | 12/2013 | Burns et al. |
| 2014/0013471 | A1 | 1/2014 | Baum et al. |
| 2014/0080755 | A1 | 3/2014 | Heck et al. |
| 2014/0194306 | A1 | 7/2014 | Andersen et al. |
| 2014/0287406 | A1 | 9/2014 | Beazley et al. |
| 2014/0325702 | A1 | 10/2014 | Boukharov et al. |
| 2014/0338072 | A1 | 11/2014 | Burns et al. |
| 2014/0366786 | A1 | 12/2014 | Carroll et al. |

FOREIGN PATENT DOCUMENTS

| | | |
|---|---|---|
| WO | WO 98/13498 | 4/1998 |
| WO | WO 98/27218 | 6/1998 |
| WO | WO 99/31248 | 6/1999 |
| WO | WO 99/35910 | 7/1999 |
| WO | WO 99/35913 | 7/1999 |
| WO | WO 2005/094340 | 10/2005 |
| WO | WO 2008/080166 | 7/2008 |
| WO | WO 2008/085729 | 7/2008 |
| WO | WO 2009/075860 A2 | 6/2009 |
| WO | WO 2009/132850 | 11/2009 |
| WO | WO 2009/149787 | 12/2009 |

OTHER PUBLICATIONS

Bannert et al., "Short-distance cross-pollination of maize in a small-field landscape as monitored by grain color markers," *Europ. J. Agronomy* vol. 29, pp. 29-32, 2008.

Bates et al., "Insect resistance management in GM crops: past, present and future," *Nature Biotechnol.* 23:57-62, 2005.

Brookes et al., 2004, "Genetically modified maize: pollen movement and crop co-existence," *PG Economics Ltd.*, Dorchester, United Kingdom (available at http://www.pgeconomics.co.uk).

Burkness et al., "Bt pollen dispersal and bt kernel mosaics: integrity of non-bt refugia for lepidopteran resistance management in maize," *Journal of Economic Entomology* 105(5):1773-1780, 2012.

Burkness et al., "Cross-pollination of nontransgenic corn ears with transgenic bt corn: efficacy against lepidopteran pests and implications for resistance management," *Journal of Economic Entomology* 104(5):1476-1479, 2011.

Chilcutt et al., "Contamination of refuges by bacillus thuringiensis toxin genes from transgenic maize," *PNAS* 101(20):7526-7529, 2004.

Cohen et al., "Bt rice: practical steps to sustainable use," *International Rice Research Notes*, 25:4-10, 2000.

Crickmore et al., "Bacillus thuringiensis toxin nomenclature," http://www.lifesci.sussex.ac.uk/home/Neil_Crickmore/Bt/intro.html, accessed on Apr. 1, 2009.

Crickmore et al., "Revision of the nomenclature for the bacillus thuringiensis pesticidal crystal proteins," *Microbiol. Mol. Biol. Rev.* 62:807-813, 1998.

Davis et al., "Seed Mixtures as a Resistance Management Strategy for European Corn Borers (Lepidoptera: Crambidae) Infesting Transgenic Corn Expressing Cry1Ab Protein," *J. Econ. Entomol.* 93(3):937-948, 2000.

Environmental Protection Agency (EPA), "Pesticide Fact Sheet," http://www.epa.gov/pesticides/biopesticides/pips/smartstax-factsheet.pdf., undated.

Environmental Protection Agency (EPA), "Transmittal of the Final Report of the FIFRA Scientific Advisory Subpanel on Bacillus thuringiensis (Bt) Plant-Pesticides and Resistance Management, Meeting held on Feb. 9 and 10, 1998."

Final Office Action in U.S. Appl. No. 11/686,725, dated Jul. 24, 2012.

Final Office Action regarding U.S. Appl. No. 10/780,151, dated Oct. 20, 2008.

Final Office Action regarding U.S. Appl. No. 11/686,725 dated Dec. 27, 2013.

Final Office Action regarding U.S. Appl. No. 12/651,174, dated Feb. 11, 2014.

Gould et al., "Sustainability of transgenic insecticidal cultivars: integrating pest genetics and ecology," *Annu. Rev. Entomol.* 43:701-726, 1998.

International Search Report issued in PCT/US2013/040173, dated Dec. 16, 2013.

Jansens et al., "Transgenic corn expressing a Cry9C insecticidal protein from Bacillus thuringiensis protected from European corn borer damage," *Crop Sci.* 37(5):1616-1624, 1997.

Kennedy et al., "Managing pest resistance to bacillus thuringiensis endotoxins: constraints and incentives to implementation," *J. Econ Entomol.* 88:454-460, 1995.

Lambert et al., "Effects of natural enemy conservation and planting date on the susceptibility of BT cotton to *Helicoverpa zea* in North Carolina," *Proceedings/Beltwide Cotton Conference* 2:931-935, 1996.

Li et al., "Effects of Bt cotton expressing Cry1ac and Cry2ab and non-Bt cotton on behavior, survival and development of trichoplusia ni (Lepidoptera:noctuidae)," *Crop Protect J.* 25-940-948, 2006.

Mallet et al., "Preventing insect adaptation to insect-resistant crops: are seed mixtures or refugia the best strategy," *Proc. R. Soc. Lond. B* 250:165-169, 1992.

Maqbool et al., "Multiple traits of agronomic importance in transgenic indica rice plants: analysis of transgene integration patterns, expression levels and stability," *Molecular Breeding* 5:471-480, 1999.

Moellenbeck et al., "Insecticidal proteins from *Bacillus thuringiensis* protect corn from rootworms," *Nature Biotechnology* 19:668-672, 2001.

Non-Final Office Action in U.S. Appl. No. 12/651,174, dated Jul. 20, 2012.

Final Office Action in U.S. Appl. No. 12/651,174, dated Jan. 6, 2012.

Non-Final Office Action regarding U.S. Appl. No. 10/780,151, dated Jun. 19, 2014.

Non-Final Office Action regarding U.S. Appl. No. 11/686,725, dated Jun. 5, 2013.

Non-Final Office Action regarding U.S. Appl. No. 12/651,174, dated Aug. 26, 2013.

Notice of Appeal regarding U.S. Appl. No. 10/780,151, dated Mar. 20, 2009.

Office Action regarding U.S. Appl. No. 10/599,307, dated Jan. 7, 2009.

Non-Final Office Action regarding U.S. Appl. No. 10/780,151, dated Dec. 17, 2009.

Final Office Action regarding U.S. Appl. No. 10/780,151, dated Jun. 29, 2010.

Non-Final Office Action regarding U.S. Appl. No. 10/780,151, dated Mar. 26, 2008.

Non-Final Office Action regarding U.S. Appl. No. 11/686,725, dated Aug. 22, 2011.

Non-Final Office Action regarding U.S. Appl. No. 11/686,725, dated Dec. 20, 2010.

Non-Final Office Action regarding U.S. Appl. No. 11/686,725, filed Jan. 26, 2012.

Non-Final Office Action regarding U.S. Appl. No. 12/651,174, dated Dec. 2, 2010.

Non-Final Office Action regarding U.S. Appl. No. 12/651,174, dated Jul. 12, 2011.

(56) References Cited

OTHER PUBLICATIONS

Onstad et al., "Seeds of change: corn seed mixtures for resistance management and integrated pest management," *Journal of Economic Entomology* 104(2):343-352, 2011.
Ostlie, "Crafting crop resistance to corn rootworms," *Nature Biotechnology* 19:624-625, 2001.
Ramachandran et al., "Intraspecific competition of an insect-resistant transgenic canola in seed mixtures," *Agron. J.* 92:368-374, 2000.
Request for Continued Examination regarding U.S. Appl. No. 10/780,151, dated Mar. 7, 2011.
Request for Continued Examination regarding U.S. Appl. No. 10/780,151, dated Sep. 18, 2009.
Response to Final Office Action regarding U.S. Appl. No. 11/686,725, dated Sep. 26, 2014, and Declaration of Graham Head, Ph.D. Under 37 C.F.R. § 1.132.
Response to Final Office Action regarding U.S. Appl. No. 12/651,174, dated Jun. 11, 2014.
Response to Non-Final Office Action regarding U.S. Appl. No. 10/780,151, dated Sep. 9, 2014 and Declaration of Graham Head, Ph.D. Under 37 C.F.R. § 1.132.
Response to Non-Final Office Action regarding U.S. Appl. No. 10/780,151, dated Jul. 22, 2008.
Response to Final Office Action regarding U.S. Appl. No. 10/780,151, dated Mar. 7, 2011.
Response to Final Office Action regarding U.S. Appl. No. 10/780,151, dated Sep. 18, 2009.
Response to Non-Final Office Action regarding U.S. Appl. No. 11/686,725, dated Oct. 7, 2013.
Response to Non-Final Office Action regarding U.S. Appl. No. 11/686,725, dated Mar. 18, 2011.
Response to Non-Final Office Action regarding U.S. Appl. No. 11/686,725, filed Dec. 13, 2011.
Response to Final Office Action regarding U.S. Appl. No. 11/686,725, filed Jan. 24, 2013.
Response to Non-Final Office Action regarding U.S. Appl. No. 12/651,174, dated Nov. 26, 2013.
Response to Non-Final Office Action regarding U.S. Appl. No. 12/651,174, dated Apr. 28, 2011.
Response to Non-Final Office Action regarding U.S. Appl. No. 12/651,174, filed Dec. 12, 2011.
Response to Non-Final Office Action regarding U.S. Appl. No. 12/651,174, filed Jan. 22, 2013.
Roush, "Advances in Insect Control: The Role of Transgenic Plants," N. Carozzi et al., eds., Taylor and Francis, London, pp. 271-294, 1997.
Roush, "Two-toxin strategies for management of insecticidal transgenic crops: can pyramiding succeed where pesticide mixtures have not?" *The Royal Society, Phil. Trans. R. Soc. Lond. B* 353:1777-1786, 1998.
Tabashnik, "Delaying insect adaptation to transgenic plants: seedmixtures and refugia reconsidered," *Proc. Royal Soc. Lond. B* 255(1342):7-12, 1994.
Vaughn et al., "A method of controlling corn rootworm feeding using a Bacillus thuringiensis protein expressed in transgenic maize," *Crop Sci.* 45:931-938, 2005.
Whalon et al., "Bacillus thuringiensis: use and resistance management," In: Insecticides with Novel Modes of Action: Mechanism and Application, Ishaaya (Eds.), Springer, pp. 106-137, Berlin, 1998.
Zhao et al., "Transgenic plants expressing two *Bacillus thuringiensis* toxins delay insect resistance evolution," *Nature Biotechnol.* 21:1493-1497, 2003.

\* cited by examiner

Figure 2

| Construct | LB | [2] | [3] | Left PIP trait Cassette [4] | [5] | [6] | [7] | Right PIP trait Cassette [8] | [9] | [10] | [11] | Herbicide Tolerance Cassette [12] [13] [14] [15] | RB [16] |
|---|---|---|---|---|---|---|---|---|---|---|---|---|---|
| 417 (SEQ ID NO: 26) | | Ps.RbcS2-E9 3' UTR | Dv_Snf7o 240-mer INVERTED REPEAT | Corn DnaK intron | CaMV 35S leader | eCaMV 35S promoter | Corn PHG promoter | Wheat Lhcb1 leader | Rice Act1 intron | cry3Bb ORF | Wheat Hsp17 3' UTR | | |
| 415 (SEQ ID NO: 27) | | Ps.RbcS2-E9 3' UTR | Dv_Snf7o 240-mer INVERTED REPEAT | Corn DnaK intron | CaMV 35S leader | eCaMV 35S promoter | Rice Rcc3 promoter | Wheat Lhcb1 leader | Rice Act1 intron | cry3Bb ORF | Wheat Hsp17 3' UTR | | |
| 418 (SEQ ID NO: 28) | | Ps.RbcS2-E9 3' UTR | Dv_Snf7o 240-mer INVERTED REPEAT | Corn DnaK intron | CaMV 35S leader | eCaMV 35S promoter | cry3Bb ORF | Wheat Lhcb1 leader | Rice Act1 intron | ENH FMV 35S promoter | | | |
| 419 (SEQ ID NO: 29) | | Ps.RbcS2-E9 3' UTR | Dv_Snf7o 240-mer INVERTED REPEAT | Corn DnaK intron | CaMV 35S leader | eCaMV 35S promoter | cry3Bb ORF | Wheat Lhcb1 leader | Rice Act1 intron | Rice Rcc3 promoter | | Rice TubA (promoter, leader, intron) CTP CP4 EPSPS Rice TubA 3' UTR | |
| 402 (SEQ ID NO: 30) | | Ps.RbcS2-E9 3' UTR | Dv_Snf7o 240-mer INVERTED REPEAT | Corn DnaK intron | Wheat Lhcb1 leader | eFMV 35S promoter | Rice Rcc3 promoter | Wheat Lhcb1 leader | Rice Act1 intron | cry3Bb ORF | Wheat Hsp17 3' UTR | | |
| 403 (SEQ ID NO: 31) | | Ps.RbcS2-E9 3' UTR | Dv_Snf7o 240-mer INVERTED REPEAT | Corn DnaK intron | Wheat Lhcb1 leader | eFMV 35S promoter | cry3Bb ORF | Wheat Lhcb1 leader | Rice Act1 intron | cry3Bb ORF | Wheat Hsp17 3' UTR | | |
| 404 (SEQ ID NO: 32) | | Ps.RbcS2-E9 3' UTR | Dv_Snf7o 240-mer INVERTED REPEAT | Corn DnaK intron | Wheat Lhcb1 leader | eCaMV 35S promoter | Corn PHG promoter | Wheat Lhcb1 leader | Rice Act1 intron | cry3Bb ORF | Wheat Hsp17 3' UTR | | |
| 423 (SEQ ID NO: 33) | | Wheat Hsp17 3' UTR | cry3Bb ORF | Corn DnaK intron | Lhcb1 + 35S leaders | eCaMV 35S promoter | Dv_Snf7o 240-mer INVERTED REPEAT | Wheat Lhcb1 leader | Corn DnaK intron | eFMV 35S promoter | Wheat Hsp17 3' UTR | | |
| 405 (SEQ ID NO: 34) | | Ps.RbcS2-E9 3' UTR | Dv_Snf7o 240-mer INVERTED REPEAT | Corn DnaK intron | FMV 35S promoter | | eCaMV 35S promoter | CaMV 35S leader | Rice Act1 intron | cry3Bb ORF | Wheat Hsp17 3' UTR | No 3rd cassette | |
| 406 (SEQ ID NO: 35) | | eCaMV 35S promoter | CaMV 35S leader | Rice Act1 intron | cry3Bb ORF | Wheat Hsp17 3' UTR | Corn ePHG promoter | CaMV 35S leader | Corn DnaK intron | cry3Bb ORF | Ps.RbcS2-E9 3' UTR | No 3rd cassette | |
| 890 (SEQ ID NO: 36) | | Ps.RbcS2-E9 3' UTR | Dv_Snf7o 240-mer INVERTED REPEAT | | | | | | | | | No 2nd or 3rd cassette | |

 Designates a right-to-left directionality of the cassette.

 Designates a left-to-right directionality of the cassette.

Figure 4

| Construct | Border | Cassette 1 | Cassette 2 | Cassette 3 | Border |
|---|---|---|---|---|---|
| pMON120413 | LB | e35s:Dv_SnfTo 240mer IR/T-E9:1:1 | Zm.PHG/Ta.Lhcb1:Os.Act:Cry3Bb/Ta.Hsp17:1:1 | Os.TubA3/CTP2-EPSPS CP4/TubA3:1:3 | RB |
| pMON120434 | LB | e35s:Dv_SnfTo 240mer IR/T-E9:1:1 | Zm.PHG/Ta.Lhcb1:Os.Act:Cry3Bb/Ta.Hsp17:1:1 | Os.TubA3/CTP2-EPSPS CP4/TubA3:1:3 | RB |
| pMON120416 | LB | e35s:Dv_SnfTo 240mer IR/T-E9:1:1 | Os.Rcc3/Ta.Lhcb1:Os.Act:Cry3Bb/Ta.Hsp17:1:1 | Os.TubA3/CTP2-EPSPS CP4/TubA3:1:3 | RB |
| pMON120419 | LB | e35s:Dv_SnfTo 240mer IR/T-E9:1:1 | Os.Rcc3/Ta.Lhcb1:Os.Act:Cry3Bb/Ta.Hsp17:1:1 | Os.TubA3/CTP2-EPSPS CP4/TubA3:1:3 | RB |

COMPOSITIONS AND METHODS FOR DEPLOYING A TRANSGENIC REFUGE SEED BLEND

REFERENCE TO RELATED APPLICATIONS

This application claims the benefit of U.S. Provisional Application No. 61/821,227, filed May 8, 2013, which is herein incorporated by reference in its entirety.

INCORPORATION OF SEQUENCE LISTING

The sequence listing contained in the file named "MONS334US_ST25.txt", which is 229 kilobytes (size as measured in Microsoft Windows®) and was created on Apr. 24, 2014, is filed herewith by electronic submission and is incorporated by reference herein.

FIELD OF THE INVENTION

The invention relates to seed blends of transgenic crops comprising *Zea mays* event MON 87411 and refugia seeds. The invention also relates to the control of pests that cause damage to crop plants, for instance through feeding. Transgenic crops of the present invention comprising *Zea mays* event MON 87411 exhibit dual modes of action for resistance to corn rootworm infestations and tolerance to the herbicide glyphosate.

BACKGROUND OF THE INVENTION

The deployment of an insect "refuge" is an important part of insect resistance management (IRM) for transgenic pest resistant crops. Governmental agencies, such as the Environmental Protection Agency in the United States, require that transgenic insect resistant crops be planted along with or along side a refuge crop.

Corn (*Zea mays*) is an important crop in many areas of the world, and the methods of biotechnology have been applied to this crop in order to produce corn with desirable traits. The expression of an insect resistance or herbicide tolerance transgene in a plant can confer the desirable traits of insect resistance and/or herbicide tolerance on the plant, but expression of such transgenes may be influenced by many different factors including the orientation and composition of the cassettes driving expression of the individual genes transferred to the plant chromosome, and the chromosomal location and the genomic result of the transgene insertion. For example, there can be variation in the level and pattern of transgene expression among individual events that are otherwise identical except for the chromosomal insertion site of the transgene. There may also be undesirable phenotypic or agronomic differences between some events. Therefore, it is often necessary to produce and analyze a large number of individual plant transformation events in order to select an event having superior properties relative to the desirable trait and the optimal phenotypic and agricultural characteristics necessary to make it suitable for commercial purposes. Such selection often requires extensive molecular characterization as well as greenhouse and field trials with many events over multiple years, in multiple locations, and under a variety of conditions so that a significant amount of agronomic, phenotypic, and molecular data may be collected. The resulting data and observations must then be analyzed by teams of scientists and agronomists with the goal of selecting a commercially suitable event. Once selected, such an event may then be used for introgressing the desirable trait into other genetic backgrounds using plant breeding methods, and thus producing a number of different crop varieties that contain the desirable trait and are suitably adapted to specific local growing conditions.

To make a transgenic plant containing a single transformation event, a portion of a recombinant DNA construct is transferred into the genome of a corn cell, and the corn cell is subsequently grown into a plant. A corn cell into which the event is initially transferred is regenerated to produce the $R_0$ generation. The $R_0$ plant and progeny plants from the $R_0$ plant can be tested for any desired trait(s), but the effectiveness of the event can be impacted by cis and/or trans factors relative to the integration site in the transformation event. The phenotype conferred by the event can also be impacted by the size and design of the DNA construct, which can vary by the combination of genetic elements in an expression cassette, number of transgenes, number of expression cassettes, and configuration of such elements and such cassettes. Identifying an event with desirable traits can be further complicated by factors such as plant developmental, diurnal, temporal, or spatial patterns of transgene expression; or by extrinsic factors, e.g., environmental plant growth conditions, water availability, nitrogen availability, heat, or stress. Thus, the ability to obtain an event conferring a desirable set of phenotypic traits is not readily predictable.

SUMMARY OF THE INVENTION

In one aspect, the invention provides, a seed blend comprising refuge crop seeds and at least one variety of transgenic crop seeds in a uniform mixture, wherein the mixture consists of from about 80% to about 99% first transgenic crop seed, wherein the first transgenic crop seed comprises event MON 87411 and the refuge crop seed does not comprise said event MON 87411, and wherein a representative sample of seed comprising the event MON 87411 has been deposited under ATCC Accession No. PTA-12669. In one embodiment, the mixture consists of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% first transgenic crop seed. In another embodiment, the mixture consists of from about 1% to about 20%, from about 1% to about 10%, from about 1% to about 5%, from about 2% to about 20%, from about 2% to about 10%, from about 2% to about 5%, from about 5% to about 20%, from about 5% to about 10%, or from about 10% to about 20% refuge crop seeds.

In a further embodiment, the seed blend of the invention comprises a refuge crop seed that is transgenic. In yet a further embodiment, the refuge crop seeds and the at least one variety of transgenic crop seeds comprise a transgene that confers tolerance to at least a first herbicide for instance dicamba, 2,4-D, glyphosate and glufosinate. In still a further embodiment, the first transgenic crop seed comprises at least one additional transgenic event that confers pest resistance, and wherein the refuge crop seed does not comprise the additional transgenic event. In another embodiment, additional transgenic event confers resistance to a lepidopteran pest. In still another embodiment, the additional transgenic event is selected from the group consisting of MON810, MON 89034, TC1507, DAS-06275-8, MIR162, BT176, and BT11. In a further embodiment, the additional transgenic event confers resistance to a coleopteran pest. In yet further embodiment, the additional transgenic event is selected from the group consisting of DAS-59122-7, MIR604, and 5307.

In another aspect, the invention provides a population of plants produced by growing the seed blend of the invention. In yet another aspect, the invention provides a method for producing a refuge seed blend comprising: a) blending a first transgenic crop seed comprising event MON 87411 with a refuge crop seed lacking said event MON 87411; and b) ensuring a uniform mixture of the first transgenic crop seed and the refuge crop seed is provided, wherein the mixture consists of from about 80% to about 99% first transgenic crop seed, and wherein a representative sample of seed comprising event MON 87411 has been deposited under ATCC Accession No. PTA-12669. In still another aspect, the invention provides a method for deploying a refuge crop in a field of transgenic pest resistant crops comprising: a) obtaining a seed blend of the invention; and b) planting said seed blend in a field.

The inventors have identified a transgenic corn event MON 87411 exhibiting superior properties and performance compared to existing transgenic corn plants and to new events constructed in parallel. The corn event MON 87411 contains three linked expression cassettes which collectively confer the traits of corn rootworm resistance and glyphosate herbicide tolerance to corn cells, corn tissues, corn seed and corn plants containing the transgenic event MON 87411. The corn event MON 87411 provides two modes of action against corn rootworm pest species (including Diabrotica spp., especially when the pest is Diabrotica virgifera virgifera (Western Corn Rootworm, WCR), Diabrotica barberi (Northern Corn Rootworm, NCR), Diabrotica virgifera zeae (Mexican Corn Rootworm, MCR), Diabrotica balteata (Brazilian Corn Rootworm (BZR) or Brazilian Corn Rootworm complex (BCR) consisting of Diabrotica viridula and Diabrotica speciosa), or Diabrotica undecimpunctata howardii (Southern Corn Rootworm, SCR)). Dual modes of action provide redundancy and reduces significantly the likelihood of the development of resistance to the pest control traits.

The event MON 87411 is characterized by specific unique DNA segments that are useful in detecting the presence of the event in a sample. A sample is intended to refer to a composition that is either substantially pure corn DNA or a composition that contains corn DNA. In either case, the sample is a biological sample, i.e., it contains biological materials, including but not limited to DNA obtained or derived from, either directly or indirectly, from the genome of corn event MON 87411. "Directly" refers to the ability of the skilled artisan to directly obtain DNA from the corn genome by fracturing corn cells (or by obtaining samples of corn that contain fractured corn cells) and exposing the genome DNA for the purposes of detection. "Indirectly" refers to the ability of the skilled artisan to obtain the target or specific reference DNA, i.e. a novel and unique junction segment described herein as being diagnostic for the presence of the event MON 87411 in a particular sample, by means other than by direct via fracturing of corn cells or obtaining a sample of corn that contains fractured corn cells. Such indirect means include but are not limited to amplification of a DNA segment that contains the DNA sequence targeted by a particular probe designed to bind with specificity to the target sequence, or amplification of a DNA segment that can be measured and characterized, i.e. measured by separation from other segments of DNA through some efficient matrix such as an agarose or acrylamide gel or the like, or characterized by direct sequence analysis of the amplicon or cloning of the amplicon into a vector and direct sequencing of the inserted amplicon present within such vector. Alternatively, a segment of DNA corresponding to the position within the corn chromosome at which the transgenic DNA was inserted into the corn chromosome and which can be used to define the event MON 87411, can be cloned by various means and then identified and characterized for its presence in a particular sample or in a particular corn genome. Such DNA segments are referred to as junction segments or sequences, and can be any length of inserted DNA and adjacent (flanking) corn chromosome DNA so long as the point of joining between the inserted DNA and the corn genome is included in the segment. SEQ ID NO:12 and SEQ ID NO:21 and the reverse complement of each of these are representative of such segments.

The specific sequences identified herein may be present uniquely in event MON 87411, or the construct comprised therein, and the identification of these sequences, whether by direct sequence analysis, by detecting probes bound to such sequences, or by observing the size and perhaps the composition of particular amplicons described herein, when present in a particular corn germplasm or genome and/or present in a particular biological sample containing corn DNA, are diagnostic for the presence of the event MON 87411, or the construct comprised therein, in such sample. It is known that the flanking genomic segments (i.e., the corn genome segments of DNA sequence adjacent to the inserted transgenic DNA) are subject to slight variability and as such, the limitation of at least 99% or greater identity is with reference to such anomalies or polymorphisms from corn genome to corn genome. Nucleotide segments that are completely complementary across their length in comparison to the particular diagnostic sequences referenced herein are intended to be within the scope of the present invention.

The position of the nucleotide segments of the present invention relative to each other and within the corn genome are illustrated in FIG. 3 and the nucleotide sequence of each is illustrated as set forth in SEQ ID NO:1. Nucleotide segments that characterize the event MON 87411 and which are diagnostic for the presence of event MON 87411, or the construct comprised therein, in a sample include SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:18, SEQ ID NO:19, SEQ ID NO:20, SEQ ID NO:21, SEQ ID NO:22, SEQ ID NO:23, SEQ ID NO:24, and SEQ ID NO:25; SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52. These presence of one, or two, or more of these nucleotide sequences in a sample, when such sample contains corn tissue and thus corn DNA, are diagnostic for the presence of the event MON 87411, or the construct comprised therein.

It is intended by use of the word "derived", that a particular DNA molecule is in the corn plant genome, or is capable of being detected in corn plant DNA. "Capable of being detected" refers to the ability of a particular DNA segment to be amplified and its size and or sequence characterized or elucidated by DNA sequence analysis, and can also refer to the ability of a probe to bind specifically to the particular DNA segment, i.e. the target DNA segment, and the subsequent ability to detect the binding of the probe to the target. The particular DNA segment or target DNA segment of the present invention is present within corn that contains the insertion event MON 87411.

By reference to corn it is intended that corn cells, corn seed, corn plant parts and corn plants are within the scope of the present invention so long as each embodiment contains a detectable amount of DNA corresponding to any one, two, or more of the segments that are described herein as being diagnostic for the presence of the corn event MON 87411 DNA.

Corn plant parts include cells; pollen; ovules pods; flowers and flower parts such as the cob, silk, and tassel; root tissue; stem tissue; and leaf tissue. Commodity products that are made from corn in which a detectable amount of the segments of DNA described herein as being diagnostic for the presence of the event MON 87411 are within the scope of the invention. Such commodity products may include whole or processed corn seeds, animal feed containing corn or corn by-products, corn oil, corn meal, corn flour, corn starch, corn flakes, corn bran, corn biomass and stover, and fuel products and fuel by-products when made from corn or corn plants and plant parts.

The DNA of corn event MON 87411 is typically present in each cell and in each chromosome of the corn plant, corn seed, and corn tissues containing the event. As the corn genome is transmitted to progeny in Mendelian fashion, if a corn plant were homozygous, each progeny corn plant and cell would contain the event DNA on each of the parental chromosomes generated to the progeny from the parent(s). However, if the corn genome containing the event MON 87411 DNA is a heterozygous or hybrid parent, then only fifty percent of the pollen and fifty percent of the ovules engaged in mating from hybrid parents will contain the corn event MON 87411 DNA, resulting in a mixed population of progeny that contain the event MON 87411 DNA, and the percentage of such progeny arising from such crosses with hybrids can range anywhere from about fifty to about seventy five percent having the event MON 87411 DNA transmitted to such progeny.

The DNA molecules of the present invention may be unique to the corn event MON 87411 inserted DNA or the two junctions between the transgenic inserted DNA and the corn genome DNA that is adjacent to either end of the inserted DNA. These molecules, when present in a particular sample analyzed by the methods described herein using the probes, primers and in some cases using DNA sequence analysis, may be diagnostic for the presence of an amount of event MON 87411 corn in that sample. Such DNA molecules unique to the corn event MON 87411 DNA can be identified and characterized in a number of ways, including by use of probe nucleic acid molecules designed to bind specifically to the unique DNA molecules followed by detection of the binding of such probes to the unique DNA, and by thermal amplification methods that use at least two different DNA molecules that act as probes but the sequence of such molecules may be somewhat less specific than the probes described above. The skilled artisan understands that contacting a particular target DNA with a probe or primer under appropriate hybridization conditions will result in the binding of the probe or primer to the targeted DNA segment.

The DNA molecules of the present invention that are target segments of DNA are capable of amplification and, when detected as one or more amplicons of the represented length obtained by amplification methods of a particular sample, may be diagnostic for the presence of event MON 87411, or the construct comprised therein, in such sample. Such DNA molecules or polynucleotide segments have the nucleotide sequences as set forth in each of, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, and SEQ ID NO:52, and are further defined herein and in the examples below. Primer molecules and/or probes may be provided in kit form along with the necessary reagents, including controls, and packaged together with instructions for use.

Recombinant DNA molecules of the present invention are deemed to be within the scope of the present invention when present within or derived from a microorganism. A microorganism is intended to include any microscopic cell, whether prokaryote or eukaryote or otherwise that contains DNA within a genome or chromosome or an extra-chromosomal DNA structure more commonly referred to as a plasmid or vector. Microscopic organisms include bacteria (prokaryotes) and cells corresponding to higher life forms (eukaryotes) which are beneath the visual range of the average human, typically beneath fifty cubic microns and more generally beneath ten cubic microns. Bacteria are common microscopic microorganisms that more likely than not could contain a vector or plasmid that contains one or more or all of the novel DNA segments of the present invention, including each of the respective expression cassettes present as set forth in SEQ ID NO: 1. Plant cells and particularly corn plant cells are within the scope of the invention when these contain any one, two, or more or all of the novel DNA segments of the present invention.

Probes for use herein are typically characterized as DNA molecules or polynucleotide segments of sufficient length to function under stringent hybridization conditions as defined herein to bind with a particular target DNA segment, i.e., a unique segment of DNA present within and diagnostic for the presence of, event MON 87741 DNA in a sample. Such a probe can be designed to bind only to a single junction or other novel sequence present only in the corn event MON 87411 DNA, or to two or more such single junction segments. In any event, the detection of the binding of such a probe to a DNA molecule in a particular sample suspected of containing corn DNA is diagnostic for the presence of corn event MON 87411 in the sample.

Primers are typically provided as pairs of different oligonucleotides or polynucleotide segments for use in a thermal amplification reaction which amplifies a particular DNA target segment. Each primer in the pair is designed to bind to a rather specific segment of DNA within or near to a segment of DNA of interest for amplification. The primers bind in such way that these then act as localized regions of nucleic acid sequence polymerization resulting in the production of one or more amplicons (amplified target segments of DNA). In the present invention, use of primers designed to bind to unique segments of corn event MON 87411 DNA in a particular biological sample and that amplify particular amplicons containing one or more of the junction segments described herein, and the detection and or characterization of such amplicons upon completion or termination of the polymerase reaction, is diagnostic for the presence of the corn event MON 87411 in the particular sample. The skilled artisan is well familiar with this amplification method and no recitation of the specifics of amplification is necessary here.

Corn plants, corn plant cells, corn plant tissues and corn seed are insensitive to glyphosate herbicide applications due to expression of a glyphosate insensitive CP4 EPSPS enzyme from a rice Rcc3 promoter in an expression cassette at the 3' distal end as set forth in SEQ ID NO:1. Such seed may be sown into a field. Several days after germination and the appearance of shoots, a weed controlling effective amount of glyphosate herbicide may be applied, which will eliminate substantially all of the weeds in the field but will allow for the continued growth and development of corn plants containing the corn event MON 87411 DNA. The plants are also resistant to infestation by corn rootworms of all known species of rootworm *Diabrotica*, including but not limited to *Diabrotica*

*virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR) or Brazilian Corn Rootworm complex (BCR) consisting of *Diabrotica viridula* and *Diabrotica speciosa*), and *Diabrotica undecimpunctata howardii* (Southern Corn Rootworm, SCR). The resistance to *Diabrotica* species arises in connection with the expression of two different DNA segments that are operably and covalently linked within the inserted transgenic DNA: a dsRNA is transcribed from the expression cassette at the 5' proximal end of the inserted transgenic DNA as set forth in SEQ ID NO:1 and as illustrated in FIG. 1 by the position of [G] SEQ ID NO:12, and targets for suppression an essential gene in corn rootworms; and a coleopteran toxic Cry3Bb protein is expressed from an expression cassette (approximately centered in SEQ ID NO:1 as shown in FIG. 1 by the position of [H] SEQ ID NO: 14) centered between the cassette expressing dsRNA [G] and the cassette at the 3' distal end of the inserted transgenic DNA as set forth in SEQ ID NO:1 (a glyphosate tolerance expression cassette illustrated in FIG. 1 by [I] SEQ ID NO:16). The dsRNA targets for suppression a yeast orthologous gene referred to as snf7 and is expressed from a CAMV e35S promoter, while the Cry3Bb protein is expressed from a *Zea mays* PIIG promoter. The dsRNA and the Cry3Bb protein are agents toxic to corn rootworm species.

The promoters driving expression of the dsRNA and Cry3Bb toxic agents are divergently positioned so that expression from each promoter of the respective toxic agent is away from a point centered between the two promoters, i.e., transcription of each expression cassette proceeds in opposite directions and does not converge. The glyphosate tolerance CP4 EPSPS expression cassette is downstream of, i.e. proximal to the 3' end as set forth in SEQ ID NO:1 and 3' distal to the cassette driving expression of the Cry3Bb protein. The cassettes driving expression of Cry3Bb and EPSPS produce their respective proteins using a tandem orientation of transcription, Cry3Bb upstream of the EPSPS, and transcribed in the same orientation, but each from their separate respective promoters. Leaving the dsRNA expression cassette and the glyphosate tolerance cassette intact and positioned at the distal ends of the DNA segment intended for insertion into the corn genome, other variant constructs were produced in which the orientation of the Cry3Bb cassette was inverted or reversed relative to the design present in the event MON 87411 DNA. These variant constructs utilized the *Zea mays* PIIG promoter or a rice Rcc3 promoter to drive expression of Cry3Bb.

Transgenic events containing only these variant constructs/orientations of the Cry3Bb expression cassette were compared to the event MON 87411 and to the currently available commercial events MON863 (containing only a Cry3Bb expression cassette), MON88017 (containing a Cry3Bb expression cassette operably linked to a CP4 EPSPS expression cassette), and DAS-59122-7 (containing three operably linked expression cassettes, two expressing in tandem the dual Bt toxin components Cry34 and Cry35 along with a gene conferring glufosinate tolerance). The results as illustrated below in the examples show that the event MON 87411 exhibited superior properties for root directed expression of the Cry3Bb protein and the plurality of transgenic events produced using the construct used for generating the event MON 87411 were each more likely than other events produced with other constructs to exhibit efficacious control of corn rootworms.

Corn plants of the present invention and parts thereof including seed, each containing the DNA corresponding to event MON 87411, are within the scope of the present invention. Such plants are resistant to corn rootworm infestation and are insensitive to applications of the herbicide glyphosate. Such plants include hybrids containing only one MON 87411 allele, i.e., a genome characterized as heterozygous with reference to the locus corresponding to the event MON 87411 DNA. Such hybrids are produced by breeding with desirable germplasm to insure hybrid vigor and other agriculturally desirable properties of corn. Hybrids may be produced by any number of methods but a preferred method takes advantage of a first inbred (homozygous) parent that contains the event MON 87411 specific allele on both chromosomes at the locus at which the event MON 87411 DNA is inserted, and breeding the first inbred together with a second inbred which does not contain the MON 87411 DNA. Both parental inbred varieties will have one or more advantageous properties desirable in the progeny seed, i.e. the hybrid seed.

A transgenic property or allele conferring some additional trait to a plant containing the event MON 87411 DNA is particularly desirable. Such transgenic alleles include other transgenic events conferring corn rootworm resistance, including but not limited to events such as DAS-59122-7; MIR604; and 5307. Each of these events provides a supplemental corn rootworm toxic agent (DAS-59122-7 provides PS149B1 (Cry34/Cry35) exhibiting rootworm toxic properties and herbicide tolerance to glufosinate; MIR604 provides a modified Cry3Aa exhibiting rootworm toxic properties; event 5307 provides FR8a gene exhibiting rootworm toxic properties). Providing additional corn rootworm resistance traits such as these may decrease the likelihood of the development of resistance to any one of the corn rootworm toxic agents provided. Other desirable traits include yield and stress resistance or tolerance traits, nitrogen fixation traits, traits modulating the use of water, resistance to fungal infestation, resistance to herbicides such as dicamba (MON 87427), glufosinate, and the like, as well as resistance to lepidopteran infestations. Lepidopteran infestation resistance traits have been provided in the art and include the transgenic corn events (and respective lepidopteran active proteins) MON810 (Cry1Ab), MON 89034 (Cry1A.105 and Cry2Ab); TC1507 (Cry1Ac and Cry1Fa); DAS-06275-8 also known as TC-6275 (Cry1Fa and bar (providing glufosinate tolerance)); MIR162 (Vip3Aa), BT176 (Cry1Ab); and BT11 (Cry1Ab).

An alternative to providing any combination or all of these traits in a single plant, particularly the insect resistance traits corresponding to the event MON 87411 traits, the other listed corn rootworm resistance traits, or the lepidopteran resistance traits, would be to provide these in various combinations of seed blends, in which certain seed in the blend contain the MON 87411 traits and some combination of only the listed coleopteran resistance traits and act together below the ground to prevent infestations of corn rootworms, while other seed in the blend contain only the lepidopteran resistance traits and confer resistance to lepidopteran infestations of corn above the ground. In this way, the seed in the blend provide refuge for each other, i.e. the coleopteran protected seed and plants act as a refuge for the plants conferring lepidopteran resistance, and vice versa. Typically however, these traits would be provided in some trait combination or package in which the MON 87411 traits would be provided together in a single plant by breeding with one or more of the lepidopteran resistance traits to provide a complete package of pest resistance to the crop in the field, and a small percentage of the seed (perhaps between 1 and 20 percent or any number in between including 2, 3, 4, 5, 6, 7, 8, 9, 10, 11, 12, 13, 14, 15, 16, 17, 18, or 19 percent) would be traited only for herbicide tolerance and would lack any pest protection traits and would be planted into the field in a mix randomly with the pest resistance traited seed or as a structured (separate) stand of crops would act as a refuge both for the pests that attack corn plants above the ground and pests that attack corn plants below the ground.

In one aspect, the invention therefore provides a method of protecting a field of corn plants comprising cultivating a field of corn plants comprised of from about 50 to about 100 percent of corn plants comprising corn event MON 87411.

The construct inserted into the event MON 87411 provides particular advantages relative to the EPSPS expression cassette. First, the presence of this cassette provides for ease of selection of the transgenic events into which the construct has been inserted. Second, the cassette provides for control of weeds in a field into which seed corresponding to event MON 87411 have been planted. The field containing such MON 87411 plants can be sprayed with an effective amount of glyphosate to control the growth of weeds in the field that are susceptible to glyphosate. For weeds that are not susceptible to glyphosate as noted above, other transgenic events that provide for tolerance to other herbicides such as to dicamba or to glufosinate can be bred into a single hybrid along with the event MON 87411, thus providing an efficient means for controlling weeds in a field by applying two or more of the herbicides glyphosate, dicamba, or glufosinate, as the likelihood that weeds would be present that exhibit tolerance to two or more of these herbicides would be unlikely, and in such case, the corn crop would consist of hybrids that exhibit resistance to such applications of herbicide combinations.

In one aspect, the invention provides a DNA molecule comprising (a) the recombinant polynucleotide as set forth in SEQ ID NO:12; and (b) the recombinant polynucleotide as set forth in SEQ ID NO:14; and (c) the recombinant polynucleotide as set forth in SEQ ID NO:16, wherein said recombinant polynucleotide sequences are linked together by phosphodiester linkage. In one embodiment, the DNA molecule comprises SEQ ID NO:4.

BRIEF DESCRIPTION OF THE DRAWINGS

FIG. 2 illustrates eleven different DNA constructs, (417, 416, 418, 419, 402, 403, 404, 423, 405, 406, and 890) engineered to express up to three distinct cassettes, including two plant-incorporated protectant (PIP) cassettes, targeting Western corn rootworm (WCR), and a single herbicide tolerance cassette. The two PIP cassettes include (a) an expression cassette for a Dv_Snf7o 240-mer inverted repeat, and (b) an expression cassette for a Cry3Bb protein. Each of the constructs depicted comprise these expression cassettes in varying order and orientation. Constructs 405 and 406 contain no herbicide tolerance cassette and construct 890 comprises only a single expression cassette for a Dv_Snf7o 240-mer inverted repeat. The three constructs comprise a total of sixteen genetic elements from the Left Border (LB) through to the Right Border (RB): [1] LB; [2] Ps.RbcS2-E9 3' UTR; [3] 240-mer Dv_Snf7o inverted repeat gene; [4] Corn DnaK intron; [5] CaMV 35S leader; [6] eCaMV 35S promoter; [7] Corn PIIG promoter; [8] Wheat Lhcb1 leader; [9] Rice Act1 intron; [10] cry3Bb ORF; [11] Wheat Hsp17 3' UTR; [12] Rice TubA (promoter, leader, intron); [13] CTP; [14] CP4 EPSPS; [15] Rice TubA 3' UTR; and [16] RB.

Figure 1:
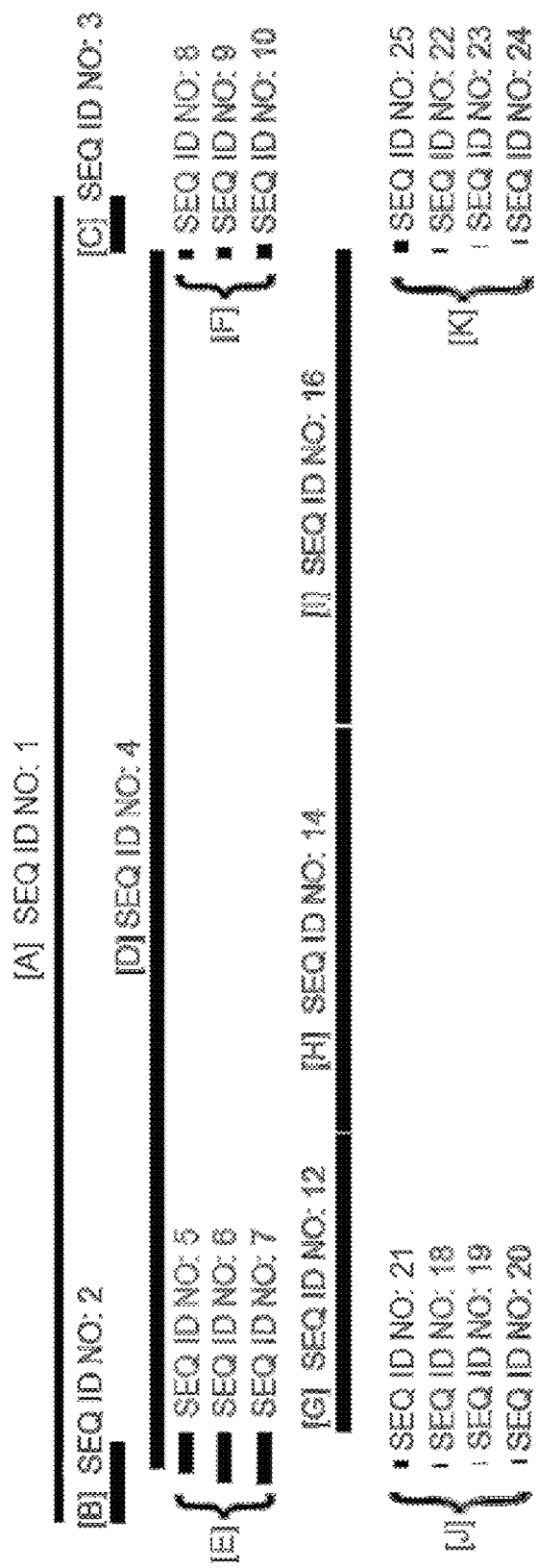
FIG. 1 is a diagrammatical representation of the transgenic insert in the genome of corn event MON 87411: [A] represents SEQ ID NO:1, which is the contiguous sequence of the transgenic DNA insert integrated into the genome of corn LH244 and 5' and 3' genomic DNA flanking the inserted DNA; [B] and [C] correspond to the relative positions of SEQ ID NOs:2 and 3, which form the 5' and 3' transgene/genomic DNA junction sequences of event MON 87411, respectively; [D] represents SEQ ID NO:4, which is the sequence of the transgenic DNA insert integrated into the genome resulting in event MON 87411; [E] corresponds to the relative positions of SEQ ID NO:5, SEQ ID NO:6 and SEQ ID NO:7, each spanning the 5' junction between the terminal ends of the transgenic inserted DNA and the flanking genomic DNA; [F] corresponds to the relative positions of SEQ ID NO:8, SEQ ID NO:9 and SEQ ID NO:10, each spanning the 3' junction between the terminal ends of the transgenic inserted DNA and the flanking genomic DNA; [G], [H] and [I] respectively represent the three different expression cassettes corresponding to the transgenic DNA construct inserted into the corn plant genome resulting in event MON 87411; [J], and [K] represent oligonucleotide primers, oligonucleotide probes, and DNA amplicons corresponding to the junctions of event MON 87411.

[A] nucleotide position 1-500 as set forth in SEQ ID NO:1 corresponds to corn genome DNA adjacent to the transgenic inserted DNA in corn event MON 87411, which in this case is arbitrarily assigned as the 5' end of the transgenic inserted DNA.

[B] nucleotide position 807-1439 as set forth in SEQ ID NO:1 corresponds to the reverse complement sequence of a *Pisum sativum* ribulose bis phosphate carboxylase small subunit E9 3' transcription termination and polyadenylation signal.

[C] nucleotide position 1469-2098 as set forth in SEQ ID NO:1 corresponds to the reverse complement sequence designed to be expressed as an RNA molecule that folds into a 240 nucleotide dsRNA and 150 nucleotide hairpin structure that is designed to target for suppression the *Diabrotica* species orthologue of a yeast gene encoding an Snf7 protein when provided in the diet of a *Diabrotica* species. A first 240 nucleotide segment corresponding to a portion of the *Diabrotica* snf7 orthologous gene is provided at nucleotide position 1469-1708 as set forth in SEQ ID NO:1, a second 240 nucleotide segment corresponding to the reverse complement of the first segment is set forth at nucleotide position 1850-2098 as set forth in SEQ ID NO:1, and the first and the second segments are operably linked by a 150 nucleotide spacer at nucleotide position 1709-1858 as set forth in SEQ ID NO:1.

[D] nucleotide position 2135-2938 as set forth in SEQ ID NO:1 corresponds to the reverse complement sequence of an intron derived from a *Zea mays* dnaK gene.

[E] nucleotide position 2839-3298 as set forth in SEQ ID NO:1 corresponds to the reverse complement of a Cauliflower mosaic virus enhanced 35S promoter sequence and an untranslated 5' leader sequence. This promoter, the associated untranslated leader, the intron element [D] and the transcription termination and polyadenylation element [B] regulate the expression of element [C] in corn plant cells.

[F] nucleotide position 3586-4534 as set forth in SEQ ID NO:1 corresponds to a promoter sequence derived from a *Zea mays* physical impedance induced protein gene (Zm.PIIG).

This promoter, the associated untranslated leader [G], the intron element [H] and the transcription termination and polyadenylation element [J] regulate the expression of element [I]. This promoter is oriented relative to the promoter [E] such that each promoter ([E] and [F]) will drive divergent expression of their respective elements ([C] and [I]) (see block arrows in FIG. 2 where the arrows are representative of the respective promoters ([E] and [F]) in the indicated direction of expression from the respective promoter).

[G] nucleotide position 4541-4601 as set forth in SEQ ID NO:1 corresponds to an untranslated 5' leader sequence derived from a *Triticum aestivum* light harvesting complex b1 gene (Ta.Lhcb1).

[H] nucleotide position 4618-5097 as set forth in SEQ ID NO:1 corresponds to an intron sequence derived from an *Oryza sativa* Actin-1 gene (Os.Act1).

[I] nucleotide position 5107-7068 as set forth in SEQ ID NO:1 corresponds to the nucleotide sequence encoding a Cry3Bb corn rootworm toxic protein (cry3Bb). The encoded Cry3Bb protein is pesticidal when provided in the diet of a *Diabrotica* (corn rootworm) species.

[J] nucleotide position 7088-7297 as set forth in SEQ ID NO:1 corresponds to the sequence of a *Triticum aestivum* heat shock protein 17 (HSP17) transcription termination and polyadenylation signal.

[K] nucleotide position 7346-9526 as set forth in SEQ ID NO:1 corresponds to a contiguous promoter-leader-intron sequence derived from an *Oryza sativa* alpha tubulin-3 gene (TubA-3). This promoter, with the associated leader and intron, and the transcription termination and polyadenylation element [M] regulate the expression of element [L].

[L] nucleotide position 9531-11126 as set forth in SEQ ID NO:1 corresponds to sequence of an *Arabidopsis thaliana* cytoplasmic targeting peptide (CTP; from nucleotide position 9531-9758), and a sequence of an EPSPS derived from *Agrobacterium* CP4 (from nucleotide position 9759-11126). When this sequence is transcribed and translated into protein in a corn plant cell, the CTP is operably linked to the EPSPS. When expressed in corn plant cells comprising event MON 87411, this CTP-EPSPS provides tolerance to the herbicide glyphosate.

[M] nucleotide position 11134-11715 as set forth in SEQ ID NO:1 corresponds to the sequence of an *Oryza sativa* alpha tubulin-3 gene (TubA-3) transcription termination and polyadenylation signal.

[N] nucleotide position 11749-12248 as set forth in SEQ ID NO:1 corresponds to corn genome DNA adjacent to the transgenic inserted DNA in corn event MON 87411, which in this case is arbitrarily assigned as the 3' end of the transgenic inserted DNA.

[aa] nucleotide position 501-806 as set forth in SEQ ID NO:1 corresponds to the portion of the *Agrobacterium tumefaciens* octopine left border sequence of the 417 construct adjacent to the genome at the arbitrarily assigned 5' end of the transgenic DNA inserted into the corn genome to form event MON 87411. The 5' end of [aa] as set forth in SEQ ID NO: 1 is linked to the 3' end of element [A] to form the unique 5' transgenic inserted DNA/corn genome junction encompassed by SEQ ID NO:5, SEQ ID NO:6, SEQ ID NO:7, and SEQ ID NO:21. The 3' end of element [aa] is linked to the 5' end of element [B] to form a unique junction within the transgenic inserted DNA that is encompassed by SEQ ID NO:41.

[bb] nucleotide position 1440-1468 as set forth in SEQ ID NO:1 corresponds to the an intervening sequence between elements [B] and [C]. The 5' end of [bb] as set forth in SEQ ID NO:1 is linked to the 3' end of element [B], and the 3' end of element [bb] is linked to the 5' end of element [C] to form a unique junction, encompassed by SEQ ID NO:42, within the transgenic DNA inserted into the corn genome to form event MON 87411.

[cc] nucleotide position 2099-2134 as set forth in SEQ ID NO:1 corresponds to the an intervening sequence between elements [C] and [D]. The 5' end of [cc] as set forth in SEQ ID NO:1 is linked to the 3' end of element [C], and the 3' end of element [cc] is linked to the 5' end of element [D] to form a unique junction, encompassed by SEQ ID NO:43, within the transgenic DNA inserted into the corn genome to form event MON 87411.

[ee] nucleotide position 3299-3585 as set forth in SEQ ID NO:1 corresponds to the an intervening sequence between elements [E] and [F]. The 5' end of [ee] as set forth in SEQ ID NO:1 is linked to the 3' end of element [E], and the 3' end of element [ee] is linked to the 5' end of element [F] to form a unique junction, encompassed by SEQ ID NO:44, within the transgenic DNA inserted into the corn genome to form event MON 87411.

[ff] nucleotide position 4535-4540 as set forth in SEQ ID NO:1 corresponds to the an intervening sequence between elements [F] and [G]. The 5' end of [ff] as set forth in SEQ ID NO:1 is linked to the 3' end of element [F], and the 3' end of element [ff] is linked to the 5' end of element [G] to form a unique junction, encompassed by SEQ ID NO:45, within the transgenic DNA inserted into the corn genome to form event MON 87411.

[gg] nucleotide position 4602-4617 as set forth in SEQ ID NO:1 corresponds to the an intervening sequence between elements [G] and [H]. The 5' end of [gg] as set forth in SEQ ID NO:1 is linked to the 3' end of element [G], and the 3' end of element [gg] is linked to the 5' end of element [H] to form a junction, encompassed by SEQ ID NO:46, within the transgenic DNA inserted into the corn genome to form event MON 87411, but which is not unique to event MON 87411.

[hh] nucleotide position 5098-5106 as set forth in SEQ ID NO:1 corresponds to the an intervening sequence between elements [H] and [I]. The 5' end of [hh] as set forth in SEQ ID NO:1 is linked to the 3' end of element [H], and the 3' end of element [hh] is linked to the 5' end of element [I] to form a junction, encompassed by SEQ ID NO:47, within the transgenic DNA inserted into the corn genome to form event MON 87411, but which is not unique to event MON 87411.

[ii] nucleotide position 7069-7087 as set forth in SEQ ID NO:1 corresponds to the an intervening sequence between elements [I] and [J]. The 5' end of [ii] as set forth in SEQ ID NO:1 is linked to the 3' end of element [I], and the 3' end of element [ii] is linked to the 5' end of element [J] to form a junction, encompassed by SEQ ID NO:48, within the transgenic DNA inserted into the corn genome to form event MON 87411, but which is not unique to event MON 87411.

[jj] nucleotide position 7298-7345 as set forth in SEQ ID NO:1 corresponds to the intervening sequence between elements [J] and [K]. The 5' end of [jj] as set forth in SEQ ID NO:1 is linked to the 3' end of element [J], and the 3' end of element [jj] is linked to the 5' end of element [K] to form a unique junction, encompassed by SEQ ID NO:49, within the transgenic DNA inserted into the corn genome to form event MON 87411.

[kk] nucleotide position 9527-9530 as set forth in SEQ ID NO:1 corresponds to the intervening sequence between elements [K] and [L]. The 5' end of [kk] as set forth in SEQ ID NO:1 is linked to the 3' end of element [K], and the 3' end of element [kk] is linked to the 5' end of element [L] to form a unique junction, encompassed by SEQ ID NO:50, within the transgenic DNA inserted into the corn genome to form event MON 87411.

[ll] nucleotide position 11127-11133 as set forth in SEQ ID NO:1 corresponds to the an intervening sequence between elements [L] and [M]. The 5' end of [ll] as set forth in SEQ ID NO:1 is linked to the 3' end of element [L], and the 3' end of element [ll] is linked to the 5' end of element [M] to form a unique junction, encompassed by SEQ ID NO:51, within the transgenic DNA inserted into the corn genome to form event MON 87411.

[mm] nucleotide position 11716-11748 as set forth in SEQ ID NO:1 corresponds to the a portion of the *Agrobacterium tumefaciens* nopaline right border sequence of the 417 construct adjacent to the genome at the arbitrarily assigned 3' end of the transgenic DNA inserted into the corn genome to form event MON 87411. The 5' end of [mm] as set forth in SEQ ID NO:1 is linked to the 3' end of element [M], and the 3' end of element [mm] is linked to the 5' end of element [N] to form a unique transgenic inserted DNA/corn genome junction encompassed by SEQ ID NO:52.

FIG. 4 Illustration of cassette orientation for vectors tested to show higher efficacy of divergent promoters driving expression of corn rootworm toxic agents compared to vectors with a tandem orientation of promoters driving expression of corn rootworm toxic agents.

BRIEF DESCRIPTION OF THE SEQUENCES

SEQ ID NO:1 is a nucleotide sequence of event MON 87411, and represents from 5' to 3', a segment of the 5' genomic DNA flanking (adjacent to) the inserted transgenic DNA (500 nucleotides), the inserted transgenic DNA (11,248 nucleotides), and a segment of the 3' genomic DNA flanking (adjacent to) the inserted transgenic DNA (500 nucleotides) in event MON 87411.

SEQ ID NO:2 is a nucleotide junction sequence of event MON 87411, and represents from 5' to 3', a segment of the 5' genomic DNA adjacent to the inserted transgenic DNA (500 nucleotides), and the inserted transgenic DNA border remnant (263 nucleotides) of event MON 87411.

SEQ ID NO:3 is a nucleotide junction sequence of event MON 87411, and represents from 5' to 3', the inserted transgenic DNA border remnant (15 nucleotides), and a segment of the 3' genomic DNA adjacent to the inserted genomic DNA (500 nucleotides) of event MON 87411.

SEQ ID NO:4 is a nucleotide sequence of event MON 87411, and represents the inserted genomic DNA (11248 nucleotides) of event MON 87411.

SEQ ID NO:5 is a nucleotide junction sequence of event MON 87411, and represents from 5' to 3', a segment of the 5' genomic DNA adjacent to the inserted transgenic DNA (50 nucleotides), and the inserted transgenic DNA border remnant (263 nucleotides) of event MON 87411.

SEQ ID NO:6 is a nucleotide junction sequence of event MON 87411, and represents from 5' to 3', a segment of the '5 genomic DNA adjacent to the inserted transgenic DNA (110 nucleotides), and the inserted transgenic DNA border remnant (263 nucleotides) of event MON 87411.

SEQ ID NO:7 is a nucleotide junction sequence of event MON 87411, and represents from 5' to 3', a segment of the 5' genomic DNA adjacent to the inserted transgenic DNA (145 nucleotides), and the inserted transgenic DNA border remnant (263 nucleotides) of event MON 87411.

SEQ ID NO:8 is a nucleotide junction sequence of event MON 87411, and represents from 5' to 3', a segment of the inserted transgenic DNA (83 nucleotides), and a segment of the 3' genomic DNA adjacent to the inserted transgenic DNA (34 nucleotides) of event MON 87411.

SEQ ID NO:9 is a nucleotide junction sequence of event MON 87411, and represents from 5' to 3', a segment of the inserted transgenic DNA (83 nucleotides), and a segment of the 3' genomic DNA adjacent to the inserted transgenic DNA (90 nucleotides) of event MON 87411.

SEQ ID NO:10 is a nucleotide junction sequence of event MON 87411, and represents from 5' to 3', a segment of the inserted transgenic DNA (83 nucleotides), and a segment of the 3' genomic DNA adjacent to the inserted transgenic DNA (255 nucleotides) of event MON 87411.

SEQ ID NO:11 is a nucleotide sequence of a cDNA sequence from *Diabrotica virgifera virgifera* (Western Corn Rootworm) encoding an ESCRT-III complex subunit that is orthologous to yeast Snf7.

SEQ ID NO:12 is a nucleotide sequence representing the antisense strand of a DNA expression cassette that includes a recombinant gene engineered to express an inverted repeat RNA molecule. The inverted repeat DNA segments correspond to positions 663 through 902 and to positions 1292 through 1053. The inverted repeat DNA sequences correspond to the nucleotide sequence of SEQ ID NO:11 from nucleotide position 151-390.

SEQ ID NO:13 is a ribonucleotide sequence transcribed from the DNA as set forth in SEQ ID NO:12.

SEQ ID NO:14 is a nucleotide sequence representing the sense strand of a DNA expression cassette that includes a recombinant gene engineered to encode and express a corn rootworm toxic Cry3Bb protein.

SEQ ID NO:15 is an amino acid sequence translation of a polynucleotide corresponding to positions 1522-3480 of SEQ ID NO:14, and representing a corn rootworm toxic Cry3Bb protein.

SEQ ID NO:16 is a nucleotide sequence representing the sense strand of a DNA expression cassette that includes a recombinant gene engineered to encode and express a 5-enolpyruvylshikimate-3-phosphate synthase (EPSPS) protein.

SEQ ID NO:17 is an amino acid sequence translation of a polynucleotide corresponding to positions 2186 through 3781 of SEQ ID NO:16, and representing an EPSPS protein that exhibits insensitivity to the herbicide glyphosate.

SEQ ID NO:18 is a nucleotide sequence of a synthetic oligonucleotide referred to as SQ27011, and is identical to the nucleotide sequence corresponding to positions 462-490 of SEQ ID NO:1.

SEQ ID NO:19 is a nucleotide sequence of a synthetic oligonucleotide referred to as PB3552, and is identical to the reverse complement of the nucleotide sequence corresponding to positions 502-515 of SEQ ID NO:1. PB3552 can be 5' labeled with a 6-carboxyfluorescein moiety (6-FAM™) and 3' labeled with a quencher moiety for use in combination with a pair of thermal amplification primers, e.g., SQ27011 and SQ9085, and capable of use in TAQMAN® DNA amplification method to detect the presence of event MON 87411 DNA in a biological sample that contains corn event MON 87411 DNA.

SEQ ID NO:20 is a nucleotide sequence of a synthetic oligonucleotide referred to as SQ9085, and is identical to the reverse complement of the nucleotide sequence corresponding to positions 516-541 of SEQ ID NO:1.

SEQ ID NO:21 is a nucleotide sequence of event MON 87411, and corresponds to positions 462-541 of SEQ ID NO:1. An amplicon exhibiting this sequence can be produced with a pair of thermal amplification primers, e.g., SQ27011 and SQ9085.

SEQ ID NO:22 is a nucleotide sequence of a synthetic oligonucleotide referred to as SQ27066, and is identical to the nucleotide sequence corresponding to positions 11710-11728 of SEQ ID NO:1.

SEQ ID NO:23 is a nucleotide sequence of a synthetic oligonucleotide referred to as PB11300, and is identical to the nucleotide sequence corresponding to positions 11731-11755 of SEQ ID NO:1. PB11300 can be 5' labeled with a 6-carboxyfluorescein moiety (6-FAM™) and 3' labeled with a quencher moiety. Labeled this way, PB11300 can be used in combination with a pair of PCR primers, e.g., SQ27066 and SQ26977, to detect event MON 87411 in a TAQMAN® assay.

SEQ ID NO:24 is a nucleotide sequence of a synthetic oligonucleotide referred to as SQ26977, and is identical to the reverse complement of the nucleotide sequence corresponding to positions 11756-11784 of SEQ ID NO:1.

SEQ ID NO:25 is a nucleotide sequence of event MON 87411, and corresponds to positions 11710-11784 of SEQ ID NO:1. An amplicon exhibiting this sequence can be amplified with a pair of primers, e.g. SQ27066 and SQ26977, and is diagnostic of event MON 87411.

SEQ ID NO:26 is a nucleotide sequence representing the DNA construct #417.

SEQ ID NO:27 is a nucleotide sequence representing the DNA construct #416.

SEQ ID NO:28 is a nucleotide sequence representing the DNA construct #418.

SEQ ID NO:29 is a nucleotide sequence representing the DNA construct #419.

SEQ ID NO:30 is a nucleotide sequence representing the DNA construct #402.

SEQ ID NO:31 is a nucleotide sequence representing the DNA construct #403.

SEQ ID NO:32 is a nucleotide sequence representing the DNA construct #404.

SEQ ID NO:33 is a nucleotide sequence representing the DNA construct #423.

SEQ ID NO:34 is a nucleotide sequence representing the DNA construct #405.

SEQ ID NO:35 is a nucleotide sequence representing the DNA construct #406.

SEQ ID NO:36 is a nucleotide sequence representing the DNA construct #890.

SEQ ID NO:37 is a nucleotide sequence of the LH244 corn plant representing the wild-type allele of event MON 87411. An amplicon exhibiting this nucleotide sequence can be produced with a pair of PCR primers, e.g., SQ27011 and SQ26977, and is diagnostic of the wild-type allele of event MON 87411.

SEQ ID NO:38 is a nucleotide sequence of a synthetic oligonucleotide referred to as SQ20221.

SEQ ID NO:39 is a nucleotide sequence of a synthetic oligonucleotide referred to as PB10065. PB10065 can be 5' labeled with VIC™ and 3' labeled with a quencher moiety. Labeled this way, PB10065 can be used in combination with a pair of PCR primers, e.g., SQ10065 and SQ20222, to detect the presence of a segment of an endogenous gene of corn in a TAQMAN® assay.

SEQ ID NO:40 is a nucleotide sequence of a synthetic oligonucleotide referred to as SQ20222.

Figure 3:
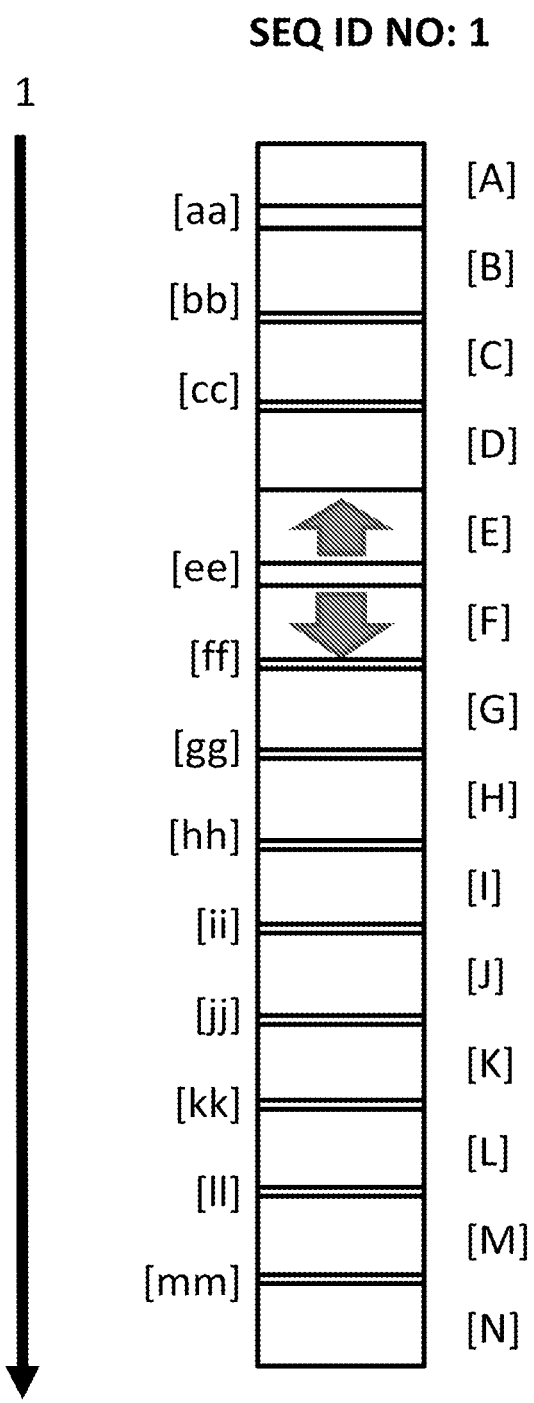
FIG. 3 [A]-[N] and [aa]-[mm] illustrate the operably linked elements and flanking corn genome and their position relative to each other as these are presented within the transgenic DNA insertion position in the corn event MON 87411 genome. The following descriptions identify the composition, function and position for each of the elements as set forth in SEQ ID NO:1.

SEQ ID NOs:41-52 are nucleotide sequences of regions of SEQ ID NO:1, where each SEQ ID NO encompasses a junction formed by intervening sequence and the expression cassette elements as detailed in the brief description for FIG. 3.

DETAILED DESCRIPTION

Resistance management provides for reducing or eliminating the likelihood of development of resistance to one or more recombinant traits, such as an insecticide, that is/are either present within a recombinant plant or present adjacent to one or more parts or tissues of a plant. One approach for achieving resistance management is though a seed mix or seed blend refuge composition. To obtain such a composition a first transgenic crop seed, such as a seed comprising event MON 87411 of the present invention, is selected to be mixed with a refuge seed to form a seed blend. The seed blend consists at least of a first transgenic crop seed, which contains at least a first transgene, and at least one type of refuge plant seed.

The refuge plant seed can be uniform in nature, in that it is composed of a single type of seed from a single variety of plant, or can be non-uniform in nature and consist of two or more varieties of plant. In one embodiment, the refuge seed is similar in variety (or agronomic characteristics) to the first transgenic crop seed. The refuge seed can be non-transgenic or can be transgenic. A refuge seed that is a transgenic seed can contain any transgene so long as it is not a transgene that is present in the first transgenic crop seed. In one embodiment, the transgene in a transgenic refuge seed is a transgene selected from an insecticidal gene, a herbicide tolerance gene, a fungicide tolerance gene, and the like. Refuge seeds may be grown into plants that act as a refuge for pests that either feed directly on a particular crop species, or other pests, the presence of which within the local proximity of a particular crop species, results in the damage, decrease in viability, infertility, or decrease in yield of a crop produced from such crop species.

The refuge strategy of the present invention assists with delaying the onset of resistance development. For instance, deploying into a field of crops some percentage of the seeds which sprout and develop into mature refuge plants, but do not contain a transgene that is present in the crop seed, allows susceptible larva to survive to adults on the refuge plants. Although this strategy is acceptable on low to moderate levels of insect pressure, under very high levels of insect pressure the non-protected plants, i.e. refuge plants, may be damaged such that this insect resistance management strategy is not commercially viable. Refuge plants may however be protected by either a transgene that is insecticidal against a different insect or against the same insect using a different mode of action. With this strategy the refuge plants are sufficiently protected but still allow for larval survivorship to adults, and the refuge seed mix becomes commercially viable under all levels of insect pressure. At the same time, two modes of action are achieved, ensuring the longest possible term for commercial viability and utility of the transgenic crop seeds with a minimal risk to the development of resistance races of insects.

One means of deploying a transgenic refuge into a field of recombinant crops would comprise a seed mixture comprising from about 1% to about 10% refuge seed, or from about 5% to about 10% refuge seed. Alternatively, the refuge seed may comprise up to about 50% of the seed in a seed mixture. That is, the insect-protected transgenic seed might comprise from about 50% to about 60%, 70%, 75%, 80%, 90%, 95% or even up to about 99% of the seed mixture.

The inventors have identified a transgenic corn event MON 87411 exhibiting superior properties and performance compared to existing transgenic corn plants. The corn event MON 87411 contains three operably linked expression cassettes which collectively confer the traits of corn rootworm resistance and glyphosate herbicide tolerance to corn cells, corn tissues, corn seed and corn plants containing the transgenic event MON 87411. The corn event MON 87411 provides two modes of action against corn rootworm pest species (including *Diabrotica* spp., especially when the pest is *Diabrotica*

*virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR) or Brazilian Corn Rootworm complex (BCR) consisting of *Diabrotica viridula* and *Diabrotica speciosa*), or *Diabrotica undecimpunctata howardii* (Southern Corn Rootworm, SCR)). Other transgenic corn events have been referenced in the art that provide various embodiments conferred singly, such as MON863 (conferring the trait of resistance to corn rootworms by expression of a Cry3Bb insecticidal toxin protein), or transgenic corn events providing two or more traits such as in corn event MON88017 (conferring the trait of resistance to corn rootworms by expression of a Cry3Bb insecticidal toxin protein and the trait of resistance to glyphosate herbicide by expression of a glyphosate insensitive EPSPS) and corn event DAS 59122-7 (conferring the trait of resistance to corn rootworms by expression of a binary *Bacillus thuringiensis* toxin PS149B1, also known as Cry34/Cry35, and the trait of tolerance to the herbicide glufosinate). Other art discloses the combination by breeding of the traits conferred by the corn events MON88017 or DAS 59122-7 with a transgenic corn event conferring the trait of corn rootworm resistance resulting from the expression of a dsRNA targeting for suppression a corn rootworm gene essential for the rootworms' survival (U.S. Pat. No. 7,943,819). Inherent in such combinations are the problems associated with the need for breeding these multiple traits located in multiple different loci and on multiple chromosomes within the corn genome together into a single corn plant and maintaining those traits as hybrids in dozens if not hundreds of different corn germplasm varieties. The solution for such problems would be to include combinations of these traits together in a single locus. The inventors herein provide one such solution to the problem in the form of the corn event MON 87411, which combines three covalently linked expression cassettes together in a single locus within the corn genome, these expression cassettes conferring the traits of corn rootworm resistance and glyphosate herbicide tolerance to the corn cells, corn tissues, corn seed and corn plants containing the transgenic event MON 87411. Use of corn event MON 87411 provides major benefits to corn growers: a) protection from economic losses due to the corn rootworm larvae by providing two different corn rootworm resistance modes of action, and b) the ability to apply glyphosate containing agricultural herbicides to the corn crop for broad-spectrum weed control. Additionally, the transgenes encoding the corn rootworm and glyphosate tolerant traits are linked on the same DNA segment and occur at a single locus in the genome of MON 87411, providing for enhanced breeding efficiency and enables the use of molecular markers to track the transgene insert in the breeding populations and progeny thereof.

The corn event MON 87411 was produced by an *Agrobacterium* mediated transformation process of an inbred corn line with the plasmid construct pMON120417. This plasmid construct contains the linked plant expression cassettes with the regulatory genetic elements necessary for expression in corn plant cells of a CP4 EPSPS protein, as well as a Cry3Bb protein and a dsRNA targeting for suppression an essential gene in the cells of corn rootworms when corn cells containing corn event MON 87411 are provided in the diet of such corn rootworms. Corn cells were regenerated into intact corn plants and individual plants were selected from the population of plants that showed integrity of the plant expression cassettes and resistance to glyphosate and corn rootworm larvae feeding damage. A corn plant that contains in its genome the linked plant expression cassettes present in corn event MON 87411 is an aspect of the present invention.

The plasmid DNA inserted into the genome of corn event MON 87411 was characterized by detailed molecular analyses. These analyses included: the insert number (number of integration sites within the corn genome), the copy number (the number of copies of the T-DNA within one locus), and the integrity of the transgenic inserted DNA. The plasmid construct containing the three linked expression cassettes inserted into the corn genome giving rise to the event MON 87411 contains multiple segments (junction sequences between elements used to build or construct the several expression cassettes) that are not known to appear naturally in the corn genome nor in other vectors or transgenic events of corn or otherwise (for example, sequences as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52). In addition, the transformation event that gave rise to the inserted transgenic DNA in the event MON 87411 is characterized herein as an insertion into a single locus in the corn genome, resulting in two new loci or junction sequences between the inserted DNA and the corn genome DNA (additional junction sequences) that are of sufficient length to be unique only to a corn genome comprising event MON 87411. These junction sequences are useful for detecting the presence of the event MON 87411 DNA in corn cells, tissue, seed and plants or plant products (commodity products). DNA molecular probes and primer pairs are described herein that have been developed for use in identifying the presence of these various junction segments in biological samples containing or suspected of containing corn cells, seed, plant parts or plant tissue that contain the event MON 87411 DNA. The data show that event MON 87411 contains a single T-DNA insertion with one copy of the inserted transgenic DNA. No additional elements from the transformation vector pMON120714 other than portions of the *Agrobacterium tumefaciens* left and right border regions used for transgenic DNA transfer from the plant transformation plasmid to the corn genome have been identified in event MON 87411. Finally, thermal amplification producing specific amplicons diagnostic for the presence of such event MON 87411 DNA in a sample, and DNA sequence analyses were performed to determine the arbitrarily assigned 5' and 3' insert-to-plant genome junctions, confirm the organization of the elements within the insert, and determine the complete DNA sequence of the inserted transgene DNA in corn plant event MON 87411 (SEQ ID NO:1).

Dozens of transgenic events were produced using the construct used to produce the transgenic event MON 87411, and different constructs were produced and used to produce many dozens of other transgenic corn events which were compared to the MON 87411 and similar events. These events were all tested for efficacy for controlling corn rootworms in diet bioassays in which the transgenic corn plant event tissues were provided in the diet of corn rootworm larvae. It was determined that the orientation of expression of the two different expression cassettes responsible for conferring the corn rootworm resistance traits to the various events was critical to the efficacy of the events in providing corn rootworm control when the corn event cells expressing these resistance traits were provided in the diet of the corn rootworm larvae. Two different promoters, CAMV e35S and Zm.PIIG, were observed to provide surprising and superior efficacy of corn events containing expression cassettes expressing the dsRNA corn rootworm protectant from the e35S promoter and the Cry3Bb corn rootworm toxic protein from an a Zm.PIIG promoter that was adjacent to and divergent from the e35S promoter. When these promoters were in this particular orientation significantly improved ratios of transgenic events exhibiting efficacy were obtained.

Unless otherwise noted herein, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. As used herein, the term "corn" means *Zea mays* and includes all plant varieties that can be bred with corn plants comprising MON 87411. As used herein, the term "comprising" means "including but not limited to".

The present invention provides for transgenic plants which have been transformed with a DNA construct that contains at least three expression cassettes; a first expression cassette expressing a corn rootworm toxic amount of a dsRNA designed to suppress a corn rootworm essential gene orthologous to a yeast snf7 gene, a second expression cassette expresses corn rootworm toxic amounts of Cry3Bb delta-endotoxin, and a third expression cassette that expresses a glyphosate tolerance enzyme CP4 EPSPS that is insensitive to glyphosate inhibition. Corn plants transformed according to the methods and with the DNA construct disclosed herein are resistant to CRW and tolerant to applications of glyphosate herbicide. The linked agronomic traits provide ease in maintaining these traits together in a breeding population, and exhibit greater corn rootworm efficacy than plants containing only a single corn rootworm inhibition gene or that contain the same corn rootworm inhibition genes (Cry3Bb and dsRNA) that are combined as a breeding stack.

A transgenic "plant" is produced by transformation of a plant cell with heterologous DNA, i.e., a polynucleic acid construct that includes a transgene of interest; regeneration of a population of plants resulting from the insertion of the transgene into the genome of the plant cell, and selection of a particular plant characterized by insertion into a particular genome location. The term "event" refers to the original transformant plant and progeny of the transformant that include the heterologous DNA. The term "event" also includes progeny produced by a sexual outcross between the event and another plant wherein the progeny includes the heterologous DNA. Even after repeated back-crossing to a recurrent parent, the inserted DNA and flanking genomic DNA from the transformed parent event is present in the progeny of the cross at the same chromosomal location. The term "event" also refers to DNA from the original transformant comprising the inserted DNA, and flanking genomic sequence immediately adjacent to the inserted DNA, that would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA. The present invention is related to the transgenic event, corn plant comprising MON 87411, progeny thereof, and DNA compositions contained therein.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from MON 87411 whether from a MON 87411 plant or from a sample that includes MON 87411 DNA. Probes according to the present invention include not only deoxyribonucleic or ribonucleic acids, but also polyamides and other probe materials that bind specifically to a target DNA sequence and can be used to detect the presence of that target DNA sequence.

DNA primers are isolated polynucleic acids that are annealed to a complementary target DNA strand by nucleic acid hybridization to form a hybrid between the primer and the target DNA strand, then extended along the target DNA strand by a polymerase, e.g., a DNA polymerase. A DNA primer pair or a DNA primer set of the present invention refer to two DNA primers useful for amplification of a target nucleic acid sequence, e.g., by the polymerase chain reaction (PCR) or other conventional polynucleic acid amplification methods.

DNA probes and DNA primers are generally 11 polynucleotides or more in length, often 18 polynucleotides or more, 24 polynucleotides or more, or 30 polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules.

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules, also referred to as nucleic acid segments, or fragments thereof are capable of specifically hybridizing to other nucleic acid molecules under certain circumstances. As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NOs: 1, 2, 3, 4, 5, 6, 7, 8, 9, 10, 12, 14, 16, 21, 25, 41, 42, 43, 44, 45, 49, 50, 51, or 52 or complements thereof or fragments of either under moderately stringent conditions, for example at about 2.0× SSC and about 65° C. In a particularly preferred embodiment, a nucleic acid of the present invention will specifically hybridize to one or more of the nucleic acid molecules set forth in SEQ ID NOs: 1, 2, 3, 4, 5, 6, 7, 8, 9, 10, 12, 14, 16, 21, 25, 41, 42, 43, 44, 45, 49, 50, 51, or 52 or complements or fragments of either under high stringency conditions. In one aspect of the present invention, a preferred marker nucleic acid molecule of the present invention has the nucleic acid sequence set forth in SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8, or SEQ ID NO:9, or SEQ ID NO:10; or SEQ ID NO:12, or SEQ ID NO:14, OR SEQ ID NO:16, or SEQ ID NO:21, or SEQ ID NO:25, or SEQ ID NO: 41, or SEQ ID NO: 42, or SEQ ID NO: 43, or SEQ ID NO: 44, or SEQ ID NO: 45, or SEQ ID NO: 49, or SEQ ID NO: 50, or SEQ ID NO: 51, or SEQ ID NO: 52 or complements thereof or fragments of either. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a corn plant resulting from a sexual cross contains transgenic plant genomic DNA from a corn plant comprising MON 87411 of the present invention, DNA that is extracted from a corn plant tissue sample may be subjected to a polynucleic acid amplification method using a primer pair that includes a primer derived from a DNA sequence in the genome of a MON 87411 comprising plant adjacent to the insertion site of the inserted heterologous DNA (transgene DNA), and a second primer derived from the inserted heterologous DNA to produce an amplicon that is diagnostic for the presence of the MON 87411 plant DNA. The diagnostic amplicon is of a length and has a DNA sequence that is also diagnostic for the plant genomic DNA. The amplicon may range in length from the combined length of the primer pair plus one nucleotide base pair, preferably plus about fifty nucleotide base pairs, more preferably plus about two hundred-fifty nucleotide base pairs, and even more preferably plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion of SEQ ID NO:1 and a reverse primer isolated from the genomic portion of SEQ ID NO:1 that amplifies a DNA molecule comprising the a junction sequence identified herein in the event MON 87411 genome). A member of a primer pair derived from the plant genomic sequence adjacent to the inserted transgenic DNA is located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Polynucleic acid amplification can be accomplished by any of the various polynucleic acid amplification methods known in the art, including the polymerase chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA sequence from event MON 87411 can be verified (and corrected if necessary) by amplifying such DNA molecules from event MON 87411 comprising seed or plants grown from the seed deposited with the ATCC having accession no. PTA-12669, using primers derived from the sequences provided herein, followed by standard DNA sequencing of the PCR amplicon or cloned DNA fragments thereof.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. A kit that contains DNA primers that are homologous or complementary to any portion of the corn genomic region as set forth in SEQ ID NO:1 and to any portion of the inserted transgenic DNA as set forth in SEQ ID NO:1 is an object of the invention. DNA molecules useful as DNA primers can be selected from the disclosed transgene/genomic DNA sequence of MON 87411 (SEQ ID NO:1) by those skilled in the art of DNA amplification.

The diagnostic amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits can be developed using the compositions disclosed herein and the methods well known in the art of DNA detection. The kits are useful for identification of corn event MON 87411 DNA in a sample and can be applied to methods for breeding corn plants containing MON 87411 DNA. A kit contains DNA molecules that are useful as primers or probes and that are homologous or complementary to at least the applicable portions of SEQ ID NO:1 as described herein. The DNA molecules can be used in DNA amplification methods (PCR) or as probes in polynucleic acid hybridization methods, i.e., Southern analysis, northern analysis.

Junction sequences may be represented by a sequence from the group consisting of SEQ ID NO:2, SEQ ID NO:3, SEQ ID NO:5, SEQ ID NO:6, SEQ ID NO:7, SEQ ID NO:8, SEQ ID NO:9, SEQ ID NO:10; SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, and SEQ ID NO:52. For example, the junction sequences may be arbitrarily represented by the nucleotide sequences provided as SEQ ID NO:5 and SEQ ID NO:8. Alternatively, the junction sequences may be arbitrarily represented by the nucleotide sequences provided as SEQ ID NO:6 and SEQ ID NO:9. Alternatively, the junction sequences may be arbitrarily represented by the nucleotide sequences provided as SEQ ID NO:7 and SEQ ID NO:10. These nucleotides are connected by phosphodiester linkage and in corn event MON 87411 are present as part of the recombinant plant cell genome. The identification of one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:2, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52 in a sample derived from a corn plant, seed, or plant part is determinative that the DNA was obtained from corn event MON 87411 and is diagnostic for the presence in a sample containing DNA from corn event MON 87411. The invention thus provides a DNA molecule that contains at least one of the nucleotide sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52. Any segment of DNA derived from transgenic corn event MON 87411 that is sufficient to include at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52 is within the scope of the invention. In addition, any polynucleotide comprising a sequence complementary to any of the sequences described within this paragraph is within the scope of the invention.

The invention provides exemplary DNA molecules that can be used either as primers or probes for detecting the presence of DNA derived from a corn plant comprising event MON 87411 DNA in a sample. Such primers or probes are specific for a target nucleic acid sequence and as such are useful for the identification of corn event MON 87411 nucleic acid sequence by the methods of the invention described herein.

A "primer" is typically a highly purified, isolated polynucleotide that is designed for use in specific annealing or hybridization methods that involve thermal amplification. A pair of primers may be used with template DNA, such as a sample of corn genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques. An amplicon of the invention comprises at least one of the sequences provided as SEQ ID NO:21 or SEQ ID NO:25. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to the use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. A primer pair useful for this application should comprise a first DNA molecule and a second DNA molecule that is different from the first DNA molecule, and wherein both are each of sufficient length of contiguous nucleotides of a DNA sequence to function as DNA primers that, when used together in a thermal amplification reaction with template DNA derived from corn event MON 87411, to produce an amplicon diagnostic for corn event MON 87411 DNA in a sample. Exemplary DNA molecules useful as primers are provided as SEQ ID NO:18, SEQ ID NO:20, SEQ ID NO:22, or SEQ ID NO:24.

A "probe" is an isolated nucleic acid that is complementary to a strand of a target nucleic acid. Probes include not only deoxyribonucleic or ribonucleic acids but also polyamides and other probe materials that bind specifically to a target DNA sequence and the detection of such binding can be useful in diagnosing, discriminating, determining, detecting, or confirming the presence of that target DNA sequence in a particular sample. A probe may be attached to a conventional detectable label or reporter molecule, e.g., a radioactive isotope, ligand, chemiluminescent agent, or enzyme. Exemplary DNA molecules useful as probes are provided as SEQ ID NO:19 and SEQ ID NO:23.

Probes and primers may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from corn event MON 87411 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985).

Any number of methods well known to those skilled in the art can be used to isolate and manipulate a DNA molecule, or fragment thereof, disclosed in the invention, including thermal amplification methods. DNA molecules, or fragments thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying corn event MON 87411, selecting plant varieties or hybrids comprising corn event MON 87411, detecting the presence of DNA derived from the transgenic corn event MON 87411 in a sample, and monitoring samples for the presence and/or absence of corn event MON 87411 or plant parts derived from corn plants comprising event MON 87411.

The invention provides corn plants, progeny, seeds, plant cells, plant parts (such as pollen, ovule, ear or silk tissue, tassel tissue, root tissue, stem tissue, and leaf tissue), and commodity products. These plants, progeny, seeds, plant cells, plant parts, and commodity products contain a detectable amount of a polynucleotide of the invention, i.e., such as a polynucleotide having at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, or SEQ ID NO:52. Plants, progeny, seeds, plant cells, and plant parts of the invention may also contain one or more additional transgenes. Such additional transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a corn plant lacking such additional transgene.

The invention provides corn plants, progeny, seeds, plant cells, and plant part such as pollen, ovule, ear or silk tissue, tassel tissue, root or stem tissue, and leaves derived from a transgenic corn plant comprising event MON 87411. A representative sample of corn seed comprising event MON 87411 has been deposited according to the Budapest Treaty with the American Type Culture Collection (ATCC). The ATCC depository has assigned the Patent Deposit Designation PTA-12669 to the event MON 87411 comprising seed.

The invention provides a microorganism comprising a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO:41, SEQ ID NO:42, SEQ ID NO:43, SEQ ID NO:44, SEQ ID NO:45, SEQ ID NO:49, SEQ ID NO:50, SEQ ID NO:51, and SEQ ID NO:52 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The transgenic plant cell's new or altered genetic composition and phenotype is a technical effect created by the integration of the heterologous DNA into the genome of the cell. Microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event DNA, including the transgene, to progeny. As used herein, "progeny" includes any plant, seed, plant cell, and/or regenerable plant part comprising the event DNA derived from an ancestor plant and/or comprising a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO:52. Plants, progeny, and seeds may be homozygous or heterozygous for the transgene. Progeny may be grown from seeds produced by a corn event MON 87411 containing plant and/or from seeds produced by a plant fertilized with pollen from a corn event MON 87411 containing plant.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be outcrossed, e.g., bred with another unrelated plant, to produce a varietal or a hybrid seed or plant. The other unrelated plant may be transgenic or nontransgenic. A varietal or hybrid seed or plant of the invention may thus be derived by crossing a first parent that lacks the specific and unique DNA of the corn event MON 87411 with a second parent comprising corn event MON 87411, resulting in a hybrid comprising the specific and unique DNA of the corn event MON 87411. Each parent can be a hybrid or an inbred/varietal, so long as the cross or breeding results in a plant or seed of the invention, i.e., a seed having at least one allele containing the DNA of corn event MON 87411 and/or a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. Two different transgenic plants may thus be crossed to produce hybrid offspring that contain two independently segregating, added, exogenous genes. For example, the event MON 87411 corn containing resistance to corn rootworm infestations and glyphosate tolerance can be crossed with different transgenic corn plants to produce a hybrid or inbred plant having the characteristics of both transgenic parents. One example of this would be a cross of event MON 87411 containing resistance to corn rootworm infestations and glyphosate tolerance with a corn plant having one or more additional traits such as herbicide tolerance and/or insect control, resulting in a progeny plant or seed that is resistant to corn rootworm infestations and tolerant to glyphosate and has at least one or more additional traits. Back-crossing to a parental plant and outcrossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

The invention provides a plant part that is derived from corn plants comprising event MON 87411. As used herein, a "plant part" refers to any part of a plant which is comprised of material derived from a corn plant comprising event MON 87411. Plant parts include but are not limited to pollen, ovule, ear or silk, tassel, root or stem tissue, fibers, and leaves. Plant parts may be viable, nonviable, regenerable, and/or nonregenerable.

The invention provides a commodity product that is derived from corn plants comprising event MON 87411 and that contains a detectable amount of a nucleic acid specific for event MON 87411. As used herein, a "commodity product" refers to any composition or product which contains material derived from a corn plant, whole or processed corn seed, one or more plant cells and/or plant parts containing the corn event MON 87411 DNA. Commodity products may be sold to consumers and may be viable or nonviable. Nonviable commodity products include but are not limited to nonviable corn seeds; processed corn seeds, corn seed parts, and corn plant parts; corn seeds and corn plant parts processed for feed or food, oil, meal, flour, flakes, bran, biomasses, and fuel products. Viable commodity products include but are not limited to corn seeds, corn plants, and corn plant cells. The corn plants comprising event MON 87411 can thus be used to manufacture any commodity product typically acquired from corn. Any such commodity product that is derived from corn plants containing corn event MON 87411 DNA that contains at least a detectable amount of one or more specific and unique DNA molecules, the presence of which are determinative of corn event MON 87411, and specifically may contain a detectable amount of a polynucleotide comprising a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO:52. Any standard method of detection for nucleotide molecules may be used, including methods of detection disclosed herein. A commodity product is within the scope of the invention if there is any detectable amount of a DNA molecule having at least one diagnostic sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25; SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 in the commodity product.

The plants, progeny, seeds, plant cells, plant parts (such as pollen, ovule, ear or silk, tassel, root or stem tissue, and leaves), and commodity products of the invention are therefore useful for, among other things, growing plants for the purpose of producing seed and/or plant parts comprising corn event MON 87411 for agricultural purposes, producing progeny comprising corn event MON 87411 for plant breeding and research purposes, use with microbiological techniques for industrial and research applications, and sale to consumers.

The invention provides methods for controlling weeds and methods for producing plants using glyphosate herbicide and corn event MON 87411. A method for controlling weeds in a field is provided and consists of planting corn event MON 87411 containing varietal or hybrid plants in a field and applying a herbicidally effective dose of glyphosate to the field for the purpose of controlling weeds in the field without injuring the MON 87411 containing plants. Such application of glyphosate herbicide may be pre-emergence, i.e., any time after MON 87411 containing seed is planted and before MON 87411 containing plants emerge, or post-emergence, i.e., any time after MON 87411 containing plants emerge. Another method for controlling weeds in a field is also provided and consists of applying an effective dose of glyphosate herbicide to control weeds in a field and then planting corn plants comprising event MON 87411 in the field. Such application of glyphosate herbicide would be pre-planting, i.e., before MON 87411 containing seed is planted, and could be done any time pre-planting including, but not limited to, about 14 days pre-planting to about 1 day pre-planting. The invention also provides a method for producing corn seed essentially free of weed seeds by planting seeds of a glyphosate tolerant corn plant comprising MON 87411 in a field, applying a post-emergence effective dose of glyphosate herbicide sufficient to kill the weed to the field, and harvesting seed from the field. A herbicidally effective dose of glyphosate for use in the field should consist of a range from about 0.125 pounds per acre to about 6.4 pounds per acre of glyphosate over a growing season. In one embodiment, a total of about 1.5 pounds per acre of glyphosate is applied over a growing season. Multiple applications of glyphosate may be used over a growing season, for example, two applications (such as a pre-planting application and a post-emergence application or a pre-emergence application and a post-emergence application) or three applications (such as a pre-planting application, a pre-emergence application, and a post-emergence application).

Methods for producing an insect and herbicide tolerant corn plant comprising the DNA sequences specific and unique to event MON 87411 of the invention are provided. Transgenic plants used in these methods may be homozygous or heterozygous for the transgene. Progeny plants produced by these methods may be varietal or hybrid plants; may be grown from seeds produced by a corn event MON 87411 containing plant and/or from seeds produced by a plant fertilized with pollen from a corn event MON 87411 containing plant; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant.

Methods of detecting the presence of DNA derived from a corn cell, tissue, seed, or plant comprising corn event MON 87411 in a sample are provided. One method consists of (i) extracting a DNA sample from at least one corn cell, tissue, seed, or plant, (ii) contacting the DNA sample with at least one primer that is capable of producing DNA sequence specific to event MON 87411 DNA under conditions appropriate for DNA sequencing, (iii) performing a DNA sequencing reaction, and then (iv) confirming that the nucleotide sequence comprises a nucleotide sequence specific for event MON 87411, or the construct comprised therein, such as one selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. Another method consists of (i) extracting a DNA sample from at least one corn cell, tissue, seed, or plant, (ii) contacting the DNA sample with a primer pair that is capable of producing an amplicon from event MON 87411 DNA under conditions appropriate for DNA amplification, (iii) performing a DNA amplification reaction, and then (iv) detecting the amplicon molecule and/or confirming that the nucleotide sequence of the amplicon comprises a nucleotide sequence specific for event MON 87411, such as one selected from the group consisting of SEQ ID NO:21 and SEQ ID NO:25. The amplicon should be one that is specific for event MON 87411, such as an amplicon that comprises SEQ ID NO:21 or SEQ ID NO:25. The detection of a nucleotide sequence specific for event MON 87411 in the amplicon is determinative and/or diagnostic for the presence of the corn event MON 87411 specific DNA in the sample. An example of a primer pair that is capable of producing an amplicon from event MON 87411 DNA under conditions appropriate for DNA amplification is provided as SEQ ID NO:18, SEQ ID NO:24, SEQ ID NO:20, and SEQ ID NO:22. Other primer pairs may be readily designed by one of skill in the art and would produce an amplicon comprising SEQ ID NO:21 or SEQ ID NO:25, wherein such a primer pair comprises at least one primer within the genomic region flanking the insert and a second primer within the insert. Another method of detecting the presence of DNA derived from a corn cell, tissue, seed, or plant comprising corn event MON 87411 in a sample consists of (i) extracting a DNA sample from at least one corn cell, tissue, seed, or plant, (ii) contacting the DNA sample with a DNA probe specific for event MON 87411 DNA, (iii) allowing the probe and the DNA sample to hybridize under stringent hybridization conditions, and then (iv) detecting hybridization between the probe and the target DNA sample. An example of the sequence a DNA probe that is specific for event MON 87411 DNA is provided as SEQ ID NO:19 or SEQ ID NO:23. Other probes may be readily designed by one of skill in the art and would comprise at least one fragment of genomic DNA flanking the insert and at least one fragment of insert DNA, such as sequences provided in, but not limited to, SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:21, and SEQ ID NO:25. Detection of probe hybridization to the DNA sample is diagnostic for the presence of corn event MON 87411 specific DNA in the sample. Absence of hybridization is alternatively diagnostic of the absence of corn event MON 87411 specific DNA in the sample.

DNA detection kits are provided that are useful for the identification of corn event MON 87411 DNA in a sample and can also be applied to methods for breeding corn plants containing the appropriate event DNA. Such kits contain DNA primers and/or probes comprising fragments of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. One example of such a kit comprises at least one DNA molecule of sufficient length of contiguous nucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 to function as a DNA probe useful for detecting the presence and/or absence of DNA derived from transgenic corn plants comprising event MON 87411 in a sample. The DNA derived from transgenic corn plants comprising event MON 87411 would comprise a DNA molecule having at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52. A DNA molecule sufficient for use as a DNA probe is provided that is useful for determining, detecting, or diagnosing the presence and/or absence of corn event MON 87411 DNA in a sample is provided as SEQ ID NO:19 and SEQ ID NO:23. Other probes may be readily designed by one of skill in the art and should comprise a sufficient number of contiguous nucleic acids, including at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:14, SEQ ID NO:16, SEQ ID NO:21, SEQ ID NO:25, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 and be sufficiently unique to corn event MON 87411 DNA in order to identify DNA derived from the event. Another type of kit comprises a primer pair useful for producing an amplicon useful for detecting the presence and/or absence of DNA derived from transgenic corn event MON 87411 in a sample. Such a kit would employ a method comprising contacting a target DNA sample with a primer pair as described herein, then performing a nucleic acid amplification reaction sufficient to produce an amplicon comprising a DNA molecule having at least one sequence selected from the group consisting of SEQ ID NO:21 and SEQ ID NO:25, and then detecting the presence and/or absence of the amplicon. Such a method may also include sequencing the amplicon or a fragment thereof, which would be determinative of, i.e. diagnostic for, the presence of the corn event MON 87411 specific DNA in the target DNA sample. Other primer pairs may be readily designed by one of skill in the art and should comprise a sufficient number of contiguous nucleic acids, including at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of sequences provided in, but not limited to SEQ ID NO:1, SEQ ID NO:2, SEQ ID NO:3, SEQ ID NO:5, SEQ ID NO:6, SEQ ID NO:7, SEQ ID NO:8, SEQ ID NO:9, or SEQ ID NO:10, SEQ ID NO:12, SEQ ID NO:14, SEQ ID NO:16, SEQ ID NO: 41, SEQ ID NO: 42, SEQ ID NO: 43, SEQ ID NO: 44, SEQ ID NO: 45, SEQ ID NO: 49, SEQ ID NO: 50, SEQ ID NO: 51, and SEQ ID NO: 52 and be sufficiently unique to corn event MON 87411 DNA in order to identify DNA derived from the event.

The kits and detection methods of the invention are useful for, among other things, identifying corn event MON 87411, selecting plant varieties or hybrids comprising corn event MON 87411, detecting the presence of DNA derived from the transgenic corn plants comprising event MON 87411 in a sample, and monitoring samples for the presence and/or absence of corn plants comprising event MON 87411 or plant parts derived from corn plants comprising event MON 87411.

The sequence of the heterologous DNA insert, junction sequences, or flanking sequences from corn event MON 87411 can be verified (and corrected if necessary) by amplifying such sequences from the event using primers derived from the sequences provided herein followed by standard DNA sequencing of the amplicon or of the cloned DNA.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

DEPOSIT INFORMATION

A deposit of a representative sample of corn seed comprising event MON 87411 has been made on Mar. 14, 2012 according to the Budapest Treaty with the American Type Culture Collection (ATCC) having an address at 10801 University Boulevard, Manassas, Va. USA, Zip Code 20110, and assigned ATCC Accession No. PTA-12669. Access to the deposits will be available during the pendency of the application to the Commissioner of Patents and Trademarks and persons determined by the Commissioner to be entitled thereto upon request. Upon issuance of the patent, all restrictions upon availability to the public will be irrevocably removed. The deposit will be maintained in the depository for a period of 30 years, or 5 years after the last request, or for the effective life of the patent, whichever is longer, and will be replaced as necessary during that period.

EXAMPLES

Example 1

This example describes the design and selection of a construct designated 417 and the engineering and evaluation of different DNA constructs. Table 1 tabulates these DNA constructs by test criteria and results.

DNA constructs were engineered to express an RNA-based plant-incorporated protectant (PIP) in corn, targeting Western corn rootworm (WCR). Variations of the RNA transcript were tested for different target genes of WCR (Group 1), different lengths of RNA (Group 2), with or without neutral RNA carrier (Group 2), different secondary structures (Group 4), and different target segments of Dv_Snf7o (Groups 2 and 3). Variations on multiple transgenes were also tested, e.g., the RNA transcript+a WCR-active protein (Groups 3 and 5), and two RNA transcripts targeting two WCR targets (Groups 1 and 4). Variations on the number and configuration of expression cassettes and elements used were also tested (all groups).

TABLE 1

Forty-five DNA constructs were stably transformed into corn plants. Progeny plants from multiple transformation events per DNA construct were evaluated.

| Construct | Group | Criteria and Results |
|---|---|---|
| 043 | 1 | Tested inhibition of WCR activity on plants expressing |
| 043 | | vector stacked combinations of RNA segments targeting |
| 059 | | transcripts of 4 different WCR endogenous genes. |
| | | WCR activity was inhibited on plants expressing an RNA |
| | | segment targeting the Dv_Snf7o gene transcript. |
| 503 | 2 | Tested inhibition of WCR activity on plants expressing |
| 475 | | various sizes of RNA segments targeting the Dv_Snf7o |
| 970 | | gene transcript (from a 27-mer up to a 429-mer) |
| 474 | | engineered to express as an inverted-repeat RNA (IR). |
| 477 | | Also tested a 150-mer neutral IR carrier that was |
| 306 | | embedded with and without a 27-mer targeting |
| 476 | | Dv_Snf7o. |
| 713 | | Optimal WCR activity was observed on plants expressing |
| | | Dv_Snf7o target segments equal or longer than 100 base |
| | | pairs in length. |
| 868 | 3 | Tested inhibition of WCR activity on plants expressing: |
| 870 | | (a) a 240-mer Dv_Snf7o IR, and (b) a pair of proteins |
| 871 | | TIC809 and TIC810 having WCR inhibitory activity; |
| 875 | | both under one expression cassette in one DNA |
| 310 | | construct. |
| 311 | | Tested inhibition of WCR activity on plants expressing: |
| 330 | | (a) the 240-mer Dv_Snf7o IR, and (b) the pair of |
| 331 | | proteins TIC809 and TIC810 having WCR inhibitory |
| 950 | | activity; each independently- and operably-linked to |
| 890 | | separate expression cassettes in one DNA construct. |
| 867 | | Tested these IR + protein combinations using different |
| 946 | | combinations of different promoters and expression |
| 878 | | cassette configurations. |
| 823 | | In-planta expression of the 240-mer Dv_Snf7o IR |
| 879 | | inhibited WCR activity on such plants, with or without |
| 880 | | expression of the TIC809 and TIC810 protein pair. |
| 401 | | |
| 354 | 4 | Tested progeny plants of a hybrid cross between plants |
| 253 | | containing events harboring DNA construct #503 (a 429- |
| 254 | | mer Dv_Snf7o IR) and plants comprising event MON |
| 255 | | 88017 (Cry3Bb). |
| 256 | | Tested inhibition of WCR activity on plants expressing a |
| 892 | | 150- or 240-mer Dv_Snf7o IR. |
| 365 | | Tested inhibition of WCR activity on plants expressing: (a) Dv_Snf7o IR, and (b) vATPase A IR. |
| | | Tested IR versus non-IR secondary RNA structures for suppressing Dv_Snf7o, vATPase A, and the combination. |
| | | In-planta Expression of the 240-mer Dv_Snf7o IR inhibited WCR activity, with or without expression of the vATPase A RNA segment. |
| | | WCR inhibition was better in-planta when Dv_Snf7o IR was expressed together with Cry3Bb, when compared to expressing Dv_Snf7o IR alone or Cry3Bb alone. |
| 416 | 5 | Tested inhibition of WCR activity on plants expressing |
| 417 | | both (a) the 240-mer Dv_Snf7o IR, and (b) the Cry3Bb |
| 418 | | protein having Diabrotica virgifera pesticidal activity; |
| 419 | | each transgene in separate expression cassettes in a DNA |
| 423 | | construct. |
| 402 | | Tested ten DNA constructs having combinations of |
| 403 | | different promoters, and combinations of different |
| 404 | | expression cassette configurations. |
| 405 | | DNA construct #417 was selected. |
| 406 | | |

Using the DNA constructs of Group 2 as an example, 7 DNA constructs were engineered to test the targeting of various lengths of Dv_Snf7o (from 27 up to 429 nt in length). Each DNA construct was produced, plant cells transformed, plants obtained, and inbreds evaluated in growth chamber efficacy bioassays. Results showed a correlation between length of inverted repeat RNA (IR) and WCR activity (Table 2, columns (B) and (H)).

TABLE 2

Correlation between length of IR and WCR-activity.

| (A) DNA Construct No. | (B) Dv_Snf7o RNA segment length (nt) | (C) No. of embryos transformed | (D) No. of embryos w/shoots | (E) No. of $R_0$ plants to soil | (F) No. of $R_0$ plants expected to harbor a single event | (G) No. of events advanced for multi-plant testing | (H) WCR-activity on plants? |
|---|---|---|---|---|---|---|---|
| 503 | 429 | 2085 | 433 | 308 | 233 | 78 | +++++ |
| 475 | 150 | 230 | 57 | 45 | 39 | 23 | +++++ |
| 970 | 27† | 220 | 79 | 47 | 44 | 21 | ++ |
| 474 | 27 | 230 | 81 | 51 | 49 | 23 | − |
| 477 | 50 | 220 | 50 | 36 | 31 | 23 | ++ |
| 306 | 75 | 230 | 37 | 27 | 18 | 15 | ++ |
| 476 | 100 | 220 | 53 | 40 | 33 | 22 | +++++ |

Column (B) displays the variable lengths of Dv_Snf7o target RNA engineered to express as an inverted repeat RNA (IR) secondary structure in corn plants. Column (C) displays the number of corn embryos that were transformed. Column (D) displays the number of corn embryos that developed shoots. Column (E) displays the number of regenerated corn plants (designated as generation R0) viable on soil. Column (F) displays the number of R0 plants expected to harbor a single copy of insert DNA in the transformation event. Column (G) displays the number of R0 plants that were expected to harbor a single transformation event, and that produced enough seed for multi-plant growth chamber bioassay. Column (H) displays the results of plant growth chamber studies designed to evaluate WCR-activity. "+++++" indicates average RDR was less than 0.5 RDR. "++" indicates average RDR was between 0.5 RDR and 2.0 RDR. "−" means average RDR was about 2.0 RDR, which was comparable to negative controls in growth chamber efficacy studies.

Study results guided the design of the DNA constructs of Group 5 to contain (a) an expression cassette for a 240-mer Dv_Snf7o IR, and (b) an expression cassette for a Cry3Bb protein (FIG. 2). The 240-mer Dv_Snf7o IR was selected because (a) plants expressing the identical 240-mer Dv_Snf7o IR were repeatedly successful in inhibiting CRW activity (Groups 2-4), (b) segments larger than 100 nt in length decrease the probability of development of WCR resistance, and (c) segments larger than 240 nt would make it more difficult to transfer intact into the corn genome. The DNA constructs were designed to test different regulatory genetic elements in each expression cassette and different configurations of each expression cassette in the DNA construct. DNA constructs of Group 5 also included constructs with and without glyphosate tolerance expression cassettes; and a control construct from group 3 that expressed only the 240-mer Dv_Snf7o IR. Each DNA construct was designed, plant cells transformed, plants obtained, and inbreds evaluated in growth chamber efficacy bioassays (Table 3 (C) through (H)).

TABLE 3

Plant production numbers from transformation of Group 5 DNA constructs.

| | (A) DNA Construct No. | (B) DNA construct composition | (C) Number of embryos transformed | (D) Number of embryos w/shoots | (E) Number of R₀ plants to soil | (F) Number of R₀ plants expected to harbor a single event | (G) Number of R₀ events advanced to growth chamber | (H) Inbred and hybrid progeny plant performance |
|---|---|---|---|---|---|---|---|---|
| (1) | 416 | Dv_Snf7o IR + Cry3Bb + EPSPS | 820 | 72 | 72 | 42 | 27 | +++++ |
| (2) | 417 | | 521 | 212 | 94 | 71 | 44 | +++++ |
| (3) | 418 | | 588 | 79 | 65 | 44 | 28 | +++++ |
| (4) | 419 | | 651 | 106 | 95 | 68 | 43 | ++++ |
| (5) | 423 | | 754 | 93 | 84 | 66 | 41 | ++++ |
| (6) | 402 | | 786 | 84 | 84 | 58 | 43 | ++++ |
| (7) | 403 | | 714 | 199 | 84 | 46 | 40 | ++++ |
| (8) | 404 | | 740 | 50 | 50 | 34 | 29 | ++++ |
| (9) | 405 | Dv_Snf7o IR + Cry3Bb | 21663 | 1586 | 1586 | 86 | 58 | +++ |
| (10) | 406 | | 21965 | 1539 | 1539 | 170 | 112 | ++++ |
| (11) | 890 | Dv_Snf7o IR | 3996 | 656 | 394 | 235 | 136 | +++ |

Column (A) lists the DNA constructs tested in stage 5 (also see FIG. 2 for breakdown of the genetic elements).
Column (B) displays the combination of transgene.
Column (C) displays the number of corn embryos that were transformed.
Column (D) displays the number of corn embryos that developed shoots.
Column (E) displays the number of regenerated corn plants (designated as generation R₀) viable on soil.
Column (F) displays the number of R₀ plants expected to harbor a single transformation event.
Column (G) displays the number of R₀ plants expected to harbor a single transformation event, and that produced enough seed for subsequent multi-plant testing.
Column (H) summarizes the performance of plants infested with WCR (See following paragraph for details).

† the same 27-mer as in DNA construct #474 but embedded in a neutral 150-mer IR. To evaluate WCR activity on plants grown in growth chambers, 6 to 8 plants for each of 10-20 events per construct were grown in peat pots. Plants were tested for the presence of the insert DNA and for expression of the transgene(s) in both leaf and root tissues. Plants confirmed to have expression of the transgene were then transplanted into larger pots infested with WCR eggs. Non-transgenic corn lines LH59 and LH244 were included as negative controls. Plants containing event MON 88017 (expressing Cry3Bb) were included as positive controls. Root damage of the growing corn plants was assessed after 4 weeks. Root damage ratings (RDR) were assessed on a three-point scale, with 0 RDR having no root damage and 3 RDR having maximum root damage.

As shown in Table 3, column (H), "+++++" describes DNA constructs that on average provided the highest sustained gene expression to transgenic plants throughout their development, most WCR inhibition during development, and most WCR inhibition in self-fertilized and cross-hybridized generations. "++++" describes DNA constructs that on average provided WCR inhibition to transgenic plants but lower gene expression when compared to the "+++++" plants. "+++" describes DNA constructs that on average provided lower WCR inhibition to transgenic plants when compared to the "++++" and "+++++" plants. Therefore, DNA construct #417 was advanced for further analysis. This construct has sixteen genetic elements organized into three expression cassettes from the Left Border (LB) through to the Right Border (RB). The construct is shown in FIG. 2 and the sequence given in SEQ ID NO:26. The vector components are as follows:

[1] LB: Corresponds to the reverse complement of positions 1 through 442 of SEQ ID NO:26. This element represents the octopine Left border sequence from *Agrobacterium tumefaciens*.

[2] Ps.RbcS2-E9 3' UTR: Corresponds to the reverse complement of positions 486 through 1118 of SEQ ID NO:26. Represents 3' untranslated region (UTR) from the ribulose 1,5-bisphosphate carboxylase small subunit E9 (rbcS-E9) gene transcript from *Pisum sativum* (pea).

[3] 240-mer Dv_Snf7o inverted repeat gene: Corresponds to the reverse complement of positions 1148 through 1777 of SEQ ID NO:26. This gene transcribes RNA containing two 240-mer ribonucleotide segments that align identically to each other in reverse complement fashion, separated by a neutral segment of 150 ribonucleotides, and forming an inverted repeat RNA (IR). The sequence of the 240-bp segment aligns to a WCR gene orthologous to yeast Snf7.

[4] Corn DnaK intron: Corresponds to the reverse complement of positions 1814 through 2617 of SEQ ID NO:26. This element consists of 10 nucleotides of exon 1, intron 1, and 11 nucleotides of exon 2 from the heat shock protein 70 gene from *Zea mays* (corn). The 11 nucleotides of exon 2 were modified to remove an initiating methionine residue.

[5] CaMV 35S leader: Corresponds to the reverse complement of positions 2618-2626 of SEQ ID NO:26. Represents the 5' untranslated region (UTR) from the 35S RNA transcript of the Cauliflower mosaic virus (CaMV) beginning at the +1 position of the mRNA transcriptional start of the gene.

[6] eCaMV 35S promoter: Corresponds to the reverse complement of positions 2627-3238 of SEQ ID NO:26. Represents the promoter of 35S RNA from Cauliflower mosaic virus (CaMV) containing a duplication of the −90 to −350 region.

[7] Corn PIIG promoter: Corresponds to positions 3265-4213 of SEQ ID NO:26. This genetic element represents the promoter of the physical impedance induced protein (PIIG) gene from *Zea mays*.

[8] Wheat Lhcb1 leader: Corresponds to positions 4220-4280 of SEQ ID NO:26. This genetic element represents the 5' untranslated region (UTR) of the light harvesting complex b1 (Lhcb1) gene from *Triticum aestivum* (wheat).

[9] Rice Act1 intron: Corresponds to positions 4297-4776 of SEQ ID NO:26. Consists of a contiguous sequence of 12 nucleotides of exon 1, intron 1, and 7 nucleotides of exon 2 from the Actin 1 (Act1) gene of *Oryza sativa* (rice).

[10] Cry3Bb ORF: Corresponds to positions 4786-6747 of SEQ ID NO:26. Represents the coding region of a non-naturally occurring pesticidal Cry3B protein engineered to exhibit modifications H231R, S311L, N313T, E317K, and Q349R as compared to the native Bt Cry3Bb protein encoding gene. The nucleotide sequence aligns to the cry3Bb gene sequence contained in event MON 88017.

[11] Wheat Hsp17 3' UTR: Corresponds to positions 6767-6976 of SEQ ID NO:26. This genetic element represents the 3' UTR of the heat shock protein 17 (HSP17) gene from *Triticum aestivum* (wheat).

[12] Rice TubA (promoter, leader, intron): Corresponds to positions 7025-9205 of SEQ ID NO:26. Represents the contiguous promoter, leader, intron, and 4 nucleotides of exon 2 from the alpha tubulin gene (TubA-3) of *Oryza sativa* (rice).

[13] CTP: Corresponds to positions 9210-9437 of SEQ ID NO:26. Represents engineered coding region encoding the N-terminal CTP from 5-enolpyruvylshikimate-3-phosphate synthase (EPSPS) from *A. thaliana*. This element differs from the native gene (GenBank Accession No. X06613) at the last GAG codon (glutamic acid) by modification to TGC (cysteine).

[14] CP4 EPSPS: Corresponds to positions 9438-10805 of SEQ ID NO:26. Represents engineered coding region of the EPSPS from *Agrobacterium* CP4. Differs from the native *Agrobacterium* gene at the second codon by modification from encoding serine to CTT (leucine) and four silent substitutions.

[15] Rice TubA 3' UTR: Corresponds to positions 10813-11394 of SEQ ID NO:26. Represents the 3' untranslated region (UTR) of an alpha tubulin gene (TubA-3) from *Oryza sativa* (rice).

[16] RB: Corresponds to positions 11413-11743 of SEQ ID NO:26. Represents nopaline right border sequence from *A. tumefaciens*.

Example 2

This example describes the transformation and selection of event MON 87411 from among a plurality of transgenic events.

Embryos were excised from kernels of corn line LH244, and inoculated with recombinant *Agrobacterium* harboring DNA construct #417. Co-cultured embryos were transferred onto selection and growth media to generate transgenic callus tissue with developing shoots. Developing shoots were transferred to rooting medium for development into plantlets. Plantlets were regenerated into whole $R_0$ plants in soil. $R_0$ plants recovered this way were screened for a single copy of introduced construct DNA. As shown in Table 3, putative single-copy events were provided in 71 unique $R_0$ transformants. Each $R_0$ transformant was placed under nursery conditions to produce progeny $R_1$ seed. Forth-four events were advanced. At least 8 $R_1$ seeds produced by each of the 44 $R_0$ plants were planted in soil and $R_1$ plants were grown to produce $R_2$ seed. A single $R_1$ plant per event was selected to continue each line containing each separate event, and seed from the single $R_1$ plant was bulked for subsequent testing by (a) self-fertilization ($R_{3, 4, \ldots, N}$), and (b) cross-fertilization with other corn lines, e.g., corn line 93IDI3. Plants representing events from transformation of DNA construct #890 (row 11 of Table 3) were also regenerated to serve as comparative controls for subsequent field trials described below and in this example.

Of the 44 events, 25 events were chosen to go forward based on a phenotype including Cry3Bb expression. The $R_1$ plants representing these 25 events were further evaluated for WCR inhibition in growth chamber efficacy methods described in Example 1, and for copy-number of multiple genetic elements of the insert DNA. Seventeen events out of the 25 events were taken forward, as four events exhibited more than one copy of the Ps.RbcS2-E9 3' UTR genetic element, and $R_1$ plants representing 4 other events exhibited root damage ratings greater than 0.8 RDR.

Progeny plants comprising the remaining 17 events, i.e., "A", MON 87411, and "C" through "Q", were further analyzed in parallel for molecular and for in-field performance (see Tables 4 and 5).

TABLE 4

Molecular analysis of 17 transgenic corn events harboring insert DNA from DNA transformation vector #417.

| Event | (A) Backbone absent | (B) Single Insert and Single Copy-number | (C) Intact insert | (D) Above threshold Cry3Bb protein expression | (E) Above threshold IR Dv_Snf7o dsRNA expression | (F) Neutral insertion site | (G) Expected transcript size |
|---|---|---|---|---|---|---|---|
| A | + | + | + | + | + | + | + |
| MON 87411 | + | + | + | + | + | + | + |
| C | + | + | + | + | + | + | + |
| D | + | + | − | + | + | + | + |
| E | + | + | + | + | + | − | NA |
| F | + | + | + | + | + | − | NA |
| G | + | + | + | + | + | − | NA |
| H | + | + | NA | NA | NA | NA | NA |
| I | + | + | NA | NA | NA | NA | NA |
| J | + | + | NA | NA | NA | NA | NA |
| K | + | − | NA | NA | NA | NA | NA |
| L | − | − | NA | NA | NA | NA | NA |
| M | − | + | NA | NA | NA | NA | NA |
| N | − | − | NA | NA | NA | NA | NA |
| O | − | + | NA | NA | NA | NA | NA |
| P | − | − | NA | NA | NA | NA | NA |
| Q | − | − | NA | NA | NA | NA | NA |

"−" indicates that the event did not meet the molecular criteria of the corresponding molecular analysis.
"+" indicates that the event met the molecular criteria of the corresponding molecular analysis.
"NA" indicates that the data was not available.

Events were screened for backbone DNA segments of the *Agrobacterium* transformation vector and for single copy-number of all portions of the intended insert DNA (Table 4, Columns (A) and (B)). Seven events (MON 87411, A, C, D, E, F, and G) were analyzed for sequence of the inserted DNA which identical to the transformation vector #417, with the exception of nick site variations at the *agrobacterium* left and right borders that occur during Agro-mediated insertion, event D failed this sequence analysis (Table 4, Column (C)). These 7 events were also evaluated for sustained plant expression of Cry3Bb protein and Dv_Snf7o IR RNA throughout plant development and several generations, and all 7 events met the passing criteria for sustained plant expression (Table 4, Column (D)). Each of the 7 events were analyzed for genomic insertion site characteristics (i.e., neutral insertion site), such as DNA displacement, duplications and repetitiveness, proximity to an endogenous gene, interruption of an endogenous gene, and proximity to QTLs and biotech traits, events E, F, and G failed this analysis (Table 4, Column (F)). Northern blots were performed on plant tissue containing events MON 87411, A, C, and D to determine if the expected sizes of the two RNA transcript encoding Cry3Bb, or producing the Dv_Snf7o IR RNA were present in RNA from the events, and all events evaluated passed this criteria (Table 4, Column (G)).

These 17 events were evaluated in agronomic, insect efficacy and glyphosate tolerance efficacy field trials, the results are summarized in Table 5. The column headers of Table 5 describe the type of field trial ("Agronomics", "Insect", or "Glyphosate"), the controls to which the events were being compared/contrasted are listed, and the genetic inbred used to generate event hybrid is also listed. The field trials summarized in columns (A) through (C) were planted one calendar year before the field trials summarized in columns (D) through (H), and two years before the field trials summarized in column (I).

TABLE 5

Results from Agronomic, Insect efficacy, and glyphosate efficacy field trials of events generated with transformation vector #417.

| Type of field trial | (A) Agronomics | (B) Agronomics | (C) Insect Efficacy | (D) Agronomics | (F) Glyphosate Efficacy | (G) Glyphosate Efficacy | (H) Insect Efficacy | (I) Agronomics |
|---|---|---|---|---|---|---|---|---|
| Controls used as comparison | LH244, #890 | LH244 x 93ID13, #890 | LH244, MON 88017, #890 | LH244, MON 88017 | MON 88017 | MON 88017 | MON 88017, #890 | LH244, #890 |
| Inbred or Hybrid | R3 inbred | R3 inbred | R2 inbred X 93ID13 | R5 inbred | R5 inbred | R4 inbred X MON 89034 | R4 inbred X MON 89034 | R5 inbred |
| Test Event |  |  |  |  |  |  |  |  |
| A | = | = | <0.10 RDR | = | = | = | ~0.10 RDR | − |
| MON 87411 | = | = | NA | = | = | = | ~0.10 RDR | = |
| C | = | = | ~0.10 RDR | = | − | NA | NA | NA |
| D | = | = | ~0.10 RDR | + | = | = | ~0.20 RDR | NA |
| E | = | = | NA | + | = | = | ~0.15 RDR | = |
| F | = | = | NA | + | − | NA | NA | NA |

TABLE 5-continued

Results from Agronomic, Insect efficacy, and glyphosate efficacy field trials of events generated with transformation vector #417.

| Type of field trial | (A) Agronomics | (B) Agronomics | (C) Insect Efficacy | (D) Agronomics | (F) Glyphosate Efficacy | (G) Glyphosate Efficacy | (H) Insect Efficacy | (I) Agronomics |
|---|---|---|---|---|---|---|---|---|
| G | = | = | NA | + | = | = | ~0.15 RDR | = |
| H‡ | − | = | ~0.10 RDR | NA | NA | NA | NA | NA |
| I‡ | − | = | NA | NA | NA | NA | NA | NA |
| J‡ | = | = | NA | NA | NA | NA | NA | NA |
| K | − | = | ~0.15 RDR | = | NA | NA | NA | NA |
| L | = | = | NA | = | NA | NA | NA | NA |
| M | = | = | ~0.20 RDR | + | NA | NA | NA | NA |
| N | − | = | NA | − | NA | NA | NA | NA |
| O | = | = | NA | NA | NA | NA | NA | NA |
| P | − | = | NA | NA | NA | NA | NA | NA |
| Q | = | = | NA | NA | NA | NA | NA | NA |

Events were compared to control(s) in each field trial. Data for each field trial were averaged by replicate plots over multiple locations. LH244 is the control for the transformation line. The DNA vector "#890" was used to produce events expressing only the 240-mer Dv_Snf7o IR. The commercial event, MON 88017, which provides coleopteran resistance and glyphosate tolerance to corn plants was used as a control. "$R_N$ inbred" specifies the $N^{th}$ generation progeny. Hybrid events evaluated in the field trials were grown from seed harvested from a cross with one parent from the event under evaluation (MON 87411, or A through Q), and one parent as indicated in Table 5 (Column C, G, or H). Specifically, in Table 5, column R2 inbred X 93IDI3 specifies that an R2 inbred of the event under evaluation was crossed with inbred corn line 93IDI3 to make the hybrid seed. Similarly, in Table 5, columns G and H, R4 inbred X MON 89034 specifies that an R4 inbred progeny of the event under evaluation was crossed with a plant containing event MON 89034 to make the hybrid seed. "NA" indicates that data for this test event was not available. "=" represents trait equivalency compared to controls. "−" represents a trait hit compared to controls. "+" represents an increase in performance compared to controls. "RDR" is root damage rating. "‡" represents that contemporaneous greenhouse studies showed that the applicable event exhibited phenotypic off-types in plants grown in the nursery. "†" represents that contemporaneous greenhouse studies showed that the applicable event did not provide WCR efficacy.

Agronomic field trials were conducted at multiple North American and South American locations, the results were averaged across all locations. as summarized Table 5, columns A, B, D, and I. For these agronomic field trials, corn kernels were planted in a randomized complete block (RCB) design in triplicate plots per event per location. Each replicate plot consisted of 100 kernels. Trial maintenance was designed to optimize grain production and eliminate natural WCR pressure One or more of the following standard agronomic field trial ratings were collected: degree units to 50% shed (GDU), Breeder's score (BR), seedling vigor (SDV), stalk lodging (STLC), root lodging (RTLC), ear height of mature plants (EHT), plant height of mature plants (PHT), grain moisture (MST), and grain test weight (TWT), phenotypic off-types, and grain yield. Both inbred and hybrid events were evaluated and the results are summarized in Table 5, columns A, B, D, and I. Appropriate controls were included in triplicate plots per control per location. The ratings were averaged by plot across all locations. Data were subjected to an analysis of variance and means separated at the least significant difference at the 5% probability level (LSD (0.05)).

Results of insect efficacy field trials that included analyses for WCR damage averaged across multiple North American locations are summarized in Table 5, columns C and H. For these efficacy field trials, corn kernels were planted in a RCB design in triplicate plots per event per location; each replicate plot consisted of 25 kernels. Test events were presented in hybrid plants. Appropriate controls were included in triplicate plots per control per location. When plots of corn reached their V2 growth stage, 5 plants per plot were infested with WCR eggs at a rate of 3,330 eggs per plant. During the V10 growth stage, the roots of the 5 infested plants per plot were dug up, washed, and evaluated for feeding damage based on a root damage rating (RDR) of 0 to 3, with 0 RDR having no root damage and 3 RDR having maximum root damage. RDRs for test events and control plants were averaged by plant across all plots in all locations. Negative control plants of each insect efficacy field trial exhibited respective average RDRs of 1.7 and 1.5 RDR. Commercial checks of each insect efficacy field trial exhibited respective average RDRs of 0.25 and 0.20 RDR. Plants containing events from DNA construct #890 exhibited a range of RDRs from about 0.35 to 0.50 RDR. Events from DNA Construct #417 consistently provided plants with average RDR scores less than the economic injury threshold of 0.25 RDR.

Results of efficacy field trials evaluating vegetative tolerance to glyphosate herbicide treatments were conducted across multiple North American locations and are summarized in Table 5, columns F and G. For these efficacy field trials, the glyphosate application regimen used for the specific trial is presented in Table 6 (corresponding to Table 5, column F) and Table 7 (corresponding to Table 5, column G).

TABLE 6

Herbicide Field Trial Treatments.

| Treatment | Rate (lbs ae/A) | Schedule (by plant stage) |
|---|---|---|
| Glyphosate | 1.5 | V2 |
| Glyphosate | 1.5, 0.75, 0.75 | V2, V8, V10 |
| Glyphosate | 1.5, 1.125, 1.125 | V2, V8, V10 |

"lbs ae" indicates pound acid equivalent. "A" indicates acre.

TABLE 7

Herbicide Field Trial Treatments.

| Treatment | Rate (lbs ae/A) | Schedule (by plant stage) |
|---|---|---|
| Untreated | 0.0 | n/a |
| Glyphosate | 1.5, 1.5 | V4, V8 |
| Glyphosate | 3.0, 3.0 | V4, V8 |
| Glyphosate | 4.5, 4.5 | V4, V8 |

"lbs ae" indicates pound acid equivalent. "A" indicates acre.

Each plot of 100 plants was rated for crop injury 7-10 days after the last spray of each treatment. Crop injury ratings included chlorosis, malformation, and average lower plant height, all of which indicate lower tolerance to the glyphosate herbicide. Each plot was also rated for PHT, EHT, days to 50% pollen shed (D50P), days to 50% silk emergence (D50S), TWT, MST, and yield. Events were provided as inbred plants and hybrid plants and compared to event MON 88017. Events "A", MON 87411, "D", "E", and "G" were equivalent to event MON 88017 relative to crop injury, PHT, EHT, D50P, D50S, TWT, MST, and yield ratings. Based on these results coupled with the significant RDR advantage of event MON 87411 compared to other events and to the commercial MON88017 event, event MON 87411 was selected.

Example 3

This example describes the molecular characterization of event MON 87411. A sample of Leaf tissue was sampled from an ($R_0$) MON 87411 plant. Sequencing of the genomic DNA corresponding to the transgenic insertion site in event MON 87411 was obtained and no differences were observed compared to the sequence in the transformation vector corresponding to vector #417.

The flanking sequences were mapped to corn genome reference sequences, including the maize B73 reference genome (Ref B73). Event MON 87411 was determined to be physically located on chromosome 9. The flanking sequence ending at the left flank/insert DNA junction corresponds to position ZM_B73_CR09:39261797. The flanking sequence ending at the right flank/insert DNA junction corresponds to position ZM_B73_CR09:39261915. The flanking sequences for event MON 87411 were analyzed for genome duplications, repeats, and endogenous genes. None were detected.

The sequence analysis of the inserted DNA in event MON 87411 confirmed that only 263 nucleotides of the *Agrobacterium* left border (arbitrarily set as the 5' end of the insert), and only 15 nucleotides of the *Agrobacterium* right border (arbitrarily set as the 3' end of the insert) were retained in the inserted DNA at the genomic insertion site of event MON 87411.

A comparative analysis of the genomic sequence flanking the inserted DNA of event MON 87411 and the corresponding genomic region of the site of insertion in the wild-type allele from LH244 was conducted. This analysis determined that a 118 base pair segment of LH244 genomic DNA was displaced by the inserted DNA of the transformation vector #417 in the process of generating event MON 87411.

Example 4

This example describes methods which are useful in identifying the presence of DNA derived from event MON 87411 in a corn sample. A pair of primers and a probe were designed for the purpose of identifying the unique junction formed between the genomic DNA and the arbitrarily assigned 5' end of the inserted DNA of event MON 87411 (i.e., the left junction) and encompassed in SEQ ID NO:1, SEQ ID NO:2, SEQ ID NO:4, SEQ ID NO:5, SEQ ID NO:6, SEQ ID NO:7, or SEQ ID NO:21. The sequence of the oligonucleotide forward primer SQ27011 (SEQ ID NO:18) is identical to the nucleotide sequence corresponding to positions 462 through 490 of SEQ ID NO:1 and SEQ ID NO:2, positions 107 through 135 of SEQ ID NO:7, positions 72 through 100 of SEQ ID NO:6, positions 12 through 40 of SEQ ID NO:5, and positions 1 through 29 of SEQ ID NO:21. The sequence of the oligonucleotide reverse primer SQ9085 (SEQ ID NO:20) is identical to the reverse complement of the nucleotide sequence corresponding to positions 516 through 541 of SEQ ID NO:1 and SEQ ID NO:2, positions 161 through 186 of SEQ ID NO:7, positions 126 through 151 of SEQ ID NO:6, positions 66 through 91 of SEQ ID NO:5, positions 16 through 41 of SEQ ID NO:4, and positions 55 through 80 of SEQ ID NO:21. The sequence of the oligonucleotide probe PB3552 (SEQ ID NO:19) is identical to the reverse complement of the nucleotide sequence corresponding to positions 502 through 515 of SEQ ID NO:1 and SEQ ID NO:2, positions 147 through 160 of SEQ ID NO:7, positions 112 through 125 of SEQ ID NO:6, positions 52 through 65 of SEQ ID NO:5, positions 2 through 15 of SEQ ID NO:4, and positions 41 through 54 of SEQ ID NO:21. The PCR primers SQ27011 (SEQ ID NO:18) and SQ9085 (SEQ ID NO:20) amplify a 79 nucleotide amplicon of the unique the genomic/insert DNA at the left junction of event MON 87411. This same primer pair with probe PB3552 (SEQ ID NO:19), which has been fluorescently labeled (i.e., a 6FAM™ fluorescent label), can be used in an Endpoint TaqMan® PCR assay to identify the presence of DNA derived from event MON 87411 in a sample.

A pair of primers and a probe were designed for the purpose of identifying the unique junction formed between the genomic DNA and the arbitrarily assigned 3' end of the inserted DNA of event MON 87411 (i.e., the right junction) and encompassed in SEQ ID NO:1, SEQ ID NO:3, SEQ ID NO:4, SEQ ID NO:8, SEQ ID NO:9, SEQ ID NO:10, or SEQ ID NO:25. The sequence of the oligonucleotide forward primer SQ27066 (SEQ ID NO:22) is identical to the nucleotide sequence corresponding to positions 11710 through 11728 of SEQ ID NO:1, positions 11210 through 11228 of SEQ ID NO:4, positions 45 through 63 of SEQ ID NO:8, SEQ ID NO:9, and SEQ ID NO:10, and positions 1 through 19 of SEQ ID NO:25. The sequence of the oligonucleotide reverse primer SQ26977 (SEQ ID NO:24) is identical to the reverse complement of the nucleotide sequence corresponding to positions 11756 through 11784 of SEQ ID NO:1, positions 91 through 117 of SEQ ID NO:8, positions 91 through 119 of SEQ ID NO:9 and SEQ ID NO:10, positions 23 through 51 of SEQ ID NO:3, and positions 47 through 75 of SEQ ID NO:25. The sequence of the oligonucleotide probe PB11300 (SEQ ID NO:23) is identical to the nucleotide sequence corresponding to positions 11731 through 11755 of SEQ ID NO:1, positions 11231 through 11248 of SEQ ID NO:4, positions 66 through 90 of SEQ ID NO:8, SEQ ID NO:9, and SEQ ID NO:10, positions 1 through 22 of SEQ ID NO:3, and positions 22 through 46 of SEQ ID NO:25. The PCR primers SQ27066 (SEQ ID NO:22) and SQ26977 (SEQ ID NO:24) amplify a 75 nucleotide amplicon of the unique the genomic/insert DNA at the right junction of event MON 87411. This same primer pair with probe PB11300 (SEQ ID NO:23), which has been fluorescently labeled (i.e., a 6FAM™ fluorescent label), can be used in an Endpoint TaqMan® PCR assay to identify the presence of DNA derived from event MON 87411 in a sample.

In addition to SQ27011, SQ9085, PB3552, SQ27066, SQ26977, and PB11300, it should be apparent to persons skilled in the art that other primers and/or probes can be designed to either amplify and/or hybridize to sequences within SEQ ID NO:1 which are unique to, and useful for, detecting the presence of DNA derived from event MON 87411 in a sample.

Based on molecular and sequence analysis, PCR assays for event identification assays were developed for event MON 87411. Following standard molecular biology laboratory practices, the parameters of either a standard PCR assay or a TaqMan® PCR assay were optimized with each set of primer pairs and probes (i.e. probes labeled with a fluorescent tag such as 6FAM™) used to detect the presence of DNA derived from event MON 87411 in a sample (SQ27011, SQ9085, and/or PB3552, or SQ27066, SQ26977, and/or PB11300). Generally, the parameters which were optimized included primer and probe concentration, amount of template DNA, and PCR amplification cycling parameters. A control for the PCR reaction included primers (SQ20221 (SEQ ID NO:38) and SQ20222 (SEQ ID NO:40)) and/or probe (PB10065 (SEQ ID NO:39)) (probe labeled with a fluorescent tag such as VIC™), which are specific for an internal control, single copy gene in the corn genome. One of skill in the art will know how to design other PCR primers specific for a single copy gene in the corn genome which can be used to amplify an amplicon to be used as an internal control probe, or as an internal control in a PCR assay (e.g. TaqMan®). DNA was extracted from leaf tissue for each of the following: [1] leaf sample to be analyzed; [2] negative control (non-transgenic corn DNA); [3] negative water control (no template); and [4] positive control MON 87411 DNA. Detection of the amplicons from a standard PCR assay would be visualization by DNA gel electrophoresis, and for a TaqMan® PCR assay by fluorescence detection.

A zygosity assay is useful for determining if a plant comprising an event is homozygous for the event DNA; that is comprising the exogenous DNA in the same location on each chromosome of a chromosomal pair; or heterozygous for an event DNA, that is comprising the exogenous DNA on only one chromosome of a chromosomal pair; or is null for the event DNA, that is wildtype. The zygosity of a corn plant containing event MON 87411 can be determined by thermal amplification (PCR) or by endpoint TaqMan® methods. For example, for PCR amplification, the primer pair SQ27011 (SEQ ID NO:18) and SQ26977 (SEQ ID NO:22) hybridize within the genomic DNA flanking the event MON 87411 insert. This primer pair will generate an amplicon which is 11323 nucleotides in length when DNA derived from event MON 87411 is present in the sample. This same primer pair will generate an amplicon which is only about 150 nucleotides long when corn DNA in the sample is not derived from event MON 87411. On DNA gel electrophoresis, a single band of 11323 bp is indicative that the DNA in the sample is from a homozygous MON 87411 event, a single band of about 150 bp is indicative that the DNA in the sample is not from a MON 87411 event, and the presence of both a band of 11323 bp and a band of about 150 bp is indicative that the DNA in the sample is from a corn plant heterozygous for MON 87411 event.

A TaqMan® assay can be developed to determine the zygosity of a corn plant containing event MON 87411. For this assay, three or four primers and two probes would be designed where [1] a first primer pair and a first probe are specific for detecting the presence of event MON 87411 DNA in a sample, and [2] a second primer pair, different from the first primer pair, and a second probe, different from the first probe, are specific for detecting the presence of wildtype corn DNA (i.e., sample not containing event MON 87411). In a TaqMan®, or similar assay, a fluorescent signal only from the first probe is indicative of and diagnostic for a plant homozygous for event MON 87411; a fluorescent signal from both the first probe and second probe is indicative of and diagnostic for a plant heterozygous for event MON 87411; and a fluorescent signal only from the second probe is indicative of and diagnostic for a plant which is homozygous for the wildtype allele (i.e., is null for event MON 87411).

Example 5

This example describes the superior protection of plant comprising event MON 87411 from corn rootworm damage when compared to current commercial products (MON 88017 and DAS-59122-7) and negative control plants. Efficacy field trials were conducted comparing 135 plants each of event MON 87411, MON 88017, DAS-59122-7, and negative controls. Root damage ratings (RDR) were collected, and the percentage plants with an RDR less than the economic injury level (0.25 RDR) is shown in Table 8.

Table 8 shows that only about 4% of plants containing event MON 87411 exhibited RDRs greater than the economic threshold of 0.25 RDR. In contrast, 22% of the commercially available plants containing MON 88017 exhibited RDRs greater than the economic threshold of 0.25 RDR. And, 20% of the commercially available plants containing DAS-59122-7 exhibited RDRs greater than the economic threshold of 0.25 RDR. And, 96% of the negative control plants exhibited RDRs greater than the economic threshold of 0.25 RDR. The conclusion from these data is that event MON 87411 is clearly superior at providing protection from corn rootworm damage as compared to commercial products MON 88071 and DAS-59122-7, and a negative control.

TABLE 8

Results of efficacy field trial with the approximate percentage of plants exhibiting ≤0.25 RDR.

| Event tested | Approximate percentage of plants exhibiting ≤0.25 RDR |
| --- | --- |
| event MON 87411 | 96 |
| MON 88017 | 78 |
| DAS-59122-7 | 80 |
| negative control plants | 4 |

Trial included 135 plants for each event tested.

Efficacy green house trials were conducted to test the performance of event MON 87411 with extreme infestation pressure of corn root worm. In this trial the following event were evaluated: event MON 87411, an event from transformation with DNA vector #890 expressing only the dsRNA; MON 88017; DAS-59122-7; and negative control. For these high-pressure efficacy trials, the corn plants under evaluation were grown in pots in a green house. Extreme infestation pressure was achieved by sequential infestation of each potted plant with approximately 2,000 WCR eggs per pot at their V2 growth stage, and, at 4 additional times occurring at 1 to 1½ week intervals with approximately 1,000 WCR eggs per pot per infestation for a total of approximately 6,000 WCR eggs added to each pot. Plant roots were removed, washed, and rated for RDR at their VT growth stage. The roots from all thirteen (N=13) negative control plants exhibited maximum root damage, or an absolute RDR of 3 RDR. These results illustrate that event MON 87411 is more superior to other corn events available for controlling corn rootworm (Table 9).

TABLE 9

Root Damage Rating (RDR) under high corn rootworm infestation pressure.

| Event | Average RDR | Lower and Upper 95% confidence limits |
|---|---|---|
| Negative Control (N = 13) | 3.0 | Absolute |
| only dsRNA (N = 11) | 0.36 | 0.17/0.54 |
| MON 88017(N = 11) | 2.1 | 1.8/2.4 |
| DAS-59122-7 (N = 16) | 0.29 | 0.17/0.42 |
| MON 87411 (N = 13) | 0.06 | 0.03/0.08 |

(N = the number of plants evaluated).

One measure of efficacy of corn rootworm transgenic events is by a determining the emergence of adult beetles from the potted soil of plants cultivated in a green house. To determine adult corn rootworm beetle emergence from the soil of event MON 87411 plants grown in pots, 10 to 15 plants were germinated in pots containing soil infested with WCR eggs, similar to that described above. Throughout the growth period, each corn plant was covered with mesh bag to contain any emerging adult beetles.

Counts of above ground adult beetles were made at 6, 12, and 18 weeks after plant emergence, and at the end of the trial the roots were evaluated for RDR. Plants containing event MON 87411 were compared to negative control plants, and other corn rootworm protective transgenic events. The results were that significantly fewer beetles were observed to emerge from soils in which event MON 87411 plants were potted compared to the other corn rootworm protective transgenic events, illustrating the superior properties of event MON 87411 to protect against corn rootworm damage.

Example 6

This example illustrates that the orientation of expression of two different promoters in a corn cell, each driving expression of a different corn rootworm toxic agent, can result in significantly improved ratios of transgenic events exhibiting efficacy when provided in the diet of corn rootworm larvae.

Corn cells were transformed with one of four different plant transformation vectors, pMON120417, pMON120434, pMON120416, or pMON120419, and transgenic events were obtained that were regenerated into transgenic corn plants.

With reference to FIG. 4, all of the plant transformation vectors contain three expression cassettes 1, 2, and 3, bounded on one end by an *Agrobacterium* left border (LB), and at the opposite end by an *Agrobacterium* right border (RB). A corn rootworm toxic dsRNA is expressed from cassette 1 in all four vectors from an enhanced Cauliflower mosaic virus 35S (e35S) promoter. A corn rootworm toxin protein, Cry3Bb, in vectors pMON120417, pMON120434 is expressed from cassette 2 from a Zm.PIIG promoter. A corn rootworm toxin protein, Cry3Bb, in vectors pMON120416, pMON120419 is expressed from cassette 2 from an Os.Rcc3 promoter. In all four vectors, a protein, conferring glyphosate herbicide tolerance, CTP-EPSPS CP4, is expressed from cassette 3 from an Os.TubA3 promoter. In all four vectors cassette 1 and cassette 3 are in the same relative orientation. With reference to FIG. 4, the block arrows indicate the direction of expression from the promoter in each of the respective cassettes.

The relative orientation of cassette 2 in vectors pMON120417 and pMON120434 is reversed, as illustrated by the block arrows (FIG. 4) indicating the direction of expression from the promoter. Expression of Cry3Bb corn rootworm toxin protein in pMON120417 from cassette 2 is divergent from the direction of expression of the corn rootworm toxic dsRNA expressed from cassette 1. Expression of Cry3Bb corn rootworm toxin protein in pMON120434 from cassette 2 is in the same orientation as expression of the corn rootworm toxic dsRNA from cassette 1.

The relative orientation of cassette 2 in vectors pMON120416 and pMON120419 is reversed, as illustrated by the block arrows (FIG. 4) indicating the direction of expression from the promoter. Expression of Cry3Bb corn rootworm toxin protein in pMON120416 from cassette 2 is divergent from the direction of expression of the corn rootworm toxic dsRNA expressed from cassette 1. Expression of Cry3Bb corn rootworm toxin protein in pMON120419 from cassette 2 is in the same orientation as expression of the corn rootworm toxic dsRNA from cassette 1.

As seen from Table 10, when tissue from transgenic corn plants was provided in the diet of *Diabrotica* species of corn root worm, the plants generated by transformation with either construct pMON120417 or pMON120416 (divergent expression of the corn rootworm toxic components) was more efficacious with respect to pesticidal activity when compared to plants generated by transformation with either construct pMON120434 or pMON120419 (tandem or same orientation of expression) (Table 10). The ratio of efficacious events generated from transformation using the vectors pMON120417 and pMON120416, compared to the ratio of efficacious events from the vectors pMON120416 and pMON120419, was significantly greater as shown by the data in Table 10. For example, for events generated from vector pMON120417 with the divergent promoter driven expression of the corn rootworm toxic components, 11 of 43 events, or almost 25% of the events exhibited rootworm efficacious control. In contrast, there were no efficacious events obtained for events generated from vector pMON120434 with the promoter driven expression in the tandem orientation of the corn rootworm toxic components. For events generated from vector pMON120416 with the divergent promoter driven expression of the corn rootworm toxic components, 17 of 27 events, or about 63% of the events exhibited rootworm efficacious control. In contrast, there only about 18.5% efficacious events obtained for events generated from vector pMON120419 with the promoter driven expression in the tandem orientation of the corn rootworm toxic components. These data demonstrate the significantly improved number of efficacious events, and improved ratios of transgenic events exhibiting efficacy, when transgenic corn plants are generated from a plant transformation vector with two different promoters each driving expression in divergent directions of two different corn rootworm toxic agents, and the transgenic corn plants are provided in the diet of corn rootworm larvae.

TABLE 10

Results showing the number of R0 events and the number efficacious events obtained from four plant transformation vectors.

| Construct | No. of R0 Events | # Efficacious events |
|---|---|---|
| pMON120417 | 43 | 11 |
| pMON120434 | 8 | 0 |
| pMON120416 | 27 | 17 |
| pMON120419 | 43 | 8 |

Example 7

To produce corn plants or plant parts thereof which comprise enhanced agronomic, insecticidal, or herbicidal properties, corn plants containing event MON 87411 can be crossed with corn plants containing potentially any other corn event or combination thereof and phenotypes evaluated to determine the resulting properties of the progeny plants. As a non-limiting example, MON 87411 can be crossed with corn plants including one or more combinations, of the following: DAS-59122-7; MIR604; MON 89034; MON 87411; MON 87427; TC1507; 5307; DAS-06275-8; BT176; BT11; and MIR162.

Example 8

This example illustrates the use of a seed blend to protect a field of crop plants comprising event MON 87411 and illustrates a few of the various combinations of transgenic crop plants and refuge crop plants that can be present in a seed blend. One of skill in the art will recognize the many various combinations available based on the present disclosure and knowledge in the art.

A blend containing various ratios of transgenic or non-transgenic seeds is deployed as refuge seed in a mixture with transgenic crop seed comprising event MON 87411. Use of such send blends provides an effective means for allowing adequate survival of susceptible corn rootworms in fields of transgenic crops to prevent or slow the rate of resistance evolution and still reduce economic loss due to corn rootworm infestation.

Transgenic seeds comprising event MON 87411 and a combination of events or transgenes conferring coleopteran resistance, such as events DAS-59122-7, MIR604, or 5307, are mixed with between 1% and 20% refuge seed that contain only events or transgenes conferring lepidopteran resistance, such as events MON810, MON 89034, TC1507, DAS-06275-8, MIR162, BT176, or BT11. The seeds in the blend therefore provide refuge for each other, i.e. the coleopteran protected seed and plants act as a refuge for the plants conferring lepidopteran resistance, and vice versa.

Alternatively, transgenic corn seed comprising event MON 87411 are bred to further comprise an event or transgene conferring coleopteran resistance, such as events DAS-59122-7, MIR604, or 5307; or an event conferring lepidopteran resistance, such as events MON810, MON 89034, TC1507, DAS-06275-8, MIR162, BT176, or BT11; or combinations thereof. This transgenic corn seed is then mixed with between 1% and 20% refuge seed that contain only an event or transgene conferring herbicide tolerance and lacking pest protection events or transgenes. In this case, the herbicide tolerant, insect sensitive plants grown from the refuge seed act as a refuge for the transgenic corn maize insect resistant plants.

The seed blends are planted in a field as a random mixture of the seed comprising event MON 87411 and the refuge seed not comprising event MON 87411. Alternatively, the transgenic crop seed comprising event MON 87411 are planted in a field with the refuge seed planted as a structured (separate) stand of crops.

What is claimed is:

1. A seed blend comprising refuge corn crop seed and at least one variety of transgenic corn crop seed in a uniform mixture, wherein the mixture consists of from about 80% to about 99% first transgenic corn crop seed, wherein the first transgenic corn crop seed comprises event MON 87411 and the refuge crop seed does not comprise said event MON 87411, and wherein a representative sample of seed corn comprising the event MON 87411 has been deposited under ATCC Accession No. PTA-12669.

2. The seed blend of claim 1, wherein said mixture consists of from about 2% to about 5% refuge corn crop seed, from about 5% to about 10% refuge corn crop seed, from about 1% to about 10% refuge corn crop seed, or from about 10% to about 20% refuge corn crop seed.

3. The seed blend of claim 1, wherein the refuge corn crop seed is transgenic.

4. The seed blend of claim 3, wherein the refuge corn crop seed and the at least one variety of transgenic corn crop seed comprise a transgene that confers tolerance to at least a first herbicide.

5. The seed blend of claim 4, wherein the herbicide is selected from the group consisting of dicamba, 2,4-D, glyphosate and glufosinate.

6. The seed blend of claim 1, wherein the first transgenic corn crop seed comprises at least one additional transgenic event that confers pest resistance, and wherein the refuge corn crop seed does not comprise the at least one additional transgenic event.

7. The seed blend of claim 6, wherein the at least one additional transgenic event confers resistance to a lepidopteran pest.

8. The seed blend of claim 7, wherein the at least one additional transgenic event is selected from the group consisting of MON810, MON 89034, TC1507, MIR162, and BT11.

9. The seed blend of claim 6, wherein the at least one additional transgenic event confers resistance to a coleopteran pest.

10. The seed blend of claim 9, wherein the at least one additional transgenic event is selected from the group consisting of DAS-59122-7, MIR604, and 5307.

11. A population of plants produced by growing the seed blend of claim 1.

12. A method for producing a refuge crop seed blend comprising:
   a) blending a first transgenic corn crop seed comprising event MON 87411 with a refuge crop corn seed lacking said event MON 87411; and
   b) ensuring a uniform mixture of the first transgenic corn crop seed and the refuge corn crop seed is provided to produce a refuge crop seed blend, wherein the mixture consists of from about 80% to about 99% first transgenic corn crop seed, and wherein a representative sample of seed corn comprising event MON 87411 has been deposited under ATCC Accession No. PTA-12669.

13. A method for deploying a refuge crop in a field of transgenic pest resistant crops comprising:
   a) obtaining a seed blend according to claim 1; and
   b) planting said seed blend in a field.

14. The method of claim 13, wherein said seed blend consists of from about 2% to about 5% refuge corn crop seed, from about 5% to about 10% refuge corn crop seed, from about 1% to about 10% refuge corn crop seed, or from about 10% to about 20% refuge corn crop seed.

15. The method of claim 13, wherein the refuge corn crop seed is transgenic.

16. The method of claim 15, wherein the refuge corn crop seed and the at least one variety of transgenic corn crop seed comprise a transgene that confers tolerance to at least a first herbicide.

17. The method of claim 16, wherein the herbicide is selected from the group consisting of dicamba, 2,4-D, glyphosate and glufosinate.

18. The method of claim 13, wherein the first transgenic corn crop seed comprises at least one additional transgenic event that confers pest resistance, and wherein the refuge corn crop seed does not comprise the at least one additional transgenic event.

19. The method of claim 18, wherein the at least one additional transgenic event confers resistance to a lepidopteran pest.

20. The method of claim 19, wherein the at least one additional transgenic event is selected from the group consisting of MON810, MON 89034, TC1507, MIR162, and BT11.

21. The method of claim 18, wherein the at least one additional transgenic event confers resistance to a coleopteran pest.

22. The method of claim 21, wherein the at least one additional transgenic event is selected from the group consisting of DAS-59122-7, MIR604, and 5307.

* * * * *

SEQUENCE LISTING

```
<160> NUMBER OF SEQ ID NOS: 52

<210> SEQ ID NO 1
<211> LENGTH: 12248
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(500)
<223> OTHER INFORMATION: represents the genomic DNA flanking the left
      border of the TDNA
<220> FEATURE:
<221> NAME/KEY: misc_feature
<222> LOCATION: (501)..(11748)
<223> OTHER INFORMATION: represents the TDNA
<220> FEATURE:
<221> NAME/KEY: promoter
<222> LOCATION: (2948)..(3559)
<223> OTHER INFORMATION: represents the reverse complement sequence of
      an enhanced CaMV 35S promoter
<220> FEATURE:
<221> NAME/KEY: promoter
<222> LOCATION: (2948)..(4534)
<223> OTHER INFORMATION: represents a divergent promoter region that
      promotes bidirectional transcription
<220> FEATURE:
<221> NAME/KEY: promoter
<222> LOCATION: (3586)..(4534)
<223> OTHER INFORMATION: represents a Corn PIIG promoter
<220> FEATURE:
<221> NAME/KEY: misc_feature
<222> LOCATION: (11749)..(12248)
<223> OTHER INFORMATION: represents the genomic DNA flanking the right
      border of the TDNA

<400> SEQUENCE: 1
```

```
ccctagcgtt gggcccaact agtcagtctg ccttccctcc cagtcgctga cctccttggt      60
ccacttgtca gctttcgcgc tcagatctaa tctcaactgt cgatctgtga tcgggtggcc     120
gagatcaccc gatgcccgtt cgtttgcaaa agttgttaaa agaccctctg tttcttagaa     180
aataacctac attcatgttt cttgcgatta ggccctggt ttcttgtaga gaagccctt      240 gctttatttt aatcacaaaa ataaatctaa tttagtgttt tgaattctaa aacttgtgaa     300
tttcatatct tttgcatatg aactctaaat tgggtggttt aaattgcaaa atgatcataa     360
tattattctc tatctgttta aattataata tttcactgtc tacatgtatg tattttatga     420
ctagacaata ggttcattta aagtgatgga ttatttatta aaaggaaaat aaaaaggcaa     480
aacactaatg aatagttaag tggcttcatg tccgggaaat ctacatggat cagcaatgag     540
tatgatggtc aatatggaga aaagaaaga gtaattacca attttttttc aattcaaaaa     600
tgtagatgtc cgcagcgtta ttataaatg aaagtacatt ttgataaaac gacaaattac     660
gatccgtcgt attatagggc gaaagcaata aacaaattat tctaattcgg aaatcttttat    720 ttcgacgtgt ctacattcac gtccaaatgg gggcttagat gagaaacttc acgatcgatg     780
cggccaccac tcgaggtcga ggtaccgttg tcaatcaatt ggcaagtcat aaaatgcatt     840
aaaaaatatt ttcatactca actacaaatc catgagtata actataatta taaagcaatg     900
attagaatct gacaaggatt ctggaaaatt acataaagga aagttcataa atgtctaaaa     960
cacaagagga catacttgta ttcagtaaca tttgcagctt ttctaggtct gaaaatatat    1020
ttgttgccta gtgaataagc ataatggtac aactacaagt gttttactcc tcatattaac    1080
ttcggtcatt agaggccacg atttgacaca ttttttactca aaacaaaatg tttgcatatc    1140
tcttataatt tcaaattcaa cacacaacaa ataagagaaa aaacaaataa tattaatttg    1200
agaatgaaca aaaggaccat atcattcatt aactcttctc catccatttc catttcacag    1260
ttcgatagcg aaaaccgaat aaaaaacaca gtaaattaca agcacaacaa atggtacaag    1320
aaaaacagtt ttcccaatgc cataatactc aaactcagta ggattctggt gtgtgcgcaa    1380
tgaaactgat gcattgaact tgacgaacgt tgtcgaaacc gatgatacga acgaaagcta    1440
ggcctcagcg agtaccgctg gcgatctaat ccatgtatat gtgaacatca tctacattca    1500
aattcttatg agctttctta agggcatctg cagcatttt catagaatct aatacagcag    1560
tatttgtgct agctccttcg agggcttccc tctgcatttc aatagttgta agggttccat    1620
ctatttgtag ttgggtcttt tccaatcgtt tcttcttttt gagggcttgg agtgcaactc    1680
ttttattttt cgacgcattt ttcttttgcgc tcctgcaggc ggccgcgtgg atgaggagtt    1740
aatcggtcgt gtgagagtag tgatcgagtg gatgtcgtcg agagtgatga gtgttgatgt    1800
tgttagtgat atgtggtaga aggtatcgtg ataaagcgtt aacgcgatcg cagtacttgc    1860
aaagaaaaat gcgtcgaaaa ataaaagagt tgcactccaa gccctcaaaa agaagaaacg    1920
attggaaaag acccaactac aaatagatgg aaccccttaca actattgaaa tgcagaggga    1980
agccctcgaa ggagctagca caaatactgc tgtattagat tctatgaaaa atgctgcaga    2040
tgcccttaag aaagctcata agaatttgaa tgtagatgat gttcacgata tcatggatgg    2100
tatcgcacag cgactgctga gggacgtcga gctcccgctt ggtatctgca ttacaatgaa    2160
atgagcaaag actatgtgag taacactggt caacactagg gagaaggcat cgagcaagat    2220
acgtatgtaa agagaagcaa tatagtgtca gttggtagaa actagatacc atcaggaggt    2280
aaggagagca acaaaaagga aactcttttat ttttaaattt tgttacaaca aacaagcaga    2340
tcaatgcatc aaaatactgt cagtacttat ttcttcagac aacaatattt aaaacaagtg    2400
```

```
catctgatct tgacttatgg tcacaataaa ggagcagaga taaacatcaa aatttcgtca    2460
tttatattta ttccttcagg cgttaacaat ttaacagcac acaaacaaaa acagaatagg    2520
aatatctaat tttggcaaat aataagctct gcagacgaac aaattattat agtatcgcct    2580
ataatatgaa tccctatact attgacccat gtagtatgaa gcctgtgcct aaattaacag    2640
caaacttctg aatccaagtg ccctataaca ccaacatgtg cttaaataaa taccgctaag    2700
caccaaatta cacatttctc gtattgctgt gtaggttcta tcttcgtttc gtactaccat    2760
gtccctatat tttgctgcta caaaggacgg caagtaatca gcacaggcag aacacgattt    2820
cagagtgtaa ttctagatcc agctaaacca ctctcagcaa tcaccacaca agagagcatt    2880
cagagaaacg tggcagtaac aaaggcagag ggcggagtga gcgcgtaccg aagacggttc    2940
agcgtgtcct ctccaaatga aatgaacttc cttatataga ggaagggtct tgcgaaggat    3000
agtgggattg tgcgtcatcc cttacgtcag tggagatatc acatcaatcc acttgctttg    3060
aagacgtggt tggaacgtct tcttttttcca cgatgctcct cgtgggtggg ggtccatctt    3120
tgggaccact gtcggcagag gcatcttcaa cgatggcctt tcctttatcg caatgatggc    3180
atttgtagga gccaccttcc ttttccacta tcttcacaat aaagtgacag atagctgggc    3240
aatggaatcc gaggaggttt ccggatatta cccctttgttg aaaagtctca atcggaccat    3300
cacatcaatc cacttgcttt gaagacgtgg ttggaacgtc ttcttttcc acgatgctcc    3360 tcgtgggtgg gggtccatct tgggaccac tgtcggcaga ggcatcttca acgatggcct    3420
ttcctttatc gcaatgatgg catttgtagg agccaccttc cttttccact atcttcacaa    3480
taaagtgaca gatagctggg caatggaatc cgaggaggtt tccggatatt acccctttgtt    3540 gaaaagtctc aatcggacct gcagcctgca ggctagcggc gcgccacaaa tcacaggcca    3600
tgaaccctac tcatgcttcg atttgtccaa cacacactta ccaaaactca aatcatgtcc    3660
ttgacagtca ctcgggactc ataacatggg tacgtatcga ctatgtcaac tatatgtgtt    3720
ctcatcagat tatagattgg cctagtacgt agtgatattt ccactagcac tgtggttatg    3780
gctgtacctg atagtgatat cagcaccggg tcatggctct actaccaggt agtgagagtg    3840
acctttatac tgtcagactg taactaagga tttccaatca ctgttcggat cctaggctta    3900
gaattaagta aaactctatc actataggct gcagcacact cggtatatat tgatgggcca    3960
acagaaattg tgcgtactat gcgcgatgta aatggacat aaaccctacc catatacaat    4020
gcaataactt ttgtccggtc tgggccaccg gttagcagag gtcctgattt cggtggtagt    4080
ggtagcttga tctggtcgtc gtatcgtaga gggatatata aaatcatgtc acttttgaag    4140
ggagcgctca cagaaataat aggtattcgc gggagccgcc cccgcagaac acaaaataag    4200
gcgagcacgc acacgcatca gtttcgataa aataataata gcgccagctg atcggaacaa    4260
ttccagctag cactaatgta tttctgcatt gatctgttta tacaacatgc tacctcgttg    4320
agtgattttg acatgatttg tcaacttgct ccgatcctat atctcgatcg atctccacat    4380
gacgatggtt gttgtcctgt atcccatgac aaccaggcaa cgctcaaagc acacatgcgt    4440
tgccgattac ccgtgcatgc cgccaagcac gaaagcacct ccctccacac cgtccatcag    4500
ctataaaaac catgccaagc accctgtgaa aagccccggg aaccatcttc cacacactca    4560
agccacacta ttggagaaca cacagggaca acacaccata agatccaagg gaggcctccg    4620
ccgccgccgg taaccacccc gccctctcc tctttctttc tccgtttttt tttccgtctc    4680
ggtctcgatc tttggccttg gtagtttggg tgggcgagag gcggcttcgt gcgcgcccag    4740
```

```
atcggtgcgc gggaggggcg ggatctcgcg gctggggctc tcgccggcgt ggatccggcc    4800
cggatctcgc ggggaatggg gctctcggat gtagatctgc gatccgccgt tgttggggga    4860
gatgatgggg ggtttaaaat ttccgccgtg ctaaacaaga tcaggaagag gggaaaaggg    4920
cactatggtt tatattttta tatatttctg ctgcttcgtc aggcttagat gtgctagatc    4980
tttctttctt cttttttgtgg gtagaatttg aatccctcag cattgttcat cggtagtttt    5040
tcttttcatg atttgtgaca aatgcagcct cgtgcggagc ttttttgtag gtagaagtga    5100
tcaaccatgg ccaaccccaa caatcgctcc gagcacgaca cgatcaaggt cacccccaac    5160
tccgagctcc agaccaacca caaccagtac ccgctggccg acaacccccaa ctccaccctg    5220 gaagagctga actacaagga gttcctgcgc atgaccgagg actcctccac ggaggtcctg    5280
gacaactcca ccgtcaagga cgccgtcggg accggcatct ccgtcgttgg gcagatcctg    5340
ggcgtcgttg gcgtcccctt cgcaggtgct ctcacctcct tctaccagtc cttcctgaac    5400
accatctggc cctccgacgc cgaccctgg aaggccttca tggcccaagt cgaagtcctg    5460
atcgacaaga agatcgagga gtacgccaag tccaaggccc tggccgagct gcaaggcctg    5520
caaaacaact tcgaggacta cgtcaacgcg ctgaactcct ggaagaagac gcctctgtcc    5580
ctgcgctcca agcgctccca ggaccgcatc cgcgagctgt tctcccaggc cgagtcccac    5640
ttccgcaact ccatgccgtc cttgccgtc tccaagttcg aggtcctgtt cctgcccacc    5700
tacgcccagg ctgccaacac ccacctcctg ttgctgaagg acgcccaggt cttcggcgag    5760
gaatggggct actcctcgga ggacgtcgcc gagttctacc gtcgccagct gaagctgacc    5820
caacagtaca ccgaccactg cgtcaactgg tacaacgtcg gcctgaacgg cctgaggggc    5880
tccacctacg acgcatgggt caagttcaac cgcttccgca gggagatgac cctgaccgtc    5940
ctggacctga tcgtcctgtt ccccttctac gacatccgcc tgtactccaa gggcgtcaag    6000
accgagctga cccgcgacat cttcacggac cccatcttcc tgctcacgac cctccagaag    6060
tacggtccca ccttcctgtc catcgagaac tccatccgca gcccacct gttcgactac    6120 ctccagggca tcgagttcca cacgcgcctg aggccaggct acttcggcaa ggactccttc    6180
aactactggt ccggcaacta cgtcgagacc aggccctcca tcggctcctc gaagacgatc    6240 acctccccctt tctacggcga caagtccacc gagcccgtcc agaagctgtc cttcgacggc    6300
cagaaggtct accgcaccat cgccaacacc gacgtcgcgg cttggccgaa cggcaaggtc    6360
tacctgggcg tcacgaaggt cgacttctcc cagtacgatg accagaagaa cgagacctcc    6420
acccagacct acgactccaa gcgcaacaat ggccacgtct ccgcccagga ctccatcgac    6480
cagctgccgc ctgagaccac tgacgagccc ctggagaagg cctactccca ccagctgaac    6540
tacgcggagt gcttcctgat gcaagaccgc aggggcacca tccccttctt cacctggacc    6600
caccgctccg tcgacttctt caacaccatc gacgccgaga agatcaccca gctgccgtg    6660 gtcaaggcct acgccctgtc ctcgggtgcc tccatcattg agggtccagg cttcaccggt    6720
ggcaacctgc tgttcctgaa ggagtcctcg aactccatcg ccaagttcaa ggtcacccctg    6780 aactccgctg ccttgctgca acgctaccgc gtccgcatcc gctacgcctc caccacgaac    6840
ctgcgcctgt tcgtccagaa ctccaacaat gacttcctgg tcatctacat caacaagacc    6900
atgaacaagg acgatgacct gacctaccag accttcgacc tcgccaccac gaactccaac    6960
atgggcttct cgggcgacaa gaatgaactg atcattggtg ctgagtcctt cgtctccaac    7020
gagaagatct acatcgacaa gatcgagttc atccccgtcc agctgtgata ggaactctga    7080
ttgaattctg catgcgtttg gacgtatgct cattcaggtt ggagccaatt tggttgatgt    7140
```

```
gtgtgcgagt tcttgcgagt ctgatgagac atctctgtat tgtgtttctt tccccagtgt    7200
tttctgtact tgtgtaatcg gctaatcgcc aacagattcg gcgatgaata aatgagaaat    7260
aaattgttct gattttgagt gcaaaaaaaa aggaattaga tctgtgtgtg ttttttggat    7320
cccattttcg acaagcttgc ctcgagacaa caacatgctt ctcatcaaca tggagggaag    7380
agggagggag aaagtgtcgc ctggtcacct ccattgtcac actagccact ggccagctct    7440
cccacaccac caatgccagg ggcgagcttt agcacagcca ccgcttcacc tccaccaccg    7500
cactacccta gcttcgccca acagccaccg tcaacgcctc ctctccgtca acataagaga    7560
gagagagaag aggagagtag ccatgtgggg aggaggaata gtacatgggg cctaccgttt    7620
ggcaagttat tttgggttgc caagttaggc caataagggg agggatttgg ccatccggtt    7680
ggaaaggtta ttggggtagt atcttttac tagaattgtc aaaaaaaaat agtttgagag    7740
ccatttggag aggatgttgc ctgttagagg tgctcttagg acatcaaatt ccataaaaac    7800
atcagaaaaa ttctctcgat gaagatttat aaccactaaa actgccctca attcgaaggg    7860
agttcaaaac aattaaaatc atgttcgaat tgagtttcaa tttcacttta acccctttga    7920
aatctcaatg gtaaaacatc aacccgtcag gtagcatggt tcttttattt cctttcaaaa    7980
agagttaatt acaaacagaa tcaaaactaa cagttaggcc caaggcccat ccgagcaaac    8040
aatagatcat gggccaggcc tgccaccacc ctcccctcc tggctcccgc tcttgaattt    8100
caaaatccaa aaatatcggc acgactggcc gccgacggag cgggcggaaa atgacggaac    8160 aaccctcga attctacccc aactacgccc accaacccac acgccactga caatccggtc    8220
ccacccttgt gggcccacct acaagcgaga cgtcagtcgc tcgcagcaac cagtgggccc    8280
acctcccagt gagcggcggg tagatctgga ctcttaccca cccacactaa acaaaacggc    8340
atgaatattt tgcactaaaa ccctcagaaa aattccgata ttccaaacca gtacagttcc    8400
tgaccgttgg aggagccaaa gtggagcgga gtgtaaaatt gggaaactta atcgaggggg    8460
ttaaacgcaa aaacgccgag gcgcctcccg ctctatagaa aggggaggag tgggaggtgg    8520 aaacccctacc acaccgcaga gaaaggcgtc ttcgtactcg cctctctccg cgccctcctc    8580
cgccgccgct cgccgccgtt cgtctccgcc gccaccggct agccatccag gtaaaacaaa    8640
caaaaacgga tctgatgctt ccattcctcc gtttctcgta gtagcgcgct tcgatctgtg    8700
ggtggatctg ggtgatcctg gggtgtggtt cgttctgttt gatagatctg tcggtggatc    8760
tggccttctg tggttgtcga tgtccggatc tgcgttttga tcagtggtag ttcgtggatc    8820
tggcgaaatg ttttggatct ggcagtgaga cgctaagaat cgggaaatga tgcaatatta    8880
gggggttttc ggatggggat ccactgaatt agtctgtctc cctgctgata atctgttcct    8940
ttttggtaga tctggttagt gtatgtttgt ttcggataga tctgatcaat gcttgtttgt    9000
tttttcaaat tttctaccta ggttgtatag gaatggcatg cggatctggt tggattgcca    9060
tgatccgtgc tgaaatgccc ctttggttga tggatcttga tattttactg ctgttcacct    9120
agatttgtac tcccgtttat acttaatttg ttgcttatta tgaatagatc tgtaacttag    9180
gcacatgtat ggacggagta tgtggatctg tagtatgtac attgctgcga gctaagaact    9240
atttcagagc aagcacagaa aaaaatattt agacagattg gcaactatt tgatggtctt    9300 tggtatcatg ctttgtagtg ctcgtttctg cgtagtaatc ttttgatctg atctgaagat    9360
aggtgctatt atattcttaa aggtcattag aacgctatct gaaaggctgt attatgtgga    9420
ttggttcacc tgtgactccc tgttcgtctt gtcttgataa atcctgtgat aaaaaaaatt    9480
```

```
cttaaggcgt aatttgttga aatcttgttt tgtcctatgc agcctgatcc atggcgcaag      9540
ttagcagaat ctgcaatggt gtgcagaacc catctcttat ctccaatctc tcgaaatcca      9600
gtcaacgcaa atctcccttta tcggtttctc tgaagacgca gcagcatcca cgagcttatc    9660
cgatttcgtc gtcgtgggga ttgaagaaga gtgggatgac gttaattggc tctgagcttc      9720
gtcctcttaa ggtcatgtct tctgtttcca cggcgtgcat gcttcacggt gcaagcagcc     9780
ggcccgcaac cgcccgcaaa tcctctggcc tttccggaac cgtccgcatt cccggcgaca      9840
agtcgatctc ccaccggtcc ttcatgttcg gcggtctcgc gagcggtgaa acgcgcatca     9900
ccggccttct ggaaggcgag gacgtcatca atacgggcaa ggccatgcag gcgatgggcg     9960
cccgcatccg taaggaaggc gacacctgga tcatcgatgg cgtcggcaat ggcggcctcc     10020
tggcgcctga ggcgccgctc gatttcggca atgccgccac gggctgccgc ctgacgatgg     10080
gcctcgtcgg ggtctacgat ttcgacagca ccttcatcgg cgacgcctcg ctcacaaagc     10140
gcccgatggg ccgcgtgttg aacccgctgc gcgaaatggg cgtgcaggtg aaatcggaag     10200
acggtgaccg tcttcccgtt accttgcgcg ggccgaagac gccgacgccg atcacctacc     10260
gcgtgccgat ggcctccgca caggtgaagt ccgccgtgct gctcgccggc ctcaacacgc     10320
ccggcatcac gacggtcatc gagccgatca tgacgcgcga tcatacggaa aagatgctgc     10380
agggctttgg cgccaacctt accgtcgaga cggatgcgga cggcgtgcgc accatccgcc     10440
tggaaggccg cggcaagctc accggccaag tcatcgacgt gccgggcgac ccgtcctcga     10500
cggccttccc gctggttgcg gccctgcttg ttccgggctc cgacgtcacc atcctcaacg     10560
tgctgatgaa ccccacccgc accggcctca tcctgacgct gcaggaaatg ggcgccgaca     10620
tcgaagtcat caacccgcgc cttgccggcg gcgaagacgt ggcggacctg cgcgttcgct     10680
cctccacgct gaagggcgtc acggtgccgg aagaccgcgc gccttcgatg atcgacgaat     10740
atccgattct cgctgtcgcc gccgccttcg cggaaggggc gaccgtgatg aacggtctgg     10800
aagaactccg cgtcaaggaa agcgaccgcc tctcggccgt cgccaatggc ctcaagctca     10860
atggcgtgga ttgcgatgag ggcgagacgt cgctcgtcgt gcgtggccgc cctgacggca     10920
aggggctcgg caacgcctcg ggcgccgccg tcgccaccca tctcgatcac cgcatcgcca     10980
tgagcttcct cgtcatgggc ctcgtgtcgg aaaaccctgt cacggtggac gatgccacga     11040
tgatcgccac gagcttcccg gagttcatgg acctgatggc cgggctgggc gcgaagatcg     11100
aactctccga tacgaaggct gcctgatgag ctccagggtt cttgcctggt gccttggcaa     11160
tgcttgatta ctgctgctat cctatgatct gtccgtgtgg gcttctatct atcagttttgt    11220 gtgtctggtt ttgaaaaaca tttgcttttc gattatgtag ggtttgcttg tagctttcgc     11280
tgctgtgacc tgtgttgttt atgtgaacct tcttttgtgc atctttaata tccaagttcg     11340
tggtttgtcg taaaacgaag cctctacttc gtaaagttgt gtctatagca ttgaaatcgt     11400
ttttttgctc gagaataatt gtgacccttta gttggcgtga aactagtttt ggatatctga     11460
ttctctggtt cgcaatcttg agatcgtcgc tgcttaggtg agctaagtga tgttcctaag     11520
taaatgctcc tcaccagaat acgtagctgt gtgaaaagag aacgcgtgaa tacgtagctg     11580
tgtaaagatt gtgtcccaag taaacctcag tgattttttgt ttggatttt aatttagaaa     11640 cattcgactg ggagcggcta gagccacacc caagttccta actatgataa agttgctctg     11700
taacagaaaa caccatctag agcggccgcg tttaaactat cagtgtttag agaatcacaa     11760
acctctagat gtattaatct accctagaac tagttcactt ttgtgtgcat acttttctat     11820
tgaactggtg ttcactttgt tgcatatgtt ttgtgtactg tttatttgtc attgcccaaa     11880
```

```
tgtgtttaat gagtgattgc tttgcgtaga caacgagcag ttcaaggttt ccgagtgtgt    11940
tgcaaaagac ttccctgagc agcaacctgg tgaaggtaag tgtcctctga cccattatgt    12000
catatttact ttataattat atccttaaca atatgattaa agattaacac caaattatat    12060
acatacatat gttaaaattt taaatgtcaa ataattcaga tgtttagaat gcatccctaa    12120
gacggccagt gcaggctcgt acgatgcata cgaaaaccta tccctagtgt tcgcttcgaa    12180
ttaatgccga cagtttaaac tactgcatct gcaatctata gagacaaaaa cactatgaaa    12240
atagtaga                                                            12248
```

```
<210> SEQ ID NO 2
<211> LENGTH: 763
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(500)
<223> OTHER INFORMATION: represents the genomic DNA flanking the left
      border of the TDNA
<220> FEATURE:
<221> NAME/KEY: misc_feature
<222> LOCATION: (501)..(763)
<223> OTHER INFORMATION: left border remnant

<400> SEQUENCE: 2
```

```
ccctagcgtt gggcccaact agtcagtctg ccttccctcc cagtcgctga cctccttggt     60
ccacttgtca gctttcgcgc tcagatctaa tctcaactgt cgatctgtga tcgggtggcc    120
gagatcaccc gatgcccgtt cgtttgcaaa agttgttaaa agaccctctg tttcttagaa    180
aataacctac attcatgttt cttgcgatta ggccctggt ttcttgtaga gaagccccctt    240 gctttatttt aatcacaaaa ataaatctaa tttagtgttt tgaattctaa aacttgtgaa    300
tttcatatct tttgcatatg aactctaaat tgggtggttt aaattgcaaa atgatcataa    360
tattattctc tatctgttta aattataata tttcactgtc tacatgtatg tattttatga    420
ctagacaata ggttcattta aagtgatgga ttatttatta aaaggaaaat aaaaaggcaa    480
aacactaatg aatagttaag tggcttcatg tccgggaaat ctacatggat cagcaatgag    540
tatgatggtc aatatggaga aaagaaaga gtaattacca attttttttc aattcaaaaa    600
tgtagatgtc cgcagcgtta ttataaaatg aaagtacatt ttgataaaac gacaaattac    660
gatccgtcgt atttataggc gaaagcaata aacaaattat tctaattcgg aaatctttat    720
ttcgacgtgt ctacattcac gtccaaatgg gggcttagat gag                     763
```

```
<210> SEQ ID NO 3
<211> LENGTH: 515
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(15)
<223> OTHER INFORMATION: right border remnant
<220> FEATURE:
<221> NAME/KEY: misc_feature
<222> LOCATION: (16)..(515)
<223> OTHER INFORMATION: represents the genomic DNA flanking the right
      border of the TDNA

<400> SEQUENCE: 3
```

```
aaactatcag tgtttagaga atcacaaacc tctagatgta ttaatctacc ctagaactag      60
ttcacttttg tgtgcatact tttctattga actggtgttc actttgttgc atatgttttg     120
tgtactgttt atttgtcatt gcccaaatgt gtttaatgag tgattgcttt gcgtagacaa     180
cgagcagttc aaggtttccg agtgtgttgc aaaagacttc cctgagcagc aacctggtga     240
aggtaagtgt cctctgaccc attatgtcat atttacttta taattatatc cttaacaata     300
tgattaaaga ttaacaccaa attatataca tacatatgtt aaaattttaa atgtcaaata     360
attcagatgt ttagaatgca tccctaagac ggccagtgca ggctcgtacg atgcatacga     420
aaacctatcc ctagtgttcg cttcgaatta atgccgacag tttaaactac tgcatctgca     480
atctatagag acaaaaacac tatgaaaata gtaga                                515

<210> SEQ ID NO 4
<211> LENGTH: 11248
<212> TYPE: DNA
<213> ORGANISM: Artificial Sequence
<220> FEATURE:
<223> OTHER INFORMATION: is a nucleotide sequence of Event MON 87411,
      and represents the TDNA of event MON 87411
<220> FEATURE:
<221> NAME/KEY: misc_feature
<222> LOCATION: (1)..(263)
<223> OTHER INFORMATION: left border remnant
<220> FEATURE:
<221> NAME/KEY: promoter
<222> LOCATION: (2086)..(4034)
<223> OTHER INFORMATION: Corn PIIG promoter
<220> FEATURE:
<221> NAME/KEY: promoter
<222> LOCATION: (2448)..(3059)
<223> OTHER INFORMATION: represents the reverse complement sequence of
      an enhanced CaMV 35S promoter
<220> FEATURE:
<221> NAME/KEY: promoter
<222> LOCATION: (2448)..(4034)
<223> OTHER INFORMATION: represents a divergent promoter region that
      promotes bidirectional transcription
<220> FEATURE:
<221> NAME/KEY: misc_feature
<222> LOCATION: (11233)..(11248)
<223> OTHER INFORMATION: right border remnant

<400> SEQUENCE: 4
tggcttcatg tccgggaaat ctacatggat cagcaatgag tatgatggtc aatatggaga      60 aaagaaaga gtaattacca attttttttc aattcaaaaa tgtagatgtc cgcagcgtta     120
ttataaaatg aaagtacatt ttgataaaac gacaaattac gatccgtcgt atttataggc     180
gaaagcaata aacaaattat tctaattcgg aaatctttat ttcgacgtgt ctacattcac     240
gtccaaatgg gggcttagat gagaaacttc acgatcgatg cggccaccac tcgaggtcga     300
ggtaccgttg tcaatcaatt ggcaagtcat aaaatgcatt aaaaaatatt ttcatactca     360
actacaaatc catgagtata actataatta taaagcaatg attagaatct gacaaggatt     420
ctggaaaatt acataaagga aagttcataa atgtctaaaa cacaagagga catacttgta     480
ttcagtaaca tttgcagctt ttctaggtct gaaaatatat ttgttgccta gtgaataagc     540
ataatggtac aactacaagt gttttactcc tcatattaac ttcggtcatt agaggccacg     600
atttgacaca ttttactca aaacaaaatg tttgcatatc tcttataatt tcaaattcaa     660
cacacaacaa ataagagaaa aaacaaataa tattaatttg agaatgaaca aaaggaccat     720
atcattcatt aactcttctc catccatttc catttcacag ttcgatagcg aaaaccgaat     780
aaaaaacaca gtaaattaca agcacaacaa atggtacaag aaaaacagtt ttcccaatgc     840
```

```
cataatactc aaactcagta ggattctggt gtgtgcgcaa tgaaactgat gcattgaact    900
tgacgaacgt tgtcgaaacc gatgatacga acgaaagcta ggcctcagcg agtaccgctg    960
gcgatctaat ccatgatatc gtgaacatca tctacattca aattcttatg agctttctta   1020
agggcatctg cagcatttt catagaatct aatacagcag tatttgtgct agctccttcg   1080
agggcttccc tctgcatttc aatagttgta agggttccat ctatttgtag ttgggtcttt   1140
tccaatcgtt tcttctttt gagggcttgg agtgcaactc ttttatttt cgacgcattt   1200 ttctttgcgc tcctgcaggc ggccgcgtgg atgaggagtt aatcggtcgt gtgagagtag   1260
tgatcgagtg gatgtcgtcg agagtgatga gtgttgatgt tgttagtgat atgtggtaga   1320
aggtatcgtg ataaagcgtt aacgcgatcg cagtacttgc aaagaaaaat gcgtcgaaaa   1380
ataaaagagt tgcactccaa gccctcaaaa agaagaaacg attggaaaag acccaactac   1440
aaatagatgg aacccttaca actattgaaa tgcagaggga agccctcgaa ggagctagca   1500
caaatactgc tgtattagat tctatgaaaa atgctgcaga tgcccttaag aaagctcata   1560
agaatttgaa tgtagatgat gttcacgata tcatggatgg tatcgcacag cgactgctga   1620
gggacgtcga gctcccgctt ggtatctgca ttacaatgaa atgagcaaag actatgtgag   1680
taacactggt caacactagg gagaaggcat cgagcaagat acgtatgtaa agagaagcaa   1740
tatagtgtca gttggtagat actagatacc atcaggaggt aaggagagca acaaaaagga   1800
aactctttat ttttaaattt tgttacaaca acaagcaga tcaatgcatc aaaatactgt   1860
cagtacttat ttcttcagac aacaatattt aaaacaagtg catctgatct tgacttatgg   1920
tcacaataaa ggagcagaga taaacatcaa aatttcgtca tttatattta ttccttcagg   1980
cgttaacaat ttaacagcac acaaacaaaa acagaatagg aatatctaat tttggcaaat   2040
aataagctct gcagacgaac aaattattat agtatcgcct ataatgaa tccctatact   2100 attgacccat gtagtatgaa gcctgtgcct aaattaacag caaacttctg aatccaagtg   2160
ccctataaca ccaacatgtg cttaaataaa taccgctaag caccaaatta cacatttctc   2220
gtattgctgt gtaggttcta tcttcgtttc gtactaccat gtccctatat tttgctgcta   2280
caaaggacgg caagtaatca gcacaggcag aacacgattt cagagtgtaa ttctagatcc   2340
agctaaacca ctctcagcaa tcaccacaca agagagcatt cagagaaacg tggcagtaac   2400
aaaggcagag ggcggagtga gcgcgtaccg aagacggttc agcgtgtcct ctccaaatga   2460
aatgaacttc cttatataga ggaagggtct tgcgaaggat agtgggattg tgcgtcatcc   2520
cttacgtcag tggagatatc acatcaatcc acttgctttg aagacgtggt tggaacgtct   2580 tcttttcca cgatgctcct cgtgggtggg ggtccatctt tgggaccact gtcggcagag   2640
gcatcttcaa cgatggcctt ccttttatcg caatgatggc atttgtagga gccaccttcc   2700
ttttccacta tcttcacaat aaagtgacag atagctgggc aatggaatcc gaggaggttt   2760
ccggatatta ccctttgttg aaaagtctca atcggaccat cacatcaatc cacttgcttt   2820
gaagacgtgg ttgaacgtc ttcttttcc acgatgctcc tcgtgggtgg gggtccatct   2880
ttgggaccac tgtcggcaga ggcatcttca cgatggcct ttccttatc gcaatgatgg   2940 catttgtagg agccaccttc cttttccact atcttcacaa taaagtgaca gatagctggg   3000
caatggaatc cgaggaggtt tccggatatt acccttgtt gaaaagtctc aatcggacct   3060
gcagcctgca ggctagcggc gcgccacaaa tcacaggcca tgaaccctac tcatgcttcg   3120
atttgtccaa cacacactta ccaaaactca aatcatgtcc ttgacagtca ctcgggactc   3180
ataacatggg tacgtatcga ctatgtcaac tatatgtgtt ctcatcagat tatagattgg   3240
```

```
cctagtacgt agtgatattt ccactagcac tgtggttatg gctgtacctg atagtgatat    3300
cagcaccggg tcatggctct actaccaggt agtgagagtg acctttatac tgtcagactg    3360
taactaagga tttccaatca ctgttcggat cctaggctta gaattaagta aaactctatc    3420
actataggct gcagcacact cggtatatat tgatgggcca acagaaattg tgcgtactat    3480
gcgcgatgta aaatggacat aaaccctacc catatacaat gcataacctt ttgtccggtc    3540
tgggccaccg gttagcagag gtcctgattt cggtggtagt ggtagcttga tctggtcgtc    3600
gtatcgtaga gggatatata aaatcatgtc acttttgaag ggagcgctca cagaaataat    3660
aggtattcgc gggagccgcc cccgcagaac acaaaataag gcgagcacgc acacgcatca    3720
gtttcgataa aataataata gcgccagctg atcggaacaa ttccagctag cactaatgta    3780
tttctgcatt gatctgttta tacaacatgc tacctcgttg agtgattttg acatgatttg    3840
tcaacttgct ccgatcctat atctcgatcg atctccacat gacgatggtt gttgtcctgt    3900
atcccatgac aaccaggcaa cgctcaaagc acacatgcgt tgccgattac ccgtgcatgc    3960
cgccaagcac gaaagcacct ccctccacac cgtccatcag ctataaaaac catgccaagc    4020
accctgtgaa aagccccggg aaccatcttc cacacactca agccacacta ttggagaaca    4080
cacagggaca acacaccata agatccaagg gaggcctccg ccgccgccgg taaccacccc    4140
gccctctcc tctttctttc tccgtttttt tttccgtctc ggtctcgatc tttgcccttg    4200
gtagtttggg tgggcgagag gcggcttcgt gcgcgcccag atcggtgcgc gggaggggcg    4260
ggatctcgcg gctggggctc tcgccggcgt ggatccggcc cggatctcgc ggggaatggg    4320
gctctcggat gtagatctgc gatccgccgt tgttgggga gatgatgggg ggtttaaaat    4380
ttccgccgtg ctaaacaaga tcaggaagag gggaaaaggg cactatggtt tatattttta    4440
tatatttctg ctgcttcgtc aggcttagat gtgctagatc tttctttctt cttttgtgg    4500
gtagaattg aatccctcag cattgttcat cggtagtttt tcttttcatg atttgtgaca    4560
aatgcagcct cgtgcggagc tttttttgtag gtagaagtga tcaaccatgg ccaacccaa    4620
caatcgctcc gagcacgaca cgatcaaggt cacccccaac tccgagctcc agaccaacca    4680
caaccagtac ccgctggccg acaaccccaa ctccacccgg gaagagctga actacaagga    4740
gttcctgcgc atgaccgagg actcctccac ggaggtcctg gacaactcca ccgtcaagga    4800
cgccgtcggg accggcatct ccgtcgttgg gcagatcctg ggcgtcgttg gcgtcccctt    4860
cgcaggtgct ctcacctcct tctaccagtc cttcctgaac accatctggc cctccgacgc    4920
cgaccctgg aaggccttca tggcccaagt cgaagtcctg atcgacaaga agatcgagga    4980
gtacgccaag tccaaggccc tggccgagct gcaaggcctg caaaacaact tcgaggacta    5040
cgtcaacgcg ctgaactcct ggaagaagac gcctctgtcc ctgcgctcca agcgctccca    5100
ggaccgcatc cgcgagctgt tctcccaggc cgagtcccac ttccgcaact ccatgccgtc    5160
cttcgccgtc tccaagttcg aggtcctgtt cctgcccacc tacgcccagg ctgccaacac    5220
ccacctcctg ttgctgaagg acgcccaggt cttcggcgag gaatgggct actcctcgga    5280
ggacgtcgcc gagttctacc gtcgccagct gaagctgacc caacagtaca ccgaccactg    5340
cgtcaactgg tacaacgtcg gcctgaacgg cctgagggc tccacctacg acgcatgggt    5400
caagttcaac cgcttccgca gggagatgac cctgaccgtc ctggacctga tcgtcctgtt    5460
ccccttctac gacatccgcc tgtactccaa gggcgtcaag accgagctga cccgcgacat    5520
cttcacggac cccatcttcc tgctcacgac cctccagaag tacggtccca ccttcctgtc    5580
```

```
catcgagaac tccatccgca agccccacct gttcgactac ctccagggca tcgagttcca   5640
cacgcgcctg aggccaggct acttcggcaa ggactccttc aactactggt ccggcaacta   5700
cgtcgagacc aggccctcca tcggctcctc gaagacgatc acctcccctt tctacggcga   5760
caagtccacc gagcccgtcc agaagctgtc cttcgacggc cagaaggtct accgcaccat   5820
cgccaacacc gacgtcgcgg cttggccgaa cggcaaggtc tacctgggcg tcacgaaggt   5880
cgacttctcc cagtacgatg accagaagaa cgagacctcc acccagacct acgactccaa   5940
gcgcaacaat ggccacgtct ccgcccagga ctccatcgac cagctgccgc tgagaccac    6000
tgacgagccc ctggagaagg cctactccca ccagctgaac tacgcggagt gcttcctgat   6060
gcaagaccgc aggggcacca tccccttctt cacctggacc caccgctccg tcgacttctt   6120
caacaccatc gacgccgaga agatcaccca gctgccccgtg gtcaaggcct acgcctgtc    6180
ctcgggtgcc tccatcattg agggtccagg cttcaccggt ggcaacctgc tgttcctgaa   6240
ggagtcctcg aactccatcg ccaagttcaa ggtcaccctg aactccgctg ccttgctgca   6300
acgctaccgc gtccgcatcc gctacgcctc caccacgaac ctgcgcctgt tcgtccagaa   6360
ctccaacaat gacttcctgg tcatctacat caacaagacc atgaacaagg acgatgacct   6420
gacctaccag accttcgacc tcgccaccac gaactccaac atgggcttct cgggcgacaa   6480
gaatgaactg atcattggtg ctgagtcctt cgtctccaac gagaagatct acatcgacaa   6540
gatcgagttc atccccgtcc agctgtgata ggaactctga ttgaattctg catgcgtttg   6600
gacgtatgct cattcaggtt ggagccaatt tggttgatgt gtgtgcgagt tcttgcgagt   6660
ctgatgagac atctctgtat tgtgtttctt tccccagtgt tttctgtact tgtgtaatcg   6720
gctaatcgcc aacagattcg gcgatgaata aatgagaaat aaattgttct gattttgagt   6780
gcaaaaaaaa aggaattaga tctgtgtgtg ttttttggat cccatttcg acaagcttgc    6840
ctcgagacaa caacatgctt ctcatcaaca tggagggaag agggagggag aaagtgtcgc   6900
ctggtcacct ccattgtcac actagccact ggccagctct cccacaccac caatgccagg   6960
ggcgagcttt agcacagcca ccgcttcacc tccaccaccg cactacccta gcttcgccca   7020
acagccaccg tcaacgcctc ctctccgtca acataagaga gagagagaag aggagagtag   7080
ccatgtgggg aggaggaata gtacatgggg cctaccgttt ggcaagttat tttgggttgc   7140
caagttaggc caataagggg agggatttgg ccatccggtt ggaaaggtta ttggggtagt   7200
atcttttac tagaattgtc aaaaaaaaat agtttgagag ccatttggag aggatgttgc    7260
ctgttagagg tgctcttagg acatcaaatt ccataaaaac atcagaaaaa ttctctcgat   7320
gaagatttat aaccactaaa actgccctca attcgaaggg agttcaaaac aattaaaatc   7380
atgttcgaat tgagtttcaa tttcacttta acccctttga atctcaatg gtaaaacatc    7440
aacccgtcag gtagcatggt tctttttatt cctttcaaaa agagttaatt acaaacagaa   7500
tcaaaactaa cagttaggcc caaggcccat ccgagcaaac aatagatcat gggccaggcc   7560
tgccaccacc ctcccctcc tggctcccgc tcttgaattt caaaatccaa aaatatcggc    7620
acgactggcc gccgacggag cgggcggaaa atgacggaac aaccctcga attctacccc    7680
aactacgccc accaacccac acgccactga caatccggtc ccaccttgt gggcccacct    7740
acaagcgaga cgtcagtcgc tcgcagcaac cagtgggccc acctcccagt gagcggcggg   7800
tagatctgga ctcttaccca cccacactaa acaaaacggc atgaatattt tgcactaaaa   7860
ccctcagaaa aattccgata ttccaaacca gtacagttcc tgaccgttgg aggagccaaa   7920
gtggagcgga gtgtaaaatt gggaaactta atcgaggggg ttaaacgcaa aaacgccgag   7980
```

```
gcgcctcccg ctctatagaa aggggaggag tgggaggtgg aaaccctacc acaccgcaga    8040
gaaaggcgtc ttcgtactcg cctctctccg cgccctcctc cgccgccgct cgccgccgtt    8100
cgtctccgcc gccaccggct agccatccag gtaaaacaaa caaaaacgga tctgatgctt    8160
ccattcctcc gtttctcgta gtagcgcgct tcgatctgtg ggtggatctg ggtgatcctg    8220
gggtgtggtt cgttctgttt gatagatctg tcggtggatc tggccttctg tggttgtcga    8280
tgtccggatc tgcgttttga tcagtggtag ttcgtggatc tggcgaaatg ttttggatct    8340
ggcagtgaga cgctaagaat cgggaaatga tgcaatatta gggggttttc ggatggggat    8400
ccactgaatt agtctgtctc cctgctgata atctgttcct ttttggtaga tctggttagt    8460
gtatgtttgt ttcggataga tctgatcaat gcttgtttgt tttttcaaat tttctaccta    8520
ggttgtatag gaatggcatg cggatctggt tggattgcca tgatccgtgc tgaaatgccc    8580
ctttggttga tggatcttga tattttactg ctgttcacct agatttgtac tcccgtttat    8640
acttaatttg ttgcttatta tgaatagatc tgtaacttag gcacatgtat ggacggagta    8700
tgtggatctg tagtatgtac attgctgcga gctaagaact atttcagagc aagcacagaa    8760
aaaaatattt agacagattg ggcaactatt tgatggtctt tggtatcatg ctttgtagtg    8820
ctcgtttctg cgtagtaatc ttttgatctg atctgaagat aggtgctatt atattcttaa    8880
aggtcattag aacgctatct gaaaggctgt attatgtgga ttggttcacc tgtgactccc    8940
tgttcgtctt gtcttgataa atcctgtgat aaaaaaaatt cttaaggcgt aatttgttga    9000
aatcttgttt tgtcctatgc agcctgatcc atggcgcaag ttagcagaat ctgcaatggt    9060
gtgcagaacc catctcttat ctccaatctc tcgaaatcca gtcaacgcaa atctcctta    9120 tcggtttctc tgaagacgca gcagcatcca cgagcttatc cgatttcgtc gtcgtgggga    9180
ttgaagaaga gtgggatgac gttaattggc tctgagcttc gtcctcttaa ggtcatgtct    9240
tctgttccca cggcgtgcat gcttcacggt gcaagcagcc ggcccgcaac cgcccgcaaa    9300
tcctctggcc tttccggaac cgtccgcatt cccggcgaca agtcgatctc ccaccggtcc    9360
ttcatgttcg gcggtctcgc gagcggtgaa acgcgcatca ccggccttct ggaaggcgag    9420
gacgtcatca atacgggcaa ggccatgcag gcgatgggcg cccgcatccg taaggaaggc    9480
gacacctgga tcatcgatgg cgtcggcaat ggcggcctcc tggcgcctga ggcgccgctc    9540
gatttcggca atgccgccac gggctgccgc ctgacgatgg gcctcgtcgg ggtctacgat    9600
ttcgacagca ccttcatcgg cgacgcctcg ctcacaaagc gcccgatggg ccgcgtgttg    9660
aacccgctgc gcgaaatggg cgtgcaggtg aaatcggaag acggtgaccg tcttcccgtt    9720
accttgcgcg ggccgaagac gccgacgccg atcacctacc gcgtgccgat ggcctccgca    9780
caggtgaagt ccgccgtgct gctcgccggc ctcaacacgc ccggcatcac gacggtcatc    9840
gagccgatca tgacgcgcga tcatacggaa aagatgctgc agggctttgg cgccaacctt    9900
accgtcgaga cggatgcgga cggcgtgcgc accatccgcc tggaaggccg cggcaagctc    9960
accggccaag tcatcgacgt gccgggcgac ccgtcctcga cggccttccc gctggttgcg   10020
gccctgcttg ttccgggctc cgacgtcacc atcctcaacg tgctgatgaa ccccacccgc   10080
accggcctca tcctgacgct gcaggaaatg gcgccgaca tcgaagtcat caacccgcgc   10140
cttgccggcg gcgaagacgt ggcggacctg cgcgttcgct cctccacgct gaagggcgtc   10200
acggtgccgg aagaccgcgc gccttcgatg atcgacgaat atccgattct cgctgtcgcc   10260
gccgccttcg cggaagggc gaccgtgatg aacggtctgg aagaactccg cgtcaaggaa   10320
```

```
agcgaccgcc tctcggccgt cgccaatggc ctcaagctca atggcgtgga ttgcgatgag    10380
ggcgagacgt cgctcgtcgt gcgtggccgc cctgacggca aggggctcgg caacgcctcg    10440
ggcgccgccg tcgccaccca tctcgatcac cgcatcgcca tgagcttcct cgtcatgggc    10500
ctcgtgtcgg aaaaccctgt cacggtggac gatgccacga tgatcgccac gagcttcccg    10560
gagttcatgg acctgatggc cgggctgggc gcgaagatcg aactctccga tacgaaggct    10620
gcctgatgag ctccagggtt cttgcctggt gccttggcaa tgcttgatta ctgctgctat    10680
cctatgatct gtccgtgtgg gcttctatct atcagtttgt gtgtctggtt ttgaaaaaca    10740
tttgcttttc gattatgtag ggtttgcttg tagctttcgc tgctgtgacc tgtgttgttt    10800
atgtgaacct tctttgtggc atctttaata tccaagttcg tggtttgtcg taaaacgaag    10860
cctctacttc gtaaagttgt gtctatagca ttgaaatcgt tttttttgctc gagaataatt    10920 gtgaccttta gttggcgtga aactagtttt ggatatctga ttctctggtt cgcaatcttg    10980
agatcgtcgc tgcttaggtg agctaagtga tgttcctaag taaatgctcc tcaccagaat    11040
acgtagctgt gtgaaaagag aacgcgtgaa tacgtagctg tgtaaagatt gtgtcccaag    11100
taaacctcag tgattttttgt ttggattttt aatttagaaa cattcgactg ggagcggcta    11160
gagccacacc caagttccta actatgataa agttgctctg taacagaaaa caccatctag    11220
agcggccgcg tttaaactat cagtgttt                                       11248
```

```
<210> SEQ ID NO 5
<211> LENGTH: 313
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(50)
<223> OTHER INFORMATION: represents the genomic DNA flanking the left
      border of the TDNA
<220> FEATURE:
<221> NAME/KEY: misc_feature
<222> LOCATION: (51)..(313)
<223> OTHER INFORMATION: left border remnant

<400> SEQUENCE: 5
ttatttatta aaggaaaat aaaaaggcaa aacactaatg aatagttaag tggcttcatg      60
tccgggaaat ctacatggat cagcaatgag tatgatggtc aatatggaga aaagaaaga    120 gtaattacca atttttttttc aattcaaaaa tgtagatgtc cgcagcgtta ttataaaatg    180
aaagtacatt ttgataaaac gacaaattac gatccgtcgt atttataggc gaaagcaata    240
aacaaattat tctaattcgg aaatctttat ttcgacgtgt ctacattcac gtccaaatgg    300
gggcttagat gag                                                       313
```

```
<210> SEQ ID NO 6
<211> LENGTH: 373
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(110)
<223> OTHER INFORMATION: represents the genomic DNA flanking the left
      border of the TDNA
<220> FEATURE:
<221> NAME/KEY: misc_feature
<222> LOCATION: (111)..(373)
<223> OTHER INFORMATION: left border remnant
```

<400> SEQUENCE: 6

```
tttcactgtc tacatgtatg tattttatga ctagacaata ggttcattta aagtgatgga    60
ttatttatta aaaggaaaat aaaaaggcaa aacactaatg aatagttaag tggcttcatg   120
tccgggaaat ctacatggat cagcaatgag tatgatggtc aatatggaga aaagaaaga    180 gtaattacca attttttttc aattcaaaaa tgtagatgtc cgcagcgtta ttataaaatg   240
aaagtacatt ttgataaaac gacaaattac gatccgtcgt attatataggc gaaagcaata  300 aacaaattat tctaattcgg aaatctttat ttcgacgtgt ctacattcac gtccaaatgg   360
gggcttagat gag                                                      373
```

<210> SEQ ID NO 7
<211> LENGTH: 408
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (1)..(145)
<223> OTHER INFORMATION: represents the genomic DNA flanking the left
      border of the TDNA
<220> FEATURE:
<221> NAME/KEY: misc_feature
<222> LOCATION: (146)..(408)
<223> OTHER INFORMATION: left border remnant

<400> SEQUENCE: 7

```
cataatatta ttctctatct gtttaaatta taatatttca ctgtctacat gtatgtattt    60
tatgactaga caataggttc atttaaagtg atggattatt tattaaaagg aaaataaaaa   120
ggcaaaacac taatgaatag ttaagtggct tcatgtccgg gaaatctaca tggatcagca   180
atgagtatga tggtcaatat ggagaaaaag aaagagtaat taccaatttt ttttcaattc   240
aaaaatgtag atgtccgcag cgttattata aaatgaaagt acattttgat aaaacgacaa   300
attacgatcc gtcgtattta taggcgaaag caataaacaa attattctaa ttcggaaatc   360
tttatttcga cgtgtctaca ttcacgtcca aatgggggct tagatgag                 408
```

<210> SEQ ID NO 8
<211> LENGTH: 117
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (69)..(83)
<223> OTHER INFORMATION: right border remnant
<220> FEATURE:
<221> NAME/KEY: misc_feature
<222> LOCATION: (84)..(117)
<223> OTHER INFORMATION: represents the genomic DNA flanking the right
      border of the TDNA

<400> SEQUENCE: 8

```
acacccaagt tcctaactat gataaagttg ctctgtaaca gaaaacacca tctagagcgg    60
ccgcgtttaa actatcagtg tttagagaat cacaaacctc tagatgtatt aatctac     117
```

<210> SEQ ID NO 9
<211> LENGTH: 173
<212> TYPE: DNA
<213> ORGANISM: Artificial Sequence
<220> FEATURE:

```
<223> OTHER INFORMATION: is a nucleotide sequence of event MON 87411
<220> FEATURE:
<221> NAME/KEY: misc_feature
<222> LOCATION: (69)..(83)
<223> OTHER INFORMATION: right border remnant
<220> FEATURE:
<221> NAME/KEY: misc_feature
<222> LOCATION: (84)..(173)
<223> OTHER INFORMATION: represents the genomic DNA flanking the right
      border of the TDNA

<400> SEQUENCE: 9
acacccaagt tcctaactat gataaagttg ctctgtaaca gaaaacacca tctagagcgg     60
ccgcgtttaa actatcagtg tttagagaat cacaaacctc tagatgtatt aatctaccct    120
agaactagtt cacttttgtg tgcatacttt tctattgaac tggtgttcac ttt           173


<210> SEQ ID NO 10
<211> LENGTH: 338
<212> TYPE: DNA
<213> ORGANISM: Artificial Sequence
<220> FEATURE:
<223> OTHER INFORMATION: is a nucleotide sequence of event MON 87411
<220> FEATURE:
<221> NAME/KEY: misc_feature
<222> LOCATION: (69)..(83)
<223> OTHER INFORMATION: right border remnant
<220> FEATURE:
<221> NAME/KEY: misc_feature
<222> LOCATION: (84)..(338)
<223> OTHER INFORMATION: represents the genomic DNA flanking the right
      border of the TDNA

<400> SEQUENCE: 10
acacccaagt tcctaactat gataaagttg ctctgtaaca gaaaacacca tctagagcgg     60
ccgcgtttaa actatcagtg tttagagaat cacaaacctc tagatgtatt aatctaccct    120
agaactagtt cacttttgtg tgcatacttt tctattgaac tggtgttcac tttgttgcat    180
atgttttgtg tactgtttat ttgtcattgc ccaaatgtgt ttaatgagtg attgctttgc    240
gtagacaacg agcagttcaa ggtttccgag tgtgttgcaa aagacttccc tgagcagcaa    300
cctggtgaag gtaagtgtcc tctgacccat tatgtcat                            338


<210> SEQ ID NO 11
<211> LENGTH: 663
<212> TYPE: DNA
<213> ORGANISM: Diabrotica virgifera virgifera
<220> FEATURE:
<221> NAME/KEY: misc_feature
<222> LOCATION: (1)..(660)
<223> OTHER INFORMATION: Dv_Snf7o ORF encoding a putative ESCRT-III
      complex subunit from Diabrotica virgifera

<400> SEQUENCE: 11
atgagctttt ttggaaaatt gttcgggggg aaaaaggaag agatagcccc tagtcctggg     60
gaggctattc aaaaactcag agagactgaa gaaatgttaa taaaaaaaca ggattttttta   120
gaaaagaaga tagaagaatt taccatggta gcaaagaaaa atgcgtcgaa aaataaaaga    180
gttgcactcc aagccctcaa aaagaagaaa cgattggaaa agacccaact acaaatagat    240
ggaaccctta caactattga aatgcagagg gaagccctcg aaggagctag cacaaatact    300
gctgtattag attctatgaa aaatgctgca gatgccctta agaaagctca taagaatttg    360
aatgtagatg atgttcacga tatcatggat gacatagccg aacaacacga catagccaac    420
gaaatcacaa acgctattag caatcctgtc ggattcaccg acgatctgga tgacgatgaa    480
```

```
ttagaaaaag aattagaaga gctcgaacaa gaaggattgg aagaagacct gctccaagtg      540
ccaggtccaa ctcaactgcc ggctgtgcct gctgatgcag ttgctactaa accaatcaaa      600
ccagcagcta aaaagttga agatgatgac gatatgaaag aattggaagc ctgggcctcg      660
taa                                                                    663
```

```
<210> SEQ ID NO 12
<211> LENGTH: 2753
<212> TYPE: DNA
<213> ORGANISM: Artificial Sequence
<220> FEATURE:
<223> OTHER INFORMATION: is a nucleotide sequence representing the
      antisense strand of an inverted repeat RNA expression cassette
<220> FEATURE:
<221> NAME/KEY: 3'UTR
<222> LOCATION: (1)..(633)
<223> OTHER INFORMATION: Ps.RbcS2-E9 3' UTR antisense strand
<220> FEATURE:
<221> NAME/KEY: misc_feature
<222> LOCATION: (663)..(902)
<223> OTHER INFORMATION: inverted repeat Dv_Snf7o arm
<220> FEATURE:
<221> NAME/KEY: misc_feature
<222> LOCATION: (903)..(1052)
<223> OTHER INFORMATION: inverted repeat loop
<220> FEATURE:
<221> NAME/KEY: misc_feature
<222> LOCATION: (1053)..(1292)
<223> OTHER INFORMATION: inverted repeat Dv_Snf7o arm
<220> FEATURE:
<221> NAME/KEY: Intron
<222> LOCATION: (1329)..(2132)
<223> OTHER INFORMATION: Corn DnaK intron antisense strand
<220> FEATURE:
<221> NAME/KEY: misc_feature
<222> LOCATION: (2133)..(2141)
<223> OTHER INFORMATION: CaMV 35S leader antisense strand
<220> FEATURE:
<221> NAME/KEY: promoter
<222> LOCATION: (2142)..(2753)
<223> OTHER INFORMATION: represents the reverse complement sequence of
      an enhanced CaMV 35S promoter

<400> SEQUENCE: 12
gttgtcaatc aattggcaag tcataaaatg cattaaaaaa tattttcata ctcaactaca       60
aatccatgag tataactata attataaagc aatgattaga atctgacaag gattctggaa      120
aattacataa aggaaagttc ataaatgtct aaaacacaag aggacatact tgtattcagt      180
aacatttgca gcttttctag gtctgaaaat atatttgttg cctagtgaat aagcataatg      240
gtacaactac aagtgtttta ctcctcatat taacttcggt cattagaggc cacgatttga      300 cacatttttta ctcaaaacaa aatgtttgca tatctcttat aatttcaaat tcaacacaca      360
acaaataaga gaaaaacaa ataatattaa tttgagaatg aacaaaagga ccatatcatt      420
cattaactct tctccatcca tttccatttc acagttcgat agcgaaaacc gaataaaaaa      480
cacagtaaat tacaagcaca acaaatggta caagaaaaac agttttccca atgccataat      540
actcaaactc agtaggattc tggtgtgtgc gcaatgaaac tgatgcattg aacttgacga      600
acgttgtcga aaccgatgat acgaacgaaa gctaggcctc agcgagtacc gctggcgatc      660
taatccatga tatcgtgaac atcatctaca ttcaaattct tatgagcttt cttaagggca      720
tctgcagcat ttttcataga atctaataca gcagtatttg tgctagctcc ttcgagggct      780
tccctctgca tttcaatagt tgtaagggtt ccatctattt gtagttgggt cttttccaat      840
cgtttcttct ttttgagggc ttggagtgca actcttttat ttttcgacgc atttttcttt      900
gcgctcctgc aggcggccgc gtggatgagg agttaatcgg tcgtgtgaga gtagtgatcg      960
```

-continued

```
agtggatgtc gtcgagagtg atgagtgttg atgttgttag tgatatgtgg tagaaggtat   1020
cgtgataaag cgttaacgcg atcgcagtac ttgcaaagaa aaatgcgtcg aaaaataaaa   1080
gagttgcact ccaagccctc aaaaagaaga aacgattgga aaagacccaa ctacaaatag   1140
atggaaccct tacaactatt gaaatgcaga gggaagccct cgaaggagct agcacaaata   1200
ctgctgtatt agattctatg aaaaatgctg cagatgccct taagaaagct cataagaatt   1260
tgaatgtaga tgatgttcac gatatcatgg atggtatcgc acagcgactg ctgagggacg   1320
tcgagctccc gcttggtatc tgcattacaa tgaaatgagc aaagactatg tgagtaacac   1380
tggtcaacac tagggagaag gcatcgagca agatacgtat gtaaagagaa gcaatatagt   1440
gtcagttggt agatactaga taccatcagg aggtaaggag agcaacaaaa aggaaactct   1500 ttattttaa attttgttac aacaaacaag cagatcaatg catcaaaata ctgtcagtac   1560
ttatttcttc agacaacaat atttaaaaca agtgcatctg atcttgactt atggtcacaa   1620
taaaggagca gagataaaca tcaaaatttc gtcatttata tttattcctt caggcgttaa   1680
caatttaaca gcacacaaac aaaaacagaa taggaatatc taattttggc aaataataag   1740
ctctgcagac gaacaaatta ttatagtatc gcctataata tgaatcccta tactattgac   1800
ccatgtagta tgaagcctgt gcctaaatta acagcaaact tctgaatcca agtgccctat   1860
aacaccaaca tgtgcttaaa taaataccgc taagcaccaa attacacatt tctcgtattg   1920
ctgtgtaggt tctatcttcg tttcgtacta ccatgtccct atattttgct gctacaaagg   1980
acggcaagta atcagcacag gcagaacacg atttcagagt gtaattctag atccagctaa   2040
accactctca gcaatcacca cacaagagag cattcagaga aacgtggcag taacaaaggc   2100
agagggcgga gtgagcgcgt accgaagacg gttcagcgtg tcctctccaa atgaaatgaa   2160
cttccttata tagaggaagg gtcttgcgaa ggatagtggg attgtgcgtc atcccttacg   2220
tcagtggaga tatcacatca atccacttgc tttgaagacg tggttggaac gtcttctttt   2280
tccacgatgc tcctcgtggg tgggggtcca tctttgggac cactgtcggc agaggcatct   2340
tcaacgatgg ccttcctttt atcgcaatga tggcatttgt aggagccacc ttccttttcc   2400
actatcttca caataaagtg acagatagct gggcaatgga atccgaggag gtttccggat   2460 attaccctt tgttgaaaagt ctcaatcgga ccatcacatc aatccacttg ctttgaagac   2520
gtggttggaa cgtcttcttt ttccacgatg ctcctcgtgg gtgggggtcc atctttggga   2580
ccactgtcgg cagaggcatc ttcaacgatg ccttccttt atcgcaatg atggcatttg   2640 taggagccac cttcctttc cactatcttc acaataaagt gacagatagc tgggcaatgg   2700
aatccgagga ggtttccgga tattacccctt tgttgaaaag tctcaatcgg acc          2753
```

<210> SEQ ID NO 13
<211> LENGTH: 240
<212> TYPE: RNA
<213> ORGANISM: Artificial Sequence
<220> FEATURE:
<223> OTHER INFORMATION: is a ribonucleotide sequence representing the Dv_Snf7o RNA inverted repeat

<400> SEQUENCE: 13

```
gcaaagaaaa augcgucgaa aaauaaaaga guugcacucc aagcccucaa aagaagaaa     60 cgauuggaaa agacccaacu acaaauagau ggaacccuua caacuauuga aaugcagagg   120
gaagcccucg aaggagcuag cacaaauacu gcuguauuag auucuaugaa aaaugcugca   180
gaugcccuua agaaagcuca uaagaauuug aauguagaug auguucacga uaucauggau   240
```

```
<210> SEQ ID NO 14
<211> LENGTH: 3712
<212> TYPE: DNA
<213> ORGANISM: Artificial Sequence
<220> FEATURE:
<223> OTHER INFORMATION: is a nucleotide sequence representing the sense
      strand of a DNA expression cassette that includes a recombinant
      gene engineered to encode and express a Cry3Bb protein
<220> FEATURE:
<221> NAME/KEY: promoter
<222> LOCATION: (1)..(949)
<223> OTHER INFORMATION: Corn PIIG promoter
<220> FEATURE:
<221> NAME/KEY: misc_feature
<222> LOCATION: (956)..(1016)
<223> OTHER INFORMATION: Wheat Lhcb1 leader sense strand
<220> FEATURE:
<221> NAME/KEY: Intron
<222> LOCATION: (1033)..(1512)
<223> OTHER INFORMATION: Rice Act1 intron sense strand
<220> FEATURE:
<221> NAME/KEY: CDS
<222> LOCATION: (1522)..(3483)
<223> OTHER INFORMATION: cry3B2 ORF sense strand
<220> FEATURE:
<221> NAME/KEY: 3'UTR
<222> LOCATION: (3503)..(3712)
<223> OTHER INFORMATION: Wheat Hsp17 3' UTR sense strand

<400> SEQUENCE: 14
acaaatcaca ggccatgaac cctactcatg cttcgatttg tccaacacac acttaccaaa        60
actcaaatca tgtccttgac agtcactcgg gactcataac atgggtacgt atcgactatg       120
tcaactatat gtgttctcat cagattatag attggcctag tacgtagtga tatttccact       180
agcactgtgg ttatggctgt acctgatagt gatatcagca ccgggtcatg gctctactac       240
caggtagtga gagtgaccct tatactgtca gactgtaact aaggatttcc aatcactgtt       300
cggatcctag gcttagaatt aagtaaaact ctatcactat aggctgcagc acactcggta       360
tatattgatg ggccaacaga aattgtgcgt actatgcgcg atgtaaaatg gacataaacc       420
ctacccatat acaatgcaat aacttttgtc cggtctgggc caccggttag cagaggtcct       480
gatttcggtg gtagtggtag cttgatctgg tcgtcgtatc gtagagggat atataaaatc       540
atgtcacttt tgaagggagc gctcacagaa ataataggta ttcgcgggag ccgccccgc       600 agaacacaaa ataaggcgag cacgcacacg catcagtttc gataaaataa taatagcgcc       660
agctgatcgg aacaattcca gctagcacta atgtatttct gcattgatct gtttatacaa       720
catgctacct cgttgagtga ttttgacatg atttgtcaac ttgctccgat cctatatctc       780
gatcgatctc cacatgacga tggttgttgt cctgtatccc atgacaacca ggcaacgctc       840
aaagcacaca tgcgttgccg attcccgtg catgccgcca agcacgaaag cacctccctc       900
cacaccgtcc atcagctata aaaccatgc caagcaccct gtgaaaagcc ccgggaacca       960
tcttccacac actcaagcca cactattgga gaacacacag gacaacaca ccataagatc       1020 caagggaggc ctccgccgcc gccggtaacc accccgcccc tctcctcttt ctttctccgt       1080 tttttttcc gtctcggtct cgatctttgg ccttggtagt ttgggtgggc gagaggcggc       1140
ttcgtgcgcg cccagatcgg tgcgcgggag gggcgggatc tcgcggctgg ggctctcgcc       1200
ggcgtggatc cggcccggat ctcgcgggga atggggctct cggatgtaga tctgcgatcc       1260
gccgttgttg ggggagatga tgggggggttt aaaatttccg ccgtgctaaa caagatcagg       1320
aagaggggaa aagggcacta tggtttatat ttttatatat ttctgctgct tcgtcaggct       1380
```

```
tagatgtgct agatctttct ttcttctttt tgtgggtaga atttgaatcc ctcagcattg    1440
ttcatcggta gttttctttt tcatgatttg tgacaaatgc agcctcgtgc ggagcttttt    1500
tgtaggtaga agtgatcaac c atg gcc aac ccc aac aat cgc tcc gag cac      1551
                         Met Ala Asn Pro Asn Asn Arg Ser Glu His
                         1               5                   10 gac acg atc aag gtc acc ccc aac tcc gag ctc cag acc aac cac aac      1599
Asp Thr Ile Lys Val Thr Pro Asn Ser Glu Leu Gln Thr Asn His Asn
                15                  20                  25 cag tac ccg ctg gcc gac aac ccc aac tcc acc ctg gaa gag ctg aac      1647
Gln Tyr Pro Leu Ala Asp Asn Pro Asn Ser Thr Leu Glu Glu Leu Asn
            30                  35                  40 tac aag gag ttc ctg cgc atg acc gag gac tcc tcc acg gag gtc ctg      1695
Tyr Lys Glu Phe Leu Arg Met Thr Glu Asp Ser Ser Thr Glu Val Leu
        45                  50                  55 gac aac tcc acc gtc aag gac gcc gtc ggg acc ggc atc tcc gtc gtt      1743
Asp Asn Ser Thr Val Lys Asp Ala Val Gly Thr Gly Ile Ser Val Val
    60                  65                  70 ggg cag atc ctg ggc gtc gtt ggc gtc ccc ttc gca ggt gct ctc acc      1791
Gly Gln Ile Leu Gly Val Val Gly Val Pro Phe Ala Gly Ala Leu Thr
75                  80                  85                  90 tcc ttc tac cag tcc ttc ctg aac acc atc tgg ccc tcc gac gcc gac      1839
Ser Phe Tyr Gln Ser Phe Leu Asn Thr Ile Trp Pro Ser Asp Ala Asp
                95                  100                 105 ccc tgg aag gcc ttc atg gcc caa gtc gaa gtc ctg atc gac aag aag      1887
Pro Trp Lys Ala Phe Met Ala Gln Val Glu Val Leu Ile Asp Lys Lys
            110                 115                 120 atc gag gag tac gcc aag tcc aag gcc ctg gcc gag ctg caa ggc ctg      1935
Ile Glu Glu Tyr Ala Lys Ser Lys Ala Leu Ala Glu Leu Gln Gly Leu
        125                 130                 135 caa aac aac ttc gag gac tac gtc aac gcg ctg aac tcc tgg aag aag      1983
Gln Asn Asn Phe Glu Asp Tyr Val Asn Ala Leu Asn Ser Trp Lys Lys
    140                 145                 150 acg cct ctg tcc ctg cgc tcc aag cgc tcc cag gac cgc atc cgc gag      2031
Thr Pro Leu Ser Leu Arg Ser Lys Arg Ser Gln Asp Arg Ile Arg Glu
155                 160                 165                 170 ctg ttc tcc cag gcc gag tcc cac ttc cgc aac tcc atg ccg tcc ttc      2079
Leu Phe Ser Gln Ala Glu Ser His Phe Arg Asn Ser Met Pro Ser Phe
                175                 180                 185 gcc gtc tcc aag ttc gag gtc ctg ttc ctg ccc acc tac gcc cag gct      2127
Ala Val Ser Lys Phe Glu Val Leu Phe Leu Pro Thr Tyr Ala Gln Ala
            190                 195                 200 gcc aac acc cac ctc ctg ttg ctg aag gac gcc cag gtc ttc ggc gag      2175
Ala Asn Thr His Leu Leu Leu Leu Lys Asp Ala Gln Val Phe Gly Glu
        205                 210                 215 gaa tgg ggc tac tcc tcg gag gac gtc gcc gag ttc tac cgt cgc cag      2223
Glu Trp Gly Tyr Ser Ser Glu Asp Val Ala Glu Phe Tyr Arg Arg Gln
    220                 225                 230 ctg aag ctg acc caa cag tac acc gac cac tgc gtc aac tgg tac aac      2271
Leu Lys Leu Thr Gln Gln Tyr Thr Asp His Cys Val Asn Trp Tyr Asn
235                 240                 245                 250 gtc ggc ctg aac ggc ctg agg ggc tcc acc tac gac gca tgg gtc aag      2319
Val Gly Leu Asn Gly Leu Arg Gly Ser Thr Tyr Asp Ala Trp Val Lys
                255                 260                 265 ttc aac cgc ttc cgc agg gag atg acc ctg acc gtc ctg gac ctg atc      2367
Phe Asn Arg Phe Arg Arg Glu Met Thr Leu Thr Val Leu Asp Leu Ile
            270                 275                 280 gtc ctg ttc ccc ttc tac gac atc cgc ctg tac tcc aag ggc gtc aag      2415
Val Leu Phe Pro Phe Tyr Asp Ile Arg Leu Tyr Ser Lys Gly Val Lys
        285                 290                 295
```

```
acc gag ctg acc cgc gac atc ttc acg gac ccc atc ttc ctg ctc acg      2463
Thr Glu Leu Thr Arg Asp Ile Phe Thr Asp Pro Ile Phe Leu Leu Thr
300                 305                 310 acc ctc cag aag tac ggt ccc acc ttc ctg tcc atc gag aac tcc atc      2511
Thr Leu Gln Lys Tyr Gly Pro Thr Phe Leu Ser Ile Glu Asn Ser Ile
315                 320                 325                 330 cgc aag ccc cac ctg ttc gac tac ctc cag ggc atc gag ttc cac acg      2559
Arg Lys Pro His Leu Phe Asp Tyr Leu Gln Gly Ile Glu Phe His Thr
                335                 340                 345 cgc ctg agg cca ggc tac ttc ggc aag gac tcc ttc aac tac tgg tcc      2607
Arg Leu Arg Pro Gly Tyr Phe Gly Lys Asp Ser Phe Asn Tyr Trp Ser
        350                 355                 360 ggc aac tac gtc gag acc agg ccc tcc atc ggc tcg aag acg atc          2655
Gly Asn Tyr Val Glu Thr Arg Pro Ser Ile Gly Ser Lys Thr Ile
365                 370                 375 acc tcc cct ttc tac ggc gac aag tcc acc gag ccc gtc cag aag ctg      2703
Thr Ser Pro Phe Tyr Gly Asp Lys Ser Thr Glu Pro Val Gln Lys Leu
380                 385                 390 tcc ttc gac ggc cag aag gtc tac cgc acc atc gcc aac acc gac gtc      2751
Ser Phe Asp Gly Gln Lys Val Tyr Arg Thr Ile Ala Asn Thr Asp Val
395                 400                 405                 410 gcg gct tgg ccg aac ggc aag gtc tac ctg ggc gtc acg aag gtc gac      2799
Ala Ala Trp Pro Asn Gly Lys Val Tyr Leu Gly Val Thr Lys Val Asp
                415                 420                 425 ttc tcc cag tac gat gac cag aag aac gag acc tcc acc cag acc tac      2847
Phe Ser Gln Tyr Asp Asp Gln Lys Asn Glu Thr Ser Thr Gln Thr Tyr
        430                 435                 440 gac tcc aag cgc aac aat ggc cac gtc tcc gcc cag gac tcc atc gac      2895
Asp Ser Lys Arg Asn Asn Gly His Val Ser Ala Gln Asp Ser Ile Asp
445                 450                 455 cag ctg ccg cct gag acc act gac gag ccc ctg gag aag gcc tac tcc      2943
Gln Leu Pro Pro Glu Thr Thr Asp Glu Pro Leu Glu Lys Ala Tyr Ser
460                 465                 470 cac cag ctg aac tac gcg gag tgc ttc ctg atg caa gac cgc agg ggc      2991
His Gln Leu Asn Tyr Ala Glu Cys Phe Leu Met Gln Asp Arg Arg Gly
475                 480                 485                 490 acc atc ccc ttc ttc acc tgg acc cac cgc tcc gtc gac ttc ttc aac      3039
Thr Ile Pro Phe Phe Thr Trp Thr His Arg Ser Val Asp Phe Phe Asn
                495                 500                 505 acc atc gac gcc gag aag atc acc cag ctg ccc gtg gtc aag gcc tac      3087
Thr Ile Asp Ala Glu Lys Ile Thr Gln Leu Pro Val Val Lys Ala Tyr
        510                 515                 520 gcc ctg tcc tcg ggt gcc tcc atc att gag ggt cca ggc ttc acc ggt      3135
Ala Leu Ser Ser Gly Ala Ser Ile Ile Glu Gly Pro Gly Phe Thr Gly
525                 530                 535 ggc aac ctg ctg ttc ctg aag gag tcc tcg aac tcc atc gcc aag ttc      3183
Gly Asn Leu Leu Phe Leu Lys Glu Ser Ser Asn Ser Ile Ala Lys Phe
540                 545                 550 aag gtc acc ctg aac tcc gct gcc ttg ctg caa cgc tac cgc gtc cgc      3231
Lys Val Thr Leu Asn Ser Ala Ala Leu Leu Gln Arg Tyr Arg Val Arg
555                 560                 565                 570 atc cgc tac gcc tcc acc acg aac ctg cgc ctg ttc gtc cag aac tcc      3279
Ile Arg Tyr Ala Ser Thr Thr Asn Leu Arg Leu Phe Val Gln Asn Ser
                575                 580                 585 aac aat gac ttc ctg gtc atc tac atc aac aag acc atg aac aag gac      3327
Asn Asn Asp Phe Leu Val Ile Tyr Ile Asn Lys Thr Met Asn Lys Asp
        590                 595                 600 gat gac ctg acc tac cag acc ttc gac ctc gcc acc acg aac tcc aac      3375
Asp Asp Leu Thr Tyr Gln Thr Phe Asp Leu Ala Thr Thr Asn Ser Asn
```

```
                 605                 610                 615
atg ggc ttc tcg ggc gac aag aat gaa ctg atc att ggt gct gag tcc        3423
Met Gly Phe Ser Gly Asp Lys Asn Glu Leu Ile Ile Gly Ala Glu Ser
620                 625                 630 ttc gtc tcc aac gag aag atc tac atc gac aag atc gag ttc atc ccc        3471
Phe Val Ser Asn Glu Lys Ile Tyr Ile Asp Lys Ile Glu Phe Ile Pro
635                 640                 645                 650 gtc cag ctg tga taggaactct gattgaattc tgcatgcgtt tggacgtatg            3523
Val Gln Leu ctcattcagg ttggagccaa tttggttgat gtgtgtgcga gttcttgcga gtctgatgag      3583
acatctctgt attgtgtttc tttccccagt gttttctgta cttgtgtaat cggctaatcg      3643
ccaacagatt cggcgatgaa taaatgagaa ataaattgtt ctgattttga gtgcaaaaaa      3703
aaaggaatt                                                              3712
```

<210> SEQ ID NO 15
<211> LENGTH: 653
<212> TYPE: PRT
<213> ORGANISM: Artificial Sequence
<220> FEATURE:
<223> OTHER INFORMATION: Synthetic Construct

<400> SEQUENCE: 15

```
Met Ala Asn Pro Asn Asn Arg Ser Glu His Asp Thr Ile Lys Val Thr
1               5                   10                  15

Pro Asn Ser Glu Leu Gln Thr Asn His Asn Gln Tyr Pro Leu Ala Asp
            20                  25                  30

Asn Pro Asn Ser Thr Leu Glu Leu Asn Tyr Lys Glu Phe Leu Arg
        35                  40                  45

Met Thr Glu Asp Ser Ser Thr Glu Val Leu Asp Asn Ser Thr Val Lys
50                  55                  60

Asp Ala Val Gly Thr Gly Ile Ser Val Val Gly Gln Ile Leu Gly Val
65                  70                  75                  80

Val Gly Val Pro Phe Ala Gly Ala Leu Thr Ser Phe Tyr Gln Ser Phe
                85                  90                  95

Leu Asn Thr Ile Trp Pro Ser Asp Ala Asp Pro Trp Lys Ala Phe Met
            100                 105                 110

Ala Gln Val Glu Val Leu Ile Asp Lys Lys Ile Glu Glu Tyr Ala Lys
        115                 120                 125

Ser Lys Ala Leu Ala Glu Leu Gln Gly Leu Gln Asn Asn Phe Glu Asp
    130                 135                 140

Tyr Val Asn Ala Leu Asn Ser Trp Lys Lys Thr Pro Leu Ser Leu Arg
145                 150                 155                 160

Ser Lys Arg Ser Gln Asp Arg Ile Arg Glu Leu Phe Ser Gln Ala Glu
                165                 170                 175

Ser His Phe Arg Asn Ser Met Pro Ser Phe Ala Val Ser Lys Phe Glu
            180                 185                 190

Val Leu Phe Leu Pro Thr Tyr Ala Gln Ala Ala Asn Thr His Leu Leu
        195                 200                 205

Leu Leu Lys Asp Ala Gln Val Phe Gly Glu Glu Trp Gly Tyr Ser Ser
    210                 215                 220

Glu Asp Val Ala Glu Phe Tyr Arg Arg Gln Leu Lys Leu Thr Gln Gln
225                 230                 235                 240

Tyr Thr Asp His Cys Val Asn Trp Tyr Asn Val Gly Leu Asn Gly Leu
                245                 250                 255
```

Arg Gly Ser Thr Tyr Asp Ala Trp Val Lys Phe Asn Arg Phe Arg Arg
                260                 265                 270

Glu Met Thr Leu Thr Val Leu Asp Leu Ile Val Leu Phe Pro Phe Tyr
            275                 280                 285

Asp Ile Arg Leu Tyr Ser Lys Gly Val Lys Thr Glu Leu Thr Arg Asp
        290                 295                 300

Ile Phe Thr Asp Pro Ile Phe Leu Leu Thr Thr Leu Gln Lys Tyr Gly
305                 310                 315                 320

Pro Thr Phe Leu Ser Ile Glu Asn Ser Ile Arg Lys Pro His Leu Phe
                325                 330                 335

Asp Tyr Leu Gln Gly Ile Glu Phe His Thr Arg Leu Arg Pro Gly Tyr
            340                 345                 350

Phe Gly Lys Asp Ser Phe Asn Tyr Trp Ser Gly Asn Tyr Val Glu Thr
        355                 360                 365

Arg Pro Ser Ile Gly Ser Ser Lys Thr Ile Thr Ser Pro Phe Tyr Gly
370                 375                 380

Asp Lys Ser Thr Glu Pro Val Gln Lys Leu Ser Phe Asp Gly Gln Lys
385                 390                 395                 400

Val Tyr Arg Thr Ile Ala Asn Thr Asp Val Ala Ala Trp Pro Asn Gly
            405                 410                 415

Lys Val Tyr Leu Gly Val Thr Lys Val Asp Phe Ser Gln Tyr Asp Asp
        420                 425                 430

Gln Lys Asn Glu Thr Ser Thr Gln Thr Tyr Asp Ser Lys Arg Asn Asn
                435                 440                 445

Gly His Val Ser Ala Gln Asp Ser Ile Asp Gln Leu Pro Pro Glu Thr
450                 455                 460

Thr Asp Glu Pro Leu Glu Lys Ala Tyr Ser His Gln Leu Asn Tyr Ala
465                 470                 475                 480

Glu Cys Phe Leu Met Gln Asp Arg Arg Gly Thr Ile Pro Phe Phe Thr
            485                 490                 495

Trp Thr His Arg Ser Val Asp Phe Phe Asn Thr Ile Asp Ala Glu Lys
        500                 505                 510

Ile Thr Gln Leu Pro Val Val Lys Ala Tyr Ala Leu Ser Ser Gly Ala
            515                 520                 525

Ser Ile Ile Glu Gly Pro Gly Phe Thr Gly Gly Asn Leu Leu Phe Leu
530                 535                 540

Lys Glu Ser Ser Asn Ser Ile Ala Lys Phe Lys Val Thr Leu Asn Ser
545                 550                 555                 560

Ala Ala Leu Leu Gln Arg Tyr Arg Val Arg Ile Arg Tyr Ala Ser Thr
                565                 570                 575

Thr Asn Leu Arg Leu Phe Val Gln Asn Ser Asn Asn Asp Phe Leu Val
            580                 585                 590

Ile Tyr Ile Asn Lys Thr Met Asn Lys Asp Asp Asp Leu Thr Tyr Gln
        595                 600                 605

Thr Phe Asp Leu Ala Thr Thr Asn Ser Asn Met Gly Phe Ser Gly Asp
            610                 615                 620

Lys Asn Glu Leu Ile Ile Gly Ala Glu Ser Phe Val Ser Asn Glu Lys
625                 630                 635                 640

Ile Tyr Ile Asp Lys Ile Glu Phe Ile Pro Val Gln Leu
                645                 650

<210> SEQ ID NO 16
<211> LENGTH: 4370
<212> TYPE: DNA

<213> ORGANISM: Artificial Sequence
<220> FEATURE:
<223> OTHER INFORMATION: is a nucleotide sequence representing the sense strand of a DNA expression cassette that includes a recombinant gene engineered to encode and express a 5-enolpyruvylshikimate-3-phosphate synthase (EPSPS) protein

<400> SEQUENCE: 16

```
gacaacaaca tgcttctcat caacatggag ggaagaggga gggagaaagt gtcgcctggt      60
cacctccatt gtcacactag ccactggcca gctctcccac accaccaatg ccaggggcga     120
gctttagcac agccaccgct tcacctccac caccgcacta ccctagcttc gcccaacagc     180
caccgtcaac gcctcctctc cgtcaacata agagagagag agaagaggag agtagccatg     240
tggggaggag gaatagtaca tggggcctac cgtttggcaa gttattttgg gttgccaagt     300
taggccaata aggggaggga tttggccatc cggttggaaa ggttattggg gtagtatctt     360
tttactagaa ttgtcaaaaa aaaatagttt gagagccatt tggagaggat gttgcctgtt     420
agaggtgctc ttaggacatc aaattccata aaaacatcag aaaaattctc tcgatgaaga     480
tttataacca ctaaaactgc cctcaattcg aagggagttc aaaacaatta aaatcatgtt     540
cgaattgagt ttcaatttca ctttaacccc tttgaaatct caatggtaaa acatcaaccc     600
gtcaggtagc atggttcttt ttattccttt caaaagagt taattacaaa cagaatcaaa     660
actaacagtt aggcccaagg cccatccgag caaacaatag atcatgggcc aggcctgcca     720
ccaccctccc cctcctggct cccgctcttg aatttcaaaa tccaaaaata tcggcacgac     780
tggccgccga cggagcgggc ggaaaatgac ggaacaaccc ctcgaattct accccaacta     840
cgcccaccaa cccacacgcc actgacaatc cggtcccacc cttgtgggcc cacctacaag     900
cgagacgtca gtcgctcgca gcaaccagtg ggcccacctc ccagtgagcg gcgggtagat     960
ctggactctt acccacccac actaaacaaa acggcatgaa tattttgcac taaaaccctc    1020
agaaaaattc cgatattcca aaccagtaca gttcctgacc gttggaggag ccaaagtgga    1080
gcggagtgta aaattgggaa acttaatcga ggggttaaa cgcaaaaacg ccgaggcgcc    1140
tcccgctcta tagaaagggg aggagtggga ggtggaaacc ctaccacacc gcagagaaag    1200
gcgtcttcgt actcgcctct ctccgcgccc tcctccgccg ccgctcgccg ccgttcgtct    1260
ccgccgccac cggctagcca tccaggtaaa acaaacaaaa acggatctga tgcttccatt    1320
cctccgtttc tcgtagtagc gcgcttcgat ctgtgggtgg atctgggtga tcctggggtg    1380
tggttcgttc tgtttgatag atctgtcggt ggatctggcc ttctgtggtt gtcgatgtcc    1440
ggatctgcgt tttgatcagt ggtagttcgt ggatctggcg aaatgttttg gatctggcag    1500
tgagacgcta agaatcggga aatgatgcaa tattaggggg gtttcggatg gggatccact    1560
gaattagtct gtctccctgc tgataatctg ttccttttg gtagatctgg ttagtgtatg    1620
tttgtttcgg atagatctga tcaatgcttg tttgttttt caaattttct acctaggttg    1680
tataggaatg gcatgcggat ctggttggat tgccatgatc cgtgctgaaa tgccccttg    1740
gttgatggat cttgatattt tactgctgtt cacctagatt tgtactcccg tttatactta    1800
atttgttgct tattatgaat agatctgtaa cttaggcaca tgtatggacg gagtatgtgg    1860
atctgtagta tgtacattgc tgcgagctaa gaactatttc agagcaagca cagaaaaaaa    1920
tatttagaca gattgggcaa ctatttgatg gtctttggta tcatgctttg tagtgctcgt    1980
ttctgcgtag taatcttttg atctgatctg aagataggtg ctattatatt cttaaaggtc    2040
attagaacgc tatctgaaag gctgtattat gtggattggt tcacctgtga ctccctgttc    2100
```

```
gtcttgtctt gataaatcct gtgataaaaa aaattcttaa ggcgtaattt gttgaaatct    2160
tgttttgtcc tatgcagcct gatccatggc gcaagttagc agaatctgca atggtgtgca    2220
gaacccatct cttatctcca atctctcgaa atccagtcaa cgcaaatctc ccttatcggt    2280
ttctctgaag acgcagcagc atccacgagc ttatccgatt tcgtcgtcgt ggggattgaa    2340
gaagagtggg atgacgttaa ttggctctga gcttcgtcct cttaaggtca tgtcttctgt    2400
ttccacggcg tgcatgcttc acggtgcaag cagccggccc gcaaccgccc gcaaatcctc    2460 tggccttttcc ggaaccgtcc gcattccggg cgacaagtcg atctcccacc ggtccttcat    2520
gttcggcggt ctcgcgagcg gtgaaacgcg catcaccggc cttctggaag gcgaggacgt    2580
catcaatacg ggcaaggcca tgcaggcgat gggcgcccgc atccgtaagg aaggcgacac    2640
ctggatcatc gatggcgtcg gcaatggcgg cctcctggcg cctgaggcgc cgctcgattt    2700
cggcaatgcc gccacgggct gccgcctgac gatgggcctc gtcggggtct acgatttcga    2760
cagcaccttc atcggcgacg cctcgctcac aaagcgcccg atgggccgcg tgttgaaccc    2820
gctgcgcgaa atgggcgtgc aggtgaaatc ggaagacggt gaccgtcttc ccgttacctt    2880
gcgcgggccg aagacgccga cgccgatcac ctaccgcgtg ccgatggcct ccgcacaggt    2940
gaagtccgcc gtgctgctcg ccggcctcaa cacgcccggc atcacgacgg tcatcgagcc    3000
gatcatgacg cgcgatcata cggaaaagat gctgcagggc tttggcgcca accttaccgt    3060
cgagacggat gcggacggcg tgcgcaccat ccgcctggaa ggccgcggca agctcaccgg    3120
ccaagtcatc gacgtgccgg gcgacccgtc ctcgacggcc ttcccgctgg ttgcggccct    3180
gcttgttccg ggctccgacg tcaccatcct caacgtgctg atgaaccca cccgcaccgg    3240 cctcatcctg acgctgcagg aaatgggcgc cgacatcgaa gtcatcaacc cgcgccttgc    3300
cggcggcgaa gacgtggcgg acctgcgcgt tcgctcctcc acgctgaagg gcgtcacggt    3360
gccggaagac cgcgcgcctt cgatgatcga cgaatatccg attctcgctg tcgccgccgc    3420
cttcgcggaa ggggcgaccg tgatgaacgg tctggaagaa ctccgcgtca aggaaagcga    3480
ccgcctctcg gccgtcgcca tggcctcaa gctcaatggc gtggattgcg atgagggcga    3540
gacgtcgctc gtcgtgcgtg gccgcccctga cggcaagggg ctcggcaacg cctcgggcgc    3600
cgccgtcgcc acccatctcg atcaccgcat cgccatgagc ttcctcgtca tgggcctcgt    3660
gtcggaaaac cctgtcacgg tggacgatgc cacgatgatc gccacgagct tcccggagtt    3720
catggacctg atggccgggc tgggcgcgaa gatcgaactc tccgatacga aggctgcctg    3780
atgagctcca gggttcttgc ctggtgcctt ggcaatgctt gattactgct gctatcctat    3840
gatctgtccg tgtgggcttc tatctatcag tttgtgtgtc tggttttgaa aaacatttgc    3900
ttttcgatta tgtagggttt gcttgtagct ttcgctgctg tgacctgtgt tgtttatgtg    3960
aaccttcttt gtggcatctt taatatccaa gttcgtggtt tgtcgtaaaa cgaagcctct    4020
acttcgtaaa gttgtgtcta tagcattgaa atcgttttt tgctcgagaa taattgtgac    4080
ctttagttgg cgtgaaacta gttttggata tctgattctc tggttcgcaa tcttgagatc    4140
gtcgctgctt aggtgagcta agtgatgttc ctaagtaaat gctcctcacc agaatacgta    4200
gctgtgtgaa aagagaacgc gtgaatacgt agctgtgtaa agattgtgtc ccaagtaaac    4260
ctcagtgatt tttgtttgga tttttaattt agaaacattc gactgggagc ggctagagcc    4320
acacccaagt tcctaactat gataaagttg ctctgtaaca gaaaacacca              4370
```

<210> SEQ ID NO 17
<211> LENGTH: 531

<212> TYPE: PRT
<213> ORGANISM: Artificial Sequence
<220> FEATURE:
<223> OTHER INFORMATION: is an amino acid sequence translation of
      nucleotide positions 2186 through 3781 of SEQ ID NO: 16
<220> FEATURE:
<221> NAME/KEY: misc_feature
<222> LOCATION: (1)..(76)
<223> OTHER INFORMATION: chloroplast transit peptide (CTP) from
      Arabidopsis thaliana (thale cress)
<220> FEATURE:
<221> NAME/KEY: misc_feature
<222> LOCATION: (77)..(531)
<223> OTHER INFORMATION: 5-enolpyruvylshikimate-3-phosphate synthase
      gene (EPSPS) from Agrobacterium sp strain CP4

<400> SEQUENCE: 17

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
50                  55                  60

Pro Leu Lys Val Met Ser Ser Val Ser Thr Ala Cys Met Leu His Gly
65                  70                  75                  80

Ala Ser Ser Arg Pro Ala Thr Ala Arg Lys Ser Ser Gly Leu Ser Gly
                85                  90                  95

Thr Val Arg Ile Pro Gly Asp Lys Ser Ile Ser His Arg Ser Phe Met
            100                 105                 110

Phe Gly Gly Leu Ala Ser Gly Glu Thr Arg Ile Thr Gly Leu Leu Glu
        115                 120                 125

Gly Glu Asp Val Ile Asn Thr Gly Lys Ala Met Gln Ala Met Gly Ala
130                 135                 140

Arg Ile Arg Lys Glu Gly Asp Thr Trp Ile Ile Asp Gly Val Gly Asn
145                 150                 155                 160

Gly Gly Leu Leu Ala Pro Glu Ala Pro Leu Asp Phe Gly Asn Ala Ala
                165                 170                 175

Thr Gly Cys Arg Leu Thr Met Gly Leu Val Gly Val Tyr Asp Phe Asp
            180                 185                 190

Ser Thr Phe Ile Gly Asp Ala Ser Leu Thr Lys Arg Pro Met Gly Arg
        195                 200                 205

Val Leu Asn Pro Leu Arg Glu Met Gly Val Gln Val Lys Ser Glu Asp
210                 215                 220

Gly Asp Arg Leu Pro Val Thr Leu Arg Gly Pro Lys Thr Pro Thr Pro
225                 230                 235                 240

Ile Thr Tyr Arg Val Pro Met Ala Ser Ala Gln Val Lys Ser Ala Val
                245                 250                 255

Leu Leu Ala Gly Leu Asn Thr Pro Gly Ile Thr Thr Val Ile Glu Pro
            260                 265                 270

Ile Met Thr Arg Asp His Thr Glu Lys Met Leu Gln Gly Phe Gly Ala
        275                 280                 285

Asn Leu Thr Val Glu Thr Asp Ala Asp Gly Val Arg Thr Ile Arg Leu
290                 295                 300

Glu Gly Arg Gly Lys Leu Thr Gly Gln Val Ile Asp Val Pro Gly Asp
305                 310                 315                 320

Pro Ser Ser Thr Ala Phe Pro Leu Val Ala Ala Leu Leu Val Pro Gly

```
              325                 330                 335
Ser Asp Val Thr Ile Leu Asn Val Leu Met Asn Pro Thr Arg Thr Gly
        340                 345                 350

Leu Ile Leu Thr Leu Gln Glu Met Gly Ala Asp Ile Glu Val Ile Asn
            355                 360                 365

Pro Arg Leu Ala Gly Gly Glu Asp Val Ala Asp Leu Arg Val Arg Ser
370                 375                 380

Ser Thr Leu Lys Gly Val Thr Val Pro Glu Asp Arg Ala Pro Ser Met
385                 390                 395                 400

Ile Asp Glu Tyr Pro Ile Leu Ala Val Ala Ala Phe Ala Glu Gly
                405                 410                 415

Ala Thr Val Met Asn Gly Leu Glu Glu Leu Arg Val Lys Glu Ser Asp
                420                 425                 430

Arg Leu Ser Ala Val Ala Asn Gly Leu Lys Leu Asn Gly Val Asp Cys
            435                 440                 445

Asp Glu Gly Glu Thr Ser Leu Val Val Arg Gly Arg Pro Asp Gly Lys
        450                 455                 460

Gly Leu Gly Asn Ala Ser Gly Ala Ala Val Ala Thr His Leu Asp His
465                 470                 475                 480

Arg Ile Ala Met Ser Phe Leu Val Met Gly Leu Val Ser Glu Asn Pro
                485                 490                 495

Val Thr Val Asp Asp Ala Thr Met Ile Ala Thr Ser Phe Pro Glu Phe
                500                 505                 510

Met Asp Leu Met Ala Gly Leu Gly Ala Lys Ile Glu Leu Ser Asp Thr
            515                 520                 525

Lys Ala Ala
    530

<210> SEQ ID NO 18
<211> LENGTH: 29
<212> TYPE: DNA
<213> ORGANISM: artificial sequence
<220> FEATURE:
<223> OTHER INFORMATION: is a nucleotide sequence of a synthetic
      oligonucleotide, and is referred to as SQ27011

<400> SEQUENCE: 18
aaggaaaata aaaggcaaa acactaatg                                          29

<210> SEQ ID NO 19
<211> LENGTH: 14
<212> TYPE: DNA
<213> ORGANISM: artificial sequence
<220> FEATURE:
<223> OTHER INFORMATION: is a nucleotide sequence of a synthetic
      oligonucleotide, and is referred to as PB3552

<400> SEQUENCE: 19
ccggacatga agcc                                                         14

<210> SEQ ID NO 20
<211> LENGTH: 26
<212> TYPE: DNA
<213> ORGANISM: artificial sequence
<220> FEATURE:
<223> OTHER INFORMATION: is a nucleotide sequence of a synthetic
      oligonucleotide, and is referred to as SQ9085

<400> SEQUENCE: 20
actcattgct gatccatgta gatttc                                            26
```

```
<210> SEQ ID NO 21
<211> LENGTH: 80
<212> TYPE: DNA
<213> ORGANISM: artificial sequence
<220> FEATURE:
<223> OTHER INFORMATION: is a nucleotide sequence of Event MON 87411
      corresponding to positions 462 through 541 of SEQ ID NO: 1

<400> SEQUENCE: 21
aaggaaaata aaaaggcaaa acactaatga atagttaagt ggcttcatgt ccgggaaatc    60
tacatggatc agcaatgagt                                                80

<210> SEQ ID NO 22
<211> LENGTH: 19
<212> TYPE: DNA
<213> ORGANISM: artificial sequence
<220> FEATURE:
<223> OTHER INFORMATION: is a nucleotide sequence of a synthetic
      oligonucleotide referred to as SQ27066

<400> SEQUENCE: 22
acaccatcta gagcggccg                                                 19

<210> SEQ ID NO 23
<211> LENGTH: 25
<212> TYPE: DNA
<213> ORGANISM: artificial sequence
<220> FEATURE:
<223> OTHER INFORMATION: is a nucleotide sequence of a synthetic
      oligonucleotide referred to as PB11300

<400> SEQUENCE: 23
tttaaactat cagtgtttag agaat                                          25

<210> SEQ ID NO 24
<211> LENGTH: 29
<212> TYPE: DNA
<213> ORGANISM: artificial sequence
<220> FEATURE:
<223> OTHER INFORMATION: is a nucleotide sequence of a synthetic
      oligonucleotide referred to as SQ26977

<400> SEQUENCE: 24
gggtagatta atacatctag aggtttgtg                                      29

<210> SEQ ID NO 25
<211> LENGTH: 75
<212> TYPE: DNA
<213> ORGANISM: artificial sequence
<220> FEATURE:
<223> OTHER INFORMATION: is a nucleotide sequence of Event MON 87411
      corresponding to positions 11710 through 11784 of SEQ ID NO: 1

<400> SEQUENCE: 25
acaccatcta gagcggccgc gtttaaacta tcagtgttta gagaatcaca aacctctaga    60
tgtattaatc taccc                                                     75

<210> SEQ ID NO 26
<211> LENGTH: 11743
<212> TYPE: DNA
<213> ORGANISM: Artificial Sequence
<220> FEATURE:
<223> OTHER INFORMATION: DNA construct 417
<220> FEATURE:
<221> NAME/KEY: promoter
```

```
<222> LOCATION: (2627)..(3238)
<223> OTHER INFORMATION: represents the reverse complement sequence of
      an enhanced CaMV 35S promoter
<220> FEATURE:
<221> NAME/KEY: promoter
<222> LOCATION: (2627)..(4213)
<223> OTHER INFORMATION: represents a divergent promoter region that
      promotes bidirectional transcription
<220> FEATURE:
<221> NAME/KEY: promoter
<222> LOCATION: (3265)..(4213)
<223> OTHER INFORMATION: Corn PIIG promoter

<400> SEQUENCE: 26
```

| | | | | | |
|---|---|---|---|---|---|
| aaaagtccca | tgtggatcac | tccgttgccc | cgtcgctcac | cgtgttgggg | ggaaggtgca | 60 |
| catggctcag | ttctcaatgg | aaattatctg | cctaaccggc | tcagttctgc | gtagaaacca | 120 |
| acatgcaagc | tccaccgggt | gcaaagcggc | agcggcggca | ggatatattc | aattgtaaat | 180 |
| ggcttcatgt | ccgggaaatc | tacatggatc | agcaatgagt | atgatggtca | atatggagaa | 240 |
| aaagaaagag | taattaccaa | ttttttttca | attcaaaaat | gtagatgtcc | gcagcgttat | 300 |
| tataaaatga | aagtacattt | tgataaaacg | acaaattacg | atccgtcgta | tttataggcg | 360 |
| aaagcaataa | acaaattatt | ctaattcgga | aatctttatt | tcgacgtgtc | tacattcacg | 420 |
| tccaaatggg | ggcttagatg | agaaacttca | cgatcgatgc | ggccaccact | cgaggtcgag | 480 |
| gtaccgttgt | caatcaattg | gcaagtcata | aaatgcatta | aaaatatttt | tcatactcaa | 540 |
| ctacaaatcc | atgagtataa | ctataattat | aaagcaatga | ttagaatctg | acaaggattc | 600 |
| tggaaaatta | cataaaggaa | agttcataaa | tgtctaaaac | acaagaggac | atacttgtat | 660 |
| tcagtaacat | ttgcagcttt | tctaggtctg | aaaatatatt | tgttgcctag | tgaataagca | 720 |
| taatggtaca | actacaagtg | ttttactcct | catattaact | tcggtcatta | gaggccacga | 780 |
| tttgacacat | ttttactcaa | aacaaaatgt | ttgcatatct | cttataattt | caaattcaac | 840 |
| acacaacaaa | taagagaaaa | aacaaataat | attaatttga | gaatgaacaa | aaggaccata | 900 |
| tcattcatta | actcttctcc | atccatttcc | atttcacagt | tcgatagcga | aaaccgaata | 960 |
| aaaaacacag | taattacaa | gcacaacaaa | tggtacaaga | aaaacagttt | tcccaatgcc | 1020 |
| ataatactca | aactcagtag | gattctggtg | tgtgcgcaat | gaaactgatg | cattgaactt | 1080 |
| gacgaacgtt | gtcgaaaccg | atgatacgaa | cgaaagctag | gcctcagcga | gtaccgctgg | 1140 |
| cgatctaatc | catgatatcg | tgaacatcat | ctacattcaa | attcttatga | gctttcttaa | 1200 |
| gggcatctgc | agcattttc | atagaatcta | atacagcagt | atttgtgcta | gctccttcga | 1260 |
| gggcttccct | ctgcatttca | atagttgtaa | gggttccatc | tatttgtagt | tgggtctttt | 1320 |
| ccaatcgttt | cttcttttg | agggcttgga | gtgcaactct | tttatttttc | gacgcatttt | 1380 |
| tctttgcgct | cctgcaggcg | gccgcgtgga | tgaggagtta | atcggtcgtg | tgagagtagt | 1440 |
| gatcgagtgg | atgtcgtcga | gagtgatgag | tgttgatgtt | gttagtgata | tgtggtagaa | 1500 |
| ggtatcgtga | taaagcgtta | acgcgatcgc | agtacttgca | aagaaaaatg | cgtcgaaaaa | 1560 |
| taaaagagtt | gcactccaag | ccctcaaaaa | gaagaaacga | ttggaaaaga | cccaactaca | 1620 |
| aatagatgga | acccttacaa | ctattgaaat | gcagagggaa | gccctcgaag | gagctagcac | 1680 |
| aaatactgct | gtattagatt | ctatgaaaaa | tgctgcagat | gcccttaaga | aagctcataa | 1740 |
| gaatttgaat | gtagatgatg | ttcacgatat | catggatggt | atcgcacagc | gactgctgag | 1800 |
| ggacgtcgag | ctcccgcttg | gtatctgcat | tacaatgaaa | tgagcaaaga | ctatgtgagt | 1860 |
| aacactggtc | aacactaggg | agaaggcatc | gagcaagata | cgtatgtaaa | gagaagcaat | 1920 |

-continued

```
atagtgtcag ttggtagata ctagatacca tcaggaggta aggagagcaa caaaaaggaa    1980
actctttatt tttaaatttt gttacaacaa acaagcagat caatgcatca aaatactgtc    2040
agtacttatt tcttcagaca acaatattta aacaagtgc atctgatctt gacttatggt     2100
cacaataaag gagcagagat aaacatcaaa atttcgtcat ttatatttat tccttcaggc    2160
gttaacaatt taacagcaca caaacaaaaa cagaatagga atatctaatt ttggcaaata    2220
ataagctctg cagacgaaca aattattata gtatcgccta atatgaat ccctatacta      2280 ttgacccatg tagtatgaag cctgtgccta aattaacagc aaacttctga atccaagtgc    2340
cctataacac caacatgtgc ttaaataaat accgctaagc accaaattac acatttctcg    2400
tattgctgtg taggttctat cttcgtttcg tactaccatg tccctatatt ttgctgctac    2460
aaaggacggc aagtaatcag cacaggcaga acacgatttc agagtgtaat tctagatcca    2520
gctaaaccac tctcagcaat caccacacaa gagagcattc agagaaacgt ggcagtaaca    2580
aaggcagagg gcggagtgag cgcgtaccga agacggttca gcgtgtcctc tccaaatgaa    2640
atgaacttcc ttatatagag gaagggtctt gcgaaggata gtgggattgt gcgtcatccc    2700
ttacgtcagt ggagatatca catcaatcca cttgctttga agacgtggtt ggaacgtctt    2760 cttttttccac gatgctcctc gtgggtgggg gtccatcttt gggaccactg tcggcagagg   2820
catcttcaac gatggccttt cctttatcgc aatgatggca tttgtaggag ccaccttcct    2880
tttccactat cttcacaata aagtgacaga tagctgggca atggaatccg aggaggtttc    2940
cggatattac cctttgttga aaagtctcaa tcggaccatc acatcaatcc acttgctttg    3000
aagacgtggt tggaacgtct tcttttttcca cgatgctcct cgtgggtggg ggtccatctt    3060
tgggaccact gtcggcagag gcatcttcaa cgatggcctt tcctttatcg caatgatggc    3120
atttgtagga gccaccttcc ttttccacta tcttcacaat aaagtgacag atagctgggc    3180
aatggaatcc gaggaggttt ccggatatta ccctttgttg aaaagtctca atcggacctg    3240
cagcctgcag gctagcggcg cgccacaaat cacaggccat gaaccctact catgcttcga    3300
tttgtccaac acacacttac caaaactcaa atcatgtcct tgacagtcac tcgggactca    3360
taacatgggt acgtatcgac tatgtcaact atatgtgttc tcatcagatt atagattggc    3420
ctagtacgta gtgatatttc cactagcact gtggttatgg ctgtacctga tagtgatatc    3480
agcaccgggt catggctcta ctaccaggta gtgagagtga cctttatact gtcagactgt    3540
aactaaggat ttccaatcac tgttcggatc ctaggcttag aattaagtaa aactctatca    3600
ctataggctg cagcacactc ggtatatatt gatgggccaa cagaaattgt gcgtactatg    3660
cgcgatgtaa aatggacata aaccctaccc atatacaatg caataacttt tgtccggtct    3720
gggccaccgg ttagcagagg tcctgatttc ggtggtagtg gtagcttgat ctggtcgtcg    3780
tatcgtagag ggatatataa aatcatgtca cttttgaagg gagcgctcac agaaataata    3840
ggtattcgcg ggagccgccc ccgcagaaca caaataaggg cgagcacgca cacgcatcag    3900
tttcgataaa ataataatag cgccagctga tcggaacaat ccagctagc actaatgtat     3960 ttctgcattg atctgtttat acaacatgct acctcgttga gtgattttga catgatttgt    4020
caacttgctc cgatcctata tctcgatcga tctccacatg acgatggttg ttgtcctgta    4080
tcccatgaca accaggcaac gctcaaagca cacatgcgtt gccgattacc cgtgcatgcc    4140
gccaagcacg aaagcacctc cctccacacc gtccatcagc tataaaaacc atgccaagca    4200
ccctgtgaaa agccccggga accatcttcc acacactcaa gccacactat tggagaacac    4260
acagggacaa cacaccataa gatccaaggg aggcctccgc cgccgccggt aaccacccg    4320
```

```
ccctctcct ctttctttct ccgttttttt ttccgtctcg gtctcgatct ttggccttgg   4380
tagtttgggt gggcgagagg cggcttcgtg cgcgcccaga tcggtgcgcg ggaggggcgg   4440
gatctcgcgg ctggggctct cgccggcgtg gatccggccc ggatctcgcg gggaatgggg   4500
ctctcggatg tagatctgcg atccgccgtt gttggggag atgatggggg gtttaaaatt    4560
tccgccgtgc taaacaagat caggaagagg ggaaaagggc actatggttt atatttttat   4620
atatttctgc tgcttcgtca ggcttagatg tgctagatct ttctttcttc ttttgtggg    4680 tagaatttga atccctcagc attgttcatc ggtagttttt cttttcatga tttgtgacaa   4740
atgcagcctc gtgcggagct tttttgtagg tagaagtgat caaccatggc caaccccaac   4800
aatcgctccg agcacgacac gatcaaggtc accccaact ccgagctcca gaccaaccac    4860
aaccagtacc cgctggccga caaccccaac tccaccctgg aagagctgaa ctacaaggag   4920
ttcctgcgca tgaccgagga ctcctccacg gaggtcctgg acaactccac cgtcaaggac   4980
gccgtcggga ccggcatctc cgtcgttggg cagatcctgg gcgtcgttgg cgtccccttc   5040
gcaggtgctc tcacctcctt ctaccagtcc ttcctgaaca ccatctggcc ctccgacgcc   5100
gacccctgga aggccttcat ggcccaagtc gaagtcctga tcgacaagaa gatcgaggag   5160
tacgccaagt ccaaggccct ggccgagctg caaggcctgc aaaacaactt cgaggactac   5220
gtcaacgcgc tgaactcctg gaagaagacg cctctgtccc tgcgctccaa gcgctcccag   5280
gaccgcatcc gcgagctgtt ctcccaggcc gagtcccact tccgcaactc catgccgtcc   5340
ttcgccgtct ccaagttcga ggtcctgttc ctgcccacct acgccaggc tgccaacacc    5400 cacctcctgt tgctgaagga cgcccaggtc ttcggcgagg aatggggcta ctcctcggag   5460
gacgtcgccg agttctaccg tcgccagctg aagctgaccc aacagtacac cgaccactgc   5520
gtcaactggt acaacgtcgg cctgaacggc ctgaggggct ccacctacga cgcatgggtc   5580
aagttcaacc gcttccgcag ggagatgacc ctgaccgtcc tggacctgat cgtcctgttc   5640
cccttctacg acatccgcct gtactccaag ggcgtcaaga ccgagctgac ccgcgacatc   5700
ttcacggacc ccatcttcct gctcacgacc ctccagaagt acggtccac cttcctgtcc    5760 atcgagaact ccatccgcaa gccccacctg ttcgactacc tccagggcat cgagttccac   5820
acgcgcctga ggccaggcta cttcggcaag gactccttca actactggtc cggcaactac   5880
gtcgagacca ggccctccat cggctcctcg aagacgatca cctcccctttt ctacggcgac   5940 aagtccaccg agcccgtcca gaagctgtcc ttcgacggcc agaaggtcta ccgcaccatc   6000
gccaacaccg acgtcgcggc ttggccgaac ggcaaggtct acctgggcgt cacgaaggtc   6060
gacttctccc agtacgatga ccagaagaac gagacctcca cccagaccta cgactccaag   6120
cgcaacaatg gccacgtctc cgcccaggac tccatcgacc agctgccgcc tgagaccact   6180
gacgagcccc tggagaaggc ctactcccac cagctgaact acgcggagtg cttcctgatg   6240
caagaccgca ggggcaccat ccccttcttc acctggaccc ccgctccgt cgacttcttc    6300 aacaccatcg acgccgagaa gatcacccag ctgcccgtgg tcaaggccta cgccctgtcc   6360
tcgggtgcct ccatcattga gggtccaggc ttcaccggtg gcaacctgct gttcctgaag   6420
gagtcctcga actccatcgc caagttcaag gtcaccctga actccgctgc cttgctgcaa   6480
cgctaccgcg tccgcatccg ctacgcctcc accacgaacc tgcgcctgtt cgtccagaac   6540
tccaacaatg acttcctggt catctacatc aacaagacca tgaacaagga cgatgacctg   6600
acctaccaga ccttcgacct cgccaccacg aactccaaca tgggcttctc gggcgacaag   6660
```

```
aatgaactga tcattggtgc tgagtccttc gtctccaacg agaagatcta catcgacaag    6720
atcgagttca tccccgtcca gctgtgatag gaactctgat tgaattctgc atgcgtttgg    6780
acgtatgctc attcaggttg gagccaattt ggttgatgtg tgtgcgagtt cttgcgagtc    6840
tgatgagaca tctctgtatt gtgtttcttt ccccagtgtt ttctgtactt gtgtaatcgg    6900
ctaatcgcca acagattcgg cgatgaataa atgagaaata aattgttctg attttgagtg    6960
caaaaaaaaa ggaattagat ctgtgtgtgt tttttggatc ccattttcga caagcttgcc    7020
tcgagacaac aacatgcttc tcatcaacat ggagggaaga gggagggaga aagtgtcgcc    7080
tggtcacctc cattgtcaca ctagccactg gccagctctc ccacaccacc aatgccaggg    7140
gcgagcttta gcacagccac cgcttcacct ccaccaccgc actacccctag cttcgcccaa    7200 cagccaccgt caacgcctcc tctccgtcaa cataagagag agagagaaga ggagagtagc    7260
catgtgggga ggaggaatag tacatggggc ctaccgtttg gcaagttatt ttgggttgcc    7320
aagttaggcc aataagggga gggatttggc catccggttg gaaaggttat tggggtagta    7380 tcttttact agaattgtca aaaaaaaata gtttgagagc catttggaga ggatgttgcc     7440
tgttagaggt gctcttagga catcaaattc cataaaaaca tcagaaaaat tctctcgatg    7500
aagatttata accactaaaa ctgccctcaa ttcaagggga gttcaaaaca attaaaatca    7560
tgttcgaatt gagtttcaat ttcactttaa ccccttttgaa atctcaatgg taaaacatca   7620
acccgtcagg tagcatggtt ctttttattc ctttcaaaaa gagttaatta caaacagaat    7680
caaaactaac agttaggccc aaggcccatc cgagcaaaca atagatcatg ggccaggcct    7740
gccaccaccc tccccctcct ggctcccgct cttgaatttc aaaatccaaa aatatcggca    7800
cgactggccg ccgacggagc gggcggaaaa tgacggaaca accctcgaa ttctacccca     7860 actacgccca ccaaccccaca cgccactgac aatccggtcc caccctttgtg ggcccaccta   7920 caagcgagac gtcagtcgct cgcagcaacc agtgggccca cctcccagtg agcggcgggt    7980
agatctggac tcttaccccac ccacactaaa caaaacggca tgaatatttt gcactaaaac   8040
cctcagaaaa attccgatat tccaaaccag tacagttcct gaccgttgga ggagccaaag    8100
tggagcggag tgtaaaattg ggaaacttaa tcgaggggggt taaacgcaaa aacgccgagg    8160
cgcctcccgc tctatagaaa ggggaggagt gggaggtgga aaccctacca caccgcagag    8220
aaaggcgtct tcgtactcgc ctctctccgc gccctcctcc gccgccgctc gccgccgttc    8280
gtctccgccg ccaccggcta gccatccagg taaaacaaac aaaaacggat ctgatgcttc    8340
cattcctccg tttctcgtag tagcgcgctt cgatctgtgg gtggatctgg gtgatcctgg    8400
ggtgtggttc gttctgtttg atagatctgt cggtggatct ggccttctgt ggttgtcgat    8460
gtccggatct gcgttttgat cagtggtagt tcgtggatct ggcgaaatgt tttggatctg    8520
gcagtgagac gctaagaatc gggaaatgat gcaatattag gggggtttcg gatggggatc    8580
cactgaatta gtctgtctcc ctgctgataa tctgttcctt tttggtagat ctggttagtg    8640
tatgtttgtt tcggatagat ctgatcaatg cttgtttgtt ttttcaaatt ttctacctag    8700
gttgtatagg aatggcatgc ggatctggtt ggattgccat gatccgtgct gaaatgcccc    8760
tttggttgat ggatccttgat atttttactgc tgttcaccta gatttgtact cccgtttata   8820
cttaatttgt tgcttattat gaatagatct gtaacttagg cacatgtatg gacggagtat    8880
gtggatctgt agtatgtaca ttgctgcgag ctaagaacta tttcagagca agcacagaaa    8940
aaaatattta gacagattgg gcaactattt gatggtcttt ggtatcatgc tttgtagtgc    9000
tcgtttctgc gtagtaatct tttgatctga tctgaagata ggtgctatta tattcttaaa    9060
```

```
ggtcattaga acgctatctg aaaggctgta ttatgtggat tggttcacct gtgactccct    9120
gttcgtcttg tcttgataaa tcctgtgata aaaaaaattc ttaaggcgta atttgttgaa    9180
atcttgtttt gtcctatgca gcctgatcca tggcgcaagt tagcagaatc tgcaatggtg    9240
tgcagaaccc atctcttatc tccaatctct cgaaatccag tcaacgcaaa tctcccttat    9300
cggtttctct gaagacgcag cagcatccac gagcttatcc gatttcgtcg tcgtggggat    9360
tgaagaagag tgggatgacg ttaattggct ctgagcttcg tcctcttaag gtcatgtctt    9420
ctgtttccac ggcgtgcatg cttcacggtg caagcagccg gcccgcaacc gcccgcaaat    9480
cctctggcct ttccggaacc gtccgcattc ccggcgacaa gtcgatctcc caccggtcct    9540
tcatgttcgg cggtctcgcg agcggtgaaa cgcgcatcac cggccttctg aaggcgagg     9600 acgtcatcaa tacgggcaag gccatgcagg cgatgggcgc ccgcatccgt aaggaaggcg    9660
acacctggat catcgatggc gtcggcaatg gcggcctcct ggcgcctgag gcgccgctcg    9720
atttcggcaa tgccgccacg ggctgccgcc tgacgatggg cctcgtcggg gtctacgatt    9780
tcgacagcac cttcatcggc gacgcctcgc tcacaaagcg cccgatgggc gcgtgttga    9840 acccgctgcg cgaaatgggc gtgcaggtga atcggaaga cggtgaccgt cttcccgtta    9900
ccttgcgcgg gccgaagacg ccgacgccga tcacctaccg cgtgccgatg gcctccgcac    9960
aggtgaagtc cgccgtgctg ctcgccggcc tcaacacgcc cggcatcacg acggtcatcg   10020
agccgatcat gacgcgcgat catacggaaa agatgctgca gggctttggc gccaacctta   10080
ccgtcgagac ggatgcggac ggcgtgcgca ccatccgcct ggaaggccgc ggcaagctca   10140
ccggccaagt catcgacgtg ccgggcgacc cgtcctcgac ggccttcccg ctggttgcgg   10200
ccctgcttgt tccgggctcc gacgtcacca tcctcaacgt gctgatgaac cccaccgca    10260 ccggcctcat cctgacgctg caggaaatgg gcgccgacat cgaagtcatc aacccgcgcc   10320
ttgccggcgg cgaagacgtg gcggacctgc gcgttcgctc ctccacgctg aagggcgtca   10380
cggtgccgga agaccgcgcg ccttcgatga tcgacgaata tccgattctc gctgtcgccg   10440
ccgccttcgc ggaaggggcg accgtgatga acgtctgga agaactccgc gtcaaggaaa    10500
gcgaccgcct ctcggccgtc gccaatggcc tcaagctcaa tggcgtggat tgcgatgagg   10560
gcgagacgtc gctcgtcgtg cgtggccgcc ctgacggcaa ggggctcggc aacgcctcgg   10620
gcgccgccgt cgccacccat ctcgatcacc gcatcgccat gagcttcctc gtcatgggcc   10680
tcgtgtcgga aaaccctgtc acggtggacg atgccacgat gatcgccacg agcttcccgg   10740
agttcatgga cctgatggcc gggctgggcg cgaagatcga actctccgat acgaaggctg   10800
cctgatgagc tccagggttc ttgcctggtg ccttggcaat gcttgattac tgctgctatc   10860
ctatgatctg tccgtgtggg cttctatcta tcagtttgtg tgtctggttt tgaaaaacat   10920 ttgctttcg attatgtagg gtttgcttgt agctttcgct gctgtgacct gtgttgttta    10980
tgtgaacctt ctttgtggca tctttaatat ccaagttcgt ggtttgtcgt aaaacgaagc   11040
ctctacttcg taaagttgtg tctatagcat tgaaatcgtt tttttgctcg agaataattg   11100
tgacctttag ttggcgtgaa actagttttg gatatctgat tctctggttc gcaatcttga   11160
gatcgtcgct gcttaggtga gctaagtgat gttcctaagt aaatgctcct caccagaata   11220
cgtagctgtg tgaaaagaga acgcgtgaat acgtagctgt gtaaagattg tgtcccaagt   11280
aaacctcagt gatttttgtt tggatttttta atttagaaac attcgactgg gagcggctag   11340
agccacaccc aagttcctaa ctatgataaa gttgctctgt aacagaaaac accatctaga   11400
```

```
gcggccgcgt ttaaactatc agtgtttgac aggatatatt ggcgggtaaa cctaagagaa    11460
aagagcgttt attagaataa tcggatattt aaaagggcgt gaaaaggttt atccgttcgt    11520
ccatttgtat gtgcatgcca accacagggt tcccctcggg agtgcttggc attccgtgcg    11580
ataatgactt ctgttcaacc acccaaacgt cggaaagcct gacgacgag cagcattcca    11640 aaaagatccc ttggctcgtc tgggtcggct agaaggtcga gtgggctgct gtggcttgat    11700
ccctcaacgc ggtcgcggac gtagcgcagc gccgaaaaat cct                      11743
```

<210> SEQ ID NO 27
<211> LENGTH: 12322
<212> TYPE: DNA
<213> ORGANISM: Artificial Sequence
<220> FEATURE:
<223> OTHER INFORMATION: DNA construct 416

<400> SEQUENCE: 27

```
aaaagtccca tgtggatcac tccgttgccc cgtcgctcac cgtgttgggg ggaaggtgca      60
catggctcag ttctcaatgg aaattatctg cctaaccggc tcagttctgc gtagaaacca     120
acatgcaagc tccaccgggt gcaaagcggc agcggcggca ggatatattc aattgtaaat     180
ggcttcatgt ccgggaaatc tacatggatc agcaatgagt atgatggtca atatggagaa     240
aaagaaagag taattaccaa ttttttttca attcaaaaat gtagatgtcc gcagcgttat     300
tataaaatga aagtacattt tgataaaacg acaaattacg atccgtcgta tttataggcg     360
aaagcaataa acaaattatt ctaattcgga aatctttatt tcgacgtgtc tacattcacg     420
tccaaatggg ggcttagatg agaaacttca cgatcgatgc ggccaccact cgaggtcgag     480
gtaccgttgt caatcaattg gcaagtcata aaatgcatta aaaatatttt tcatactcaa     540
ctacaaatcc atgagtataa ctataattat aaagcaatga ttagaatctg acaaggattc     600
tggaaaatta cataaggaa agttcataaa tgtctaaaac acaagaggac atacttgtat      660
tcagtaacat ttgcagcttt tctaggtctg aaaatatatt tgttgcctag tgaataagca     720
taatggtaca actacaagtg ttttactcct catattaact tcggtcatta gaggccacga     780
tttgacacat ttttactcaa aacaaaatgt ttgcatatct cttataattt caaattcaac     840
acacaacaaa taagagaaaa aacaaataat attaatttga gaatgaacaa aaggaccata     900
tcattcatta actcttctcc atccatttcc atttcacagt tcgatagcga aaaccgaata     960
aaaaacacag taaattacaa gcacaacaaa tggtacaaga aaaacagttt tcccaatgcc    1020
ataatactca aactcagtag gattctggtg tgtgcgcaat gaaactgatg cattgaactt    1080
gacgaacgtt gtcgaaaccg atgatacgaa cgaaagctag gcctcagcga gtaccgctgg    1140
cgatctaatc catgatatcg tgaacatcat ctacattcaa attcttatga gctttcttaa    1200
gggcatctgc agcattttc atagaatcta atacagcagt atttgtgcta gctccttcga    1260
gggcttccct ctgcatttca atagttgtaa gggttccatc tatttgtagt tgggtctttt    1320
ccaatcgttt cttctttttg agggcttgga gtgcaactct tttatttttc gacgcatttt    1380
tctttgcgct cctgcaggcg gccgcgtgga tgaggagtta atcggtcgtg tgagagtagt    1440
gatcgagtgg atgtcgtcga gagtgatgag tgttgatgtt gttagtgata tgtggtagaa    1500
ggtatcgtga taaagcgtta acgcgatcgc agtacttgca agaaaaatg cgtcgaaaaa     1560 taaaagagtt gcactccaag ccctcaaaaa gaagaaacga ttggaaaaga cccaactaca    1620
aatagatgga acccttacaa ctattgaaat gcagagggaa gccctcgaag gagctagcac    1680
aaatactgct gtattagatt ctatgaaaaa tgctgcagat gcccttaaga aagctcataa    1740
```

```
gaatttgaat gtagatgatg ttcacgatat catggatggt atcgcacagc gactgctgag   1800
ggacgtcgag ctcccgcttg gtatctgcat tacaatgaaa tgagcaaaga ctatgtgagt   1860
aacactggtc aacactaggg agaaggcatc gagcaagata cgtatgtaaa gagaagcaat   1920
atagtgtcag ttggtagata ctagatacca tcaggaggta aggagagcaa caaaaaggaa   1980
actctttatt tttaaatttt gttacaacaa acaagcagat caatgcatca aaatactgtc   2040
agtacttatt tcttcagaca acaatattta aacaagtgc atctgatctt gacttatggt    2100
cacaataaag gagcagagat aaacatcaaa atttcgtcat ttatatttat tccttcaggc   2160
gttaacaatt taacagcaca caaacaaaaa cagaatagga atatctaatt ttggcaaata   2220
ataagctctg cagacgaaca aattattata gtatcgccta atatgaat ccctatacta     2280 ttgacccatg tagtatgaag cctgtgccta aattaacagc aaacttctga atccaagtgc   2340
cctataacac caacatgtgc ttaaataaat accgctaagc accaaattac acatttctcg   2400
tattgctgtg taggttctat cttcgtttcg tactaccatg tccctatatt ttgctgctac   2460
aaaggacggc aagtaatcag cacaggcaga acacgatttc agagtgtaat tctagatcca   2520
gctaaaccac tctcagcaat caccacacaa gagagcattc agagaaacgt ggcagtaaca   2580
aaggcagagg gcggagtgag cgcgtaccga agacggttca gcgtgtcctc tccaaatgaa   2640
atgaacttcc ttatatagag gaagggtctt gcgaaggata gtgggattgt gcgtcatccc   2700
ttacgtcagt ggagatatca catcaatcca cttgctttga agacgtggtt ggaacgtctt   2760
ctttttccac gatgctcctc gtgggtgggg gtccatcttt gggaccactg tcggcagagg   2820
catcttcaac gatggccttt cctttatcgc aatgatggca tttgtaggag ccaccttcct   2880
tttccactat cttcacaata aagtgacaga tagctgggca atggaatccg aggaggtttc   2940
cggatattac cctttgttga aaagtctcaa tcggaccatc acatcaatcc acttgctttg   3000
aagacgtggt tggaacgtct tcttttttcca cgatgctcct cgtgggtggg ggtccatctt   3060
tgggaccact gtcggcagag gcatcttcaa cgatggcctt tcctttatcg caatgatggc   3120
atttgtagga gccaccttcc ttttccacta tcttcacaat aaagtgacag atagctgggc   3180
aatggaatcc gaggaggttt ccggatatta ccctttgttg aaaagtctca atcggacctg   3240
cagcctgcag gctagcggcg cgccggaagc taactagtca cggcgaatac atgacgacat   3300
cggcctacaa cgcacaactt cttggcataa agcttcaat ttcaatgccc ctatctggaa    3360
gccctaggcg ccgcgcaaat gtaaaacatt cgcttcgctt ggcttgttat ccaaaataga   3420
gtatggacct ccgacagatt ggcaacccgt gggtaatcga aaatggctcc atctgccct    3480 ttgtcgaagg aatcaggaaa cggccctcac ctcctggcgg agtgtagata tgtgaaagaa   3540
tctaggcgac acttgcagac tggacaacat gtgaacaaat aagaccaacg ttatggcaac   3600
aagcctcgac gctactcaag tggtgggagg ccaccgcatg ttccaacgaa gcgccaaaga   3660
aagccttgca gactctaatg ctattagtcg cctaggatat ttggaatgaa aggaaccgca   3720 gagttttca gcaccaagag cttccggtgg ctagtctgat agccaaaatt aaggaggatg    3780
ccaaaacatg ggtcttggcg ggcgcgaaac accttgatag gtggcttacc ttttaacatg   3840
ttcgggccaa aggccttgag acggtaaagt tttctatttg cgcttgcgca tgtacaattt   3900
tattcctcta ttcaatgaaa ttggtggctc actggttcat taaaaaaaaa agaatctagc   3960
ctgttcggga agaagaggat tttattcgtg agagagagag agagagagag agagagaggg   4020
agagagaagg aggaggagga ttttcaggct tcgcattgcc caacctctgc ttctgttggc   4080
```

```
ccaagaagaa tcccaggcgc ccatgggctg gcagtttacc acggacctac ctagcctacc    4140
ttagctatct aagcgggccg acctagtagc tacgtgccta gtgtagatta aagttggcgg    4200
gccagcagga agccacgctg caatggcatc ttcccctgtc cttcgcgtac gtgaaaacaa    4260
acccaggtaa gcttagaatc ttcttgcccg ttggactggg acacccacca atcccaccat    4320
gccccgatat tcctccggtc tcggttcatg tgatgtcctc tcttgtgtga tcacggagca    4380
agcattctta aacggcaaaa gaaaatcacc aacttgctca cgcagtcacg ctgcaccgcg    4440
cgaagcgacg cccgataggc caagatcgcg agataaaata caaccaatg atcataagga    4500 aacaagcccg cgatgtgtcg tgtgcagcaa tcttggtcat ttgcgggatc gagtgcttca    4560
cggctaacca aatattcggc cgatgattta acacattatc agcgtagatg tacgtacgat    4620
ttgttaatta atctacgagc cttgctaggg caggtgttct gccagccaat ccagatcgcc    4680
ctcgtatgca cgctcacatg atggcagggc agggttcaca tgagctctaa cggtcgatta    4740
attaatcccg gggctcgact ataaatacct ccctaatccc atgatcaaaa ccccgggaa    4800 ccatcttcca cacactcaag ccacactatt ggagaacaca cagggacaac acaccataag    4860
atccaaggga ggcctccgcc gccgccggta accaccccgc ccctctcctc tttctttctc    4920
cgtttttttt tccgtctcgg tctcgatctt tggccttggt agtttgggtg ggcgagaggc    4980
ggcttcgtgc gcgcccagat cggtgcgcgg gaggggcggg atctcgcggc tggggctctc    5040
gccggcgtga tccggcccg gatctcgcgg ggaatgggc tctcggatgt agatctgcga    5100
tccgccgttg ttgggggaga tgatgggggg tttaaaattt ccgccgtgct aaacaagatc    5160
aggaagaggg gaaagggca ctatggttta tattttata tatttctgct gcttcgtcag    5220
gcttagatgt gctagatctt tctttcttct ttttgtgggt agaatttgaa tccctcagca    5280
ttgttcatcg gtagttttc ttttcatgat ttgtgacaaa tgcagcctcg tgcggagctt    5340
ttttgtaggt agaagtgatc aaccatggcc aaccccaaca atcgctccga gcacgacacg    5400
atcaaggtca cccccaactc cgagctccag accaaccaca accagtaccc gctggccgac    5460
aaccccaact ccaccctgga agagctgaac tacaaggagt tcctgcgcat gaccgaggac    5520
tcctccacga aggtcctgga caactccacc gtcaaggacg ccgtcgggac cggcatctcc    5580
gtcgttgggc agatcctggg cgtcgttggc gtcccttcg caggtgctct cacctccttc    5640
taccagtcct tcctgaacac catctggccc tccgacgccg accctgaa ggccttcatg    5700 gcccaagtcg aagtcctgat cgacaagaag atcgaggagt acgccaagtc caaggccctg    5760
gccgagctgc aaggcctgca aaacaacttc gaggactacg tcaacgcgct gaactcctgg    5820
aagaagacgc ctctgtccct gcgctccaag cgctcccagg accgcatccg cgagctgttc    5880
tcccaggccg agtcccactt ccgcaactcc atgccgtcct tcgccgtctc caagttcgag    5940
gtcctgttcc tgcccaccta cgcccaggct gccaacaccc acctcctgtt gctgaaggac    6000
gcccaggtct tcggcgagga atggggctac tcctcggagg acgtcgccga gttctaccgt    6060
cgccagctga agctgaccca acagtacacc gaccactgcg tcaactggta caacgtcggc    6120
ctgaacggcc tgaggggctc cacctacgac gcatgggtca agttcaaccg cttccgcagg    6180
gagatgaccc tgaccgtcct ggacctgatc gtcctgttcc ccttctacga catccgcctg    6240
tactccaagg gcgtcaagac cgagctgacc cgcgacatct tcacggaccc catcttcctg    6300
ctcacgaccc tccagaagta cggtcccacc ttcctgtcca tcgagaactc catccgcaag    6360
ccccacctgt tcgactacct ccagggcatc gagttccaca cgcgcctgag gccaggctac    6420
ttcggcaagg actccttcaa ctactggtcc ggcaactacg tcgagaccag gcctccatc    6480
```

```
ggctcctcga agacgatcac ctcccctttc tacggcgaca agtccaccga gcccgtccag   6540
aagctgtcct tcgacggcca gaaggtctac cgcaccatcg ccaacaccga cgtcgcggct   6600
tggccgaacg gcaaggtcta cctgggcgtc acgaaggtcg acttctccca gtacgatgac   6660
cagaagaaca agacctccac ccagacctac gactccaagc gcaacaatgg ccacgtctcc   6720
gcccaggact ccatcgacca gctgccgcct gagaccactg acgagcccct ggagaaggcc   6780
tactcccacc agctgaacta cgcggagtgc ttcctgatgc aagaccgcag gggcaccatc   6840
cccttcttca cctggaccca ccgctccgtc gacttcttca acaccatcga cgccgagaag   6900
atcacccagc tgcccgtggt caaggcctac gccctgtcct cgggtgcctc catcattgag   6960
ggtccaggct tcaccggtgg caacctgctg ttcctgaagg agtcctcgaa ctccatcgcc   7020
aagttcaagg tcaccctgaa ctccgctgcc ttgctgcaac gctaccgcgt ccgcatccgc   7080
tacgcctcca ccacgaacct gcgcctgttc gtccagaact ccaacaatga cttcctggtc   7140
atctacatca acaagaccat gaacaaggac gatgacctga cctaccagac cttcgacctc   7200
gccaccacga actccaacat gggcttctcg ggcgacaaga atgaactgat cattggtgct   7260
gagtccttcg tctccaacga gaagatctac atcgacaaga tcgagttcat ccccgtccag   7320
ctgtgatagg aactctgatt gaattctgca tgcgtttgga cgtatgctca ttcaggttgg   7380
agccaatttg gttgatgtgt gtgcgagttc ttgcgagtct gatgagacat ctctgtattg   7440
tgtttctttc cccagtgttt tctgtacttg tgtaatcggc taatcgccaa cagattcggc   7500
gatgaataaa tgagaaataa attgttctga ttttgagtgc aaaaaaaaag gaattagatc   7560
tgtgtgtgtt ttttggatcc cattttcgac aagcttgcct cgagacaaca acatgcttct   7620
catcaacatg gagggaagag ggagggagaa agtgtcgcct ggtcacctcc attgtcacac   7680
tagccactgg ccagctctcc cacaccacca atgcaggggg cgagctttag cacagccacc   7740
gcttcacctc caccaccgca ctaccctagc ttcgcccaac agccaccgtc aacgcctcct   7800
ctccgtcaac ataagagaga gagagaagag gagagtagcc atgtggggag gaggaatagt   7860
acatggggcc taccgtttgg caagttattt tgggttgcca agttaggcca ataaggggag   7920
ggatttggcc atccggttgg aaaggttatt ggggtagtat cttttactaa gaattgtcaa   7980
aaaaaaatag tttgagagcc atttggagag gatgttgcct gttagaggtg ctcttaggac   8040
atcaaattcc ataaaaacat cagaaaaatt ctctcgatga agatttataa ccactaaaac   8100
tgccctcaat tcgaagggag ttcaaaacaa ttaaaatcat gttcgaattg agtttcaatt   8160
tcactttaac cccttttgaaa tctcaatggt aaaacatcaa cccgtcaggt agcatggttc   8220 ttttttattcc tttcaaaaag agttaattac aaacagaatc aaaactaaca gttaggccca   8280
aggcccatcc gagcaaacaa tagatcatgg gccaggcctg ccaccaccct ccccctcctg   8340
gctcccgctc ttgaatttca aaatccaaaa atatcggcac gactggccgc cgacggagcg   8400
ggcggaaaat gacggaacaa cccctcgaat tctaccccaa ctacgcccac caacccacac   8460
gccactgaca atccggtccc acccttgtgg gcccacctac aagcgagacg tcagtcgctc   8520
gcagcaacca gtgggcccac ctcccagtga gcggcgggta gatctggact cttacccacc   8580
cacactaaac aaaacggcat gaatattttg cactaaaacc ctcagaaaaa ttccgatatt   8640
ccaaaccagt acagttcctg accgttggag gagccaaagt ggagcggagt gtaaaattgg   8700
gaaacttaat cgaggggggtt aaacgcaaaa acgccgaggc gcctcccgct ctatagaaag   8760
gggaggagtg ggaggtggaa accctaccac accgcagaga aaggcgtctt cgtactcgcc   8820
```

```
tctctccgcg ccctcctccg ccgccgctcg ccgccgttcg tctccgccgc caccggctag    8880
ccatccaggt aaaacaaaca aaaacggatc tgatgcttcc attcctccgt ttctcgtagt    8940
agcgcgcttc gatctgtggg tggatctggg tgatcctggg gtgtggttcg ttctgtttga    9000
tagatctgtc ggtggatctg gccttctgtg gttgtcgatg tccggatctg cgttttgatc    9060
agtggtagtt cgtggatctg gcgaaatgtt ttggatctgg cagtgagacg ctaagaatcg    9120
ggaaatgatg caatattagg ggggtttcgg atggggatcc actgaattag tctgtctccc    9180
tgctgataat ctgttccttt ttggtagatc tggttagtgt atgtttgttt cggatagatc    9240
tgatcaatgc ttgtttgttt tttcaaattt tctacctagg ttgtatagga atggcatgcg    9300
gatctggttg gattgccatg atccgtgctg aaatgcccct ttggttgatg gatcttgata    9360
ttttactgct gttcacctag atttgtactc ccgtttatac ttaatttgtt gcttattatg    9420
aatagatctg taacttaggc acatgtatgg acggagtatg tggatctgta gtatgtacat    9480
tgctgcgagc taagaactat ttcagagcaa gcacagaaaa aaatatttag acagattggg    9540
caactatttg atggtctttg gtatcatgct ttgtagtgct cgtttctgcg tagtaatctt    9600
ttgatctgat ctgaagatag gtgctattat attcttaaag gtcattagaa cgctatctga    9660
aaggctgtat tatgtggatt ggttcacctg tgactccctg ttcgtcttgt cttgataaat    9720
cctgtgataa aaaaaattct taaggcgtaa tttgttgaaa tcttgttttg tcctatgcag    9780
cctgatccat ggcgcaagtt agcagaatct gcaatggtgt gcagaaccca tctcttatct    9840
ccaatctctc gaaatccagt caacgcaaat ctcccttatc ggtttctctg aagacgcagc    9900
agcatccacg agcttatccg atttcgtcgt cgtggggatt gaagaagagt gggatgacgt    9960
taattggctc tgagcttcgt cctcttaagg tcatgtcttc tgtttccacg gcgtgcatgc   10020
ttcacggtgc aagcagccgg cccgcaaccg cccgcaaatc ctctggcctt tccgaaccg    10080
tccgcattcc cggcgacaag tcgatctccc accggtcctt catgttcggc ggtctcgcga   10140
gcggtgaaac gcgcatcacc ggccttctgg aaggcgagga cgtcatcaat acgggcaagg   10200
ccatgcaggc gatgggcgcc cgcatccgta aggaaggcga cacctggatc atcgatggcg   10260
tcggcaatgg cggcctcctg gcgcctgagg cgccgctcga tttcggcaat gccgccacgg   10320
gctgccgcct gacgatgggc ctcgtcgggg tctacgattt cgacagcacc ttcatcggcg   10380
acgcctcgct cacaaagcgc ccgatgggcc gcgtgttgaa cccgctgcgc gaaatgggcg   10440
tgcaggtgaa atcggaagac ggtgaccgtc ttcccgttac cttgcgcggg ccgaagacgc   10500
cgacgccgat cacctaccgc gtgccgatgg cctccgcaca ggtgaagtcc gccgtgctgc   10560
tcgccggcct caacacgccc ggcatcacga cggtcatcga gccgatcatg acgcgcgatc   10620
atacggaaaa gatgctgcag ggcttttggcg ccaaccttac cgtcgagacg gatgcggacg   10680
gcgtgcgcac catccgcctg gaaggccgcg gcaagctcac cggccaagtc atcgacgtgc   10740
cgggcgaccc gtcctcgacg gccttccgc tggttgcggc cctgcttgtt ccgggctccg   10800
acgtcaccat cctcaacgtg ctgatgaacc ccacccgcac cggcctcatc ctgacgctgc   10860
aggaaatggg cgccgacatc gaagtcatca acccgcgcct tgccggcggc gaagacgtgg   10920
cggacctgcg cgttcgctcc tccacgctga agggcgtcac ggtgccggaa gaccgcgcgc   10980
cttcgatgat cgacgaatat ccgattctcg ctgtcgccgc cgccttcgcg aaggggcga    11040
ccgtgatgaa cggtctggaa gaactccgcg tcaaggaaag cgaccgcctc tcggccgtcg   11100
ccaatggcct caagctcaat ggcgtggatt gcgatgaggg cgagacgtcg ctcgtcgtgc   11160
gtggccgccc tgacggcaag gggctcggca acgcctcggg cgccgccgtc gccacccatc   11220
```

```
tcgatcaccg catcgccatg agcttcctcg tcatgggcct cgtgtcggaa aaccctgtca    11280
cggtggacga tgccacgatg atcgccacga gcttcccgga gttcatggac ctgatggccg    11340
ggctgggcgc gaagatcgaa ctctccgata cgaaggctgc ctgatgagct ccagggttct    11400
tgcctggtgc cttggcaatg cttgattact gctgctatcc tatgatctgt ccgtgtgggc    11460
ttctatctat cagtttgtgt gtctggtttt gaaaaacatt tgcttttcga ttatgtaggg    11520
tttgcttgta gctttcgctg ctgtgacctg tgttgtttat gtgaaccttc tttgtggcat    11580
ctttaatatc caagttcgtg gtttgtcgta aaacgaagcc tctacttcgt aaagttgtgt    11640
ctatagcatt gaaatcgttt ttttgctcga gaataattgt gacctttagt tggcgtgaaa    11700
ctagttttgg atatctgatt ctctggttcg caatcttgag atcgtcgctg cttaggtgag    11760
ctaagtgatg ttcctaagta aatgctcctc accagaatac gtagctgtgt gaaaagagaa    11820
cgcgtgaata cgtagctgtg taaagattgt gtcccaagta aacctcagtg atttttgttt    11880 ggattttttaa tttagaaaca ttcgactggg agcggctaga gccacaccca agttcctaac    11940
tatgataaag ttgctctgta acagaaaaca ccatctagag cggccgcgtt taaactatca    12000
gtgtttgaca ggatatattg gcgggtaaac ctaagagaaa agagcgttta ttagaataat    12060
cggatattta aagggcgtg aaaaggttta ccgttcgtc catttgtatg tgcatgccaa    12120
ccacagggtt cccctcggga gtgcttggca ttccgtgcga taatgacttc tgttcaacca    12180
cccaaacgtc ggaaagcctg acgacggagc agcattccaa aaagatccct tggctcgtct    12240
gggtcggcta gaaggtcgag tgggctgctg tggcttgatc cctcaacgcg gtcgcggacg    12300
tagcgcagcg ccgaaaaatc ct                                             12322
```

<210> SEQ ID NO 28
<211> LENGTH: 11787
<212> TYPE: DNA
<213> ORGANISM: Artificial Sequence
<220> FEATURE:
<223> OTHER INFORMATION: DNA construct 418

<400> SEQUENCE: 28

```
aaaagtccca tgtggatcac tccgttgccc cgtcgctcac cgtgttgggg ggaaggtgca      60
catggctcag ttctcaatgg aaattatctg cctaaccggc tcagttctgc gtagaaacca    120
acatgcaagc tccaccgggt gcaaagcggc agcggcggca ggatatattc aattgtaaat    180
ggcttcatgt ccgggaaatc tacatggatc agcaatgagt atgatggtca atatggagaa    240
aaagaaagag taattaccaa ttttttttca attcaaaaat gtagatgtcc gcagcgttat    300
tataaaatga agtacatttt tgataaaacg acaaattacg atccgtcgta tttataggcg    360
aaagcaataa acaaattatt ctaattcgga aatctttatt tcgacgtgtc tacattcacg    420
tccaaatggg ggcttagatg agaaacttca cgatcgatgc ggccaccact cgaggtcgag    480
gtaccgttgt caatcaattg gcaagtcata aaatgcatta aaaatatttt tcatactcaa    540
ctacaaatcc atgagtataa ctataattat aaagcaatga ttagaatctg acaaggattc    600
tggaaaatta cataaaggaa agttcataaa tgtctaaaac acaagaggac atacttgtat    660
tcagtaacat ttgcagcttt tctaggtctg aaaatatatt tgttgcctag tgaataagca    720
taatggtaca actacaagtg ttttactcct catattaact tcggtcatta gaggccacga    780
tttgacacat ttttactcaa aacaaaatgt ttgcatatct cttataattt caaattcaac    840
acacaacaaa taagagaaaa aacaaataat attaatttga gaatgaacaa aaggaccata    900
```

```
tcattcatta actcttctcc atccatttcc atttcacagt tcgatagcga aaaccgaata    960
aaaaacacag taaattacaa gcacaacaaa tggtacaaga aaaacagttt tcccaatgcc   1020
ataatactca aactcagtag gattctggtg tgtgcgcaat gaaactgatg cattgaactt   1080
gacgaacgtt gtcgaaaccg atgatacgaa cgaaagctag gcctcagcga gtaccgctgg   1140
cgatctaatc catgatatcg tgaacatcat ctacattcaa attcttatga gctttcttaa   1200
gggcatctgc agcatttttc atagaatcta atacagcagt atttgtgcta gctccttcga   1260
gggcttccct ctgcatttca atagttgtaa gggttccatc tatttgtagt tgggtctttt   1320
ccaatcgttt cttcttttg agggcttgga gtgcaactct tttatttttc gacgcatttt   1380
tctttgcgct cctgcaggcg gccgcgtgga tgaggagtta atcggtcgtg tgagagtagt   1440
gatcgagtgg atgtcgtcga gagtgatgag tgttgatgtt gttagtgata tgtggtagaa   1500
ggtatcgtga taaagcgtta acgcgatcgc agtacttgca aagaaaaatg cgtcgaaaaa   1560
taaaagagtt gcactccaag ccctcaaaaa gaagaaacga ttggaaaaga cccaactaca   1620
aatagatgga acccttacaa ctattgaaat gcagagggaa gccctcgaag gagctagcac   1680
aaatactgct gtattagatt ctatgaaaaa tgctgcagat gcccttaaga aagctcataa   1740
gaatttgaat gtagatgatg ttcacgatat catggatggc atcgcacagc gactgctgag   1800
ggacgtcgag ctcccgcttg gtatctgcat tacaatgaaa tgagcaaaga ctatgtgagt   1860
aacactggtc aacactaggg agaaggcatc gagcaagata cgtatgtaaa gagaagcaat   1920
atagtgtcag ttggtagata ctagatacca tcaggaggta aggagagcaa caaaaaggaa   1980
actctttatt tttaaatttt gttacaacaa acaagcagat caatgcatca aaatactgtc   2040
agtacttatt tcttcagaca acaatattta aaacaagtgc atctgatctt gacttatggt   2100
cacaataaag gagcagagat aaacatcaaa atttcgtcat ttatatttat tccttcaggc   2160
gttaacaatt taacagcaca caaacaaaaa cagaatagga atatctaatt ttggcaaata   2220
ataagctctg cagacgaaca aattattata gtatcgccta taatgaatc cctatacta   2280
ttgacccatg tagtatgaag cctgtgccta aattaacagc aaacttctga atccaagtgc   2340
cctataacac caacatgtgc ttaaataaat accgctaagc accaaattac acatttctcg   2400
tattgctgtg taggttctat cttcgtttcg tactaccatg tccctatatt ttgctgctac   2460
aaaggacggc aagtaatcag cacaggcaga acacgatttc agagtgtaat tctagatcca   2520
gctaaaccac tctcagcaat caccacacaa gagagcattc agagaaacgt ggcagtaaca   2580
aaggcagagg gcggagtgag cgcgtaccga agacggttca gcgtgtcctc tccaaatgaa   2640
atgaacttcc ttatatagag gaagggtctt gcgaaggata gtgggattgt gcgtcatccc   2700
ttacgtcagt ggagatatca catcaatcca cttgctttga agacgtggtt ggaacgtctt   2760
cttttttccac gatgctcctc gtgggtgggg gtccatcttt gggaccactg tcggcagagg   2820
catcttcaac gatggccttt cctttatcgc aatgatggca tttgtaggag ccacttcct   2880
tttccactat cttcacaata aagtgacaga tagctgggca atggaatccg aggaggtttc   2940
cggatattac cctttgttga aaagtctcaa tcggaccatc acatcaatcc acttgctttg   3000
aagacgtggt tggaacgtct tcttttttcca cgatgctcct cgtgggtggg ggtccatctt   3060
tgggaccact gtcggcagag gcatcttcaa cgatggcctt tcctttatcg caatgatggc   3120
atttgtagga gccaccttcc ttttccacta tcttcacaat aaagtgacag atagctgggc   3180
aatggaatcc gaggaggttt ccggatatta cccttgttg aaaagtctca atcggacctg   3240
cagcctgcag gctagcggcg cgccgggatc caaaaaacac acacagatct aattccttt   3300
```

```
tttttgcact caaaatcaga acaatttatt tctcatttat tcatcgccga atctgttggc    3360
gattagccga ttacacaagt acagaaaaca ctggggaaag aaacacaata cagagatgtc    3420
tcatcagact cgcaagaact cgcacacaca tcaaccaaat tggctccaac ctgaatgagc    3480
atacgtccaa acgcatgcag aattcaatca gagttcctat cacagctgga cggggatgaa    3540
ctcgatcttg tcgatgtaga tcttctcgtt ggagacgaag gactcagcac caatgatcag    3600
ttcattcttg tcgcccgaga agcccatgtt ggagttcgtg gtggcgaggt cgaaggtctg    3660
gtaggtcagg tcatcgtcct tgttcatggt cttgttgatg tagatgacca ggaagtcatt    3720
gttggagttc tggacgaaca ggcgcaggtt cgtggtggag gcgtagcgga tgcggacgcg    3780
gtagcgttgc agcaaggcag cggagttcag ggtgaccttg aacttggcga tggagttcga    3840
ggactccttc aggaacagca ggttgccacc ggtgaagcct ggaccctcaa tgatggaggc    3900
acccgaggac agggcgtagg ccttgaccac gggcagctgg gtgatcttct cggcgtcgat    3960
ggtgttgaag aagtcgacgg agcggtgggt ccaggtgaag aaggggatgg tgcccctgcg    4020
gtcttgcatc aggaagcact ccgcgtagtt cagctggtgg gagtaggcct tctccagggg    4080
ctcgtcagtg gtctcaggcg gcagctggtc gatggagtcc tgggcggaga cgtggccatt    4140
gttgcgcttg gagtcgtagg tctgggtgga ggtctcgttc ttctggtcat cgtactggga    4200
gaagtcgacc ttcgtgacgc ccaggtagac cttgccgttc ggccaagccg cgacgtcggt    4260
gttggcgatg gtgcggtaga ccttctggcc gtcgaaggac agcttctgga cgggctcggt    4320
ggacttgtcg ccgtagaaag gggaggtgat cgtcttcgag gagccgatgg agggcctggt    4380
ctcgacgtag ttgccggacc agtagttgaa ggagtccttg ccgaagtagc ctggcctcag    4440
gcgcgtgtgg aactcgatgc cctggaggta gtcgaacagg tggggcttgc ggatggagtt    4500
ctcgatggac aggaaggtgg gaccgtactt ctggagggtc gtgagcagga agatgggggtc    4560 cgtgaagatg tcgcgggtca gctcggtctt gacgcccttg gagtacaggc ggatgtcgta    4620 gaagggaac aggacgatca ggtccaggac ggtcagggtc atctccctgc ggaagcggtt    4680
gaacttgacc catgcgtcgt aggtggagcc cctcaggccg ttcaggccga cgttgtacca    4740
gttgacgcag tggtcggtgt actgttgggt cagcttcagc tggcgacggt agaactcggc    4800
gacgtcctcc gaggagtagc cccattcctc gccgaagacc tgggcgtcct tcagcaacag    4860
gaggtgggtg ttggcagcct gggcgtaggt ggcaggaac aggacctcga acttggagac    4920
ggcgaaggac ggcatggagt tgcggaagtg ggactcggcc tgggagaaca gctcgcggat    4980
gcggtcctgg gagcgcttgg agcgcaggga cagaggcgtc ttcttccagg agttcagcgc    5040
gttgacgtag tcctcgaagt tgttttgcag gccttgcagc tcggccaggg ccttggactt    5100
ggcgtactcc tcgatcttct tgtcgatcag gacttcgact tgggccatga aggccttcca    5160
ggggtcggcg tcggagggcc agatggtgtt caggaaggac tggtagaagg aggtgagagc    5220
acctgcgaag gggacgccaa cgacgcccag gatctgccca acgacggaga tgccggtccc    5280
gacggcgtcc ttgacggtgg agttgtccag gacctccgtg gaggagtcct cggtcatgcg    5340
caggaactcc ttgtagttca gctcttccag ggtggagttg gggttgtcgg ccagcgggta    5400
ctggttgtgg ttggtctgga gctcggagtt ggggtgacc ttgatcgtgt cgtgctcgga    5460
gcgattgttg gggttggcca tggttgatca cttctaccta caaaaaagct ccgcacgagg    5520
ctgcatttgt cacaaatcat gaaaagaaaa actaccgatg aacaatgctg agggattcaa    5580
attctaccca caaaaagaag aaagaaagat ctagcacatc taagcctgac gaagcagcag    5640
```

| | |
|---|---|
| aaatatataa aaatataaac catagtgccc ttttcccctc ttcctgatct tgtttagcac | 5700 |
| ggcggaaatt ttaaaccccc catcatctcc cccaacaacg gcggatcgca gatctacatc | 5760 |
| cgagagcccc attcccgcg agatccgggc cggatccacg ccggcgagag ccccagccgc | 5820 |
| gagatcccgc ccctcccgcg caccgatctg ggcgcgcacg aagccgcctc tcgcccaccc | 5880 |
| aaactaccaa ggccaaagat cgagaccgag acggaaaaaa aaacggagaa agaaagagga | 5940 |
| gaggggcggg gtggttaccg gcggcggcgg aggcctccct tggatcttat ggtgtgttgt | 6000 |
| ccctgtgtgt tctccaatag tgtggcttga gtgtgtggaa gatggttccc ggggtatctg | 6060 |
| atgatccttc aaatgggaat gaatgccttc ttatatagag ggaattcttt tgtggtcgtc | 6120 |
| actgcgttcg tcatacgcat tagtgagtgg gctgtcagga cagctctttt ccacgttatt | 6180 |
| ttgttcccca cttgtactag aggaatctgc tttatctttg caataaaggc aaagatgctt | 6240 |
| ttggtaggtg cgcctaacaa ttctgcacca ttccttttt gtctggtccc cacaagccag | 6300 |
| ctgctcgatg ttgacaagat tactttcaaa gatgcccact aactttaagt cttcggtgga | 6360 |
| tgtcttttc tgaaacttac tgaccatgat gcatgtgctg aacagtagt ttactttgat | 6420 |
| tgaagattct tcattgatct cctgtagctt ttggctaatg gtttggagac tctgtaccct | 6480 |
| gaccttgttg aggctttgga ctgagaattc ttccttacaa acctttgagg atgggagttc | 6540 |
| cttcttggtt ttggcgatac caatttgaat aaagtgatat ggctcgtacc ttgttgattg | 6600 |
| aacccaatct ggaatgctgc taaatcctga gctcaagcta attcttttgt ggtcgtcact | 6660 |
| gcgttcgtca tacgcattag tgagtgggct gtcaggacag ctcttttcca cgttattttg | 6720 |
| ttccccactt gtactagagg aatctgcttt atctttgcaa taaaggcaaa gatgcttttg | 6780 |
| gtaggtgcgc ctaacaattc tgcaccattc ctttttgtc tggtcccac aagccagctg | 6840 |
| ctcgatgttg acaagattac tttcaaagat gcccactaac tttaagtctt cggtggatgt | 6900 |
| cttttctga acttactga ccatgatgca tgtgctggaa cagtagttta ctttgattga | 6960 |
| agattcttca ttgatctcct gtagcttttg gctaatggtt tggagactct gtaccctgac | 7020 |
| cttgttgagg ctttggactg agaattattt tcgacaagct tgcctcgaga caacaacatg | 7080 |
| cttctcatca acatggaggg aagagggagg gagaaagtgt cgcctggtca cctccattgt | 7140 |
| cacactagcc actggccagc tctcccacac caccaatgcc aggggcgagc tttagcacag | 7200 |
| ccaccgcttc acctccacca ccgcactacc ctagcttcgc ccaacagcca ccgtcaacgc | 7260 |
| ctcctctccg tcaacataag agagagagag aagaggagag tagccatgtg gggaggagga | 7320 |
| atagtacatg gggcctaccg tttggcaagt tattttgggt tgccaagtta ggccaataag | 7380 |
| gggagggatt tggccatccg gttggaaagg ttattggggt agtatctttt tactagaatt | 7440 |
| gtcaaaaaaa aatagtttga gagccatttg gagaggatgt tgcctgttag aggtgctctt | 7500 |
| aggacatcaa attccataaa aacatcagaa aaattctctc gatgaagatt tataaccact | 7560 |
| aaaactgccc tcaattcgaa gggagttcaa acaattaaa atcatgttcg aattgagttt | 7620 |
| caatttcact ttaaccccctt tgaaatctca atggtaaaac atcaacccgt caggtagcat | 7680 |
| ggttcttttt attcctttca aaagagtta attacaaaca gaatcaaaac taacagttag | 7740 |
| gcccaaggcc catccgagca acaatagat catgggccag gctgccacc accctccccc | 7800 |
| tcctggctcc cgctcttgaa tttcaaaatc caaaaatatc ggcacgactg gccgccgacg | 7860 |
| gagcgggcgg aaaatgacgg aacaaccct cgaattctac cccaactacg cccaccaacc | 7920 |
| cacacgccac tgacaatccg gtcccaccct tgtgggccca cctacaagcg agacgtcagt | 7980 |
| cgctcgcagc aaccagtggg cccaccctccc agtgagcggc gggtagatct ggactcttac | 8040 |

```
ccacccacac taaacaaaac ggcatgaata ttttgcacta aaaccctcag aaaaattccg    8100
atattccaaa ccagtacagt tcctgaccgt tggaggagcc aaagtggagc ggagtgtaaa    8160
attgggaaac ttaatcgagg gggttaaacg caaaaacgcc gaggcgcctc ccgctctata    8220
gaaaggggag gagtgggagg tggaaaccct accacaccgc agagaaaggc gtcttcgtac    8280
tcgcctctct ccgcgccctc ctccgccgcc gctcgccgcc gttcgtctcc gccgccaccg    8340
gctagccatc caggtaaaac aaacaaaaac ggatctgatg cttccattcc tccgtttctc    8400
gtagtagcgc gcttcgatct gtgggtggat ctgggtgatc ctggggtgtg gttcgttctg    8460
tttgatagat ctgtcggtgg atctggcctt ctgtggttgt cgatgtccgg atctgcgttt    8520
tgatcagtgg tagttcgtgg atctggcgaa atgttttgga tctggcagtg agacgctaag    8580
aatcgggaaa tgatgcaata ttagggggt tcggatggg gatccactga attagtctgt    8640
ctccctgctg ataatctgtt cctttttggt agatctggtt agtgtatgtt tgtttcggat    8700
agatctgatc aatgcttgtt tgttttttca aattttctac ctaggttgta taggaatggc    8760
atgcggatct ggttggattg ccatgatccg tgctgaaatg ccccttttggt tgatggatct    8820 tgatatttta ctgctgttca cctagatttg tactcccgtt tatacttaat ttgttgctta    8880
ttatgaatag atctgtaact taggcacatg tatggacgga gtatgtggat ctgtagtatg    8940
tacattgctg cgagctaaga actatttcag agcaagcaca gaaaaaaata tttagacaga    9000
ttgggcaact atttgatggt ctttggtatc atgctttgta gtgctcgttt ctgcgtagta    9060
atcttttgat ctgatctgaa gataggtgct attatattct taaaggtcat tagaacgcta    9120
tctgaaaggc tgtattatgt ggattggttc acctgtgact ccctgttcgt cttgtcttga    9180
taaatcctgt gataaaaaaa attcttaagg cgtaatttgt tgaaatcttg ttttgtccta    9240
tgcagcctga tccatggcgc aagttagcag aatctgcaat ggtgtgcaga acccatctct    9300
tatctccaat ctctcgaaat ccagtcaacg caaatctccc ttatcggttt ctctgaagac    9360
gcagcagcat ccacgagctt atccgatttc gtcgtcgtgg ggattgaaga agagtgggat    9420
gacgttaatt ggctctgagc ttcgtcctct taaggtcatg tcttctgttt ccacggcgtg    9480
catgcttcac ggtgcaagca gccggcccgc aaccgcccgc aaatcctctg gccttttccgg    9540 aaccgtccgc attcccggcg acaagtcgat ctcccaccgg tccttcatgt tcggcggtct    9600
cgcgagcggt gaaacgcgca tcaccggcct tctggaaggc gaggacgtca tcaatacggg    9660
caaggccatg caggcgatgg gcgcccgcat ccgtaaggaa ggcgacacct ggatcatcga    9720
tggcgtcggc aatggcggcc tcctggcgcc tgaggcgccg ctcgatttcg gcaatgccgc    9780
cacgggctgc cgcctgacga tgggcctcgt cggggtctac gatttcgaca gcaccttcat    9840
cggcgacgcc tcgctcacaa agcgcccgat gggccgcgtg ttgaacccgc tgcgcgaaat    9900
gggcgtgcag gtgaaatcgg aagacggtga ccgtcttccc gttaccttgc gcgggccgaa    9960
gacgccgacg ccgatcacct accgcgtgcc gatggcctcc gcacaggtga agtccgccgt   10020
gctgctcgcc ggcctcaaca cgcccggcat cacgacggtc atcgagccga tcatgacgcg   10080
cgatcatacg gaaaagatgc tgcagggctt tggcgccaac cttaccgtcg agacggatgc   10140
ggacggcgtg cgcaccatcc gcctggaagg ccgcggcaag ctcaccggcc aagtcatcga   10200
cgtgccgggc gacccgtcct cgacggcctt cccgctggtt gcggccctgc ttgttccggg   10260
ctccgacgtc accatcctca cgtgctgat gaacccacc cgcaccggcc tcatcctgac   10320
gctgcaggaa atgggcgccg acatcgaagt catcaacccg cgccttgccg gcggcgaaga   10380
```

```
cgtggcggac ctgcgcgttc gctcctccac gctgaagggc gtcacggtgc cggaagaccg    10440
cgcgccttcg atgatcgacg aatatccgat tctcgctgtc gccgccgcct tcgcggaagg    10500
ggcgaccgtg atgaacggtc tggaagaact ccgcgtcaag gaaagcgacc gcctctcggc    10560
cgtcgccaat ggcctcaagc tcaatggcgt ggattgcgat gagggcgaga cgtcgctcgt    10620
cgtgcgtggc cgccctgacg gcaaggggct cggcaacgcc tcgggcgccg ccgtcgccac    10680
ccatctcgat caccgcatcg ccatgagctt cctcgtcatg ggcctcgtgt cggaaaaccc    10740
tgtcacggtg gacgatgcca cgatgatcgc cacgagcttc ccggagttca tggacctgat    10800
ggccgggctg ggcgcgaaga tcgaactctc cgatacgaag gctgcctgat gagctccagg    10860
gttcttgcct ggtgccttgg caatgcttga ttactgctgc tatcctatga tctgtccgtg    10920
tgggcttcta tctatcagtt tgtgtgtctg gttttgaaaa acatttgctt ttcgattatg    10980
tagggtttgc ttgtagcttt cgctgctgtg acctgtgttg tttatgtgaa ccttctttgt    11040
ggcatcttta atatccaagt tcgtggtttg tcgtaaaacg aagcctctac ttcgtaaagt    11100
tgtgtctata gcattgaaat cgtttttttg ctcgagaata attgtgacct ttagttggcg    11160
tgaaactagt tttggatatc tgattctctg gttcgcaatc ttgagatcgt cgctgcttag    11220
gtgagctaag tgatgttcct aagtaaatgc tcctcaccag aatacgtagc tgtgtgaaaa    11280
gagaacgcgt gaatacgtag ctgtgtaaag attgtgtccc aagtaaacct cagtgatttt    11340
tgtttggatt tttaatttag aaacattcga ctggagcggc tagagccac acccaagttc     11400 ctaactatga taaagttgct ctgtaacaga aaacaccatc tagagcggcc gcgtttaaac    11460
tatcagtgtt tgacaggata tattggcggg taaacctaag agaaaagagc gtttattaga    11520
ataatcggat attttaaagg gcgtgaaaag gttttatccgt tcgtccattt gtatgtgcat    11580
gccaaccaca gggttcccct cgggagtgct tggcattccg tgcgataatg acttctgttc    11640
aaccacccaa acgtcggaaa gcctgacgac ggagcagcat tccaaaaaga tcccttggct    11700
cgtctgggtc ggctagaagg tcgagtgggc tgctgtggct tgatccctca acgcggtcgc    11760
ggacgtagcg cagcgccgaa aaatcct                                        11787
```

<210> SEQ ID NO 29
<211> LENGTH: 12322
<212> TYPE: DNA
<213> ORGANISM: Artificial Sequence
<220> FEATURE:
<223> OTHER INFORMATION: DNA construct 419

<400> SEQUENCE: 29

```
aaaagtccca tgtggatcac tccgttgccc cgtcgctcac cgtgttgggg ggaaggtgca      60
catggctcag ttctcaatgg aaattatctg cctaaccggc tcagttctgc gtagaaacca     120
acatgcaagc tccaccgggt gcaaagcggc agcggcggca ggatatattc aattgtaaat     180
ggcttcatgt ccgggaaatc tacatggatc agcaatgagt atgatggtca atatggagaa     240
aaagaaagag taattaccaa ttttttttca attcaaaaat gtagatgtcc gcagcgttat     300
tataaaatga agtacatttt tgataaaacg acaaattacg atccgtcgta tttataggcg     360
aaagcaataa acaaattatt ctaattcgga atctttatt tcgacgtgtc tacattcacg      420
tccaaatggg ggcttagatg agaaacttca cgatcgatgc ggccaccact cgaggtcgag     480
gtaccgttgt caatcaattg gcaagtcata aaatgcatta aaaatatttt tcatactcaa     540
ctacaaatcc atgagtataa ctataattat aaagcaatga ttagaatctg acaaggattc     600
tggaaaatta cataaaggaa agttcataaa tgtctaaaac acaagaggac atacttgtat     660
```

```
tcagtaacat ttgcagcttt tctaggtctg aaaatatatt tgttgcctag tgaataagca    720
taatggtaca actacaagtg ttttactcct catattaact tcggtcatta gaggccacga    780
tttgacacat ttttactcaa acaaaatgt ttgcatatct cttataattt caaattcaac    840
acacaacaaa taagagaaaa aacaaataat attaatttga gaatgaacaa aaggaccata    900
tcattcatta actcttctcc atccatttcc atttcacagt tcgatagcga aaaccgaata    960
aaaaacacag taaattacaa gcacaacaaa tggtacaaga aaaacagttt tcccaatgcc   1020
ataatactca aactcagtag gattctggtg tgtgcgcaat gaaactgatg cattgaactt   1080
gacgaacgtt gtcgaaaccg atgatacgaa cgaaagctag gcctcagcga gtaccgctgg   1140
cgatctaatc catgatatcg tgaacatcat ctacattcaa attcttatga gctttcttaa   1200
gggcatctgc agcattttc atagaatcta atacagcagt atttgtgcta gctccttcga    1260
gggcttccct ctgcatttca atagttgtaa gggttccatc tatttgtagt tgggtctttt   1320
ccaatcgttt cttcttttg agggcttgga gtgcaactct tttatttttc gacgcatttt    1380
tctttgcgct cctgcaggcg gccgcgtgga tgaggagtta atcggtcgtg tgagagtagt   1440
gatcgagtgg atgtcgtcga gagtgatgag tgttgatgtt gttagtgata tgtggtagaa   1500
ggtatcgtga taaagcgtta acgcgatcgc agtacttgca aagaaaaatg cgtcgaaaaa   1560
taaaagagtt gcactccaag ccctcaaaaa gaagaaacga ttggaaaaga cccaactaca   1620
aatagatgga acccttacaa ctattgaaat gcagagggaa gccctcgaag gagctagcac   1680
aaatactgct gtattagatt ctatgaaaaa tgctgcagat gcccttaaga aagctcataa   1740
gaatttgaat gtagatgatg ttcacgatat catggatggt atcgcacagc gactgctgag   1800
ggacgtcgag ctcccgcttg gtatctgcat tacaatgaaa tgagcaaaga ctatgtgagt   1860
aacactggtc aacactaggg agaaggcatc gagcaagata cgtatgtaaa gagaagcaat   1920
atagtgtcag ttggtagata ctagatacca tcaggaggta aggagagcaa caaaaaggaa   1980
actctttatt tttaaatttt gttacaacaa acaagcagat caatgcatca aaatactgtc   2040
agtacttatt tcttcagaca acaatattta aaacaagtgc atctgatctt gacttatggt   2100
cacaataaag gagcagagat aaacatcaaa atttcgtcat ttatatttat tccttcaggc   2160
gttaacaatt taacagcaca caaacaaaaa cagaatagga atatctaatt ttggcaaata   2220
ataagctctg cagacgaaca aattattata gtatcgccta taatatgaat ccctatacta   2280
ttgacccatg tagtatgaag cctgtgccta aattaacagc aaacttctga atccaagtgc   2340
cctataacac caacatgtgc ttaaataaat accgctaagc accaaattac acatttctcg   2400
tattgctgtg taggttctat cttcgtttcg tactaccatg tccctatatt ttgctgctac   2460
aaaggacggc aagtaatcag cacaggcaga acacgatttc agagtgtaat tctagatcca   2520
gctaaaccac tctcagcaat caccacacaa gagagcattc agagaaacgt ggcagtaaca   2580
aaggcagagg gcggagtgag cgcgtaccga agacggttca gcgtgtcctc tccaaatgaa   2640
atgaacttcc ttatatagag gaagggtctt gcgaaggata gtgggattgt gcgtcatccc   2700
ttacgtcagt ggagatatca catcaatcca cttgctttga agacgtggtt ggaacgtctt   2760
ctttttccac gatgctcctc gtgggtgggg gtccatcttt gggaccactg tcggcagagg   2820
catcttcaac gatggccttt cctttatcgc aatgatggca tttgtaggag ccaccttcct   2880
tttccactat cttcacaata aagtgacaga tagctgggca atggaatccg aggaggtttc   2940
cggatattac cctttgttga aaagtctcaa tcggaccatc acatcaatcc acttgctttg   3000
```

```
aagacgtggt tggaacgtct tctttttcca cgatgctcct cgtgggtggg ggtccatctt    3060
tgggaccact gtcggcagag gcatcttcaa cgatggcctt tcctttatcg caatgatggc    3120
atttgtagga gccaccttcc ttttccacta tcttcacaat aaagtgacag atagctgggc    3180
aatggaatcc gaggaggttt ccggatatta ccctttgttg aaaagtctca atcggacctg    3240
cagcctgcag gctagcggcg cgccgggatc caaaaaacac acacagatct aattcctttt    3300
tttttgcact caaaatcaga acaatttatt tctcatttat tcatcgccga atctgttggc    3360
gattagccga ttacacaagt acagaaaaca ctggggaaag aaacacaata cagagatgtc    3420
tcatcagact cgcaagaact cgcacacaca tcaaccaaat tggctccaac ctgaatgagc    3480
atacgtccaa acgcatgcag aattcaatca gagttcctat cacagctgga cggggatgaa    3540
ctcgatcttg tcgatgtaga tcttctcgtt ggagacgaag gactcagcac caatgatcag    3600
ttcattcttg tcgcccgaga agcccatgtt ggagttcgtg gtggcgaggt cgaaggtctg    3660
gtaggtcagg tcatcgtcct tgttcatggt cttgttgatg tagatgacca ggaagtcatt    3720
gttggagttc tggacgaaca ggcgcaggtt cgtggtggag gcgtagcgga tgcggacgcg    3780
gtagcgttgc agcaaggcag cggagttcag ggtgaccttg aacttggcga tggagttcga    3840
ggactccttc aggaacagca ggttgccacc ggtgaagcct ggaccctcaa tgatggaggc    3900
acccgaggac agggcgtagg ccttgaccac gggcagctgg gtgatcttct cggcgtcgat    3960
ggtgttgaag aagtcgacgg agcggtgggt ccaggtgaag aaggggatgg tgcccctgcg    4020
gtcttgcatc aggaagcact ccgcgtagtt cagctggtgg gagtaggcct tctccagggg    4080
ctcgtcagtg gtctcaggcg gcagctggtc gatggagtcc tgggcggaga cgtggccatt    4140
gttgcgcttg gagtcgtagg tctgggtgga ggtctcgttc ttctggtcat cgtactggga    4200
gaagtcgacc ttcgtgacgc ccaggtagac cttgccgttc ggccaagccg cgacgtcggt    4260
gttggcgatg gtgcggtaga ccttctggcc gtcgaaggac agcttctgga cgggctcggt    4320
ggacttgtcg ccgtagaaag gggaggtgat cgtcttcgag gagccgatgg agggcctggt    4380
ctcgacgtag ttgccggacc agtagttgaa ggagtccttg ccgaagtagc ctggcctcag    4440
gcgcgtgtgg aactcgatgc cctggaggta gtcgaacagg tggggcttgc ggatggagtt    4500
ctcgatggac aggaaggtgg gaccgtactt ctggagggtc gtgagcagga agatggggtc    4560
cgtgaagatg tcgcgggtca gctcggtctt gacgcccttg gagtacaggc ggatgtcgta    4620 gaagggaac aggacgatca ggtccaggac ggtcagggtc atctccctgc ggaagcggtt    4680
gaacttgacc catgcgtcgt aggtggagcc cctcaggccg ttcaggccga cgttgtacca    4740
gttgacgcag tggtcggtgt actgttgggt cagcttcagc tggcgacggt agaactcggc    4800
gacgtcctcc gaggagtagc cccattcctc gccgaagacc tgggcgtcct tcagcaacag    4860
gaggtgggtg ttggcagcct gggcgtaggt gggcaggaac aggacctcga acttggagac    4920
ggcgaaggac ggcatggagt tgcggaagtg ggactcggcc tggagaaca gctcgcggat    4980 gcggtcctgg gagcgcttgg agcgcaggga cagaggcgtc ttcttccagg agttcagcgc    5040
gttgacgtag tcctcgaagt tgttttgcag gccttgcagc tcggccaggg ccttggactt    5100
ggcgtactcc tcgatcttct tgtcgatcag gacttcgact tgggccatga aggccttcca    5160
ggggtcggcg tcggagggcc agatggtgtt caggaaggac tggtagaagg aggtgagagc    5220
acctgcgaag gggacgccaa cgacgcccag gatctgccca acgacggaga tgccggtccc    5280 gacgcgtcc ttgacggtgg agttgtccag gacctccgtg gaggagtcct cggtcatgcg    5340
caggaactcc ttgtagttca gctcttccag ggtggagttg gggttgtcgg ccagcgggta    5400
```

```
ctggttgtgg ttggtctgga gctcggagtt gggggtgacc ttgatcgtgt cgtgctcgga   5460
gcgattgttg gggttggcca tggttgatca cttctaccta caaaaaagct ccgcacgagg   5520
ctgcatttgt cacaaatcat gaaaagaaaa actaccgatg aacaatgctg agggattcaa   5580
attctaccca caaaagaag aaagaaagat ctagcacatc taagcctgac gaagcagcag    5640
aaatatataa aaatataaac catagtgccc ttttcccctc ttcctgatct tgtttagcac   5700
ggcggaaatt ttaaaccccc catcatctcc cccaacaacg gcggatcgca gatctacatc   5760
cgagagcccc attccccgcg agatccgggc cggatccacg ccggcgagag ccccagccgc   5820
gagatcccgc ccctcccgcg caccgatctg ggcgcgcacg aagccgcctc tcgcccaccc   5880
aaactaccaa ggccaaagat cgagaccgag acggaaaaaa aaacggagaa agaaagagga   5940
gaggggcggg gtggttaccg gcggcggcgg aggcctcct tggatcttat ggtgtgttgt    6000
ccctgtgtgt tctccaatag tgtggcttga gtgtgtggaa gatggttccc ggggttttg    6060
atcatgggat tagggaggta tttatagtcg agccccggga ttaattaatc gaccgttaga   6120
gctcatgtga accctgccct gccatcatgt gagcgtgcat acgagggcga tctggattgg   6180
ctggcagaac acctgcccta gcaaggctcg tagattaatt aacaaatcgt acgtacatct   6240
acgctgataa tgtgttaaat catcggccga atatttggtt agccgtgaag cactcgatcc   6300
cgcaaatgac caagattgct gcacacgaca catcgcgggc ttgtttcctt atgatcattg   6360
gttgttattt tatctcgcga tcttggccta tcgggcgtcg cttcgcgcgg tgcagcgtga   6420
ctgcgtgagc aagttggtga ttttcttttg ccgtttaaga atgcttgctc cgtgatcaca   6480
caagagagga catcacatga accgagaccg gaggaatatc ggggcatggt gggattggtg   6540
ggtgtcccag tccaacgggc aagaagattc taagcttacc tgggtttgtt ttcacgtacg   6600
cgaaggacag gggaagatgc cattgcagcg tggcttcctg ctggcccgcc aactttaatc   6660
tacactaggc acgtagctac taggtcggcc cgcttagata gctaaggtag gctaggtagg   6720
tccgtggtaa actgccagcc catgggcgcc tgggattctt cttgggccaa cagaagcaga   6780
ggttgggcaa tgcgaagcct gaaaatcctc ctcctccttc tctctccctc tctctctctc   6840
tctctctctc tctctcacga ataaaatcct cttcttcccg aacaggctag attcttttt    6900
ttttaatgaa ccagtgagcc accaatttca ttgaatagag gaataaaatt gtacatgcgc   6960
aagcgcaaat agaaactttt accgtctcaa ggcctttggc ccgaacatgt taaaggtaa    7020
gccacctatc aaggtgtttc gcgcccgcca agacccatgt tttggcatcc tccttaattt   7080
tggctatcag actagccacc ggaagctctt ggtgctgaaa aactctgcgg ttcctttcat   7140
tccaaatatc ctaggcgact aatagcatta gagtctgcaa ggctttcttt ggcgcttcgt   7200
tggaacatgc ggtggcctcc caccacttga gtagcgtcga ggcttgttgc cataacgttg   7260
gtcttatttg ttcacatgtt gtccagtctg caagtgtcgc ctagattctt tcacatatct   7320
acactccgcc aggaggtgag ggccgtttcc tgattccttc gacaaagggg cagatggagc   7380
cattttcgat tacccacggg ttgccaatct gtcggaggtc catactctat tttggataac   7440
aagccaagcg aagcgaatgt tttacatttg cgcggcgcct agggcttcca gataggggca   7500
ttgaaattga agctttatg ccaagaagtt gtgcgttgta ggccgatgtc gtcatgtatt    7560
cgccgtgact agttagcttc cattttcgac aagcttgcct cgagacaaca acatgcttct   7620
catcaacatg gagggaagag ggagggagaa agtgtcgcct ggtcacctcc attgtcacac   7680
tagccactgg ccagctctcc cacaccacca atgccagggg cgagctttag cacagccacc   7740
```

```
gcttcacctc caccaccgca ctaccctagc ttcgcccaac agccaccgtc aacgcctcct    7800
ctccgtcaac ataagagaga gagagaagag gagagtagcc atgtggggag gaggaatagt    7860
acatggggcc taccgtttgg caagttattt tgggttgcca agttaggcca ataaggggag    7920
ggatttggcc atccggttgg aaaggttatt ggggtagtat cttttttacta gaattgtcaa    7980
aaaaaaatag tttgagagcc atttggagag gatgttgcct gttagaggtg ctcttaggac    8040
atcaaattcc ataaaaacat cagaaaaatt ctctcgatga agatttataa ccactaaaac    8100
tgccctcaat tcgaagggag ttcaaaacaa ttaaaatcat gttcgaattg agtttcaatt    8160
tcactttaac ccctttgaaa tctcaatggt aaaacatcaa cccgtcaggt agcatggttc    8220
tttttattcc tttcaaaaag agttaattac aaacagaatc aaaactaaca gttaggccca    8280
aggcccatcc gagcaaacaa tagatcatgg gccaggcctg ccaccaccct cccctcctg    8340
gctcccgctc ttgaatttca aaatccaaaa atatcggcac gactggccgc cgacggagcg    8400
ggcggaaaat gacggaacaa cccctcgaat tctaccccaa ctacgccac caacccacac    8460
gccactgaca atccggtccc acccttgtgg gcccacctac aagcgagacg tcagtcgctc    8520
gcagcaacca gtgggcccac ctcccagtga gcggcgggta gatctggact cttacccacc    8580
cacactaaac aaaacggcat gaatattttg cactaaaacc ctcagaaaaa ttccgatatt    8640
ccaaaccagt acagttcctg accgttggag gagccaaagt ggagcggagt gtaaaattgg    8700
gaaacttaat cgagggggtt aaacgcaaaa acgccgaggc gcctcccgct ctatagaaag    8760
gggaggagtg ggaggtggaa accctaccac accgcagaga aaggcgtctt cgtactcgcc    8820
tctctccgcg ccctcctccg ccgccgctcg ccgccgttcg tctccgccgc caccggctag    8880
ccatccaggt aaaacaaaca aaacggatc tgatgcttcc attcctccgt ttctcgtagt    8940
agcgcgcttc gatctgtggg tggatctggg tgatcctggg gtgtggttcg ttctgtttga    9000
tagatctgtc ggtggatctg gccttctgtg gttgtcgatg tccggatctg cgttttgatc    9060
agtggtagtt cgtggatctg gcgaaatgtt ttggatctgg cagtgagacg ctaagaatcg    9120
ggaaatgatg caatattagg ggggtttcgg atggggatcc actgaattag tctgtctccc    9180
tgctgataat ctgttccttt ttggtagatc tggttagtgt atgtttgttt cggatagatc    9240
tgatcaatgc ttgtttgttt tttcaaattt tctacctagg ttgtatagga atggcatgcg    9300
gatctggttg gattgccatg atccgtgctg aaatgcccct ttggttgatg gatcttgata    9360
ttttactgct gttcacctag atttgtactc ccgtttatac ttaatttgtt gcttattatg    9420
aatagatctg taacttaggc acatgtatgg acggagtatg tggatctgta gtatgtacat    9480
tgctgcgagc taagaactat ttcagagcaa gcacagaaaa aaatatttag acagattggg    9540
caactatttg atggtctttg gtatcatgct ttgtagtgct cgtttctgcg tagtaatctt    9600
ttgatctgat ctgaagatag gtgctattat attcttaaag gtcattagaa cgctatctga    9660
aaggctgtat tatgtggatt ggttcacctg tgactccctg ttcgtcttgt cttgataaat    9720
cctgtgataa aaaaaattct taaggcgtaa tttgttgaaa tcttgttttg tcctatgcag    9780
cctgatccat ggcgcaagtt agcagaatct gcaatggtgt gcagaaccca tctcttatct    9840
ccaatctctc gaaatccagt caacgcaaat ctcccttatc ggtttctctg aagacgcagc    9900
agcatccacg agcttatccg atttcgtcgt cgtggggatt gaagaagagt gggatgacgt    9960
taattggctc tgagcttcgt cctcttaagg tcatgtcttc tgtttccacg cgtgcatgc    10020
ttcacggtgc aagcagccgg cccgcaaccg cccgcaaatc ctctggcctt tccggaaccg    10080
tccgcattcc cggcgacaag tcgatctccc accggtcctt catgttcggc ggtctcgcga    10140
```

```
gcggtgaaac gcgcatcacc ggccttctgg aaggcgagga cgtcatcaat acgggcaagg   10200
ccatgcaggc gatgggcgcc cgcatccgta aggaaggcga cacctggatc atcgatggcg   10260
tcggcaatgg cggcctcctg gcgcctgagg cgccgctcga tttcggcaat gccgccacgg   10320
gctgccgcct gacgatgggc ctcgtcgggg tctacgattt cgacagcacc ttcatcggcg   10380
acgcctcgct cacaaagcgc ccgatgggcc gcgtgttgaa cccgctgcgc gaaatgggcg   10440
tgcaggtgaa atcggaagac ggtgaccgtc ttcccgttac cttgcgcggg ccgaagacgc   10500
cgacgccgat cacctaccgc gtgccgatgg cctccgcaca ggtgaagtcc gccgtgctgc   10560
tcgccggcct caacacgccc ggcatcacga cggtcatcga ccgatcatg acgcgcgatc   10620 atacggaaaa gatgctgcag ggctttggcg ccaaccttac cgtcgagacg gatgcggacg   10680
gcgtgcgcac catccgcctg gaaggccgcg gcaagctcac cggccaagtc atcgacgtgc   10740
cgggcgaccc gtcctcgacg gccttcccgc tggttgcggc cctgcttgtt ccgggctccg   10800
acgtcaccat cctcaacgtg ctgatgaacc caccccgcac cggcctcatc ctgacgctgc   10860
aggaaatggg cgccgacatc gaagtcatca acccgcgcct tgccggcggc gaagacgtgg   10920
cggacctgcg cgttcgctcc tccacgctga agggcgtcac ggtgccggaa gaccgcgcgc   10980
cttcgatgat cgacgaatat ccgattctcg ctgtcgccgc cgccttcgcg aagggggcga   11040
ccgtgatgaa cggtctggaa gaactccgcg tcaaggaaag cgaccgcctc tcggccgtcg   11100
ccaatggcct caagctcaat ggcgtggatt gcgatgaggg cgagacgtcg ctcgtcgtgc   11160
gtggccgccc tgacggcaag gggctcggca acgcctcggg cgccgccgtc gccacccatc   11220
tcgatcaccg catcgccatg agcttcctcg tcatgggcct cgtgtcggaa aaccctgtca   11280
cggtggacga tgccacgatg atcgccacga gcttcccgga gttcatggac ctgatggccg   11340
ggctgggcgc gaagatcgaa ctctccgata cgaaggctgc ctgatgagct ccagggttct   11400
tgcctggtgc cttggcaatg cttgattact gctgctatcc tatgatctgt ccgtgtgggc   11460
ttctatctat cagtttgtgt gtctggtttt gaaaaacatt tgcttttcga ttatgtaggg   11520
tttgcttgta gctttcgctg ctgtgacctg tgttgtttat gtgaaccttc tttgtggcat   11580
ctttaatatc caagttcgtg gtttgtcgta aaacgaagcc tctacttcgt aaagttgtgt   11640
ctatagcatt gaaatcgttt ttttgctcga gaataattgt gacctttagt tggcgtgaaa   11700
ctagttttgg atatctgatt ctctggttcg caatcttgag atcgtcgctg cttaggtgag   11760
ctaagtgatg ttcctaagta aatgctcctc accagaatac gtagctgtgt gaaaagagaa   11820
cgcgtgaata cgtagctgtg taaagattgt gtcccaagta aacctcagtg atttttgttt   11880
ggatttttaa tttagaaaca ttcgactggg agcggctaga gccacaccca agttcctaac   11940
tatgataaag ttgctctgta acagaaaaca ccatctagag cggccgcgtt taaactatca   12000
gtgtttgaca ggatatattg gcgggtaaac ctaagagaaa agagcgttta ttagaataat   12060
cggatattta aaagggcgtg aaaaggttta tccgttcgtc catttgtatg tgcatgccaa   12120
ccacagggtt cccctcggga gtgcttggca ttccgtgcga taatgacttc tgttcaacca   12180
cccaaacgtc ggaaagcctg acgacggagc agcattccaa aaagatccct tggctcgtct   12240
gggtcggcta gaaggtcgag tgggctgctg tggcttgatc cctcaacgcg gtcgcggacg   12300
tagcgcagcg ccgaaaaatc ct                                            12322

<210> SEQ ID NO 30
<211> LENGTH: 12797
<212> TYPE: DNA
```

<213> ORGANISM: Artificial Sequence
<220> FEATURE:
<223> OTHER INFORMATION: DNA construct 402

<400> SEQUENCE: 30

```
aaaagtccca tgtggatcac tccgttgccc cgtcgctcac cgtgttgggg ggaaggtgca      60
catggctcag ttctcaatgg aaattatctg cctaaccggc tcagttctgc gtagaaacca     120
acatgcaagc tccaccgggt gcaaagcggc agcggcggca ggatatattc aattgtaaat     180
ggcttcatgt ccgggaaatc tacatggatc agcaatgagt atgatggtca atatggagaa     240
aaagaaagag taattaccaa ttttttttca attcaaaaat gtagatgtcc gcagcgttat     300
tataaaatga agtacatttt tgataaaacg acaaattacg atccgtcgta tttataggcg     360
aaagcaataa acaaattatt ctaattcgga aatctttatt tcgacgtgtc tacattcacg     420
tccaaatggg ggcttagatg agaaacttca cgatcgatgc ggccaccact cgaggtcgag     480
gtaccgttgt caatcaattg gcaagtcata aaatgcatta aaaatatttt tcatactcaa     540
ctacaaatcc atgagtataa ctataattat aaagcaatga ttagaatctg acaaggattc     600
tggaaaatta cataaaggaa agttcataaa tgtctaaaac acaagaggac atacttgtat     660
tcagtaacat ttgcagcttt tctaggtctg aaaatatatt tgttgcctag tgaataagca     720
taatggtaca actacaagtg ttttactcct catattaact tcggtcatta gaggccacga     780
tttgacacat ttttactcaa aacaaaatgt ttgcatatct cttataattt caaattcaac     840
acacaacaaa taagagaaaa acaaataat attaatttga gaatgaacaa aaggaccata     900
tcattcatta actcttctcc atccatttcc atttcacagt tcgatagcga aaaccgaata     960
aaaacacag taattacaa gcacaacaaa tggtacaaga aaaacagttt tcccaatgcc    1020
ataatactca aactcagtag gattctggtg tgtgcgcaat gaaactgatg cattgaactt    1080
gacgaacgtt gtcgaaaccg atgatacgaa cgaaagctag gcctcagcga gtaccgctgg    1140
cgatctaatc catgatatcg tgaacatcat ctacattcaa attcttatga gctttcttaa    1200
gggcatctgc agcatttttc atagaatcta atacagcagt attttgtgcta gctccttcga    1260
gggcttccct ctgcatttca atagttgtaa gggttccatc tatttgtagt tgggtctttt    1320
ccaatcgttt cttctttttg agggcttgga gtgcaactct tttatttttc gacgcatttt    1380
tctttgcgct cctgcaggcg gccgcgtgga tgaggagtta atcggtcgtg tgagagtagt    1440
gatcgagtgg atgtcgtcga gagtgatgag tgttgatgtt gttagtgata tgtggtagaa    1500
ggtatcgtga taaagcgtta acgcgatcgc agtacttgca aagaaaaatg cgtcgaaaaa    1560
taaaagagtt gcactccaag ccctcaaaaa gaagaaacga ttggaaaaga cccaactaca    1620
aatagatgga acccttacaa ctattgaaat gcagagggaa gccctcgaag gagctagcac    1680
aaatactgct gtattagatt ctatgaaaaa tgctgcagat gcccttaaga aagctcataa    1740
gaatttgaat gtagatgatg ttcacgatat catggatggt atcgcacagc gactgctgag    1800
ggacgtcggt ccatggagat cctctagagg ccgcttggta tctgcattac aatgaaatga    1860
gcaaagacta tgtgagtaac actggtcaac actagggaga aggcatcgag caagatacgt    1920
atgtaaagag aagcaatata gtgtcagttg gtagatacta gataccatca ggaggtaagg    1980
agagcaacaa aaaggaaact ctttatttt aaatttttgtt acaacaaaca agcagatcaa    2040
tgcatcaaaa tactgtcagt acttattttct tcagacaaca atatttaaaa caagtgcatc    2100
tgatcttgac ttatggtcac aataaaggag cagagataaa catcaaaatt tcgtcattta    2160
tatttattcc ttcaggcgtt aacaatttaa cagcacacaa acaaaaacag aataggaata    2220
```

```
tctaattttg gcaaataata agctctgcag acgaacaaat tattatagta tcgcctataa    2280
tatgaatccc tatactattg acccatgtag tatgaagcct gtgcctaaat taacagcaaa    2340
cttctgaatc caagtgccct ataacaccaa catgtgctta ataaatacc gctaagcacc     2400 aaattacaca tttctcgtat tgctgtgtag gttctatctt cgtttcgtac taccatgtcc    2460
ctatattttg ctgctacaaa ggacggcaag taatcagcac aggcagaaca cgatttcaga    2520
gtgtaattct agatccagct aaaccactct cagcaatcac cacacaagag agcattcaga    2580
gaaacgtggc agtaacaaag gcagagggcg gagtgagcgc gtaccgaaga cggtgggccg    2640
cttatggtgt gttgtccctg tgtgttctcc aatagtgtgg cttgagtgtg tggaagatgg    2700
ttgtatctga tgatccttca aatgggaatg aatgcctcct tatatagagg gaattctttt    2760
gtggtcgtca ctgcgttcgt catacgcatt agtgagtggg ctgtcaggac agctcttttc    2820
cacgttattt tgttccccac ttgtactaga ggaatctgct ttatctttgc aataaaggca    2880
aagatgcttt tggtaggtgc gcctaacaat tctgcaccat tccttttttg tctggtcccc    2940
acaagccagc tgctcgatgt tgacaagatt actttcaaag atgcccacta actttaagtc    3000
ttcggtggat gtcttttttct gaaacttact gaccatgatg catgtgctgg aacagtagtt    3060
tactttgatt gaagattctt cattgatctc ctgtagcttt tggctaatgg tttggagact    3120
ctgtaccctg accttgttga ggctttggac tgagaattct tccttacaaa cctttgagga    3180
tgggagttcc ttcttggttt tggcgatacc aatttgaata aagtgatatg gctcgtacct    3240
tgttgattga acccaatctg gaatgctgct aaatcctgag ctcaagctaa ttcttttgtg    3300
gtcgtcactg cgttcgtcat acgcattagt gagtgggctg tcaggacagc tcttttccac    3360
gttattttgt tccccacttg tactagagga atctgcttta tctttgcaat aaaggcaaag    3420
atgcttttgg taggtgcgcc taacaattct gcaccattcc ttttttgtct ggtccccaca    3480
agccagctgc tcgatgttga caagattact ttcaaagatg cccactaact ttaagtcttc    3540
ggtggatgtc tttttctgaa acttactgac catgatgcat gtgctggaac agtagtttac    3600
tttgattgaa gattcttcat tgatctcctg tagcttttgg ctaatggttt ggagactctg    3660
taccctgacc ttgttgaggc tttggactga gaattagctt ccactcgaag cttgttaacc    3720
tgcaggctag cggcgcgccg gaagctaact agtcacggcg aatacatgac gacatcggcc    3780
tacaacgcac aacttcttgg cataaaagct tcaatttcaa tgcccctatc tggaagccct    3840
aggcgccgcg caaatgtaaa acattcgctt cgcttggctt gttatccaaa atagagtatg    3900
gacctccgac agattggcaa cccgtgggta atcgaaaatg gctccatctg cccctttgtc    3960
gaaggaatca ggaaacggcc ctcacctcct ggcggagtgt agatatgtga aagaatctag    4020
gcgacacttg cagactggac aacatgtgaa caaataagac caacgttatg gcaacaagcc    4080
tcgacgctac tcaagtggtg ggaggccacc gcatgttcca acgaagcgcc aaagaaagcc    4140
ttgcagactc taatgctatt agtcgcctag gatatttgga atgaaaggaa ccgcagagtt    4200
tttcagcacc aagagcttcc ggtggctagt ctgatagcca aaattaagga ggatgccaaa    4260
acatgggtct ggcgggcgc gaaacacctt gataggtggc ttaccttttta acatgttcgg    4320 gccaaaggcc ttgagacggt aaagttttct atttgcgctt gcgcatgtac aatttttattc    4380 ctctattcaa tgaaattggt ggctcactgg ttcattaaaa aaaaaagaat ctagcctgtt    4440
cgggaagaag aggattttat tcgtgagaga gagagagaga gagagagaga gagggagaga    4500
gaaggaggag gaggattttc aggcttcgca ttgcccaacc tctgcttctg ttggcccaag    4560
```

```
aagaatccca ggcgcccatg ggctggcagt ttaccacgga cctacctagc ctaccttagc    4620
tatctaagcg ggccgaccta gtagctacgt gcctagtgta gattaaagtt ggcgggccag    4680
caggaagcca cgctgcaatg gcatcttccc ctgtccttcg cgtacgtgaa aacaaaccca    4740
ggtaagctta gaatcttctt gcccgttgga ctgggacacc caccaatccc accatgcccc    4800
gatattcctc cggtctcggt tcatgtgatg tcctctcttg tgtgatcacg gagcaagcat    4860
tcttaaacgg caaaagaaaa tcaccaactt gctcacgcag tcacgctgca ccgcgcgaag    4920
cgacgcccga taggccaaga tcgcgagata aaataacaac caatgatcat aaggaaacaa    4980
gcccgcgatg tgtcgtgtgc agcaatcttg gtcatttgcg ggatcgagtg cttcacggct    5040
aaccaaatat tcggccgatg atttaacaca ttatcagcgt agatgtacgt acgatttgtt    5100
aattaatcta cgagccttgc tagggcaggt gttctgccag ccaatccaga tcgccctcgt    5160
atgcacgctc acatgatggc agggcagggt tcacatgagc tctaacggtc gattaattaa    5220
tcccggggct cgactataaa tacctcccta atcccatgat caaaaccccc gggaaccatc    5280
ttccacacac tcaagccaca ctattggaga acacacaggg acaacacacc ataagatcca    5340
agggaggcct ccgccgccgc cggtaaccac cccgcccctc tcctctttct ttctccgttt    5400
tttttttccgt ctcggtctcg atctttggcc ttggtagttt gggtgggcga gaggcggctt    5460
cgtgcgcgcc cagatcggtg cgcgggaggg gcgggatctc gcggctgggg ctctcgccgg    5520
cgtggatccg gcccggatct cgcggggaat ggggctctcg gatgtagatc tgcgatccgc    5580
cgttgttggg ggagatgatg gggggtttaa aatttccgcc gtgctaaaca agatcaggaa    5640
gaggggaaaa gggcactatg gtttatattt ttatatattt ctgctgcttc gtcaggctta    5700
gatgtgctag atcttttcttt cttcttttttg tgggtagaat ttgaatccct cagcattgtt    5760
catcggtagt ttttcttttc atgatttgtg acaaatgcag cctcgtgcgg agctttttttg   5820
taggtagaag tgatcaacca tggccaaccc caacaatcgc tccgagcacg acacgatcaa    5880
ggtcaccccc aactccgagc tccagaccaa ccacaaccag tacccgctgg ccgacaaccc    5940
caactccacc ctggaagagc tgaactacaa ggagttcctg cgcatgaccg aggactcctc    6000
cacggaggtc ctggacaact ccaccgtcaa ggacgccgtc gggaccggca tctccgtcgt    6060
tgggcagatc ctgggcgtcg ttggcgtccc cttcgcaggt gctctcacct ccttctacca    6120
gtccttcctg aacaccatct ggcctccga cgccgacccc tggaaggcct tcatggccca    6180
agtcgaagtc ctgatcgaca agaagatcga ggagtacgcc aagtccaagg ccctggccga    6240
gctgcaaggc ctgcaaaaca acttcgagga ctacgtcaac gcgctgaact cctggaagaa    6300
gacgcctctg tccctgcgct ccaagcgctc ccaggaccgc atccgcgagc tgttctccca    6360
ggccgagtcc cacttccgca actccatgcc gtccttcgcc gtctccaagt tcgaggtcct    6420
gttcctgccc acctacgccc aggctgccaa cacccacctc ctgttgctga aggacgccca    6480
ggtcttcggc gaggaatggg gctactcctc ggaggacgtc gccgagttct accgtcgcca    6540
gctgaagctg acccaacagt acaccgacca ctgcgtcaac tggtacaacg tcggcctgaa    6600
cggcctgagg ggctccacct acgacgcatg ggtcaagttc aaccgcttcc gcagggagat    6660
gaccctgacc gtcctggacc tgatcgtcct gttcccctttc tacgacatcc gcctgtactc    6720
caagggcgtc aagaccgagc tgacccgcga catcttcacg gaccccatct tcctgctcac    6780
gaccctccag aagtacggtc ccaccttcct gtccatcgag aactccatcc gcaagcccca    6840
cctgttcgac tacctccagg gcatcgagtt ccacacgcgc ctgaggccag gctacttcgg    6900
caaggactcc ttcaactact ggtccggcaa ctacgtcgag accaggccct ccatcggctc    6960
```

```
ctcgaagacg atcacctccc ctttctacgg cgacaagtcc accgagcccg tccagaagct    7020
gtccttcgac ggccagaagg tctaccgcac catcgccaac accgacgtcg cggcttggcc    7080
gaacggcaag gtctacctgg gcgtcacgaa ggtcgacttc tcccagtacg atgaccagaa    7140
gaacgagacc tccacccaga cctacgactc caagcgcaac aatggccacg tctccgccca    7200
ggactccatc gaccagctgc cgcctgagac cactgacgag cccctggaga aggcctactc    7260
ccaccagctg aactacgcgg agtgcttcct gatgcaagac cgcaggggca ccatcccctt    7320
cttcacctgg acccaccgct ccgtcgactt cttcaacacc atcgacgccg agaagatcac    7380
ccagctgccc gtggtcaagg cctacgccct gtcctcgggt gcctccatca ttgagggtcc    7440
aggcttcacc ggtggcaacc tgctgttcct gaaggagtcc tcgaactcca tcgccaagtt    7500
caaggtcacc ctgaactccg ctgccttgct gcaacgctac cgcgtccgca tccgctacgc    7560
ctccaccacg aacctgcgcc tgttcgtcca gaactccaac aatgacttcc tggtcatcta    7620
catcaacaag accatgaaca aggacgatga cctgacctac cagaccttcg acctcgccac    7680
cacgaactcc aacatgggct tctcgggcga caagaatgaa ctgatcattg gtgctgagtc    7740
cttcgtctcc aacgagaaga tctacatcga caagatcgag ttcatccccg tccagctgtg    7800
ataggaactc tgattgaatt ctgcatgcgt ttggacgtat gctcattcag gttggagcca    7860
atttggttga tgtgtgtgcg agttcttgcg agtctgatga gacatctctg tattgtgttt    7920 cttttccccag tgttttctgt acttgtgtaa tcggctaatc gccaacagat cggcgatga    7980 ataaatgaga aataaattgt tctgattttg agtgcaaaaa aaaggaatt agatctgtgt    8040 gtgttttttg gatcccattt tcgacaagct tgcctcgaga caacaacatg cttctcatca    8100
acatggaggg aagagggagg gagaaagtgt cgcctggtca cctccattgt cacactagcc    8160
actggccagc tctcccacac caccaatgcc agggggcgagc tttagcacag ccaccgcttc    8220
acctccacca ccgcactacc ctagcttcgc ccaacagcca ccgtcaacgc ctcctctccg    8280
tcaacataag agagagagag aagaggagag tagccatgtg gggaggagga atagtacatg    8340
gggcctaccg tttggcaagt tattttgggt tgccaagtta ggccaataag gggagggatt    8400
tggccatccg gttggaaagg ttattggggt agtatctttt tactagaatt gtcaaaaaaa    8460
aatagtttga gagccatttg gagaggatgt tgcctgttag aggtgctctt aggacatcaa    8520
attccataaa aacatcagaa aaattctctc gatgaagatt tataaccact aaaactgccc    8580
tcaattcgaa gggagttcaa aacaattaaa atcatgttcg aattgagttt caatttcact    8640
ttaacccctt tgaaatctca atggtaaaac atcaacccgt caggtagcat ggttcttttt    8700
attcctttca aaagagtta attacaaaca gaatcaaaac taacagttag gcccaaggcc    8760
catccgagca acaatagat catgggccag gcctgccacc accctccccc tcctggctcc    8820
cgctcttgaa tttcaaaatc caaaaatatc ggcacgactg gccgccgacg gagcgggcgg    8880
aaaatgacgg aacaacccct cgaattctac cccaactacg cccaccaacc cacacgccac    8940
tgacaatccg gtcccaccct tgtgggccca cctacaagcg agacgtcagt cgctcgcagc    9000
aaccagtggg cccacctccc agtgagcggc gggtagatct ggactcttac ccacccacac    9060
taaacaaaac ggcatgaata ttttgcacta aaaccctcag aaaaattccg atattccaaa    9120
ccagtacagt tcctgaccgt tggaggagcc aaagtggagc ggagtgtaaa attgggaaac    9180
ttaatcgagg gggttaaacg caaaaacgcc gaggcgcctc ccgctctata gaaagggag    9240 gagtgggagg tggaaacccc accacaccgc agagaaaggc gtcttcgtac tcgcctctct    9300
```

```
ccgcgccctc ctccgccgcc gctcgccgcc gttcgtctcc gccgccaccg gctagccatc    9360
caggtaaaac aaacaaaaac ggatctgatg cttccattcc tccgtttctc gtagtagcgc    9420
gcttcgatct gtgggtggat ctgggtgatc ctggggtgtg gttcgttctg tttgatagat    9480
ctgtcggtgg atctggcctt ctgtggttgt cgatgtccgg atctgcgttt tgatcagtgg    9540
tagttcgtgg atctggcgaa atgttttgga tctggcagtg agacgctaag aatcgggaaa    9600
tgatgcaata ttagggggt ttcggatggg gatccactga attagtctgt ctccctgctg     9660
ataatctgtt cctttttggt agatctggtt agtgtatgtt tgtttcggat agatctgatc    9720
aatgcttgtt tgtttttca aattttctac ctaggttgta taggaatggc atgcggatct     9780
ggttggattg ccatgatccg tgctgaaatg cccctttggt tgatggatct tgatattta     9840
ctgctgttca cctagatttg tactcccgtt tatacttaat ttgttgctta ttatgaatag    9900
atctgtaact taggcacatg tatggacgga gtatgtggat ctgtagtatg tacattgctg    9960
cgagctaaga actatttcag agcaagcaca gaaaaaaata tttagacaga ttgggcaact   10020
atttgatggt ctttggtatc atgctttgta gtgctcgttt ctgcgtagta atcttttgat   10080
ctgatctgaa gataggtgct attatattct taaaggtcat tagaacgcta tctgaaaggc   10140
tgtattatgt ggattggttc acctgtgact ccctgttcgt cttgtcttga taaatcctgt   10200
gataaaaaaa attcttaagg cgtaatttgt tgaaatcttg ttttgtccta tgcagcctga   10260
tccatggcgc aagttagcag aatctgcaat ggtgtgcaga acccatctct tatctccaat   10320
ctctcgaaat ccagtcaacg caaatctccc ttatcggttt ctctgaagac gcagcagcat   10380
ccacgagctt atccgatttc gtcgtcgtgg ggattgaaga agagtgggat gacgttaatt   10440
ggctctgagc ttcgtcctct taaggtcatg tcttctgttt ccacggcgtg catgcttcac   10500
ggtgcaagca gccggcccgc aaccgcccgc aaatcctctg gcctttccgg aaccgtccgc   10560
attcccggcg acaagtcgat ctcccaccgg tccttcatgt tcggcggtct cgcgagcggt   10620
gaaacgcgca tcaccggcct tctggaaggc gaggacgtca tcaatacggg caaggccatg   10680
caggcgatgg gcgcccgcat ccgtaaggaa ggcgacacct ggatcatcga tggcgtcggc   10740
aatggcggcc tcctggcgcc tgaggcgccg ctcgatttcg gcaatgccgc cacgggctgc   10800
cgcctgacga tgggcctcgt cggggtctac gatttcgaca gcaccttcat cggcgacgcc   10860
tcgctcacaa agcgcccgat gggcgcgtg ttgaacccgc tgcgcgaaat gggcgtgcag    10920
gtgaaatcgg aagacggtga ccgtcttccc gttaccttgc gcgggccgaa gacgccgacg   10980
ccgatcacct accgcgtgcc gatggcctcc gcacaggtga agtccgccgt gctgctcgcc   11040
ggcctcaaca cgcccggcat cacgacggtc atcgagccga tcatgacgcg cgatcatacg   11100
gaaaagatgc tgcagggctt tggcgccaac cttaccgtcg agacggatgc ggacggcgtg   11160
cgcaccatcc gcctggaagg ccgcggcaag ctcaccggcc aagtcatcga cgtgccgggc   11220
gaccgtcct cgacgccctt cccgctggtt gcggccctgc ttgttccggg ctccgacgtc    11280
accatcctca acgtgctgat gaacccccacc cgcaccggcc tcatcctgac gctgcaggaa   11340
atgggcgccg acatcgaagt catcaacccg cgccttgccg gcggcgaaga cgtggcggac   11400
ctgcgcgttc gctcctccac gctgaagggc gtcacggtgc cggaagaccg cgcgccttcg   11460
atgatcgacg aatatccgat tctcgctgtc gccgccgcct tcgcggaagg ggcgaccgtg   11520
atgaacggtc tggaagaact ccgcgtcaag gaaagcgacc gcctctcggc cgtcgccaat   11580
ggcctcaagc tcaatggcgt ggattgcgat gagggcgaga cgtcgctcgt cgtgcgtggc   11640
cgccctgacg gcaagggggct cggcaacgcc tcgggcgccg ccgtcgccac ccatctcgat   11700
```

```
caccgcatcg ccatgagctt cctcgtcatg ggcctcgtgt cggaaaaccc tgtcacggtg    11760
gacgatgcca cgatgatcgc cacgagcttc ccggagttca tggacctgat ggccgggctg    11820
ggcgcgaaga tcgaactctc cgatacgaag gctgcctgat gagctccagg gttcttgcct    11880
ggtgccttgg caatgcttga ttactgctgc tatcctatga tctgtccgtg tgggcttcta    11940
tctatcagtt tgtgtgtctg gttttgaaaa acatttgctt ttcgattatg tagggtttgc    12000
ttgtagcttt cgctgctgtg acctgtgttg tttatgtgaa ccttctttgt ggcatcttta    12060
atatccaagt tcgtggtttg tcgtaaaacg aagcctctac ttcgtaaagt tgtgtctata    12120
gcattgaaat cgttttttg ctcgagaata attgtgacct ttagttggcg tgaaactagt    12180
tttggatatc tgattctctg gttcgcaatc ttgagatcgt cgctgcttag gtgagctaag    12240
tgatgttcct aagtaaatgc tcctcaccag aatacgtagc tgtgtgaaaa gagaacgcgt    12300
gaatacgtag ctgtgtaaag attgtgtccc aagtaaacct cagtgatttt tgtttggatt    12360
tttaatttag aaacattcga ctgggagcgg ctagagccac acccaagttc ctaactatga    12420
taaagttgct ctgtaacaga aaacaccatc tagagcggcc gcgtttaaac tatcagtgtt    12480
tgacaggata tattgcgggt aaacctaag agaaaagagc gtttattaga ataatcggat    12540
atttaaaagg gcgtgaaaag gtttatccgt tcgtccattt gtatgtgcat gccaaccaca    12600 gggttccct cgggagtgct tggcattccg tgcgataatg acttctgttc aaccacccaa    12660
acgtcggaaa gcctgacgac ggagcagcat tccaaaaaga tcccttggct cgtctgggtc    12720
ggctagaagg tcgagtgggc tgctgtggct tgatccctca acgcggtcgc ggacgtagcg    12780
cagcgccgaa aaatcct                                                  12797

<210> SEQ ID NO 31
<211> LENGTH: 12218
<212> TYPE: DNA
<213> ORGANISM: Artificial Sequence
<220> FEATURE:
<223> OTHER INFORMATION: DNA construct 403

<400> SEQUENCE: 31
aaaagtccca tgtggatcac tccgttgccc cgtcgctcac cgtgttgggg ggaaggtgca      60
catggctcag ttctcaatgg aaattatctg cctaaccggc tcagttctgc gtagaaacca     120
acatgcaagc tccaccgggt gcaaagcggc agcggcggca ggatatattc aattgtaaat     180
ggcttcatgt ccgggaaatc tacatggatc agcaatgagt atgatggtca atatggagaa     240
aaagaaagag taattaccaa ttttttttca attcaaaaat gtagatgtcc gcagcgttat     300
tataaaatga agtacatttt tgataaaacg acaaattacg atccgtcgta tttataggcg     360
aaagcaataa acaaattatt ctaattcgga aatctttatt tcgacgtgtc tacattcacg     420
tccaaatggg ggcttagatg agaaacttca cgatcgatgc ggccaccact cgaggtcgag     480
gtaccgttgt caatcaattg gcaagtcata aatgcatta aaaatatttt tcatactcaa     540
ctacaaatcc atgagtataa ctataattat aaagcaatga ttagaatctg acaaggattc     600
tggaaaatta cataaggaa agttcataaa tgtctaaaac acaagaggac atacttgtat     660
tcagtaacat ttgcagcttt tctaggtctg aaaatatatt tgttgcctag tgaataagca     720
taatggtaca actacaagtg ttttactcct catattaact tcggtcatta gaggccacga     780
tttgacacat ttttactcaa aacaaaatgt ttgcatatct cttataattt caaattcaac     840
acacaacaaa taagagaaaa aacaaataat attaatttga gaatgaacaa aaggaccata     900
```

```
tcattcatta actcttctcc atccatttcc atttcacagt tcgatagcga aaaccgaata    960
aaaaacacag taaattacaa gcacaacaaa tggtacaaga aaaacagttt tcccaatgcc   1020
ataatactca aactcagtag gattctggtg tgtgcgcaat gaaactgatg cattgaactt   1080
gacgaacgtt gtcgaaaccg atgatacgaa cgaaagctag gcctcagcga gtaccgctgg   1140
cgatctaatc catgatatcg tgaacatcat ctacattcaa attcttatga gctttcttaa   1200
gggcatctgc agcattttc atagaatcta atacagcagt atttgtgcta gctccttcga    1260
gggcttccct ctgcatttca atagttgtaa gggttccatc tatttgtagt tgggtctttt   1320
ccaatcgttt cttcttttg agggcttgga gtgcaactct tttattttc gacgcatttt     1380
tctttgcgct cctgcaggcg gccgcgtgga tgaggagtta atcggtcgtg tgagagtagt   1440
gatcgagtgg atgtcgtcga gagtgatgag tgttgatgtt gttagtgata tgtggtagaa   1500
ggtatcgtga taaagcgtta acgcgatcgc agtacttgca aagaaaaatg cgtcgaaaaa   1560
taaaagagtt gcactccaag ccctcaaaaa gaagaaacga ttggaaaaga cccaactaca   1620
aatagatgga acccttacaa ctattgaaat gcagagggaa gccctcgaag gagctagcac   1680
aaatactgct gtattagatt ctatgaaaaa tgctgcagat gcccttaaga aagctcataa   1740
gaatttgaat gtagatgatg ttcacgatat catggatggt atcgcacagc gactgctgag   1800
ggacgtcggt ccatggagat cctctagagg ccgcttggta tctgcattac aatgaaatga   1860
gcaaagacta tgtgagtaac actggtcaac actaggagaa aggcatcgag caagatacgt   1920
atgtaaagag aagcaatata gtgtcagttg gtagatacta gataccatca ggaggtaagg   1980
agagcaacaa aaaggaaact ctttattttt aaattttgtt acaacaaaca agcagatcaa   2040
tgcatcaaaa tactgtcagt acttatttct tcagacaaca atatttaaaa caagtgcatc   2100
tgatcttgac ttatggtcac aataaaggag cagagataaa catcaaaatt tcgtcattta   2160
tatttattcc ttcaggcgtt aacaatttaa cagcacacaa acaaaaacag aataggaata   2220
tctaattttg gcaaataata agctctgcag acgaacaaat tattatagta tcgcctataa   2280
tatgaatccc tatactattg acccatgtag tatgaagcct gtgcctaaat aacagcaaa    2340
cttctgaatc caagtgccct ataacaccaa catgtgctta aataaatacc gctaagcacc   2400
aaattacaca tttctcgtat tgctgtgtag gttctatctt cgtttcgtac taccatgtcc   2460
ctatattttg ctgctacaaa ggacggcaag taatcagcac aggcagaaca cgatttcaga   2520
gtgtaattct agatccagct aaaccactct cagcaatcac cacacaagag agcattcaga   2580
gaaacgtggc agtaacaaag gcagagggcg gagtgagcgc gtaccgaaga cggtgggccg   2640
cttatggtgt gttgtccctg tgtgttctcc aatagtgtgg cttgagtgtg tggaagatgg   2700
ttgtatctga tgatccttca aatgggaatg aatgccttct tatatagagg gaattctttt   2760
gtggtcgtca ctgcgttcgt catacgcatt agtgagtggg ctgtcaggac agctctttc    2820
cacgttattt tgttccccac ttgtactaga ggaatctgct ttatctttgc aataaaggca   2880
aagatgcttt tggtaggtgc gcctaacaat tctgcaccat tcctttttg tctggtcccc    2940
acaagccagc tgctcgatgt tgacaagatt actttcaaag atgcccacta actttaagtc   3000
ttcggtggat gtcttttct gaacttact gaccatgatg catgtgctgg aacagtagtt     3060
tactttgatt gaagattctt cattgatctc ctgtagcttt tggctaatgg tttggagact   3120
ctgtaccctg accttgttga ggctttggac tgagaattct tccttacaaa cctttgagga   3180
tgggagttcc ttcttggttt tggcgatacc aatttgaata aagtgatatg gctcgtacct   3240
tgttgattga acccaatctg gaatgctgct aaaatcctgag ctcaagctaa ttctttttgtg 3300
```

```
gtcgtcactg cgttcgtcat acgcattagt gagtgggctg tcaggacagc tcttttccac    3360
gttattttgt tccccacttg tactagagga atctgcttta tctttgcaat aaaggcaaag    3420
atgcttttgg taggtgcgcc taacaattct gcaccattcc ttttttgtct ggtccccaca    3480
agccagctgc tcgatgttga caagattact ttcaaagatg cccactaact ttaagtcttc    3540
ggtggatgtc ttttcctgaa acttactgac catgatgcat gtgctggaac agtagtttac    3600
tttgattgaa gattcttcat tgatctcctg tagcttttgg ctaatggttt ggagactctg    3660
taccctgacc ttgttgaggc tttggactga gaattagctt ccactcgaag cttgttaacc    3720
tgcaggctag cggcgcgcca caaatcacag gccatgaacc ctactcatgc ttcgatttgt    3780
ccaacacaca cttaccaaaa ctcaaatcat gtccttgaca gtcactcggg actcataaca    3840
tgggtacgta tcgactatgt caactatatg tgttctcatc agattataga ttggcctagt    3900
acgtagtgat atttccacta gcactgtggt tatggctgta cctgatagtg atatcagcac    3960
cgggtcatgg ctctactacc aggtagtgag agtgacctttt atactgtcag actgtaacta    4020
aggatttcca atcactgttc ggatcctagg cttagaatta agtaaaactc tatcactata    4080
ggctgcagca cactcggtat atattgatgg gccaacagaa attgtgcgta ctatgcgcga    4140
tgtaaaatgg acataaaccc tacccatata caatgcaata acttttgtcc ggtctgggcc    4200
accggttagc agaggtcctg atttcggtgg tagtggtagc ttgatctggt cgtcgtatcg    4260
tagagggata tataaaatca tgtcactttt gaagggagcg ctcacagaaa taataggtat    4320
tcgcgggagc cgcccccgca gaacacaaaa taaggcgagc acgcacacgc atcagtttcg    4380
ataaaataat aatagcgcca gctgatcgga acaattccag ctagcactaa tgtatttctg    4440
cattgatctg tttatacaac atgctacctc gttgagtgat tttgacatga tttgtcaact    4500
tgctccgatc ctatatctcg atcgatctcc acatgacgat ggttgttgtc ctgtatccca    4560
tgacaaccag gcaacgctca aagcacacat gcgttgccga ttacccgtgc atgccgccaa    4620
gcacgaaagc acctccctcc acaccgtcca tcagctataa aaaccatgcc aagcaccctg    4680
tgaaaagccc cgggaaccat cttccacaca ctcaagccac actattggag aacacacagg    4740
gacaacacac cataagatcc aagggaggcc tccgccgccg ccggtaacca ccccgcccct    4800
ctcctctttc tttctccgtt ttttttttccg tctcggtctc gatctttggc cttggtagtt    4860
tgggtgggcg agaggcggct tcgtgcgcgc ccagatcggt gcgcgggagg ggcgggatct    4920
cgcggctggg gctctcgccg gcgtggatcc ggcccggatc tcgcggggaa tggggctctc    4980
ggatgtagat ctgcgatccg ccgttgttgg gggagatgat gggggggttta aaatttccgc    5040 cgtgctaaac aagatcagga agagggggaaa agggcactat ggtttatatt tttatatatt    5100
tctgctgctt cgtcaggctt agatgtgcta gatctttctt tcttcttttt gtgggtagaa    5160
tttgaatccc tcagcattgt tcatcggtag ttttttcttt catgatttgt gacaaatgca    5220
gcctcgtgcg gagcttttt gtaggtagaa gtgatcaacc atggccaacc ccaacaatcg    5280
ctccgagcac gacacgatca aggtcacccc caactccgag ctccagacca accacaacca    5340
gtacccgctg gccgacaacc ccaactccac cctggaagag ctgaactaca aggagttcct    5400
gcgcatgacc gaggactcct ccacggaggt cctgacaac tccaccgtca aggacgccgt    5460
cgggaccggc atctccgtcg ttgggcagat cctgggcgtc gttggcgtcc ccttcgcagg    5520
tgctctcacc tccttctacc agtccttcct gaacaccatc tggccctccg acgccgaccc    5580
ctggaaggcc ttcatggccc aagtcgaagt cctgatcgac aagaagatcg aggagtacgc    5640
```

```
caagtccaag gccctggccg agctgcaagg cctgcaaaac aacttcgagg actacgtcaa    5700
cgcgctgaac tcctggaaga agacgcctct gtccctgcgc tccaagcgct cccaggaccg    5760
catccgcgag ctgttctccc aggccgagtc ccacttccgc aactccatgc cgtccttcgc    5820
cgtctccaag ttcgaggtcc tgttcctgcc cacctacgcc caggctgcca acacccacct    5880
cctgttgctg aaggacgccc aggtcttcgg cgaggaatgg ggctactcct cggaggacgt    5940
cgccgagttc taccgtcgcc agctgaagct gacccaacag tacaccgacc actgcgtcaa    6000
ctggtacaac gtcggcctga acggcctgag gggctccacc tacgacgcat gggtcaagtt    6060
caaccgcttc cgcagggaga tgaccctgac cgtcctggac ctgatcgtcc tgttcccctt    6120
ctacgacatc cgcctgtact ccaagggcgt caagaccgag ctgacccgcg acatcttcac    6180 ggacccatc ttcctgctca cgaccctcca gaagtacggt cccaccttcc tgtccatcga    6240
gaactccatc cgcaagcccc acctgttcga ctacctccag ggcatcgagt ccacacgcg    6300 cctgaggcca ggctacttcg gcaaggactc cttcaactac tggtccggca actacgtcga    6360
gaccaggccc tccatcggct cctcgaagac gatcacctcc cctttctacg cgacaagtc    6420 caccgagccc gtccagaagc tgtccttcga cggccagaag gtctaccgca ccatcgccaa    6480
caccgacgtc gcggcttggc cgaacggcaa ggtctacctg ggcgtcacga aggtcgactt    6540
ctcccagtac gatgaccaga gaacgagac ctccacccag acctacgact ccaagcgcaa    6600
caatggccac gtctccgccc aggactccat cgaccagctg ccgcctgaga ccactgacga    6660 gccctggag aaggcctact cccaccagct gaactacgcg gagtgcttcc tgatgcaaga    6720
ccgcaggggc accatcccct tcttcacctg gacccaccgc tccgtcgact tcttcaacac    6780
catcgacgcc gagaagatca cccagctgcc cgtggtcaag gcctacgccc tgtcctcggg    6840
tgcctccatc attgagggtc caggcttcac cggtggcaac ctgctgttcc tgaaggagtc    6900
ctcgaactcc atcgccaagt tcaaggtcac cctgaactcc gctgccttgc tgcaacgcta    6960
ccgcgtccgc atccgctacg cctccaccac gaacctgcgc ctgttcgtcc agaactccaa    7020
caatgacttc ctggtcatct acatcaacaa gaccatgaac aaggacgatg acctgaccta    7080
ccagaccttc gacctcgcca ccacgaactc caacatgggc ttctcgggcg acaagaatga    7140
actgatcatt ggtgctgagt ccttcgtctc caacgagaag atctacatcg acaagatcga    7200
gttcatcccc gtccagctgt gataggaact ctgattgaat tctgcatgcg tttggacgta    7260
tgctcattca ggttggagcc aatttggttg atgtgtgtgc gagttcttgc gagtctgatg    7320
agacatctct gtattgtgtt ctttccccca gtgttttctg tacttgtgta atcggctaat    7380
cgccaacaga ttcggcgatg aataaatgag aaataaattg ttctgatttt gagtgcaaaa    7440
aaaaaggaat tagatctgtg tgtgtttttt ggatcccatt ttcgacaagc ttgcctcgag    7500
acaacaacat gcttctcatc aacatggagg gaagagggag ggagaaagtg tcgcctggtc    7560
acctccattg tcacactagc cactggccag ctctcccaca ccaccaatgc caggggcgag    7620
ctttagcaca gccaccgctt cacctccacc accgcactac cctagcttcg cccaacagcc    7680
accgtcaacg cctcctctcc gtcaacataa gagagagaga gaagaggaga gtagccatgt    7740
ggggaggagg aatagtacat ggggcctacc gtttggcaag ttattttggg ttgccaagtt    7800
aggccaataa ggggagggat ttggccatcc ggttggaaag gttattgggg tagtatcttt    7860
ttactagaat tgtcaaaaaa aaatagtttg agagccattt ggagaggatg ttgcctgtta    7920
gaggtgctct taggacatca aattccataa aaacatcaga aaaattctct cgatgaagat    7980
ttataaccac taaaactgcc ctcaattcga agggagttca aaacaattaa aatcatgttc    8040
```

-continued

```
gaattgagtt tcaatttcac tttaacccct ttgaaatctc aatggtaaaa catcaacccg    8100
tcaggtagca tggttctttt tattcctttc aaaagagtt aattacaaac agaatcaaaa    8160
ctaacagtta ggcccaaggc ccatccgagc aaacaataga tcatgggcca ggcctgccac    8220
caccctcccc ctcctggctc ccgctcttga atttcaaaat ccaaaaatat cggcacgact    8280
ggccgccgac ggagcgggcg gaaaatgacg gaacaacccc tcgaattcta ccccaactac    8340
gcccaccaac ccacacgcca ctgacaatcc ggtcccaccc ttgtgggccc acctacaagc    8400
gagacgtcag tcgctcgcag caaccagtgg gcccacctcc cagtgagcgg cgggtagatc    8460
tggactctta cccacccaca ctaaacaaaa cggcatgaat attttgcact aaaaccctca    8520
gaaaaattcc gatattccaa accagtacag ttcctgaccg ttggaggagc caaagtggag    8580
cggagtgtaa aattgggaaa cttaatcgag ggggttaaac gcaaaaacgc cgaggcgcct    8640
cccgctctat agaaagggga ggagtgggag gtggaaaccc taccacaccg cagagaaagg    8700
cgtcttcgta ctcgcctctc tccgcgcccc cctccgccgc cgctcgccgc cgttcgtctc    8760
cgccgccacc ggctagccat ccaggtaaaa caaacaaaaa cggatctgat gcttccattc    8820
ctccgtttct cgtagtagcg cgcttcgatc tgtgggtgga tctgggtgat cctggggtgt    8880
ggttcgttct gtttgataga tctgtcggtg gatctggcct tctgtggttg tcgatgtccg    8940
gatctgcgtt ttgatcagtg gtagttcgtg gatctggcga aatgttttgg atctggcagt    9000
gagacgctaa gaatcgggaa atgatgcaat attagggggg tttcggatgg ggatccactg    9060
aattagtctg tctccctgct gataatctgt tccttttggg tagatctggt tagtgtatgt    9120
ttgtttcgga tagatctgat caatgcttgt ttgtttttttc aaattttcta cctaggttgt    9180
ataggaatgg catgcggatc tggttggatt gccatgatcc gtgctgaaat gcccctttgg    9240
ttgatggatc ttgatatttt actgctgttc acctagattt gtactcccgt ttatacttaa    9300
tttgttgctt attatgaata gatctgtaac ttaggcacat gtatggacgg agtatgtgga    9360
tctgtagtat gtacattgct gcgagctaag aactatttca gagcaagcac agaaaaaaat    9420
atttagacag attgggcaac tatttgatgg tctttggtat catgctttgt agtgctcgtt    9480
tctgcgtagt aatcttttga tctgatctga agataggtgc tattatattc ttaaaggtca    9540
ttagaacgct atctgaaagg ctgtattatg tggattggtt cacctgtgac tccctgttcg    9600
tcttgtcttg ataaatcctg tgataaaaaa aattcttaag gcgtaatttg ttgaaatctt    9660
gttttgtcct atgcagcctg atccatggcg caagttagca gaatctgcaa tggtgtgcag    9720
aacccatctc ttatctccaa tctctcgaaa tccagtcaac gcaaatctcc cttatcggtt    9780
tctctgaaga cgcagcagca tccacgagct tatccgattt cgtcgtcgtg gggattgaag    9840
aagagtggga tgacgttaat tggctctgag cttcgtcctc ttaaggtcat gtcttctgtt    9900
tccacggcgt gcatgcttca cggtgcaagc agccggcccg caaccgcccg caaatcctct    9960
ggcctttccg gaaccgtccg cattcccggc gacaagtcga tctcccaccg gtccttcatg    10020
ttcggcggtc tcgcgagcgg tgaaacgcgc atcaccggcc ttctggaagg cgaggacgtc    10080
atcaatacgg gcaaggccat gcaggcgatg ggcgcccgca tccgtaagga aggcgacacc    10140
tggatcatcg atgcgtcgg caatggcggc tcctgcgcg ctgaggcgcc gctcgatttc    10200
ggcaatgccg ccacgggctg ccgcctgacg atgggcctcg tcgggtcta cgatttcgac    10260 agcaccttca tcgcgacgc ctcgctcaca aagcgcccga tgggccgcgt gttgaacccg    10320
ctgcgcgaaa tgggcgtgca ggtgaaatcg gaagacggtg accgtcttcc cgttaccttg    10380
```

```
cgcgggccga agacgccgac gccgatcacc taccgcgtgc cgatggcctc cgcacaggtg    10440
aagtccgccg tgctgctcgc cggcctcaac acgcccggca tcacgacggt catcgagccg    10500
atcatgacgc gcgatcatac ggaaaagatg ctgcagggct ttggcgccaa ccttaccgtc    10560
gagacggatg cggacggcgt gcgcaccatc cgcctggaag ccgcggcaa gctcaccggc     10620 caagtcatcg acgtgccggg cgacccgtcc tcgacggcct tcccgctggt tgcggccctg    10680
cttgttccgg gctccgacgt caccatcctc aacgtgctga tgaacccac ccgcaccggc     10740 ctcatcctga cgctgcagga aatgggcgcc gacatcgaag tcatcaaccc gcgccttgcc    10800
ggcggcgaag acgtggcgga cctgcgcgtt cgctcctcca cgctgaaggg cgtcacggtg    10860
ccggaagacc gcgcgccttc gatgatcgac gaatatccga ttctcgctgt cgccgccgcc    10920
ttcgcggaag gggcgaccgt gatgaacggt ctggaagaac tccgcgtcaa ggaaagcgac    10980
cgcctctcgg ccgtcgccaa tggcctcaag ctcaatggcg tggattgcga tgagggcgag    11040
acgtcgctcg tcgtgcgtgg ccgccctgac ggcaaggggc tcggcaacgc ctcgggcgcc    11100
gccgtcgcca cccatctcga tcaccgcatc gccatgagct tcctcgtcat gggcctcgtg    11160
tcggaaaacc ctgtcacggt ggacgatgcc acgatgatcg ccacgagctt cccggagttc    11220
atggacctga tggccgggct gggcgcgaag atcgaactct ccgatacgaa ggctgcctga    11280
tgagctccag ggttcttgcc tggtgccttg gcaatgcttg attactgctg ctatcctatg    11340
atctgtccgt gtgggcttct atctatcagt ttgtgtgtct ggttttgaaa acatttgct    11400 tttcgattat gtagggtttg cttgtagctt tcgctgctgt gacctgtgtt gtttatgtga    11460
accttctttg tggcatcttt aatatccaag ttcgtggttt gtcgtaaaac gaagcctcta    11520
cttcgtaaag ttgtgtctat agcattgaaa tcgttttttt gctcgagaat aattgtgacc    11580
tttagttggc gtgaaactag ttttggatat ctgattctct ggttcgcaat cttgagatcg    11640
tcgctgctta ggtgagctaa gtgatgttcc taagtaaatg ctcctcacca gaatacgtag    11700
ctgtgtgaaa agagaacgcg tgaatacgta gctgtgtaaa gattgtgtcc caagtaaacc    11760
tcagtgattt ttgtttggat ttttaattta gaaacattcg actgggagcg gctagagcca    11820
cacccaagtt cctaactatg ataaagttgc tctgtaacag aaaacaccat ctagagcggc    11880
cgcgtttaaa ctatcagtgt ttgacaggat atattggcgg gtaaacctaa gagaaaagag    11940
cgtttattag aataatcgga tatttaaaag ggcgtgaaaa ggtttatccg ttcgtccatt    12000
tgtatgtgca tgccaaccac agggttcccc tcgggagtgc ttggcattcc gtgcgataat    12060
gacttctgtt caaccaccca aacgtcggaa agcctgacga cggagcagca ttccaaaaag    12120
atcccttggc tcgtctgggt cggctagaag gtcgagtggg ctgctgtggc ttgatccctc    12180
aacgcggtcg cggacgtagc gcagcgccga aaaatcct                             12218
```

<210> SEQ ID NO 32  
<211> LENGTH: 12797  
<212> TYPE: DNA  
<213> ORGANISM: Artificial Sequence  
<220> FEATURE:  
<223> OTHER INFORMATION: DNA construct 404

<400> SEQUENCE: 32

```
aaaagtccca tgtggatcac tccgttgccc cgtcgctcac cgtgttgggg ggaaggtgca      60
catggctcag ttctcaatgg aaattatctg cctaaccggc tcagttctgc gtagaaacca    120
acatgcaagc tccaccgggt gcaaagcggc agcggcggga ggatatattc aattgtaaat    180
ggcttcatgt ccgggaaatc tacatggatc agcaatgagt atgatggtca atatggagaa    240
```

```
aaagaaagag taattaccaa ttttttttca attcaaaaat gtagatgtcc gcagcgttat     300
tataaaatga aagtacattt tgataaaacg acaaattacg atccgtcgta tttataggcg     360
aaagcaataa acaaattatt ctaattcgga aatctttatt tcgacgtgtc tacattcacg     420
tccaaatggg ggcttagatg agaaacttca cgatcgatgc ggccaccact cgaggtcgag     480
gtaccgttgt caatcaattg gcaagtcata aaatgcatta aaaatatttt tcatactcaa     540
ctacaaatcc atgagtataa ctataattat aaagcaatga ttagaatctg acaaggattc     600
tggaaaatta cataaaggaa agttcataaa tgtctaaaac acaagaggac atacttgtat     660
tcagtaacat ttgcagcttt tctaggtctg aaaatatatt tgttgcctag tgaataagca     720
taatggtaca actacaagtg ttttactcct catattaact tcggtcatta gaggccacga     780
tttgacacat ttttactcaa aacaaaatgt ttgcatatct cttataattt caaattcaac     840
acacaacaaa taagagaaaa acaaataat attaatttga gaatgaacaa aaggaccata     900
tcattcatta actcttctcc atccatttcc atttcacagt tcgatagcga aaaccgaata     960
aaaaacacag taaattacaa gcacaacaaa tggtacaaga aaaacagttt tcccaatgcc    1020
ataatactca aactcagtag gattctggtg tgtgcgcaat gaaactgatg cattgaactt    1080
gacgaacgtt gtcgaaaccg atgatacgaa cgaaagctag gcctcagcga gtaccgctgg    1140
cgatctaatc catgatatcg tgaacatcat ctacattcaa attcttatga gctttcttaa    1200
gggcatctgc agcattttc atagaatcta atacagcagt atttgtgcta gctccttcga    1260
gggcttccct ctgcatttca atagttgtaa gggttccatc tatttgtagt tgggtctttt    1320
ccaatcgttt cttcttttg agggcttgga gtgcaactct tttattttc gacgcatttt    1380 tctttgcgct cctgcaggcg gccgcgtgga tgaggagtta atcggtcgtg tgagagtagt    1440
gatcgagtgg atgtcgtcga gagtgatgag tgttgatgtt gttagtgata tgtggtagaa    1500
ggtatcgtga taaagcgtta acgcgatcgc agtacttgca aagaaaaatg cgtcgaaaaa    1560
taaaagagtt gcactccaag ccctcaaaaa gaagaaacga ttggaaaaga cccaactaca    1620
aatagatgga acccttacaa ctattgaaat gcagagggaa gccctcgaag gagctagcac    1680
aaatactgct gtattagatt ctatgaaaaa tgctgcagat gcccttaaga aagctcataa    1740
gaatttgaat gtagatgatg ttcacgatat catggatggt atcgcacagc gactgctgag    1800
ggacgtcggt ccatggagat cctctagagg ccgcttggta tctgcattac aatgaaatga    1860
gcaaagacta tgtgagtaac actggtcaac actagggaga aggcatcgag caagatacgt    1920
atgtaaagag aagcaatata gtgtcagttg gtagatacta gataccatca ggaggtaagg    1980
agagcaacaa aaaggaaact ctttattttt aaattttgtt acaacaaaca agcagatcaa    2040
tgcatcaaaa tactgtcagt acttatttct tcagacaaca atatttaaaa caagtgcatc    2100
tgatcttgac ttatggtcac aataaaggag cagagataaa catcaaaatt tcgtcattta    2160
tatttattcc ttcaggcgtt aacaatttaa cagcacacaa acaaaaacag aataggaata    2220
tctaattttg gcaaataata agctctgcag acgaacaaat tattatagta tcgcctataa    2280
tatgaatccc tatactattg acccatgtag tatgaagcct gtgcctaaat taacagcaaa    2340
cttctgaatc caagtgccct ataacaccaa catgtgctta aataaatacc gctaagcacc    2400
aaattacaca tttctcgtat tgctgtgtag gttctatctt cgtttcgtac taccatgtcc    2460
ctatattttg ctgctacaaa ggacggcaag taatcagcac aggcagaaca cgatttcaga    2520
gtgtaattct agatccagct aaaccactct cagcaatcac cacacaagag agcattcaga    2580
```

```
gaaacgtggc agtaacaaag gcagagggcg gagtgagcgc gtaccgaaga cggtgggccg    2640
cttatggtgt gttgtccctg tgtgttctcc aatagtgtgg cttgagtgtg tggaagatgg    2700
ttgtatctga tgatccttca aatgggaatg aatgccttct tatatagagg gaattctttt    2760
gtggtcgtca ctgcgttcgt catacgcatt agtgagtggg ctgtcaggac agctcttttc    2820
cacgttattt tgttccccac ttgtactaga ggaatctgct ttatctttgc aataaaggca    2880
aagatgcttt tggtaggtgc gcctaacaat tctgcaccat tcctttttg tctggtcccc     2940
acaagccagc tgctcgatgt tgacaagatt actttcaaag atgcccacta actttaagtc    3000
ttcggtggat gtcttttct gaaacttact gaccatgatg catgtgctgg aacagtagtt     3060
tactttgatt gaagattctt cattgatctc ctgtagcttt tggctaatgg tttggagact    3120
ctgtaccctg accttgttga ggctttggac tgagaattct tccttacaaa cctttgagga    3180
tgggagttcc ttcttggttt tggcgatacc aatttgaata aagtgatatg gctcgtacct    3240
tgttgattga acccaatctg gaatgctgct aaatcctgag ctcaagctaa ttcttttgtg    3300
gtcgtcactg cgttcgtcat acgcattagt gagtgggctg tcaggacagc tcttttccac    3360
gttattttgt tccccacttg tactagagga atctgcttta tctttgcaat aaaggcaaag    3420
atgcttttgg taggtgcgcc taacaattct gcaccattcc ttttttgtct ggtccccaca    3480
agccagctgc tcgatgttga caagattact ttcaaagatg cccactaact taagtcttc    3540
ggtggatgtc ttttctgaa acttactgac catgatgcat gtgctggaac agtagtttac    3600
tttgattgaa gattcttcat tgatctcctg tagcttttgg ctaatggttt ggagactctg    3660
taccctgacc ttgttgaggc tttggactga gaattagctt ccactcgaag cttgttaacc    3720
tgcaggctag cggcgcgccg ggatccaaaa aacacacaca gatctaattc ctttttttt    3780
gcactcaaaa tcagaacaat ttatttctca tttattcatc gccgaatctg ttggcgatta    3840
gccgattaca caagtacaga aaacactggg gaaagaaaca caatacagag atgtctcatc    3900
agactcgcaa gaactcgcac acacatcaac caaattggct ccaacctgaa tgagcatacg    3960
tccaaacgca tgcagaattc aatcagagtt cctatcacag ctggacgggg atgaactcga    4020
tcttgtcgat gtagatcttc tcgttggaga cgaaggactc agcaccaatg atcagttcat    4080
tcttgtcgcc cgagaagccc atgttggagt tcgtggtggc gaggtcgaag gtctggtagg    4140
tcaggtcatc gtccttgttc atggtcttgt tgatgtagat gaccaggaag tcattgttgg    4200
agttctggac gaacaggcgc aggttcgtgg tggaggcgta gcggatgcgg acgcggtagc    4260
gttgcagcaa ggcagcggag ttcagggtga ccttgaactt ggcgatggag ttcgaggact    4320
ccttcaggaa cagcaggttg ccaccggtga agcctggacc ctcaatgatg gaggcacccg    4380
aggacagggc gtaggccttg accacgggca gctgggtgat cttctcggcg tcgatggtgt    4440
tgaagaagtc gacggagcgg tgggtccagg tgaagaaggg gatggtgccc ctgcggtctt    4500
gcatcaggaa gcactccgcg tagttcagct ggtgggagta ggccttctcc aggggctcgt    4560
cagtggtctc aggcggcagc tggtcgatgg agtcctgggc ggagacgtgg ccattgttgc    4620
gcttggagtc gtaggtctgg gtggaggtct cgttcttctg gtcatcgtac tgggagaagt    4680
cgaccttcgt gacgcccagg tagaccttgc cgttcggcca agccgcgacg tcggtgttgg    4740
cgatggtgcg gtagaccttc tggccgtcga aggacagctt ctggacgggc tcggtggact    4800
tgtcgccgta gaaaggggag gtgatcgtct tcgaggagcc gatggagggc ctggtctcga    4860
cgtagttgcc ggaccagtag ttgaaggagt ccttgccgaa gtagcctggc ctcaggcgcg    4920
tgtggaactc gatgccctgg aggtagtcga acaggtgggg cttgcggatg gagttctcga    4980
```

```
tggacaggaa ggtgggaccg tacttctgga gggtcgtgag caggaagatg gggtccgtga   5040
agatgtcgcg ggtcagctcg gtcttgacgc ccttggagta caggcggatg tcgtagaagg   5100
ggaacaggac gatcaggtcc aggacggtca gggtcatctc cctgcggaag cggttgaact   5160
tgacccatgc gtcgtaggtg gagcccctca ggccgttcag gccgacgttg taccagttga   5220
cgcagtggtc ggtgtactgt tgggtcagct tcagctggcg acggtagaac tcggcgacgt   5280
cctccgagga gtagccccat tcctcgccga agacctgggc gtccttcagc aacaggaggg   5340
gggtgttggc agcctgggcg taggtgggca ggaacaggac ctcgaacttg gagacggcga   5400
aggacggcat ggagttgcgg aagtgggact cggcctggga gaacagctcg cggatgcggt   5460
cctgggagcg cttggagcgc agggacagag gcgtcttctt ccaggagttc agcgcgttga   5520
cgtagtcctc gaagttgttt tgcaggcctt gcagctcggc cagggccttg gacttggcgt   5580
actcctcgat cttcttgtcg atcaggactt cgacttgggc catgaaggcc ttccaggggt   5640
cggcgtcgga gggccagatg gtgttcagga aggactggta gaaggaggtg agagcacctg   5700
cgaaggggac gccaacgacg cccaggatct gcccaacgac ggagatgccg gtcccgacgg   5760
cgtccttgac ggtggagttg tccaggacct ccgtggagga gtcctcggtc atgcgcagga   5820
actccttgta gttcagctct tccagggtgg agttggggtt gtcggccagc gggtactggt   5880
tgtggttggt ctggagctcg gagttggggg tgaccttgat cgtgtcgtgc tcggagcgat   5940
tgttggggtt ggccatggtt gatcacttct acctacaaaa aagctccgca cgaggctgca   6000
tttgtcacaa atcatgaaaa gaaaaactac cgatgaacaa tgctgaggga ttcaaattct   6060
acccacaaaa agaagaaaga aagatctagc acatctaagc ctgacgaagc agcagaaata   6120
tataaaaata taaccatag tgccttttc cctcttcct gatcttgttt agcacggcgg   6180
aaattttaaa ccccccatca tctcccccaa caacggcgga tcgcagatct acatccgaga   6240
gccccattcc ccgcgagatc cgggccggat ccacgccggc gagagcccca gccgcgagat   6300
cccgcccctc ccgcgcaccg atctgggcgc gcacgaagcc gcctctcgcc cacccaaact   6360
accaaggcca aagatcgaga ccgagacgga aaaaaaacg gagaaagaaa gaggagaggg   6420
gcggggtggt taccggcggc ggcggaggcc tcccttggat cttatggtgt gttgtccctg   6480
tgtgttctcc aatagtgtgg cttgagtgtg tggaagatgg ttcccggggg ttttgatcat   6540
gggattaggg aggtatttat agtcgagccc cgggattaat taatcgaccg ttagagctca   6600
tgtgaaccct gccctgccat catgtgagcg tgcatacgag ggcgatctgg attggctggc   6660
agaacacctg ccctagcaag gctcgtagat taattaacaa atcgtacgta catctacgct   6720
gataatgtgt taaatcatcg gccgaatatt tggttagccg tgaagcactc gatcccgcaa   6780
atgaccaaga ttgctgcaca cgacacatcg cgggcttgtt tccttatgat cattggttgt   6840
tattttatct cgcgatcttg gcctatcggg cgtcgcttcg cgcggtgcag cgtgactgcg   6900
tgagcaagtt ggtgattttc ttttgccgtt taagaatgct tgctccgtga tcacacaaga   6960
gaggacatca catgaaccga gaccggagga atatcggggc atggtgggat tggtgggtgt   7020
cccagtccaa cggcaagaa gattctaagc ttacctgggt tgttttcac gtacgcgaag   7080
gacagggaa gatgccattg cagcgtggct tcctgctgga ccgccaactt taatctacac   7140
taggcacgta gctactaggt cggcccgctt agatagctaa ggtaggctag gtaggtccgt   7200
ggtaaactgc cagcccatgg gcgcctggga ttccttcttgg gccaacagaa gcagaggttg   7260
ggcaatgcga agcctgaaaa tcctcctcct ccttctctct ccctctctct ctctctctct   7320
```

```
ctctctctct cacgaataaa atcctcttct tcccgaacag gctagattct ttttttttta    7380
atgaaccagt gagccaccaa tttcattgaa tagaggaata aaattgtaca tgcgcaagcg    7440
caaatagaaa actttaccgt ctcaaggcct ttggcccgaa catgttaaaa ggtaagccac    7500
ctatcaaggt gtttcgcgcc cgccaagacc catgttttgg catcctcctt aattttggct    7560
atcagactag ccaccggaag ctcttggtgc tgaaaaactc tgcggttcct ttcattccaa    7620
atatcctagg cgactaatag cattagagtc tgcaaggctt tctttggcgc ttcgttggaa    7680
catgcggtgg cctcccacca cttgagtagc gtcgaggctt gttgccataa cgttggtctt    7740
atttgttcac atgttgtcca gtctgcaagt gtcgcctaga ttctttcaca tatctacact    7800
ccgccaggag gtgagggccg tttcctgatt ccttcgacaa aggggcagat ggagccattt    7860
tcgattaccc acgggttgcc aatcgtctgg aggtccatac tctatttttg ataacaagcc    7920
aagcgaagcg aatgttttac atttgcgcgg cgcctagggc ttccagatag gggcattgaa    7980
attgaagctt ttatgccaag aagttgtgcg ttgtaggccg atgtcgtcat gtattcgccg    8040
tgactagtta gcttccattt tcgacaagct tgcctcgaga caacaacatg cttctcatca    8100
acatggaggg aagagggagg gagaaagtgt cgcctggtca cctccattgt cacactagcc    8160
actggccagc tctcccacac caccaatgcc aggggcgagc tttagcacag ccaccgcttc    8220
acctccacca ccgcactacc ctagcttcgc ccaacagcca ccgtcaacgc ctcctctccg    8280
tcaacataag agagagagag aagaggagag tagccatgtg gggaggagga atagtacatg    8340
gggcctaccg tttggcaagt tattttgggt tgccaagtta ggccaataag gggagggatt    8400
tggccatccg gttggaaagg ttattggggt agtatctttt tactagaatt gtcaaaaaaa    8460
aatagtttga gagccatttg gagaggatgt tgcctgttag aggtgctctt aggacatcaa    8520
attccataaa aacatcagaa aaattctctc gatgaagatt tataaccact aaaactgccc    8580
tcaattcgaa gggagttcaa aacaattaaa atcatgttcg aattgagttt caatttcact    8640 ttaaccccctt tgaaatctca atggtaaaac atcaacccgt caggtagcat ggttcttttt    8700
attcctttca aaaagagtta attacaaaca gaatcaaaac taacagttag gcccaaggcc    8760
catccgagca aacaatagat catgggccag gcctgccacc accctccccc tcctggctcc    8820
cgctcttgaa tttcaaaatc caaaaatatc ggcacgactg gccgccgacg gagcgggcgg    8880
aaaatgacgg aacaaccccct cgaattctac cccaactacg cccaccaacc cacacgccac    8940
tgacaatccg gtcccacccct tgtgggccca cctacaagcg agacgtcagt cgctcgcagc    9000
aaccagtggg cccacctccc agtgagcggc gggtagatct ggactcttac ccacccacac    9060
taaacaaaac ggcatgaata ttttgcacta aaaccctcag aaaaattccg atattccaaa    9120
ccagtacagt tcctgaccgt tggaggagcc aaagtggagc ggagtgtaaa attgggaaac    9180
ttaatcgagg gggttaaacg caaaaacgcc gaggcgcctc ccgctctata gaaagggggag    9240 gagtgggagg tggaaaccct accacaccgc agagaaaggc gtcttcgtac tcgcctctct    9300
ccgcgccctc ctccgccgcc gctcgccgcc gttcgtctcc gccgccaccg gctagccatc    9360
caggtaaaac aaacaaaaac ggatctgatg cttccattcc tccgtttctc gtagtagcgc    9420
gcttcgatct gtgggtggat ctgggtgatc ctggggtgtg gttcgttctg tttgatagat    9480
ctgtcggtgg atctggcctt ctgtggttgt cgatgtccgg atctgcgttt tgatcagtgg    9540
tagttcgtgg atctggcgaa atgttttgga tctggcagtg agacgctaag aatcgggaaa    9600
tgatgcaata ttaggggggt ttcggatggg gatccactga attagtctgt ctccctgctg    9660
ataatctgtt ccttttttggt agatctggtt agtgtatgtt tgtttcggat agatctgatc    9720
```

```
aatgcttgtt tgttttttca aattttctac ctaggttgta taggaatggc atgcggatct    9780
ggttggattg ccatgatccg tgctgaaatg ccccttggt tgatggatct tgatatttta    9840
ctgctgttca cctagatttg tactcccgtt tatacttaat ttgttgctta ttatgaatag    9900
atctgtaact taggcacatg tatggacgga gtatgtggat ctgtagtatg tacattgctg    9960
cgagctaaga actatttcag agcaagcaca gaaaaaaata tttagacaga ttgggcaact   10020
atttgatggt ctttggtatc atgctttgta gtgctcgttt ctgcgtagta atcttttgat   10080
ctgatctgaa gataggtgct attatattct taaaggtcat tagaacgcta tctgaaaggc   10140
tgtattatgt ggattggttc acctgtgact ccctgttcgt cttgtcttga taaatcctgt   10200
gataaaaaaa attcttaagg cgtaatttgt tgaaatcttg ttttgtccta tgcagcctga   10260
tccatggcgc aagttagcag aatctgcaat ggtgtgcaga acccatctct tatctccaat   10320
ctctcgaaat ccagtcaacg caaatctccc ttatcggttt ctctgaagac gcagcagcat   10380
ccacgagctt atccgatttc gtcgtcgtgg ggattgaaga agagtgggat gacgttaatt   10440
ggctctgagc ttcgtcctct taaggtcatg tcttctgttt ccacggcgtg catgcttcac   10500
ggtgcaagca gccggcccgc aaccgcccgc aaatcctctg gcctttccgg aaccgtccgc   10560
attcccggcg acaagtcgat ctcccaccgg tccttcatgt tcggcggtct cgcgagcggt   10620
gaaacgcgca tcaccggcct tctggaaggc gaggacgtca tcaatacggg caaggccatg   10680
caggcgatgg gcgcccgcat ccgtaaggaa ggcgacacct ggatcatcga tggcgtcggc   10740
aatggcggcc tcctggcgcc tgaggcgccg ctcgatttcg gcaatgccgc cacgggctgc   10800
cgcctgacga tgggcctcgt cggggtctac gatttcgaca gcaccttcat cggcgacgcc   10860
tcgctcacaa agcgcccgat gggccgcgtg ttgaacccgc tgcgcgaaat gggcgtgcag   10920
gtgaaatcgg aagacggtga ccgtcttccc gttaccttgc gcgggccgaa gacgccgacg   10980
ccgatcacct accgcgtgcc gatggcctcc gcacaggtga agtccgccgt gctgctcgcc   11040
ggcctcaaca cgcccggcat cacgacggtc atcgagccga tcatgacgcg cgatcatacg   11100
gaaaagatgc tgcagggctt tggcgccaac cttaccgtcg agacggatgc ggacggcgtg   11160
cgcaccatcc gcctggaagg ccgcggcaag ctcaccggcc aagtcatcga cgtgccgggc   11220
gacccgtcct cgacggcctt cccgctggtt gcggccctgc ttgttccggg ctccgacgtc   11280
accatcctca acgtgctgat gaaccccacc cgcaccggcc tcatcctgac gctgcaggaa   11340
atgggcgccg acatcgaagt catcaacccg cgccttgccg gcggcgaaga cgtggcggac   11400
ctgcgcgttc gctcctccac gctgaagggc gtcacggtgc cggaagaccg cgcgccttcg   11460
atgatcgacg aatatccgat tctcgctgtc gccgccgcct tcgcggaagg ggcgaccgtg   11520
atgaacggtc tggaagaact ccgcgtcaag gaaagcgacc gcctctcggc cgtcgccaat   11580
ggcctcaagc tcaatggcgt ggattgcgat gagggcgaga cgtcgctcgt cgtgcgtggc   11640
cgccctgacg gcaaggggct cggcaacgcc tcggcgccg ccgtcgccac ccatctcgat   11700
caccgcatcg ccatgagctt cctcgtcatg ggcctcgtgt cggaaaaccc tgtcacggtg   11760
gacgatgcca cgatgatcgc cacgagcttc ccggagttca tggacctgat ggccgggctg   11820
ggcgcgaaga tcgaactctc cgatacgaag gctgcctgat gagctccagg gttcttgcct   11880
ggtgccttgg caatgcttga ttactgctgc tatcctatga tctgtccgtg tgggcttcta   11940
tctatcagtt tgtgtgtctg gttttgaaaa acatttgctt ttcgattatg tagggtttgc   12000
ttgtagcttt cgctgctgtg acctgtgttg tttatgtgaa ccttcttgt ggcatcttta   12060
```

| | |
|---|---|
| atatccaagt tcgtggtttg tcgtaaaacg aagcctctac ttcgtaaagt tgtgtctata | 12120 |
| gcattgaaat cgttttttg ctcgagaata attgtgacct ttagttggcg tgaaactagt | 12180 |
| tttggatatc tgattctctg gttcgcaatc ttgagatcgt cgctgcttag gtgagctaag | 12240 |
| tgatgttcct aagtaaatgc tcctcaccag aatacgtagc tgtgtgaaaa gagaacgcgt | 12300 |
| gaatacgtag ctgtgtaaag attgtgtccc aagtaaacct cagtgatttt tgtttggatt | 12360 |
| tttaatttag aaacattcga ctgggagcgg ctagagccac acccaagttc ctaactatga | 12420 |
| taaagttgct ctgtaacaga aaacaccatc tagagcggcc gcgtttaaac tatcagtgtt | 12480 |
| tgacaggata tattggcggg taaacctaag agaaaagagc gtttattaga ataatcggat | 12540 |
| atttaaaagg gcgtgaaaag gtttatccgt tcgtccattt gtatgtgcat gccaaccaca | 12600 |
| gggttcccct cgggagtgct tggcattccg tgcgataatg acttctgttc aaccacccaa | 12660 |
| acgtcggaaa gcctgacgac ggagcagcat tccaaaaaga tcccttggct cgtctgggtc | 12720 |
| ggctagaagg tcgagtgggc tgctgtggct tgatccctca acgcggtcgc ggacgtagcg | 12780 |
| cagcgccgaa aaatcct | 12797 |

<210> SEQ ID NO 33
<211> LENGTH: 11906
<212> TYPE: DNA
<213> ORGANISM: Artificial Sequence
<220> FEATURE:
<223> OTHER INFORMATION: DNA construct 423

<400> SEQUENCE: 33

| | |
|---|---|
| aaaagtccca tgtggatcac tccgttgccc cgtcgctcac cgtgttgggg ggaaggtgca | 60 |
| catggctcag ttctcaatgg aaattatctg cctaaccggc tcagttctgc gtagaaacca | 120 |
| acatgcaagc tccaccgggt gcaaagcggc agcggcggca ggatatattc aattgtaaat | 180 |
| ggcttcatgt ccgggaaatc tacatggatc agcaatgagt atgatggtca atatggagaa | 240 |
| aaagaaagag taattaccaa tttttttca attcaaaaat gtagatgtcc gcagcgttat | 300 |
| tataaaatga agtacattt tgataaaacg acaaattacg atccgtcgta tttataggcg | 360 |
| aaagcaataa acaaattatt ctaattcgga aatctttatt tcgacgtgtc tacattcacg | 420 |
| tccaaatggg ggcttagatg agaaacttca cgatcgatgc ggccaccact cgaggtcgag | 480 |
| gtaccacaca cagatctaat tccttttttt ttgcactcaa aatcagaaca atttatttct | 540 |
| catttattca tcgccgaatc tgttggcgat tagccgatta cacaagtaca gaaaacactg | 600 |
| gggaaagaaa cacaatacag agatgtctca tcagactcgc aagaactcgc acacacatca | 660 |
| accaaattgg ctccaacctg aatgagcata cgtccaaacg catgcagaat tcaatcagag | 720 |
| ttcctatcac agctggacgg ggatgaactc gatcttgtcg atgtagatct tctcgttgga | 780 |
| gacgaaggac tcagcaccaa tgatcagttc attcttgtcg cccgagaagc ccatgttgga | 840 |
| gttcgtggtg gcgaggtcga aggtctggta ggtcaggtca tcgtccttgt tcatggtctt | 900 |
| gttgatgtag atgaccagga agtcattgtt ggagttctgg acgaacaggc gcaggttcgt | 960 |
| ggtggaggcg tagcggatgc ggacgcggta gcgttgcagc aaggcagcgg agttcagggt | 1020 |
| gaccttgaac ttggcgatgg agttcgagga ctccttcagg aacagcaggt tgccaccggt | 1080 |
| gaagcctgga ccctcaatga tggaggcacc cgaggacagg gcgtaggcct tgaccacggg | 1140 |
| cagctgggtg atcttctcgg cgtcgatggt gttgaagaag tcgacggagc ggtgggtcca | 1200 |
| ggtgaagaag gggatggtgc ccctgcggtc ttgcatcagg aagcactccg cgtagttcag | 1260 |
| ctggtgggag taggccttct ccaggggctc gtcagtggtc tcaggcggca gctggtcgat | 1320 |

```
ggagtcctgg gcggagacgt ggccattgtt gcgcttggag tcgtaggtct gggtggaggt      1380
ctcgttcttc tggtcatcgt actgggagaa gtcgaccttc gtgacgccca ggtagacctt      1440
gccgttcggc caagccgcga cgtcggtgtt ggcgatggtg cggtagacct tctggccgtc      1500
gaaggacagc ttctggacgg gctcggtgga cttgtcgccg tagaaagggg aggtgatcgt      1560
cttcgaggag ccgatggagg gcctggtctc gacgtagttg ccggaccagt agttgaagga      1620
gtccttgccg aagtagcctg gcctcaggcg cgtgtggaac tcgatgccct ggaggtagtc      1680
gaacaggtgg ggcttgcgga tggagttctc gatggacagg aaggtgggac cgtacttctg      1740
gagggtcgtg agcaggaaga tggggtccgt gaagatgtcg cgggtcagct cggtcttgac      1800
gcccttggag tacaggcgga tgtcgtagaa ggggaacagg acgatcaggt ccaggacggt      1860
cagggtcatc tccctgcgga agcggttgaa cttgacccat cgtcgtagg tggagccccct      1920
caggccgttc aggccgacgt tgtaccagtt gacgcagtgg tcggtgtact gttgggtcag      1980
cttcagctgg cgacggtaga actcggcgac gtcctccgag gagtagcccc attcctcgcc      2040
gaagacctgg gcgtccttca gcaacaggag gtgggtgttg gcagcctggg cgtaggtggg      2100
caggaacagg acctcgaact ggagacggc gaaggacggc atggagttgc ggaagtggga      2160
ctcggcctgg gagaacagct cgcggatgcg gtcctgggag cgcttggagc gcagggacag      2220
aggcgtcttc ttccaggagt tcagcgcgtt gacgtagtcc tcgaagttgt tttgcaggcc      2280
ttgcagctcg gccagggcct tggacttggc gtactcctcg atcttcttgt cgatcaggac      2340
ttcgacttgg gccatgaagg ccttccaggg gtcggcgtcg gagggccaga tggtgttcag      2400
gaaggactgg tagaaggagg tgagagcacc tgcgaagggg acgccaacga cgcccaggat      2460
ctgcccaacg acggagatgc cggtcccgac ggcgtccttg acggtggagt tgtccaggac      2520
ctccgtggag gagtcctcgg tcatgcgcag gaactccttg tagttcagct cttccagggt      2580
ggagttgggg ttgtcggcca gcgggtactg gttgtggttg gtctggagct cggagttggg      2640
ggtgaccttg atcgtgtcgt gctcggagcg attgttgggg ttggccatgg ttgatcactt      2700
ctacctacaa aaaagctccg cacgaggctg catttgtcac aaatcatgaa aagaaaaact      2760
accgatgaac aatgctgagg gattcaaatt ctacccacaa aaagaagaaa gaaagatcta      2820
gcacatctaa gcctgacgaa gcagcagaaa tatataaaaa tataaaccat agtgcccttt      2880
tccctcttc ctgatcttgt ttagcacggc ggaaatttta aacccccat catctccccc        2940
aacaacggcg gatcgcagat ctacatccga gagccccatt ccccgcgaga tccgggccgg      3000
atccacgccg gcgagagccc cagccgcgag atcccgcccc tcccgcgcac cgatctgggc      3060
gcgcacgaag ccgcctctcg cccacccaaa ctaccaaggc caaagatcga gaccgagacg      3120
gaaaaaaaa cggagaaaga aagaggagag gggcggggtg gttaccggcg gcggcggagg      3180
cctcccttgg atcttatggt gtgttgtccc tgtgtgttct ccaatagtgt ggcttgagtg      3240
tgtggaagat ggttctagag gatctgctag agtcagcttg tcagcgtgtc ctctccaaat      3300
gaaatgaact tccttatata gaggaagggt cttgcgaagg atagtgggat tgtgcgtcat      3360
cccttacgtc agtggagata tcacatcaat ccacttgctt tgaagacgtg gttggaacgt      3420
cttcttttc cacgatgctc ctcgtgggtg ggggtccatc tttgggacca ctgtcggcag        3480
aggcatcttc aacgatggcc tttcctttat cgcaatgatg gcatttgtag gagccacctt      3540
ccttttccac tatcttcaca ataaagtgac agatagctgg gcaatggaat ccgaggaggt      3600
ttccggatat tacccttttgt tgaaaagtct caatcggacc atcacatcaa tccacttgct      3660
```

```
ttgaagacgt ggttggaacg tcttctttt  ccacgatgct cctcgtgggt ggggtccat    3720
ctttgggacc actgtcggca gaggcatctt caacgatggc ctttcccttta tcgcaatgat   3780
ggcatttgta ggagccacct tccttttcca ctatcttcac aataaagtga cagatagctg   3840
ggcaatggaa tccgaggagg tttccggata tacccttg   ttgaaaagtc tcaatcggac   3900
ctggtaccgt tgtcaatcaa ttggcaagtc ataaaatgca ttaaaaaata tttcatact    3960
caactacaaa tccatgagta taactataat tataaagcaa tgattagaat ctgacaagga   4020
ttctggaaaa ttacataaag gaaagttcat aaatgtctaa aacacaagag gacatacttg   4080
tattcagtaa catttgcagc ttttctaggt ctgaaaatat atttgttgcc tagtgaataa   4140
gcataatggt acaactacaa gtgttttact cctcatatta acttcggtca ttagaggcca   4200
cgatttgaca cattttact  caaaacaaaa tgtttgcata tctcttataa tttcaaattc   4260
aacacacaac aaataagaga aaaacaaat  aatattaatt tgagaatgaa caaaaggacc   4320
atatcattca ttaactcttc tccatccatt tccatttcac agttcgatag cgaaaaccga   4380
ataaaaaaca cagtaaatta caagcacaac aaatggtaca agaaaaacag ttttcccaat   4440
gccataatac tcaaactcag taggattctg gtgtgtgcgc aatgaaactg atgcattgaa   4500
cttgacgaac gttgtcgaaa ccgatgatac gaacgaaagc taggcctcag cgagtaccgc   4560
tggcgatcta atccatgata tcgtgaacat catctacatt caaattctta tgagctttct   4620
taagggcatc tgcagcattt ttcatagaat ctaatacagc agtatttgtg ctagctcctt   4680
cgagggcttc cctctgcatt tcaatagttg taagggttcc atctatttgt agttgggtct   4740
tttccaatcg tttcttcttt tgagggcttt ggagtgcaac tcttttattt ttcgacgcat   4800
ttttctttgc gctcctgcag gcggccgcgt ggatgaggag ttaatcggtc gtgtgagagt   4860
agtgatcgag tggatgtcgt cgagagtgat gagtgttgat gttgttagtg atatgtggta   4920
gaaggtatcg tgataaagcg ttaacgcgat cgcagtactt gcaaagaaaa atgcgtcgaa   4980
aaataaaaga gttgcactcc aagccctcaa aaagaagaaa cgattggaaa agacccaact   5040
acaaatagat ggaacccttaa caactattga aatgcagagg gaagccctcg aaggagctag   5100
cacaaatact gctgtattag attctatgaa aaatgctgca gatgccctta agaaagctca   5160
taagaatttg aatgtagatg atgttcacga tatcatggat ggtatcgcac agcgactgct   5220
gagggacgtc ggtccatgga gatcctctag aggccgcttg gtatctgcat tacaatgaaa   5280
tgagcaaaga ctatgtgagt aacactggtc aacactaggg agaaggcatc gagcaagata   5340
cgtatgtaaa gagaagcaat atagtgtcag ttggtagata ctagatacca tcaggaggta   5400
aggagagcaa caaaaaggaa actctttatt tttaaatttt gttacaacaa acaagcagat   5460
caatgcatca aaatactgtc agtacttatt tcttcagaca acaatattta aaacaagtgc   5520
atctgatctt gacttatggt cacaataaag gagcagagat aaacatcaaa atttcgtcat   5580
ttatatttat tccttcaggc gttaacaatt taacagcaca caaacaaaaa cagaatagga   5640
atatctaatt ttggcaaata ataagctctg cagacgaaca aattattata gtatcgccta   5700
taatatgaat ccctatacta ttgacccatg tagtatgaag cctgtgccta aattaacagc   5760
aaacttctga atccaagtgc cctataacac caacatgtgc ttaaataaat accgctaagc   5820
accaaattac acatttctcg tattgctgtg taggttctat cttcgtttcg tactaccatg   5880
tccctatatt ttgctgctac aaaggacggc aagtaatcag cacaggcaga acacgatttc   5940
agagtgtaat tctagatcca gctaaaccac tctcagcaat caccacacaa gagagcattc   6000
agagaaacgt ggcagtaaca aaggcagagg gcggagtgag cgcgtaccga agacggtggg   6060
```

```
ccgcttatgg tgtgttgtcc ctgtgtgttc tccaatagtg tggcttgagt gtgtggaaga    6120
tggttgtatc tgatgatcct tcaaatggga atgaatgcct tcttatatag agggaattct    6180
tttgtggtcg tcactgcgtt cgtcatacgc attagtgagt gggctgtcag gacagctctt    6240
ttccacgtta ttttgttccc cacttgtact agaggaatct gctttatctt tgcaataaag    6300
gcaaagatgc ttttggtagg tgcgcctaac aattctgcac cattccttt ttgtctggtc    6360 cccacaagcc agctgctcga tgttgacaag attactttca agatgccca ctaactttaa    6420 gtcttcggtg gatgtctttt tctgaaactt actgaccatg atgcatgtgc tggaacagta    6480
gtttactttg attgaagatt cttcattgat ctcctgtagc ttttggctaa tggtttggag    6540
actctgtacc ctgaccttgt tgaggctttg gactgagaat tcttccttac aaacctttga    6600
ggatgggagt tccttcttgg ttttggcgat accaatttga ataaagtgat atggctcgta    6660
ccttgttgat tgaacccaat ctggaatgct gctaaatcct gagctcaagc taattctttt    6720
gtggtcgtca ctgcgttcgt catacgcatt agtgagtggg ctgtcaggac agctcttttc    6780
cacgttattt tgttccccac ttgtactaga ggaatctgct ttatctttgc aataaaggca    6840
aagatgcttt tggtaggtgc gcctaacaat tctgcaccat tccttttttg tctggtcccc    6900
acaagccagc tgctcgatgt tgacaagatt actttcaaag atgcccacta actttaagtc    6960
ttcggtggat gtctttttct gaaacttact gaccatgatg catgtgctgg aacagtagtt    7020
tactttgatt gaagattctt cattgatctc ctgtagcttt tggctaatgg tttggagact    7080
ctgtaccctg accttgttga ggctttggac tgagaattag cttccactcg aagcttgtta    7140
acctgcaggc tagcggcgcg ccagtctagt cgacaagctt gcctcgagac aacaacatgc    7200
ttctcatcaa catggaggga agagggaggg agaaagtgtc gcctggtcac ctccattgtc    7260
acactagcca ctggccagct ctcccacacc accaatgcca ggggcgagct ttagcacagc    7320
caccgcttca cctccaccac cgcactaccc tagcttcgcc caacagccac cgtcaacgcc    7380
tcctctccgt caacataaga gagagagaga agaggagagt agccatgtgg ggaggaggaa    7440
tagtacatgg ggcctaccgt ttggcaagtt attttgggtt gccaagttag gccaataagg    7500
ggagggattt ggccatccgg ttggaaaggt tattgggta gtatcttttt actagaattg    7560
tcaaaaaaaa atagtttgag agccatttgg agaggatgtt gcctgttaga ggtgctctta    7620
ggacatcaaa ttccataaaa acatcagaaa aattctctcg atgaagattt ataaccacta    7680
aaactgccct caattcgaag ggagttcaaa acaattaaaa tcatgttcga attgagtttc    7740
aatttcactt taaccccttt gaaatctcaa tggtaaaaca tcaacccgtc aggtagcatg    7800
gttcttttta ttccttcaa aaagagttaa ttacaaacag aatcaaaact aacagttagg    7860
cccaaggccc atccgagcaa acaatagatc atgggccagg cctgccacca ccctccccct    7920
cctggctccc gctcttgaat ttcaaaatcc aaaaatatcg gcacgactgg ccgccgacgg    7980
agcgggcgga aaatgacgga acaaccctc gaattctacc ccaactacgc ccaccaaccc    8040
acacgccact gacaatccgg tcccaccctt gtgggcccac ctacaagcga gacgtcagtc    8100
gctcgcagca accagtgggc ccacctccca gtgagcggcg ggtagatctg gactcttacc    8160
cacccacact aaacaaaacg gcatgaatat tttgcactaa aaccctcaga aaaattccga    8220
tattccaaac cagtacagtt cctgaccgtt ggaggagcca agtggagcg gagtgtaaaa    8280 ttgggaaact taatcgaggg ggttaaacgc aaaaacgccg aggcgcctcc cgctctatag    8340
aaaggggagg agtgggaggt ggaaaaccta ccacaccgca gagaaaggcg tcttcgtact    8400
```

```
cgcctctctc cgcgccctcc tccgccgccg ctcgccgccg ttcgtctccg ccgccaccgg   8460
ctagccatcc aggtaaaaca aacaaaaacg gatctgatgc ttccattcct ccgtttctcg   8520
tagtagcgcg cttcgatctg tgggtggatc tgggtgatcc tggggtgtgg ttcgttctgt   8580
ttgatagatc tgtcggtgga tctggccttc tgtggttgtc gatgtccgga tctgcgtttt   8640
gatcagtggt agttcgtgga tctggcgaaa tgttttggat ctggcagtga gacgctaaga   8700
atcgggaaat gatgcaatat tagggggggtt tcggatgggg atccactgaa ttagtctgtc   8760
tccctgctga taatctgttc cttttttggta gatctggtta gtgtatgttt gtttcggata   8820
gatctgatca atgcttgttt gttttttcaa attttctacc taggttgtat aggaatggca   8880
tgcggatctg gttggattgc catgatccgt gctgaaatgc ccctttggtt gatggatctt   8940
gatattttac tgctgttcac ctagatttgt actcccgttt atacttaatt tgttgcttat   9000
tatgaataga tctgtaactt aggcacatgt atggacggag tatgtggatc tgtagtatgt   9060
acattgctgc gagctaagaa ctatttcaga gcaagcacag aaaaaaatat ttagacagat   9120
tgggcaacta tttgatggtc tttggtatca tgctttgtag tgctcgtttc tgcgtagtaa   9180
tcttttgatc tgatctgaag ataggtgcta ttatattctt aaaggtcatt agaacgctat   9240
ctgaaaggct gtattatgtg gattggttca cctgtgactc cctgttcgtc ttgtcttgat   9300
aaatcctgtg ataaaaaaaa ttcttaaggc gtaatttgtt gaaatcttgt tttgtcctat   9360
gcagcctgat ccatggcgca agttagcaga atctgcaatg gtgtgcagaa cccatctctt   9420
atctccaatc tctcgaaatc cagtcaacgc aaatctccct tatcggtttc tctgaagacg   9480
cagcagcatc cacgagctta tccgatttcg tcgtcgtggg gattgaagaa gagtgggatg   9540
acgttaattg gctctgagct tcgtcctctt aaggtcatgt cttctgtttc cacggcgtgc   9600
atgcttcacg gtgcaagcag ccggcccgca accgcccgca aatcctctgg cctttccgga   9660
accgtccgca ttcccggcga caagtcgatc tcccaccggt ccttcatgtt cggcggtctc   9720
gcgagcggtg aaacgcgcat caccggcctt ctggaaggcg aggacgtcat caatacgggc   9780
aaggccatgc aggcgatggg cgcccgcatc cgtaaggaag gcgacacctg gatcatcgat   9840
ggcgtcggca atggcggcct cctggcgcct gaggcgccgc tcgatttcgg caatgccgcc   9900
acgggctgcc gcctgacgat gggcctcgtc ggggtctacg atttcgacag caccttcatc   9960
ggcgacgcct cgctcacaaa gcgcccgatg ggccgcgtgt tgaacccgct gcgcgaaatg  10020
ggcgtgcagg tgaaatcgga agacggtgac cgtcttcccg ttaccttgcg cgggccgaag  10080
acgccgacgc cgatcaccta ccgcgtgccg atggcctccg cacaggtgaa gtccgccgtg  10140
ctgctcgccg gcctcaacac gcccggcatc acgacggtca tcgagccgat catgacgcgc  10200
gatcatacgg aaaagatgct gcagggcttt ggcgccaacc ttaccgtcga gacggatgcg  10260
gacggcgtgc gcaccatccg cctggaaggc cgcggcaagc tcaccggcca agtcatcgac  10320
gtgccgggcg accgtcctc gacgccttc ccgctggttg cggccctgct tgttccgggc  10380
tccgacgtca ccatcctcaa cgtgctgatg aaccccaccc gcaccggcct catcctgacg  10440
ctgcaggaaa tgggcgccga catcgaagtc atcaacccgc gccttgccgg cggcgaagac  10500
gtggcggacc tgcgcgttcg ctcctccacg ctgaagggcg tcacggtgcc ggaagaccgc  10560
gcgccttcga tgatcgacga atatccgatt ctcgctgtcg ccgccgcctt cgcggaaggg  10620
gcgaccgtga tgaacggtct ggaagaactc cgcgtcaagg aaagcgaccg cctctcggcc  10680
gtcgccaatg gcctcaagct caatggcgtg gattgcgatg agggcgagac gtcgctcgtc  10740
gtgcgtggcc gccctgacgg caaggggctc ggcaacgcct cgggcgccgc cgtcgccacc  10800
```

```
catctcgatc accgcatcgc catgagcttc ctcgtcatgg gcctcgtgtc ggaaaaccct    10860
gtcacggtgg acgatgccac gatgatcgcc acgagcttcc cggagttcat ggacctgatg    10920
gccgggctgg gcgcgaagat cgaactctcc gatacgaagg ctgcctgatg agctccaggg    10980
ttcttgcctg gtgccttggc aatgcttgat tactgctgct atcctatgat ctgtccgtgt    11040
gggcttctat ctatcagttt gtgtgtctgg ttttgaaaaa catttgcttt tcgattatgt    11100
agggtttgct tgtagctttc gctgctgtga cctgtgttgt ttatgtgaac cttctttgtg    11160
gcatctttaa tatccaagtt cgtggtttgt cgtaaaacga agcctctact tcgtaaagtt    11220
gtgtctatag cattgaaatc gttttttttgc tcgagaataa ttgtgacctt tagttggcgt    11280
gaaactagtt ttggatatct gattctctgg ttcgcaatct tgagatcgtc gctgcttagg    11340
tgagctaagt gatgttccta agtaaatgct cctcaccaga atacgtagct gtgtgaaaag    11400
agaacgcgtg aatacgtagc tgtgtaaaga ttgtgtccca agtaaacctc agtgattttt    11460
gtttggattt ttaatttaga aacattcgac tgggagcggc tagagccaca cccaagttcc    11520
taactatgat aaagttgctc tgtaacagaa acaccatct agagcggccg cgtttaaact    11580
atcagtgttt gacaggatat attggcgggt aaacctaaga gaaaagagcg tttattagaa    11640
taatcggata tttaaaaggg cgtgaaaagg tttatccgtt cgtccatttg tatgtgcatg    11700
ccaaccacag ggttcccctc gggagtgctt ggcattccgt gcgataatga cttctgttca    11760
accacccaaa cgtcggaaag cctgacgacg gagcagcatt ccaaaaagat cccttggctc    11820
gtctgggtcg gctagaaggt cgagtgggct gctgtggctt gatccctcaa cgcggtcgcg    11880
gacgtagcgc agcgccgaaa aatcct                                         11906

<210> SEQ ID NO 34
<211> LENGTH: 7158
<212> TYPE: DNA
<213> ORGANISM: Artificial Sequence
<220> FEATURE:
<223> OTHER INFORMATION: DNA construct 405

<400> SEQUENCE: 34
aaaagtccca tgtggatcac tccgttgccc cgtcgctcac cgtgttgggg ggaaggtgca      60
catggctcag ttctcaatgg aaattatctg cctaaccggc tcagttctgc gtagaaacca     120
acatgcaagc tccaccgggt gcaaagcggc agcggcggca ggatatattc aattgtaaat     180
ggcttcatgt ccgggaaatc tacatggatc agcaatgagt atgatggtca atatggagaa     240
aaagaaagag taattaccaa ttttttttca attcaaaaat gtagatgtcc gcagcgttat     300
tataaaatga agtacatttt tgataaaacg acaaattacg atccgtcgta tttataggcg     360
aaagcaataa acaaattatt ctaattcgga aatctttatt tcgacgtgtc tacattcacg     420
tccaaatggg ggcttagatg agaaacttca cgatcgatgc ggcccacgtg gattaccctg     480
ttatccctag aattcgatat cagttcgctc gtggccgtca cggccagcgc ctgcgttggc     540
ctagtaggcc aagcaggacg tattcgtttg ttgtgcggcc gctacctcag caaatcaacc     600
tcactctatt taaatgaggt ggtaggattt gctgaggagg ctgctccgtt gtcctgcagg     660
agacgagaaa caccctttaat taacctcagc gcgtgttctg ctggcgatcg caacaggcac     720
agcgctgagg gtaccgttgt caatcaattg gcaagtcata aaatgcatta aaaatatttt     780
tcatactcaa ctacaaatcc atgagtataa ctataattat aaagcaatga ttagaatctg     840
acaaggattc tggaaaatta cataaaggaa agttcataaa tgtctaaaac acaagaggac     900
```

```
atacttgtat tcagtaacat ttgcagcttt tctaggtctg aaaatatatt tgttgcctag    960
tgaataagca taatggtaca actacaagtg ttttactcct catattaact tcggtcatta   1020
gaggccacga tttgacacat ttttactcaa aacaaaatgt ttgcatatct cttataattt   1080
caaattcaac acacaacaaa taagagaaaa aacaaataat attaatttga gaatgaacaa   1140
aaggaccata tcattcatta actcttctcc atccatttcc atttcacagt tcgatagcga   1200
aaaccgaata aaaacacag taaattacaa gcacaacaaa tggtacaaga aaaacagttt    1260
tcccaatgcc ataatactca aactcagtag gattctggtg tgtgcgcaat gaaactgatg   1320
cattgaactt gacgaacgtt gtcgaaaccg atgatacgaa cgaaagctag gcctcagcga   1380
gtaccgctgg cgatctaatc catgatatcg tgaacatcat ctacattcaa attcttatga   1440
gctttcttaa gggcatctgc agcatttttc atagaatcta atacagcagt atttgtgcta   1500
gctccttcga gggcttccct ctgcatttca atagttgtaa gggttccatc tatttgtagt   1560
tgggtctttt ccaatcgttt cttcttttg agggcttgga gtgcaactct tttattttc    1620 gacgcatttt tctttgcgct cctgcaggcg gccgcgtgga tgaggagtta atcggtcgtg   1680
tgagagtagt gatcgagtgg atgtcgtcga gagtgatgag tgttgatgtt gttagtgata   1740
tgtggtagaa ggtatcgtga taaagcgtta acgcgatcgc agtacttgca aagaaaaatg   1800
cgtcgaaaaa taaaagagtt gcactccaag ccctcaaaaa gaagaaacga ttggaaaaga   1860
cccaactaca aatagatgga acccttacaa ctattgaaat gcagagggaa gccctcgaag   1920
gagctagcac aaatactgct gtattagatt ctatgaaaaa tgctgcagat gcccttaaga   1980
aagctcataa gaatttgaat gtagatgatg ttcacgatat catggatggt atcgcacagc   2040
gactgctgag ggacgtcgag ctcccgcttg gtatctgcat tacaatgaaa tgagcaaaga   2100
ctatgtgagt aacactggtc aacactaggg agaaggcatc gagcaagata cgtatgtaaa   2160
gagaagcaat atagtgtcag ttggtagata ctagatacca tcaggaggta aggagagcaa   2220
caaaaaggaa actctttatt tttaaatttt gttacaacaa acaagcagat caatgcatca   2280
aaatactgtc agtacttatt tcttcagaca acaatattta aaacaagtgc atctgatctt   2340
gacttatggt cacaataaag gagcagagat aaacatcaaa atttcgtcat ttatatttat   2400
tccttcaggc gttaacaatt taacagcaca caaacaaaaa cagaatagga atatctaatt   2460
ttggcaaata ataagctctg cagacgaaca aattattata gtatcgccta taatatgaat   2520
ccctatacta ttgacccatg tagtatgaag cctgtgccta aattaacagc aaacttctga   2580
atccaagtgc cctataacac caacatgtgc ttaaataaat accgctaagc accaaattac   2640
acatttctcg tattgctgtg taggttctat cttcgtttcg tactaccatg tccctatatt   2700
ttgctgctac aaaggacggc aagtaatcag cacaggcaga acacgatttc agagtgtaat   2760
tctagatcca gctaaaccac tctcagcaat caccacacaa gagagcattc agagaaacgt   2820
ggcagtaaca aaggcagagg gcggagtgag cgcgtaccga agacggtcct tcaaatggga   2880
atgaatgcct tcttatatag agggaattct tttgtggtcg tcactgcgtt cgtcatacgc   2940
attagtgagt gggctgtcag gacagctctt ttccacgtta ttttgttccc cacttgtact   3000
agaggaatct gctttatctt tgcaataaag gcaaagatgc ttttggtagg tgcgcctaac   3060
aattctgcac cattccttt ttgtctggtc cccacaagcc agctgctcga tgttgacaag    3120
attactttca aagatgccca ctaactttaa gtcttcggtg gatgtctttt tctgaaactt   3180
actgaccatg atgcatgtgc tggaacagta gtttactttg attgaagatt cttcattgat   3240
ctcctgtagc ttttggctaa tggtttggag actctgtacc ctgaccttgt tgaggctttg   3300
```

```
gactgagaat tcttccttac aaacctttga ggatgggagt tccttcttgg ttttggcgat    3360
accaatttga ataaagtgat atggctcgta ccttgttgat tgaacccaat ctggaatgcg    3420
gcgcgccaag cttctgcagg tccgattgag acttttcaac aaagggtaat atccggaaac    3480
ctcctcggat tccattgccc agctatctgt cactttattg tgaagatagt ggaaaaggaa    3540
ggtggctcct acaaatgcca tcattgcgat aaaggaaagg ccatcgttga agatgcctct    3600
gccgacagtg gtcccaaaga tggaccccca cccacgagga gcatcgtgga aaaagaagac    3660
gttccaacca cgtcttcaaa gcaagtggat tgatgtgatg gtccgattga acttttcaa     3720 caaagggtaa tatccggaaa cctcctcgga ttccattgcc cagctatctg tcactttatt    3780
gtgaagatag tggaaaagga aggtggctcc tacaaatgcc atcattgcga taaaggaaag    3840
gccatcgttg aagatgcctc tgccgacagt ggtcccaaag atggacccc acccacgagg     3900 agcatcgtgg aaaaagaaga cgttccaacc acgtcttcaa agcaagtgga ttgatgtgat    3960
atctccactg acgtaaggga tgacgcacaa tcccactatc cttcgcaaga cccttcctct    4020
atataaggaa gttcatttca tttggagagg acacgctgac aagctgactc tagcagatcc    4080
tctagaacca tcttccacac actcaagcca cactattgga gaacacacag gacaacaca     4140 ccataagatc caagggaggc ctccgccgcc gccggtaacc accccgcccc tctcctcttt    4200
ctttctccgt ttttttttcc gtctcggtct cgatctttgg ccttggtagt ttgggtgggc    4260
gagaggcggc ttcgtgcgcg cccagatcgg tgcgcgggag gggcgggatc tcgcggctgg    4320
ggctctcgcc ggcgtggatc cggcccggat ctcgcgggga atggggctct cggatgtaga    4380
tctgcgatcc gccgttgttg ggggagatga tgggggtttt aaaatttccg ccgtgctaaa    4440
caagatcagg aagaggggaa aagggcacta tggtttatat ttttatatat ttctgctgct    4500
tcgtcaggct tagatgtgct agatctttct ttcttctttt tgtgggtaga atttgaatcc    4560
ctcagcattg ttcatcggta gttttttcttt tcatgatttg tgacaaatgc agcctcgtgc    4620
ggagcttttt tgtaggtaga agtgatcaac catggccaac cccaacaatc gctccgagca    4680
cgacacgatc aaggtcaccc ccaactccga gctccagacc aaccacaacc agtacccgct    4740
ggccgacaac cccaactcca ccctggaaga gctgaactac aaggagttcc tgcgcatgac    4800
cgaggactcc tccacggagg tcctggacaa ctccaccgtc aaggacgccg tcgggaccgg    4860
catctccgtc gttgggcaga tcctgggcgt cgttggcgtc cccttcgcag gtgctctcac    4920
ctccttctac cagtccttcc tgaacaccat ctggccctcc gacgccgacc cctggaaggc    4980
cttcatggcc caagtcgaag tcctgatcga caagaagatc gaggagtacg ccaagtccaa    5040
ggccctggcc gagctgcaag gcctgcaaaa caacttcgag gactacgtca acgcgctgaa    5100
ctcctggaag aagacgcctc tgtccctgcg ctccaagcgc tcccaggacc gcatccgcga    5160
gctgttctcc caggccgagt cccacttccg caactccatg ccgtccttcg ccgtctccaa    5220
gttcgaggtc ctgttcctgc ccacctacgc ccaggctgcc aacacccacc tcctgttgct    5280
gaaggacgcc caggtcttcg gcgaggaatg gggctactcc tcggaggacg tcgccgagtt    5340
ctaccgtcgc cagctgaagc tgacccaaca gtacaccgac cactgcgtca actggtacaa    5400
cgtcggcctg aacggcctga ggggctccac ctacgacgca tgggtcaagt tcaaccgctt    5460
ccgcagggag atgaccctga ccgtcctgga cctgatcgtc ctgttcccct tctacgacat    5520
ccgcctgtac tccaagggcg tcaagaccga gctgacccgc gacatcttca cggacccccat    5580 cttcctgctc acgaccctcc agaagtacgg tcccaccttc ctgtccatcg agaactccat    5640
```

-continued

| | |
|---|---|
| ccgcaagccc cacctgttcg actacctcca gggcatcgag ttccacacgc gcctgaggcc | 5700 |
| aggctacttc ggcaaggact ccttcaacta ctggtccggc aactacgtcg agaccaggcc | 5760 |
| ctccatcggc tcctcgaaga cgatcacctc ccctttctac ggcgacaagt ccaccgagcc | 5820 |
| cgtccagaag ctgtccttcg acggccagaa ggtctaccgc accatcgcca acaccgacgt | 5880 |
| cgcggcttgg ccgaacggca aggtctacct gggcgtcacg aaggtcgact tctcccagta | 5940 |
| cgatgaccag aagaacgaga cctccaccca gacctacgac tccaagcgca caatggcca | 6000 |
| cgtctccgcc caggactcca tcgaccagct gccgcctgag accactgacg agccctgga | 6060 |
| gaaggcctac tcccaccagc tgaactacgg ggagtgcttc ctgatgcaag accgcagggg | 6120 |
| caccatcccc ttcttcacct ggacccaccg ctccgtcgac ttcttcaaca ccatcgacgc | 6180 |
| cgagaagatc acccagctgc ccgtggtcaa ggcctacgcc ctgtcctcgg gtgcctccat | 6240 |
| cattgagggt ccaggcttca ccggtggcaa cctgctgttc ctgaaggagt cctcgaactc | 6300 |
| catcgccaag ttcaaggtca ccctgaactc cgctgccttg ctgcaacgct accgcgtccg | 6360 |
| catccgctac gcctccacca cgaacctgcg cctgttcgtc cagaactcca caatgactt | 6420 |
| cctggtcatc tacatcaaca agaccatgaa caaggacgat gacctgacct accagacctt | 6480 |
| cgacctcgcc accacgaact ccaacatggg cttctcgggc gacaagaatg aactgatcat | 6540 |
| tggtgctgag tccttcgtct ccaacgagaa gatctacatc gacaagatcg agttcatccc | 6600 |
| cgtccagctg tgataggaac tctgattgaa ttctgcatgc gtttggacgt atgctcattc | 6660 |
| aggttggagc caatttggtt gatgtgtgtg cgagttcttg cgagtctgat gagacatctc | 6720 |
| tgtattgtgt ttctttcccc agtgtttct gtacttgtgt aatcggctaa tcgccaacag | 6780 |
| attcggcgat gaataaatga gaataaatt gttctgattt tgagtgcaaa aaaaaggaa | 6840 |
| ttagatctgt gtgtgtttt tggatccgtc gacagacctc aattgcgagc tttctaattt | 6900 |
| caaactattc gggcctaact tttggtgtga tgatgctgac tggcaggata tataccgttg | 6960 |
| taatttgagc tcgtgtgaat aagtcgctgt gtatgtttgt ttgattgttt ctgttggagt | 7020 |
| gcagcccatt tcaccggaca agtcggctag attgatttag ccctgatgaa ctgccgaggg | 7080 |
| gaagccatct tgagcgcgga atgggaatgg atttcgttgt acaacgagac gacagaacac | 7140 |
| ccacgggacc gagcttcg | 7158 |

<210> SEQ ID NO 35
<211> LENGTH: 8208
<212> TYPE: DNA
<213> ORGANISM: Artificial Sequence
<220> FEATURE:
<223> OTHER INFORMATION: DNA construct 406

<400> SEQUENCE: 35

| | |
|---|---|
| aaaagtccca tgtggatcac tccgttgccc cgtcgctcac cgtgttgggg ggaaggtgca | 60 |
| catggctcag ttctcaatgg aaattatctg cctaaccggc tcagttctgc gtagaaacca | 120 |
| acatgcaagc tccaccgggt gcaaagcggc agcggcggca ggatatattc aattgtaaat | 180 |
| ggcttcatgt ccgggaaatc tacatggatc agcaatgagt atgatggtca atatggagaa | 240 |
| aaagaaagag taattaccaa ttttttttca attcaaaaat gtagatgtcc gcagcgttat | 300 |
| tataaaatga agtacatttt tgataaaacg acaaattacg atccgtcgta tttataggcg | 360 |
| aaagcaataa acaaattatt ctaattcgga aatctttatt tcgacgtgtc tacattcacg | 420 |
| tccaaatggg ggcttagatg agaaacttca cgatcgatgc ggcccacgtg gattaccctg | 480 |
| ttatccctag aattcgatat cagttcgctc gtggccgtca cggccagcgc ctgcgttggc | 540 |

```
ctagtaggcc aagcaggacg tattcgtttg ttgtgcggcc gcgttaacaa gcttctgcag    600
gtccgattga gacttttcaa caaagggtaa tatccggaaa cctcctcgga ttccattgcc    660
cagctatctg tcactttatt gtgaagatag tggaaaagga aggtggctcc tacaaatgcc    720
atcattgcga taaaggaaag gccatcgttg aagatgcctc tgccgacagt ggtcccaaag    780
atggaccccc acccacgagg agcatcgtgg aaaagaaga cgttccaacc acgtcttcaa    840
agcaagtgga ttgatgtgat ggtccgattg agacttttca caaagggta atatccggaa    900 acctcctcgg attccattgc ccagctatct gtcactttat tgtgaagata gtggaaaagg    960
aaggtggctc ctacaaatgc catcattgcg ataaaggaaa ggccatcgtt gaagatgcct   1020
ctgccgacag tggtcccaaa gatggacccc cacccacgag gagcatcgtg gaaaagaag   1080 acgttccaac cacgtcttca agcaagtgg attgatgtga tatctccact gacgtaaggg   1140
atgacgcaca atcccactat ccttcgcaag acccttcctc tatataagga agttcatttc   1200
atttggagag acacgctga caagctgact ctagcagatc tctagaaacc atcttccaca   1260
cactcaagcc acactattgg agaacacaca gggacaacac accataagat ccaagggagg   1320
cctccgccgc cgccggtaac caccccgccc ctctcctctt tctttctccg ttttttttc    1380 cgtctcggtc tcgatctttg gccttggtag tttgggtggg cgagaggcgg cttcgtgcgc   1440
gcccagatcg gtgcgcggga ggggcgggat ctcgcggctg ggctctcgc cggcgtggat    1500 ccggcccgga tctcgcgggg aatggggctc tcggatgtag atctgcgatc cgccgttgtt   1560
gggggagatg atgggggggtt taaaatttcc gccgtgctaa acaagatcag gaagagggga   1620
aaagggcact atggtttata tttttatata tttctgctgc ttcgtcaggc ttagatgtgc   1680
tagatctttc tttcttcttt ttgtgggtag aatttgaatc cctcagcatt gttcatcggt   1740 agttttttctt ttcatgattt gtgacaaatg cagcctcgtg cggagctttt ttgtaggtag   1800
aagtgatcaa ccatggccaa ccccaacaat cgctccgagc acgacacgat caaggtcacc   1860
cccaactccg agctccagac caaccacaac cagtacccgc tggccgacaa ccccaactcc   1920
accctggaag agctgaacta caaggagttc ctgcgcatga ccgaggactc ctccacggag   1980
gtcctggaca actccaccgt caaggacgcc gtcgggaccg gcatctccgt cgttgggcag   2040
atcctgggcg tcgttggcgt ccccttcgca ggtgctctca cctccttcta ccagtccttc   2100
ctgaacacca tctggcccctc cgacgccgac ccctggaagg ccttcatggc ccaagtcgaa   2160
gtcctgatcg acaagaagat cgaggagtac gccaagtcca aggccctggc cgagctgcaa   2220
ggcctgcaaa caacttcga ggactacgtc aacgcgctga actcctggaa gagacgcct    2280 ctgtccctgc gctccaagcg ctcccaggac cgcatccgcg agctgttctc ccaggccgag   2340
tcccacttcc gcaactccat gccgtccttc gccgtctcca gttcgaggt cctgttcctg   2400 cccacctacg cccaggctgc caacacccac ctcctgttgc tgaaggacgc ccaggtcttc   2460
ggcgaggaat ggggctactc ctcggaggac gtcgccagt tctaccgtcg ccagctgaag   2520
ctgacccaac agtacaccga ccactgcgtc aactggtaca cgtcggcct gaacggcctg   2580 aggggctcca cctacgacgc atgggtcaag ttcaaccgct tccgcaggga gatgaccctg   2640
accgtcctgg acctgatcgt cctgttcccc ttctacgaca tccgcctgta ctccaagggc   2700
gtcaagaccg agctgacccc cgacatcttc acggacccca tcttcctgct cacgaccctc   2760
cagaagtacg tcccaccctt cctgtccatc gagaactcca tccgcaagcc ccacctgttc   2820
gactacctcc agggcatcga gttccacacg cgcctgaggc caggctactt cggcaaggac   2880
```

```
tccttcaact actggtccgg caactacgtc gagaccaggc cctccatcgg ctcctcgaag    2940
acgatcacct ccccttttcta cggcgacaag tccaccgagc ccgtccagaa gctgtccttc    3000
gacggccaga aggtctaccg caccatcgcc aacaccgacg tcgcggcttg ccgaacggc     3060
aaggtctacc tgggcgtcac gaaggtcgac ttctcccagt acgatgacca agaacgag      3120
acctccaccc agacctacga ctccaagcgc aacaatggcc acgtctccgc ccaggactcc    3180
atcgaccagc tgccgcctga gaccactgac gagcccctgg agaaggccta ctcccaccag    3240
ctgaactacg cggagtgctt cctgatgcaa gaccgcaggg gcaccatccc cttcttcacc    3300
tggacccacc gctccgtcga cttcttcaac accatcgacg ccgagaagat cacccagctg    3360
cccgtggtca aggcctacgc cctgtcctcg ggtgcctcca tcattgaggg tccaggcttc    3420
accggtggca acctgctgtt cctgaaggag tcctcgaact ccatcgccaa gttcaaggtc    3480
accctgaact ccgctgcctt gctgcaacgc taccgcgtcc gcatccgcta cgcctccacc    3540
acgaacctgc gcctgttcgt ccagaactcc aacaatgact tcctggtcat ctacatcaac    3600
aagaccatga acaaggacga tgacctgacc taccagacct tcgacctcgc caccacgaac    3660
tccaacatgg gcttctcggg cgacaagaat gaactgatca ttggtgctga gtccttcgtc    3720
tccaacgaga agatctacat cgacaagatc gagttcatcc ccgtccagct gtgataggaa    3780
ctctgattga attctgcatg cgtttggacg tatgctcatt caggttggag ccaatttggt    3840
tgatgtgtgt gcgagttctt gcgagtctga tgagacatct ctgtattgtg tttctttccc    3900
cagtgttttc tgtacttgtg taatcggcta atcgccaaca gattcggcga tgaataaatg    3960
agaaataaat tgttctgatt ttgagtgcaa aaaaaagga attagatctg tgtgtgtttt    4020
ttggatcccc ggggcggccg ctacctcagc aaatcaacct cactctattt aaatgaggtg    4080
gtaggatttg ctgaggaggc tgctccgttg tcctgcagga gacgagaaac acctttaatt    4140
aacaaatcac aggccatgaa ccctactcat gcttcgattt gtccaacaca cacttaccaa    4200
aactcaaatc atgtccttga cagtcactcg ggactcataa catgggtacg tatcgactat    4260
gtcaactata tgtgttctca tcagattata gattggccta gtacgtagtg atatttccac    4320
tagcactgtg gttatggctg tacctgatag tgatatcagc accgggtcat ggctctacta    4380
ccaggtagtg agagtgacct ttatactgtc agactgtaac taaggatttc caatcactgt    4440
tcggatccta ggcttagaat taagtaaaac tctatcacta taggctgcag cacactcggt    4500
atatattgat gggccaacag aaattgtgcg tactatgcgc gatgtaaaat ggacataaac    4560
cctacccata taactgcaa taacttttgt ccggtctggg ccaccggtta gcagaggtcc    4620
tgatttcggt ggtagtggta gcttgatctg gtcgtcgtat cgtagaggga tatataaaat    4680
catgtcactt ttgaagggag cgctcacaga aataataggt attcgcggga gccgcccccg    4740
cagaacacaa aataaggcga gcacgcacac gcatcagttt cgataaaata ataatagcgc    4800
cagctgatcg gaacaattcc agctagcact aatgtatttc tgcattgatc tgtttataca    4860
acatgctacc tcgttgagtg attttgacat gatttgtcaa cttgctccga tcctatatct    4920
cgatcgatct ccacatgacg atggttgttg tcctgtatcc catgacaacc aggcaacgct    4980
caaagcacac atgcgttgcc gattacccgt gcatgccgcc aagcacgaaa gcacctccct    5040
ccacaccgtc catcagcggt ccgattgaga cttttcaaca aagggtaata tccggaaacc    5100
tcctcggatt ccattgccca gctatctgtc actttattgt gaagatagtg gaaaggaag     5160
gtggctccta caaatgccat cattgcgata aaggaaggc catcgttgaa gatgcctctg    5220
ccgacagtgg tcccaaagat ggaccccccac ccacgaggag catcgtggaa aagaagacg    5280
```

```
ttccaaccac gtcttcaaag caagtggatt gatgtgatgg tccgattgag acttttcaac    5340
aaagggtaat atccggaaac ctcctcggat tccattgccc agctatctgt cactttattg    5400
tgaagatagt ggaaaaggaa ggtggctcct acaaatgcca tcattgcgat aaaggaaagg    5460
ccatcgttga agatgcctct gccgacagtg gtcccaaaga tggaccccca cccacgagga    5520
gcatcgtgga aaagaagac gttccaacca cgtcttcaaa gcaagtggat tgatgtgata    5580
tctccactga cgtaagggat gacgcacaat cccactatcc ttcgcaagac ccttcctcta    5640
tataaggaag ttcatttcat tggagagga cacgctgaac cgtcttcggt acgcgctcac    5700
tccgccctct gcctttgtta ctgccacgtt tctctgaatg ctctcttgtg tggtgattgc    5760
tgagagtggt ttagctggat ctagaattac actctgaaat cgtgttctgc ctgtgctgat    5820
tacttgccgt cctttgtagc agcaaaatat agggacatgg tagtacgaaa cgaagataga    5880
acctacacag caatacgaga aatgtgtaat ttggtgctta gcggtattta tttaagcaca    5940
tgttggtgtt atagggcact tggattcaga agtttgctgt taatttaggc acaggcttca    6000
tactacatgg gtcaatagta tagggattca tattataggc gatactataa taatttgttc    6060
gtctgcagag cttattattt gccaaaatta gatattccta ttctgttttt gtttgtgtgc    6120
tgttaaattg ttaacgcctg aaggaataaa tataaatgac gaaattttga tgtttatctc    6180
tgctccttta ttgtgaccat aagtcaagat cagatgcact tgttttaaat attgttgtct    6240
gaagaaataa gtactgacag tattttgatg cattgatctg cttgtttgtt gtaacaaaat    6300
ttaaaaataa agagtttcct ttttgttgct ctccttacct cctgatggta tctagtatct    6360
accaactgac actatattgc ttctctttac atacgtatct tgctcgatgc cttctcccta    6420
gtgttgacca gtgttactca catagtcttt gctcatttca ttgtaatgca gataccaagc    6480
gggagctcga cgtccctcag cagtcgctgt gcgataccat ccatgatatc gtgaacatca    6540
tctacattca aattcttatg agctttctta agggcatctg cagcattttt catagaatct    6600
aatacagcag tatttgtgct agctccttcg agggcttccc tctgcatttc aatagttgta    6660
agggttccat ctatttgtag ttgggtcttt tccaatcgtt tcttcttttt gagggcttgg    6720
agtgcaactc ttttattttt cgacgcattt ttctttgcaa gtactgcgat cgcgttaacg    6780
ctttatcacg ataccttcta ccacatatca ctaacaacat caacactcat cactctcgac    6840
gacatccact cgatcactac tctcacacga ccgattaact cctcatccac gcggccgcct    6900
gcaggagcgc aaagaaaaat gcgtcgaaaa ataaagagt tgcactccaa gccctcaaaa    6960
agaagaaacg attggaaaag acccaactac aaatagatgg aacccttaca actattgaaa    7020
tgcagaggga agccctcgaa ggagctagca caaatactgc tgtattagat tctatgaaaa    7080
atgctgcaga tgcccttaag aaagctcata agaatttgaa tgtagatgat gttcacgata    7140
tcatggatta gatcgccagc ggtactcgct gaggcctagc tttcgttcgt atcatcggtt    7200
tcgacaacgt tcgtcaagtt caatgcatca gtttcattgc gcacacacca gaatcctact    7260
gagtttgagt attatggcat tgggaaaact gttttttcttg taccatttgt tgtgcttgta    7320
atttactgtg tttttttattc ggttttcgct atcgaactgt gaaatggaaa tggatggaga    7380
agagttaatg aatgatatgg tccttttgtt cattctcaaa ttaatattat ttgttttttc    7440
tcttatttgt tgtgtgttga atttgaaatt ataagagata tgcaaacatt ttgttttgag    7500
taaaaatgtg tcaaatcgtg gcctctaatg accgaagtta atatgaggag taaaacactt    7560
gtagttgtac cattatgctt attcactagg caacaaatat attttcagac ctagaaaagc    7620
```

| | |
|---|---|
| tgcaaatgtt actgaataca agtatgtcct cttgtgtttt agacatttat gaactttcct | 7680 |
| ttatgtaatt ttccagaatc cttgtcagat tctaatcatt gctttataat tatagttata | 7740 |
| ctcatggatt tgtagttgag tatgaaaata ttttttaatg cattttatga cttgccaatt | 7800 |
| gattgacaac ggtaccgtcg gtccgagttt gcgtcttggc gcgccaagaa gaacgattcg | 7860 |
| ctaccttagg accgttatag ttagaattcg atatctagtt agggataaca gggtaatgtc | 7920 |
| gacagacctc aattgcgagc tttctaattt caaactattc gggcctaact tttggtgtga | 7980 |
| tgatgctgac tggcaggata tataccgttg taatttgagc tcgtgtgaat aagtcgctgt | 8040 |
| gtatgtttgt ttgattgttt ctgttggagt gcagcccatt tcaccggaca agtcggctag | 8100 |
| attgatttag ccctgatgaa ctgccgaggg gaagccatct tgagcgcgga atgggaatgg | 8160 |
| atttcgttgt acaacgagac gacagaacac ccacgggacc gagcttcg | 8208 |

<210> SEQ ID NO 36
<211> LENGTH: 2632
<212> TYPE: DNA
<213> ORGANISM: Artificial Sequence
<220> FEATURE:
<223> OTHER INFORMATION: DNA construct 890

<400> SEQUENCE: 36

| | |
|---|---|
| aaaagtccca tgtggatcac tccgttgccc cgtcgctcac cgtgttgggg ggaaggtgca | 60 |
| catggctcag ttctcaatgg aaattatctg cctaaccggc tcagttctgc gtagaaacca | 120 |
| acatgcaagc tccaccgggt gcaaagcggg agcggcggca ggatatattc aattgtaaat | 180 |
| ggcttcatgt ccgggaaatc tacatggatc agcaatgagt atgatggtca atatggagaa | 240 |
| aaagaaagag taattaccaa tttttttttca attcaaaaat gtagatgtcc gcagcgttat | 300 |
| tataaaatga aagtacattt tgataaaacg acaaattacg atccgtcgta tttataggcg | 360 |
| aaagcaataa acaaattatt ctaattcgga aatctttatt tcgacgtgtc tacattcacg | 420 |
| tccaaatggg ggcttagatg agaaacttca cgatcgatgc ggccgcttaa ttaaggcgcg | 480 |
| ccgctagcct gcaggctgca ggtccgattg agacttttca acaagggta atatccggaa | 540 |
| acctcctcgg attccattgc ccagctatct gtcactttat tgtgaagata gtggaaaagg | 600 |
| aaggtggctc ctacaaatgc catcattgcg ataaaggaaa ggccatcgtt gaagatgcct | 660 |
| ctgccgacag tggtcccaaa gatggacccc cacccgacgag gagcatcgtg gaaaagaag | 720 |
| acgttccaac cacgtcttca aagcaagtgg attgatgtga tggtccgatt gagacttttc | 780 |
| aacaaagggt aatatccgga aacctcctcg gattccattg cccagctatc tgtcacttta | 840 |
| ttgtgaagat agtggaaaag gaaggtggct cctacaaatg ccatcattgc gataaaggaa | 900 |
| aggccatcgt tgaagatgcc tctgccgaca gtggtcccaa agatggaccc ccacccacga | 960 |
| ggagcatcgt ggaaaagaa gacgttccaa ccacgtcttc aaagcaagtg gattgatgtg | 1020 |
| atatctccac tgacgtaagg gatgacgcac aatcccacta tccttcgcaa gacccttcct | 1080 |
| ctatataagg aagttcattt catttggaga ggacacgctg agggcccacc gtcttcggta | 1140 |
| cgcgctcact ccgccctctg cctttgttac tgccacgttt ctctgaatgc tctcttgtgt | 1200 |
| ggtgattgct gagagtggtt tagctggatc tagaattaca ctctgaaatc gtgttctgcc | 1260 |
| tgtgctgatt acttgccgtc ctttgtagca gcaaaatata gggacatggt agtacgaaac | 1320 |
| gaagatagaa cctacacagc aatacgagaa atgtgtaatt tggtgcttag cggtatttat | 1380 |
| ttaagcacat gttggtgtta tagggcactt ggattcagaa gtttgctgtt aatttaggca | 1440 |
| caggcttcat actacatggg tcaatagtat agggattcat attataggcg atactataat | 1500 |

-continued

```
aatttgttcg tctgcagagc ttattatttg ccaaaattag atattcctat tctgttttg    1560 tttgtgtgct gttaaattgt taacgcctga aggaataaat ataaatgacg aaattttgat    1620
gtttatctct gctcctttat tgtgaccata agtcaagatc agatgcactt gttttaaata    1680
ttgttgtctg aagaaataag tactgacagt attttgatgc attgatctgc ttgtttgttg    1740
taacaaaatt taaaaataaa gagtttcctt tttgttgctc tccttacctc ctgatggtat    1800
ctagtatcta ccaactgaca ctatattgct tctctttaca tacgtatctt gctcgatgcc    1860
ttctccctag tgttgaccag tgttactcac atagtctttg ctcatttcat tgtaatgcag    1920
ataccaagcg ggagctcgac gtccctcagc agtcgctgtg cgataccatc catgatatcg    1980
tgaacatcat ctacattcaa attcttatga gctttcttaa gggcatctgc agcatttttc    2040
atagaatcta atacagcagt atttgtgcta gctccttcga gggcttccct ctgcatttca    2100
atagttgtaa gggttccatc tatttgtagt tgggtctttt ccaatcgttt cttcttttg    2160 agggcttgga gtgcaactct tttatttttc gacgcatttt tctttgcaag tactgcgatc    2220
gcgttaacgc tttatcacga taccttctac cacatatcac taacaacatc aacactcatc    2280
actctcgacg acatccactc gatcactact ctcacgacg cgattaactc ctcatccacg      2340
cggccgcctg caggagcgca aagaaaaatg cgtcgaaaaa taaagagtt gcactccaag      2400 ccctcaaaaa gaagaaacga ttggaaagaa cccaactaca aatagatgga acccttacaa    2460
ctattgaaat gcagagggaa gccctcgaag gagctagcac aaatactgct gtattagatt    2520
ctatgaaaaa tgctgcagat gcccttaaga aagctcataa gaatttgaat gtagatgatg    2580
ttcacgatat catggattag atcgccagcg gtactcgctg aggcctagct tt            2632
```

<210> SEQ ID NO 37
<211> LENGTH: 193
<212> TYPE: DNA
<213> ORGANISM: Zea mays
<220> FEATURE:
<221> NAME/KEY: misc_feature
<223> OTHER INFORMATION: represents a segment of the integration site in
      the LH244 corn genome at which TDNA from DNA construct #417 was
      inserted to create Event MON 87411

<400> SEQUENCE: 37

```
aaggaaaata aaaggcaaa acactaatga atagttaagt ggttaacttt gtgaaattaa       60
tctcatgtaa tatatgatcc caccctgaa ataactttag taattcatta agatagctat      120
agttaagtta tgtaatacat tgagatgggt agtacttaga gaatcacaaa cctctagatg    180
tattaatcta ccc                                                       193
```

<210> SEQ ID NO 38
<211> LENGTH: 28
<212> TYPE: DNA
<213> ORGANISM: artificial sequence
<220> FEATURE:
<223> OTHER INFORMATION: is a nucleotide sequence representing a
      synthetic oligonucleotide, and is referred to as SQ20221

<400> SEQUENCE: 38

```
gttgctatgt actaacagaa ctgcatgt                                        28
```

<210> SEQ ID NO 39
<211> LENGTH: 24
<212> TYPE: DNA
<213> ORGANISM: artificial sequence
<220> FEATURE:

```
<223> OTHER INFORMATION: is a nucleotide sequence representing a
      synthetic oligonucleotide, and is referred to as PB10065

<400> SEQUENCE: 39
gccctatgac ttaccgagag ttca                                              24

<210> SEQ ID NO 40
<211> LENGTH: 29
<212> TYPE: DNA
<213> ORGANISM: artificial sequence
<220> FEATURE:
<223> OTHER INFORMATION: is a nucleotide sequence representing a
      synthetic oligonucleotide, and is referred to as SQ20222

<400> SEQUENCE: 40
ttgttgtgtg gctccattct gacttgtga                                         29

<210> SEQ ID NO 41
<211> LENGTH: 60
<212> TYPE: DNA
<213> ORGANISM: Artificial Sequence
<220> FEATURE:
<223> OTHER INFORMATION: is a nucleotide sequence of event MON 87411

<400> SEQUENCE: 41
gatgcggcca ccactcgagg tcgaggtacc gttgtcaatc aattggcaag tcataaaatg       60

<210> SEQ ID NO 42
<211> LENGTH: 89
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 42
ttgtcgaaac cgatgatacg aacgaaagct aggcctcagc gagtaccgct ggcgatctaa       60
tccatgatat cgtgaacatc atctacatt                                         89

<210> SEQ ID NO 43
<211> LENGTH: 96
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 43
aatgtagatg atgttcacga tatcatggat ggtatcgcac agcgactgct gagggacgtc       60
gagctcccgc ttggtatctg cattacaatg aaatga                                 96

<210> SEQ ID NO 44
<211> LENGTH: 347
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 44
taccctttgt tgaaaagtct caatcggacc atcacatcaa tccacttgct ttgaagacgt       60
ggttggaacg tcttcttttt ccacgatgct cctcgtgggt gggggtccat ctttgggacc      120
actgtcggca gaggcatctt caacgatggc ctttcctttg tcgcaatgat ggcatttgta      180
```
ggagccacct tcctttttcca ctatcttcac aataaagtga cagatagctg ggcaatggaa    240
tccgaggagg tttccggata ttacccttttg ttgaaaagtc tcaatcggac ctgcagcctg    300
caggctagcg gcgcgccaca aatcacaggc catgaaccct actcatg    347

<210> SEQ ID NO 45
<211> LENGTH: 76
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 45
gctataaaaa ccatgccaag caccctgtga aaagccccgg gaaccatctt ccacacactc    60
aagccacact attgga    76

<210> SEQ ID NO 46
<211> LENGTH: 86
<212> TYPE: DNA
<213> ORGANISM: Artificial Sequence
<220> FEATURE:
<223> OTHER INFORMATION: a junction sequence within the transgenic
      insert of event MON 87411

<400> SEQUENCE: 46
actattggag aacacacagg gacaacacac cataagatcc aagggaggcc tccgccgccg    60
ccggtaacca ccccgcccct ctcctc    86

<210> SEQ ID NO 47
<211> LENGTH: 79
<212> TYPE: DNA
<213> ORGANISM: Artificial Sequence
<220> FEATURE:
<223> OTHER INFORMATION: a junction sequence within the transgenic
      insert of event MON 87411

<400> SEQUENCE: 47
tgcagcctcg tgcggagctt ttttgtaggt agaagtgatc aaccatggcc aaccccaaca    60
atcgctccga gcacgacac    79

<210> SEQ ID NO 48
<211> LENGTH: 89
<212> TYPE: DNA
<213> ORGANISM: Artificial Sequence
<220> FEATURE:
<223> OTHER INFORMATION: a junction sequence within the transgenic
      insert of event MON 87411

<400> SEQUENCE: 48
tcgacaagat cgagttcatc cccgtccagc tgtgatagga actctgattg aattctgcat    60
gcgtttggac gtatgctcat tcaggttgg    89

<210> SEQ ID NO 49
<211> LENGTH: 108
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 49
tctgattttg agtgcaaaaa aaaaggaatt agatctgtgt gtgttttttg gatcccattt    60

-continued

```
tcgacaagct tgcctcgaga caacaacatg cttctcatca acatggag                  108

<210> SEQ ID NO 50
<211> LENGTH: 104
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 50
aattcttaag gcgtaatttg ttgaaatctt gttttgtcct atgcagcctg atccatggcg     60
caagttagca gaatctgcaa tggtgtgcag aacccatctc ttat                      104

<210> SEQ ID NO 51
<211> LENGTH: 107
<212> TYPE: DNA
<213> ORGANISM: Artificial Sequence
<220> FEATURE:
<223> OTHER INFORMATION: a unique junction sequence within the
      transgenic insert of event MON 87411

<400> SEQUENCE: 51
tggccgggct gggcgcgaag atcgaactct ccgatacgaa ggctgcctga tgagctccag     60
ggttcttgcc tggtgccttg gcaatgcttg attactgctg ctatcct                   107

<210> SEQ ID NO 52
<211> LENGTH: 103
<212> TYPE: DNA
<213> ORGANISM: Artificial Sequence
<220> FEATURE:
<223> OTHER INFORMATION: is a nucleotide sequence of event MON 87411

<400> SEQUENCE: 52
tatgataaag ttgctctgta acagaaaaca ccatctagag cggccgcgtt taaactatca     60
gtgtttagag aatcacaaac ctctagatgt attaatctac cct                       103
```